US010179769B2

(12) United States Patent
Chen et al.

(10) Patent No.: US 10,179,769 B2
(45) Date of Patent: *Jan. 15, 2019

(54) HISTONE DEMETHYLASE INHIBITORS

(71) Applicant: CELGENE QUANTICEL RESEARCH, INC., San Diego, CA (US)

(72) Inventors: Young K. Chen, San Marcos, CA (US); Toufike Kanouni, Rancho Santa Fe, CA (US); Zhe Nie, San Diego, CA (US); Jeffrey Alan Stafford, San Diego, CA (US); James Marvin Veal, Apex, NC (US); Michael Brennan Wallace, San Diego, CA (US)

(73) Assignee: Celgene Quanticel Research, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/796,667

(22) Filed: Oct. 27, 2017

(65) Prior Publication Data

US 2018/0044296 A1   Feb. 15, 2018

Related U.S. Application Data

(60) Continuation of application No. 15/636,420, filed on Jun. 28, 2017, now Pat. No. 9,828,343, which is a continuation of application No. 15/441,142, filed on Feb. 23, 2017, now Pat. No. 9,725,441, which is a continuation of application No. 15/236,142, filed on Aug. 12, 2016, now Pat. No. 9,611,221, which is a continuation of application No. 14/740,143, filed on Jun. 15, 2015, now Pat. No. 9,447,045, which is a continuation of application No. 14/592,830, filed on Jan. 8, 2015, now Pat. No. 9,085,534, which is a division of application No. 14/139,197, filed on Dec. 23, 2013, now Pat. No. 8,952,151.

(60) Provisional application No. 61/785,380, filed on Mar. 14, 2013, provisional application No. 61/745,246, filed on Dec. 21, 2012.

(51) Int. Cl.
| C07D 213/79 | (2006.01) |
| C07D 401/12 | (2006.01) |
| C07D 405/12 | (2006.01) |
| C07D 409/12 | (2006.01) |
| C07D 213/74 | (2006.01) |
| C07D 237/24 | (2006.01) |
| C07D 405/14 | (2006.01) |
| C07D 213/81 | (2006.01) |
| C07D 401/04 | (2006.01) |
| C07D 409/14 | (2006.01) |

(52) U.S. Cl.
CPC ......... *C07D 213/79* (2013.01); *C07D 213/74* (2013.01); *C07D 213/81* (2013.01); *C07D 237/24* (2013.01); *C07D 401/04* (2013.01); *C07D 401/12* (2013.01); *C07D 405/12* (2013.01); *C07D 405/14* (2013.01); *C07D 409/12* (2013.01); *C07D 409/14* (2013.01)

(58) Field of Classification Search
CPC .. C07D 213/79; C07D 401/12; C07D 405/12; C07D 409/12
See application file for complete search history.

(56) References Cited

U.S. PATENT DOCUMENTS

| 7,897,612 B2 | 3/2011 | Fitch et al. |
| 8,034,811 B2 | 10/2011 | Fensholdt et al. |
| 8,952,151 B2 | 2/2015 | Chen et al. |
| 9,242,968 B2 | 1/2016 | Boloor et al. |
| 2004/0206599 A1 | 6/2004 | Delorme et al. |
| 2014/0080802 A1 | 3/2014 | Holson et al. |
| 2014/0171432 A1 | 6/2014 | Kanouni et al. |
| 2015/0119397 A1 | 4/2015 | Chen et al. |
| 2016/0107995 A1 | 4/2016 | Boloor et al. |

FOREIGN PATENT DOCUMENTS

| WO | 2005054179 A2 | 6/2005 |
| WO | 2006002383 A2 | 1/2006 |
| WO | 2012052390 A1 | 4/2012 |
| WO | 2013143597 A1 | 10/2013 |
| WO | 2014089368 A1 | 6/2014 |
| WO | 2014100818 A1 | 6/2014 |

OTHER PUBLICATIONS

Berge et al. Pharmaceutical Salts. Journal of Pharmaceutical Sciences 66(1):1-19 (Jan. 1977).
Extended European Search, dated May 2, 2015, issued in related European Patent Application No. 13865712.7, filed Dec. 23, 2013.
International Preliminary Report on Patentability, dated Jul. 2, 2015, issued in PCT/US2013/077539, filed Dec. 23, 2013.
International Search Report and Written Opinion, dated Apr. 28, 2014, issued in PCT/US2013/077539, filed Dec. 23, 2013.
Klose et al. JmjC-domain-containing proteins and histone demethylation. Nature Reviews Genetics 7:715-727 (Sep. 2006).
Lachner et al. An epigenetic road map for histone lysine methylation. Journal of Cell Science 116:2117-2124 (Jun. 1, 2003).
Lin et al. Loss of the retinoblastoma binding protein 2 (RBP2) histone demethylase suppresses tumorigenesis in mice lacking RB1 or Men 1.PNAS108(33):13379-13386 (2011).
Mangueron et al. The key to development: interpreting the histone code? Current Opinion Genet. Dev. 15:163-176 (2005).
Stahl et al., Handbook of Pharmaceutical Salts. Verlag Helvetica Chimica Acta, Zurich (2002).
Thalhammer, A. et al., Inhibition of the histone demethylase JMJD2E by 3-substituted pyridine 2,4-dicarboxylates. Org. Biomol. Chem. 9(1)127-135 (Jan. 7, 2011).

*Primary Examiner* — Timothy R Rozof
(74) *Attorney, Agent, or Firm* — Wiley Rein LLP

(57) ABSTRACT

The present invention relates generally to compositions and methods for treating cancer and neoplastic disease. Provided herein are substituted amidopyridine or amidopyridazine derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like.

14 Claims, No Drawings

HISTONE DEMETHYLASE INHIBITORS

RELATED APPLICATIONS

This Application is a continuation of U.S. patent application Ser. No. 15/636,420, filed Jun. 28, 2017, which is a continuation of U.S. patent application Ser. No. 15/441,142 (now U.S. Pat. No. 9,725,441), filed Feb. 23, 2017, which is a continuation of U.S. patent application Ser. No. 15/236,142, filed Aug. 12, 2016 (now U.S. Pat. No. 9,611,221), which is a continuation of U.S. patent application Ser. No. 14/740,143, filed Jun. 15, 2015 (now U.S. Pat. No. 9,447,045), which is a continuation of U.S. patent application Ser. No. 14/592,830, filed Jan. 8, 2015 (now U.S. Pat. No. 9,085,534), which is a division of U.S. patent application Ser. No. 14/139,197, filed Dec. 23, 2013 (now U.S. Pat. No. 8,952,151), which claims priority benefit of U.S. Provisional Patent Applications No. 61/785,380, filed Mar. 14, 2013, and No. 61/745,246, filed Dec. 21, 2012, the contents of which are hereby incorporated by reference in their entireties for all purposes.

BACKGROUND

A need exists in the art for an effective treatment of cancer and neoplastic disease.

SUMMARY OF THE INVENTION

Provided herein are substituted pyridine and pyridazine derivative compounds and pharmaceutical compositions comprising said compounds. The subject compounds and compositions are useful for inhibition of histone demethylase. Furthermore, the subject compounds and compositions are useful for the treatment of cancer, such as prostate cancer, breast cancer, bladder cancer, lung cancer and/or melanoma and the like. The substituted pyridine and pyridazine derivative compounds described herein are based upon a disubstituted pyridine or pyridazine ring bearing at the 4-position a carboxylic acid, a carboxylic acid ester, or a carboxylic acid bioisostere thereof, and at the 3-position a substituted amino group.

One embodiment provides a compound of Formula (XI), or a pharmaceutically acceptable salt thereof,

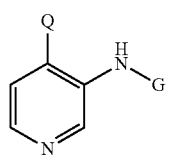

Formula (XI)

wherein:
Q is —CO$_2$R, —C(O)N(H)CN, —C(O)N(H)OH, or tetrazolyl;
R is hydrogen or optionally substituted alkyl;
G is —X—Y;
  X is —C$_1$ alkylene;
  Y is optionally substituted tetralinyl, optionally substituted tetrahydroquinolinyl, substituted pyridyl, optionally substituted naphthyl, optionally substituted indolyl, optionally substituted benzofuranyl, optionally substituted adamantyl, or optionally substituted indanyl.

One embodiment provides a compound of Formula (XI), or a pharmaceutically acceptable salt thereof,

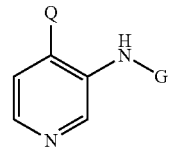

Formula (XI)

wherein:
Q is —CO$_2$R, —C(O)N(H)CN, —C(O)N(H)OH, or tetrazolyl;
R is hydrogen or optionally substituted alkyl;
G is —X—Y;
  X is —C$_1$ alkylene;
  Y is phenyl substituted with alkenyl, alkynyl, fluoro, chloro, fluoroalkyl, nitro, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$, —R$^b$—S(O)$_t$OR$^a$, —R$^b$—S(O)$_t$OR$^a$, and —R$^b$—S(O)$_t$N(R$^a$)$_2$;
  wherein:
    each R$^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl;
    each R$^b$ is independently a direct bond or a straight or branched alkylene or alkenylene chain;
    each R$^c$ is a straight or branched alkylene or alkenylene chain; and
    t is 1 or 2.

One embodiment provides a compound of Formula (XV), or a pharmaceutically acceptable salt thereof,

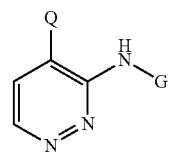

Formula (XV)

wherein,
Q is —CO$_2$R, —C(O)N(H)CN, —C(O)N(H)OH, or tetrazolyl;
R is hydrogen or optionally substituted alkyl;
G is —X—Y;
  X is —C$_1$ alkylene;
  Y is carbocyclyl, heterocyclyl, aryl, or heteroaryl;

with the proviso that G is not

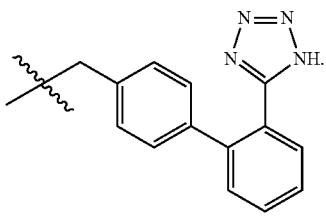 [SMILES: *Cc1ccc(-c2ccccc2-c2nnn[nH]2)cc1]

One embodiment provides a compound of Formula (XI), or a pharmaceutically acceptable salt thereof,

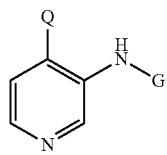

Formula (XI)

wherein:
Q is —CO$_2$R, —C(O)N(H)CN, —C(O)N(H)OH, or tetrazolyl;
R is hydrogen or optionally substituted alkyl;
G is —X—Y;
X is —C$_1$ alkylene;
Y is optionally substituted tetralinyl, optionally substituted chromanyl, optionally substituted tetrahydroquinolinyl, optionally substituted benzofuranyl, optionally substituted 2,3-dihydrobenzofuranyl, optionally substituted 2,3-dihydrobenzo[b][1,4]dioxinyl, optionally substituted naphthyl, optionally substituted indolyl, optionally substituted 1,2-dihydronaphthyl, optionally substituted indanyl, or optionally substituted thiochromanyl.

Another embodiment provides a compound of Formula (XI), or a pharmaceutically acceptable salt thereof, wherein the compound of Formula (XI) has the structure of Formula (XIa):

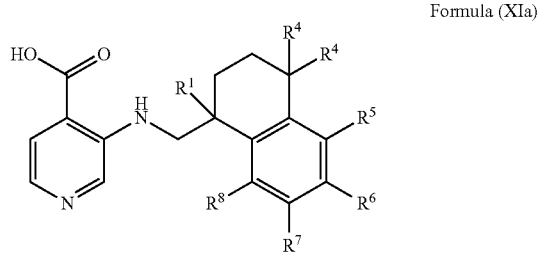

Formula (XIa)

wherein,
R$^1$ is hydrogen, methyl, or —OH;
each R$^4$ is independently hydrogen, fluoro, or methyl; and
R$^5$, R$^6$, R$^7$ and R$^8$ are each independently chosen from hydrogen, halogen, —OH, —CN, optionally substituted C$_1$-C$_6$ alkyl, optionally substituted C$_1$-C$_6$ alkoxy, optionally substituted C$_3$-C$_7$ carbocyclyl, optionally substituted C$_3$-C$_7$ carbocyclyloxy, optionally substituted C$_4$-C$_{12}$ carbocyclylalkyl, optionally substituted C$_4$-C$_{12}$ carbocyclylalkoxy, optionally substituted C$_1$-C$_6$ alkynyl, optionally substituted C$_1$-C$_6$ alkenyl, optionally substituted C$_6$-C$_{10}$ aryl, optionally substituted C$_6$-C$_{10}$ aryloxy, optionally substituted C$_6$-C$_{10}$ aryl-S—, optionally substituted C$_7$-C$_{14}$ aralkoxy, optionally substituted heteroaryl, and optionally substituted heteroaryloxy.

Another embodiment provides a compound of Formula (XI), or a pharmaceutically acceptable salt thereof, wherein the compound of Formula (XI) has the structure of Formula (XIb):

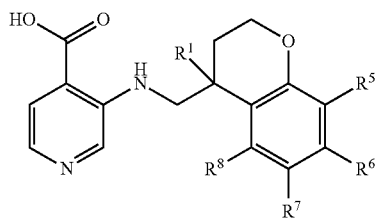

Formula (XIb)

wherein,
R$^1$ is hydrogen, methyl, or —OH; and
R$^5$, R$^6$, R$^7$ and R$^8$ are each independently chosen from hydrogen, halogen, —OH, —CN, optionally substituted C$_1$-C$_6$ alkyl, optionally substituted C$_1$-C$_6$ alkoxy, optionally substituted C$_3$-C$_7$ carbocyclyl, optionally substituted C$_3$-C$_7$ carbocyclyloxy, optionally substituted C$_4$-C$_{12}$ carbocyclylalkyl, optionally substituted C$_4$-C$_{12}$ carbocyclylalkoxy, optionally substituted C$_1$-C$_6$ alkynyl, optionally substituted C$_1$-C$_6$ alkenyl, optionally substituted C$_6$-C$_{10}$ aryl, optionally substituted C$_6$-C$_{10}$ aryloxy, optionally substituted C$_6$-C$_{10}$ aryl-S—, optionally substituted C$_7$-C$_{14}$ aralkoxy, optionally substituted heteroaryl, and optionally substituted heteroaryloxy.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising"

(and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises two to ten carbon atoms (e.g., $C_2$-$C_{10}$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula $-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula $-R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula $-R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula $-O-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula $-R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula $-O-R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxo-piperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxa-zolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo-[1,2-a]pyridinyl, carbazolyl, cinnolinyl, cyclopenta[d]pyrimidinyl, 6,7-dihydro-5H-cyclopenta[4,5]-thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexa-hydrocycloocta[d]pyrimidinyl, 5,6,7,8,9,10-hexahydrocycloocta[d]pyridazinyl, 5,6,7,8,9,10-hexa-hydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydro-quinazolinyl, naphthyridinyl, 1,6-naphthyridinonyl, oxadiazolyl, 2-oxoazepinyl, oxazolyl, oxiranyl, 5,6,6a,7,8,9,10,10a-octa-hydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]-pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydro-quinazolinyl, 5,6,7,8-tetrahydrobenzo[4,5]thieno[2,3-d]pyrimidinyl, 6,7,8,9-tetrahydro-5Hcyclo-hepta[4,5]thieno[2,3-d]pyrimidinyl, 5,6,7,8-tetrahydropyrido[4,5-c]-pyridazinyl, thiazolyl, thiadiazolyl, triazolyl, tetrazolyl, triazinyl, thieno[2,3-d]pyrimidinyl, thieno[3,2-d]-pyrimidinyl, thieno[2,3-c]pridinyl, and thiophenyl (i.e., thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—R—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

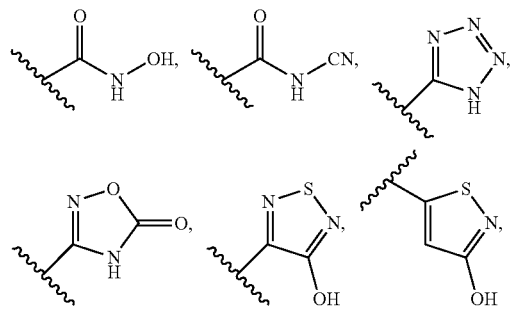

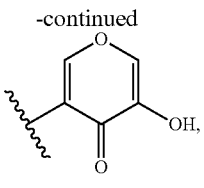

and the like.

The compounds, or their pharmaceutically acceptable salts, in some instances, contain one or more asymmetric centers and thus give rise to enantiomers, diastereomers, and other stereoisomeric forms that are defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "stereoisomer" refers to a compound made up of the same atoms bonded by the same bonds but having different three-dimensional structures, which are not interchangeable. It is contemplated that the disclosure provided herein encompasses the various stereoisomers and mixtures thereof and includes "enantiomers," which refers to two stereoisomers whose molecular structures are nonsuperimposeable mirror images of one another.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

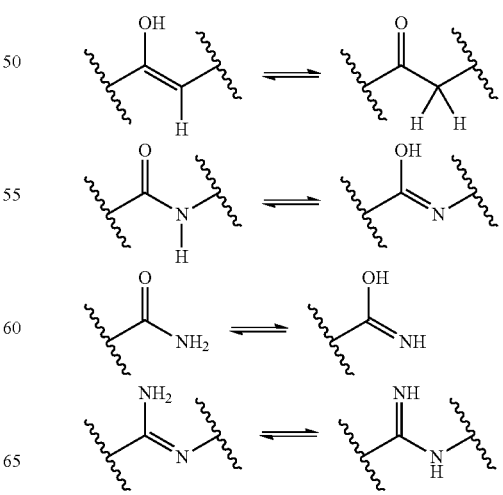

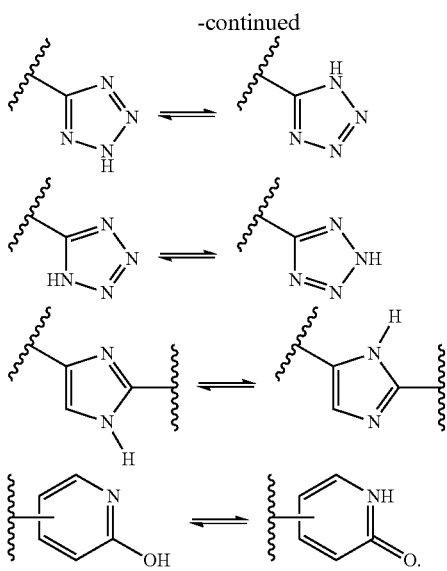

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted amidopyridine or amidopyridazine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogen-phosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitro-benzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, e.g., Berge et al., *Pharmaceutical Salts*, J. Pharm. Sci. 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, Design of Prodrugs (1985), pp. 7-9, 21-24 (Elsevier, Amsterdam).

A discussion of prodrugs is provided in Higuchi et al., *Pro-drugs as Novel Delivery Systems*, A.C.S. Symposium Series, Vol. 14; and in BIOREVERSIBLE CARRIERS IN DRUG DESIGN, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Pyridine or Pyridazine Derivative Compounds

Substituted pyridine and pyridazine derivative compounds are described herein that inhibit a histone demethylase enzyme. These compounds, and compositions comprising these compounds, are useful for the treatment of cancer and neoplastic disease. The compounds described herein may, therefore, be useful for treating prostate cancer, breast cancer, bladder cancer, lung cancer and/or melanoma and the like.

One embodiment provides a compound of Formula (I), or a tautomer, stereoisomer, geometric isomer, N-oxide, or pharmaceutically acceptable salt thereof,

Formula (I)

wherein,
R is hydrogen or alkyl;
G is —X—Y;
X is —$C_1$-$C_5$ alkylene, —($C_1$-$C_5$ alkylene)-Z—($C_1$-$C_5$ alkylene)-, or —($C_1$-$C_5$ alkylene)-Z—;
Y is carbocyclyl, heterocyclyl, aryl, or heteroaryl; and
Z is

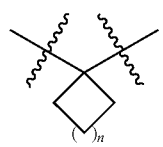

and n is 0, 1, 2, or 3;
with the provision: G is not

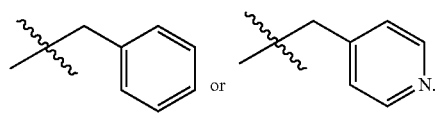 [SMILES: *Cc1ccccc1 ; *Cc1ccncc1]

Another embodiment provides the compound of Formula (I), wherein X is a $C_1$ alkylene. Another embodiment provides the compound of Formula (I), wherein X is a $C_2$ alkylene. Another embodiment provides the compound of Formula (I), wherein X is a $C_3$ alkylene. Another embodiment provides the compound of Formula (I), wherein X is —($C_1$-$C_5$ alkylene)-Z—. Another embodiment provides the compound of Formula (I), wherein X is —($C_1$ alkylene)-Z—. Another embodiment provides the compound of Formula (I), wherein X is —($C_1$ alkylene)-Z—, and n is 0, 1 or 2. Another embodiment provides the compound of Formula (I), wherein Y is carbocyclyl. Another embodiment provides the compound of Formula (I), wherein Y is heterocyclyl. Another embodiment provides the compound of Formula (I), wherein Y is aryl. Another embodiment provides the compound of Formula (I), wherein Y is heteroaryl. Another embodiment provides the compound of Formula (I), wherein $R^1$ is hydrogen. Another embodiment provides the compound of Formula (I), wherein $R^1$ is alkyl.

One embodiment provides a compound of Formula (III), or a tautomer, stereoisomer, geometric isomer, N-oxide, or pharmaceutically acceptable salt thereof,

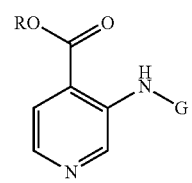

Formula (III)

wherein,
R is hydrogen or alkyl;
G is —X—Y;
X is —$C_1$-$C_5$ alkylene, —($C_1$-$C_5$ alkylene)-Z—($C_1$-$C_5$ alkylene)-, or —($C_1$-$C_5$ alkylene)-Z—;
Y is carbocyclyl, or heterocyclyl; and
Z is

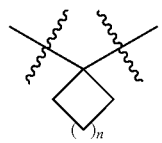

and n is 0, 1, 2, or 3.

Another embodiment provides the compound of Formula (III), wherein X is a C1 alkylene. Another embodiment provides the compound of Formula (III), wherein X is a $C_2$ alkylene. Another embodiment provides the compound of Formula (III), wherein X is a $C_3$ alkylene. Another embodiment provides the compound of Formula (III), wherein X is —($C_1$-$C_5$ alkylene)-Z—. Another embodiment provides the compound of Formula (III), wherein X is —($C_1$ alkylene)-Z—. Another embodiment provides the compound of Formula (III), wherein X is —($C_1$ alkylene)-Z—, and n is 0, 1 or 2. Another embodiment provides the compound of Formula (III), wherein Y is carbocyclyl. Another embodiment provides the compound of Formula (III), wherein Y is heterocyclyl. Another embodiment provides the compound of Formula (III), wherein $R^1$ is hydrogen. Another embodiment provides the compound of Formula (III), wherein $R^1$ is alkyl.

One embodiment provides a compound of Formula (V), or a tautomer, stereoisomer, geometric isomer, N-oxide, or pharmaceutically acceptable salt thereof,

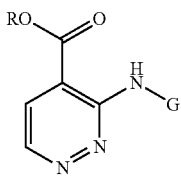

Formula (V)

wherein,

R is hydrogen or alkyl;

G is R¹ or R²;

R¹ is —CO—R³, —CO₂—R³ or —CO—N(R⁴)₂;

R³ is alkyl;

R⁴ is H or alkyl, wherein, optionally, if both R⁴ groups are alkyl, then they may, together with the nitrogen to which they are attached, join to form a ring;

R² is —X—Y;

X is —C₁-C₅ alkylene, —CO—C₁-C₅ alkylene, —(C₁-C₅ alkylene)-Z—, —(C₁-C₅ alkylene)-Z—(C₁-C₅ alkylene)-, —CO—(C₁-C₅ alkylene)-Z—, —CO—(C₁-C₅ alkylene)-Z—(C₁-C₅ alkylene)-, or —C(=N—Oalkyl)-;

Y is carbocyclyl, heterocyclyl, aryl, or heteroaryl;

Z is

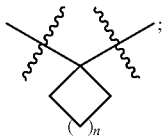

and n is 0, 1, 2, or 3;

with the provision: G is not

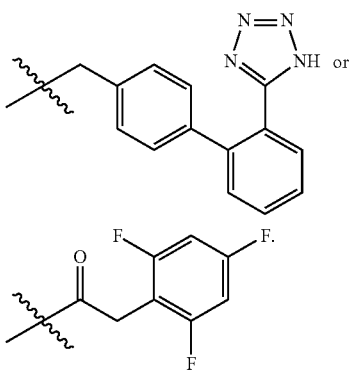

Another embodiment provides the compound of Formula (V), wherein G is R¹. Another embodiment provides the compound of Formula (V), wherein G is R².

One embodiment provides a compound of Formula (XI), or a tautomer, stereoisomer, geometric isomer, N-oxide, or pharmaceutically acceptable salt thereof,

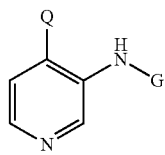

Formula (XI)

wherein,

Q is —C(O)N(H)CN, —C(O)N(H)OH, or tetrazolyl;

G is —X—Y;

X is —C₁-C₅ alkylene, —(C₁-C₅ alkylene)-Z—(C₁-C₅ alkylene)-, or —(C₁-C₅ alkylene)-Z—;

Y is carbocyclyl, heterocyclyl, aryl, or heteroaryl; and

Z is

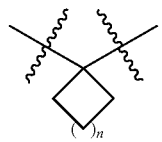

and n is 0, 1, 2, or 3.

Another embodiment provides the compound of Formula (XI) wherein G is not

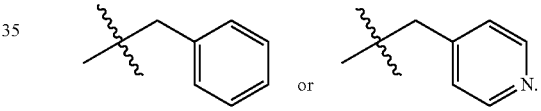

Another embodiment provides the compound of Formula (XI), wherein X is a C₁ alkylene. Another embodiment provides the compound of Formula (XI), wherein X is a C₂ alkylene. Another embodiment provides the compound of Formula (XI), wherein X is a C₃ alkylene. Another embodiment provides the compound of Formula (XI), wherein X is —(C₁-C₅ alkylene)-Z—. Another embodiment provides the compound of Formula (XI), wherein X is —(C₁ alkylene)-Z—. Another embodiment provides the compound of Formula (XI), wherein X is —(C₁ alkylene)-Z—, and n is 0, 1 or 2. Another embodiment provides the compound of Formula (XI), wherein Y is carbocyclyl. Another embodiment provides the compound of Formula (XI), wherein Y is heterocyclyl. Another embodiment provides the compound of Formula (XI), wherein Y is aryl. Another embodiment provides the compound of Formula (XI), wherein Y is heteroaryl. Another embodiment provides the compound of Formula (XI), wherein Q is tetrazolyl. Another embodiment provides the compound of Formula (XI), wherein Q is —C(O)N(H)CN. Another embodiment provides the compound of Formula (XI), wherein Q is —C(O)N(H)OH.

One embodiment provides a compound of Formula (XIII), or a tautomer, stereoisomer, geometric isomer, N-oxide, or pharmaceutically acceptable salt thereof,

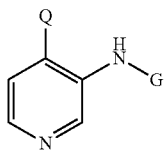

Formula (XIII)

wherein,
Q is —C(O)N(H)CN, —C(O)N(H)OH, or tetrazolyl;
G is —X—Y;
   X is —$C_1$-$C_5$ alkylene, —($C_1$-$C_5$ alkylene)-Z—($C_1$-$C_5$ alkylene)-, or —($C_1$-$C_5$ alkylene)-Z—;
   Y is carbocyclyl, or heterocyclyl; and
   Z is

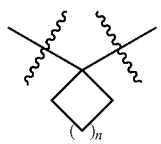

and n is 0, 1, 2, or 3.

Another embodiment provides the compound of Formula (XIII), wherein X is a C1 alkylene. Another embodiment provides the compound of Formula (XIII), wherein X is a C2 alkylene. Another embodiment provides the compound of Formula (XIII), wherein X is a C3 alkylene. Another embodiment provides the compound of Formula (XIII), wherein X is —($C_1$-$C_5$ alkylene)-Z—. Another embodiment provides the compound of Formula (XIII), wherein X is —($C_1$ alkylene)-Z—. Another embodiment provides the compound of Formula (XIII), wherein X is —($C_1$ alkylene)-Z—, and n is 0, 1 or 2. Another embodiment provides the compound of Formula (XIII), wherein Y is carbocyclyl. Another embodiment provides the compound of Formula (XIII), wherein Y is heterocyclyl. Another embodiment provides the compound of Formula (XIII), wherein Q is tetrazolyl. Another embodiment provides the compound of Formula (XIII), wherein Q is —C(O)N(H)CN. Another embodiment provides the compound of Formula (XIII), wherein Q is —C(O)N(H)OH.

One embodiment provides a compound of Formula (XV), or a tautomer, stereoisomer, geometric isomer, N-oxide, or pharmaceutically acceptable salt thereof,

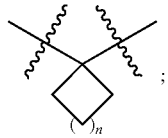

Formula (XV)

wherein,
Q is —C(O)N(H)CN, —C(O)N(H)OH, or tetrazolyl;
G is $R^1$ or $R^2$;
   $R^1$ is —CO—$R^3$, —$CO_2$—$R^3$ or —CO—N($R^4$)$_2$;
      $R^3$ is alkyl;
      $R^4$ is H or alkyl, wherein, optionally, if both $R^4$ groups are alkyl, then they may, together with the nitrogen to which they are attached, join to form a ring;
   $R^2$ is —X—Y;
   X is —$C_1$-$C_5$ alkylene, —CO—$C_1$-$C_5$ alkylene, —($C_1$-$C_5$ alkylene)-Z—, —($C_1$-$C_5$ alkylene)-Z—($C_1$-$C_5$ alkylene)-, —CO—($C_1$-$C_5$ alkylene)-Z—, —CO—($C_1$-$C_5$ alkylene)-Z—($C_1$-$C_5$ alkylene)-, or —C(=N—Oalkyl)-;
Y is carbocyclyl, heterocyclyl, aryl, or heteroaryl; and
Z is

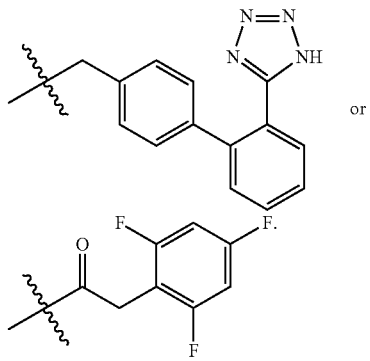

and n is 0, 1, 2, or 3.

Another embodiment provides the compound of Formula (XV), wherein G is not

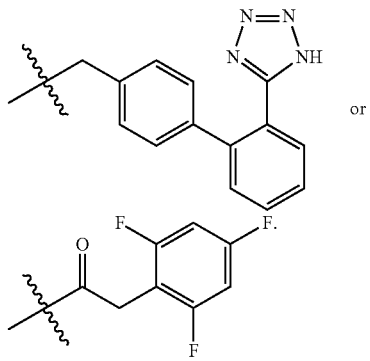

or

Another embodiment provides the compound of Formula (XV), wherein G is $R^1$. Another embodiment provides the compound of Formula (XV), wherein G is $R^2$. Another embodiment provides the compound of Formula (XV), wherein Q is tetrazolyl. Another embodiment provides the compound of Formula (XV), wherein Q is —C(O)N(H)CN. Another embodiment provides the compound of Formula (XV), wherein Q is —C(O)N(H)OH.

One embodiment provides a compound of Formula (XI), or a pharmaceutically acceptable salt thereof,

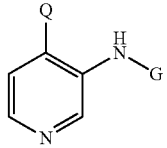

Formula (XI)

wherein:
Q is —$CO_2$R, —C(O)N(H)CN, —C(O)N(H)OH, or tetrazolyl;
R is hydrogen or optionally substituted alkyl;
G is —X—Y;
   X is —$C_1$ alkylene;
   Y is optionally substituted tetralinyl, optionally substituted tetrahydroquinolinyl, substituted pyridyl, optionally substituted naphthyl, optionally substituted indolyl, optionally substituted benzofuranyl, optionally substituted adamantyl, or optionally substituted indanyl.

One embodiment provides a compound of Formula (XI), or a pharmaceutically acceptable salt thereof,

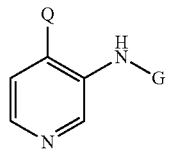

Formula (XI)

wherein:

Q is —CO₂R, —C(O)N(H)CN, —C(O)N(H)OH, or tetrazolyl;

R is hydrogen or optionally substituted alkyl;

G is —X—Y;

X is —C₁ alkylene;

Y is phenyl substituted with alkenyl, alkynyl, fluoro, chloro, fluoroalkyl, nitro, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $R^b$—$OR^a$, —$R^b$—OC(O)—$R^a$, —$R^b$—OC(O)—$OR^a$, —$R^b$—OC(O)—N($R^a$)₂, —$R^b$—N($R^a$)₂, —$R^b$—C(O)$R^a$, —$R^b$—C(O)$OR^a$, —$R^b$—O—$R^c$—C(O)N($R^a$)₂, —$R^b$—N($R^a$)C(O)$OR^a$, —$R^b$—N($R^a$)C(O)$R^a$, —$R^b$—N($R^a$)S(O)$_t$$R^a$, —$R^b$—S(O)$_t$$OR^a$, —$R^b$—S(O)$_t$$OR^a$, and —$R^b$—S(O)$_t$N($R^a$)₂;

wherein:

each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl;

each $R^b$ is independently a direct bond or a straight or branched alkylene or alkenylene chain;

each $R^c$ is a straight or branched alkylene or alkenylene chain; and t is 1 or 2.

One embodiment provides a compound of Formula (XV), or a pharmaceutically acceptable salt thereof,

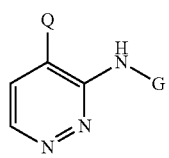

Formula (XV)

wherein,

Q is —CO₂R, —C(O)N(H)CN, —C(O)N(H)OH, or tetrazolyl;

R is hydrogen or optionally substituted alkyl;

G is —X—Y;

X is —C₁ alkylene;

Y is carbocyclyl, heterocyclyl, aryl, or heteroaryl;

with the provisio that G is not

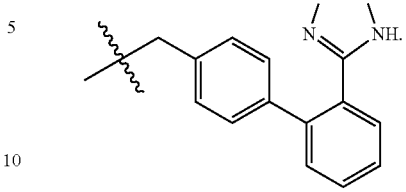

Another embodiment provides the compound or pharmaceutically acceptable salt of Formula (XI) or Formula (XV), wherein Q is —CO₂R. Another embodiment provides the compound or pharmaceutically acceptable salt of Formula (XI) or Formula (XV), wherein Q is —C(O)N(H)CN. Another embodiment provides the compound or pharmaceutically acceptable salt of Formula (XI) or Formula (XV), wherein Q is —C(O)N(H)OH. Another embodiment provides the compound or pharmaceutically acceptable salt of Formula (XI) or Formula (XV), wherein Q is tetrazolyl. Another embodiment provides the compound or pharmaceutically acceptable salt of Formula (XI) or Formula (XV), wherein R is hydrogen. Another embodiment provides the compound or pharmaceutically acceptable salt of Formula (XI) or Formula (XV), wherein R is optionally substituted alkyl. Another embodiment provides the compound or pharmaceutically acceptable salt of Formula (XI) or Formula (XV), wherein Y is optionally substituted tetralinyl. Another embodiment provides the compound or pharmaceutically acceptable salt of Formula (XI) or Formula (XV), wherein Y is optionally substituted tetrahydroquinolinyl. Another embodiment provides the compound or pharmaceutically acceptable salt of Formula (XI) or Formula (XV), wherein Y is substituted pyridyl. Another embodiment provides the compound or pharmaceutically acceptable salt of Formula (XI) or Formula (XV), wherein Y is optionally substituted naphthyl. Another embodiment provides the compound or pharmaceutically acceptable salt of Formula (XI) or Formula (XV), wherein Y is optionally substituted indolyl. Another embodiment provides the compound or pharmaceutically acceptable salt of Formula (XI) or Formula (XV), wherein Y is optionally substituted benzofuranyl. Another embodiment provides the compound or pharmaceutically acceptable salt of Formula (XI) or Formula (XV), wherein Y is optionally substituted adamantyl. Another embodiment provides the compound or pharmaceutically acceptable salt of Formula (XI) or Formula (XV), wherein Y is optionally substituted indanyl.

One embodiment provides a compound, or a pharmaceutically acceptable salt thereof, selected from the group consisting of:

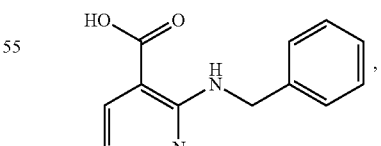

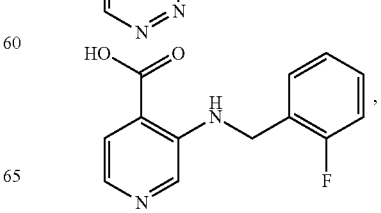

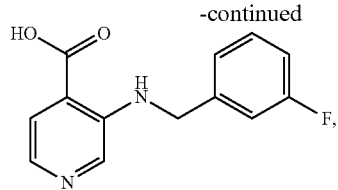
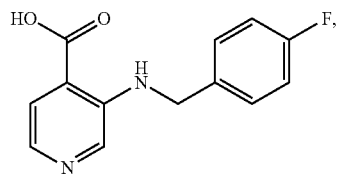
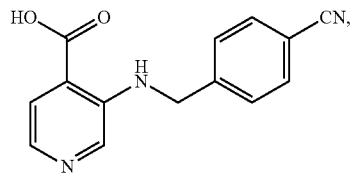
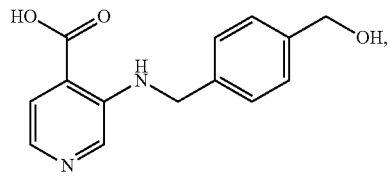
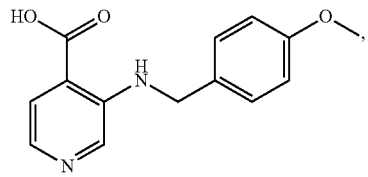
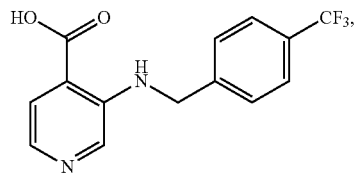
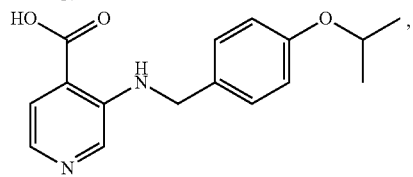
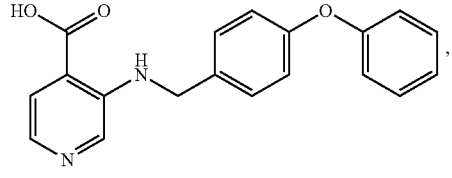
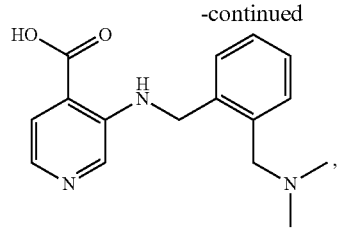
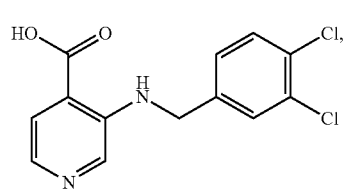
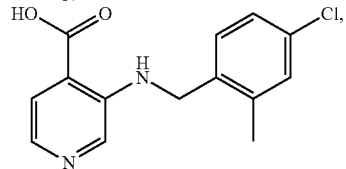
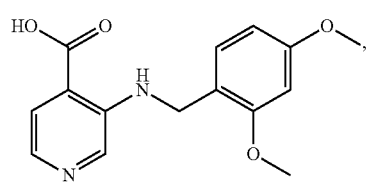
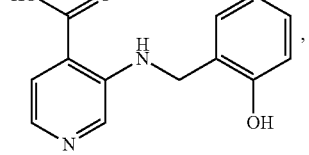
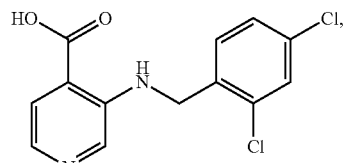
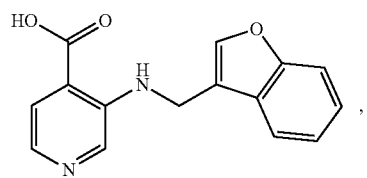
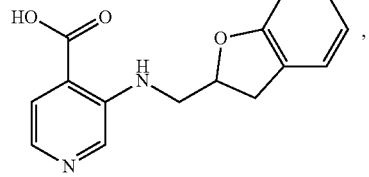
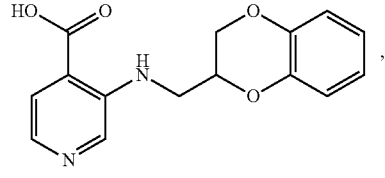

-continued

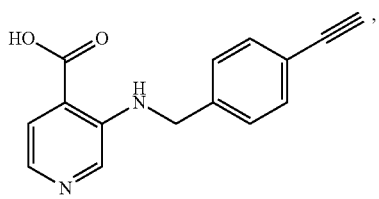

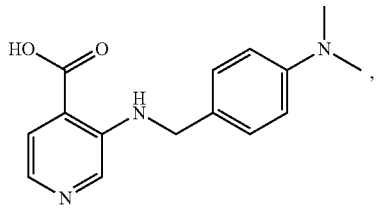

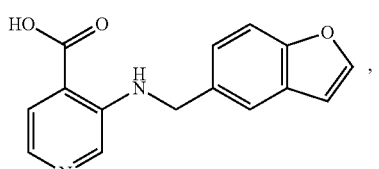

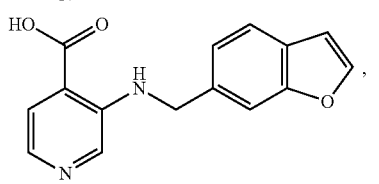

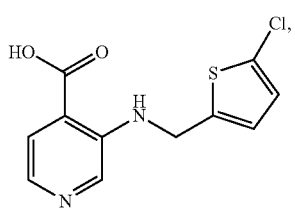

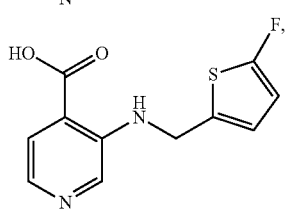

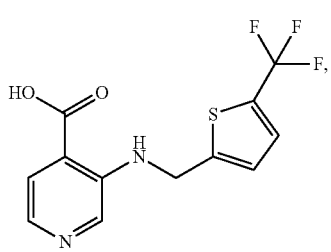

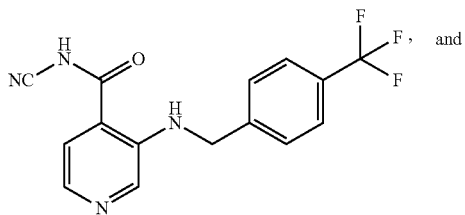 and

-continued

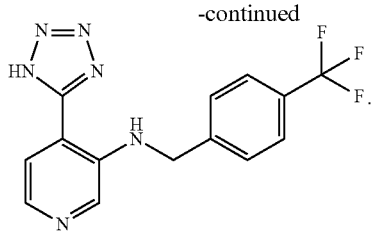

One embodiment provides a compound of Formula (XI), or a pharmaceutically acceptable salt thereof, Formula (XI)

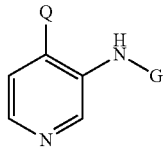

wherein:
Q is —CO$_2$R, —C(O)N(H)CN, —C(O)N(H)OH, or tetrazolyl;
R is hydrogen or optionally substituted alkyl;
G is —X—Y;
X is —C$_1$ alkylene;
Y is optionally substituted tetralinyl, optionally substituted chromanyl, optionally substituted tetrahydroquinolinyl, optionally substituted benzofuranyl, optionally substituted 2,3-dihydrobenzofuranyl, optionally substituted 2,3-dihydrobenzo[b]-[1,4]dioxinyl, optionally substituted naphthyl, optionally substituted indolyl, optionally substituted 1,2-dihydronaphthyl, optionally substituted indanyl, or optionally substituted thiochromanyl.

Another embodiment provides a compound of Formula (XI), or a pharmaceutically acceptable salt thereof, wherein Q is —CO$_2$R. Another embodiment provides a compound of Formula (XI), or a pharmaceutically acceptable salt thereof, wherein Q is —C(O)N(H)CN. Another embodiment provides a compound of Formula (XI), or a pharmaceutically acceptable salt thereof, wherein Q is —C(O)N(H)OH. Another embodiment provides a compound of Formula (XI), or a pharmaceutically acceptable salt thereof, wherein Q is tetrazolyl. Another embodiment provides a compound of Formula (XI), or a pharmaceutically acceptable salt thereof, wherein R is hydrogen. Another embodiment provides a compound of Formula (XI), or a pharmaceutically acceptable salt thereof, wherein R is optionally substituted alkyl. Another embodiment provides a compound of Formula (XI), or a pharmaceutically acceptable salt thereof, wherein Y is optionally substituted chromanyl. Another embodiment provides a compound of Formula (XI), or a pharmaceutically acceptable salt thereof, wherein Y is optionally substituted tetrahydroquinolinyl. Another embodiment provides a compound of Formula (XI), or a pharmaceutically acceptable salt thereof, wherein Y is optionally substituted benzofuranyl. Another embodiment provides a compound of Formula (XI), or a pharmaceutically acceptable salt thereof, wherein Y is optionally substituted 2,3-dihydrobenzofuranyl. Another embodiment provides a compound of Formula (XI), or a pharmaceutically acceptable salt thereof, wherein Y is optionally substituted naphthyl. Another embodiment provides a compound of Formula (XI), or a pharmaceutically acceptable salt thereof, wherein Y is optionally substituted indolyl. Another embodiment provides a compound of Formula (XI), or a pharmaceutically acceptable salt thereof, wherein Y is optionally substituted 1,2-dihydronaphthyl. Another embodiment provides a compound of Formula (XI), or a pharmaceutically acceptable salt thereof, wherein Y is optionally substituted indanyl. Another embodiment provides a compound of Formula (XI), or a pharmaceutically acceptable salt thereof, wherein Y is optionally substituted thiochromanyl. Another embodiment provides a compound of Formula (XI), or a pharmaceutically acceptable salt thereof, wherein Y is optionally substituted tetralinyl. Another embodiment provides a compound of Formula (XI), or a pharmaceutically acceptable salt thereof, wherein the optionally substituted tetralinyl is an optionally substituted 1-tetralinyl.

Another embodiment provides a compound of Formula (XI), or a pharmaceutically acceptable salt thereof, wherein the compound of Formula (XI) has the structure of Formula (XIa):

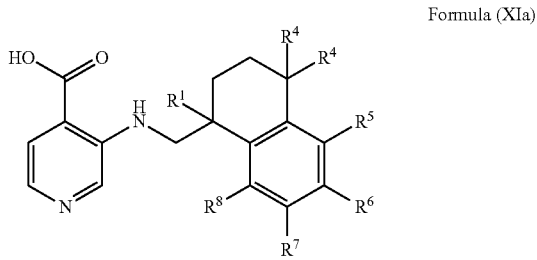

Formula (XIa)

wherein,
$R^1$ is hydrogen, methyl, or —OH;
each $R^4$ is independently hydrogen, fluoro, or methyl; and
$R^5$, $R^6$, $R^7$ and $R^8$ are each independently chosen from hydrogen, halogen, —OH, —CN, optionally substituted $C_1$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy.

Another embodiment provides a compound of Formula (XIa), wherein each $R^4$ is hydrogen. Another embodiment provides a compound of Formula (XIa), wherein each $R^4$ is fluoro. Another embodiment provides a compound of Formula (XIa), wherein each $R^4$ is methyl. Another embodiment provides a compound of Formula (XIa), wherein one $R^4$ is hydrogen. Another embodiment provides a compound of Formula (XIa), wherein one $R^4$ is fluoro.

Another embodiment provides a compound of Formula (XI), or a pharmaceutically acceptable salt thereof, wherein Y is optionally substituted chromanyl. Another embodiment provides a compound of Formula (XI), or a pharmaceutically acceptable salt thereof, wherein the optionally substituted chromanyl is an optionally substituted 4-chromanyl.

Another embodiment provides a compound of Formula (XI), or a pharmaceutically acceptable salt thereof, wherein the compound of Formula (XI) has the structure of Formula (XIb):

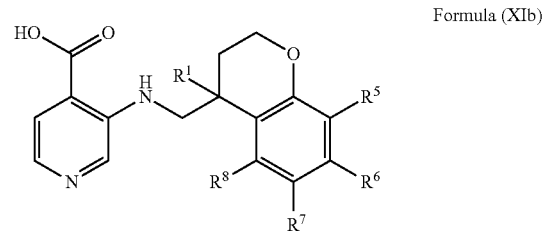

Formula (XIb)

wherein,
$R^1$ is hydrogen, methyl, or —OH; and
$R^5$, $R^6$, $R^7$ and $R^8$ are each independently chosen from hydrogen, halogen, —OH, —CN, optionally substituted $C_1$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy.

Another embodiment provides a compound of Formula (XIa) or (XIb), or a pharmaceutically acceptable salt thereof, wherein $R^1$ is hydrogen. Another embodiment provides a compound of Formula (XIa) or (XIb), wherein $R^5$ is hydrogen. Another embodiment provides a compound of Formula (XIa) or (XIb), wherein $R^6$ is hydrogen. Another embodiment provides a compound of Formula (XIa) or (XIb), wherein $R^7$ is hydrogen. Another embodiment provides a compound of Formula (XIa) or (XIb), wherein $R^8$ is hydrogen. Another embodiment provides a compound of Formula (XIa) or (XIb), wherein $R^5$ and $R^7$ are hydrogen. Another embodiment provides a compound of Formula (XIa) or (XIb), wherein $R^5$ and $R^8$ are hydrogen. Another embodiment provides a compound of Formula (XIa) or (XIb), wherein $R^7$ and $R^8$ are hydrogen. Another embodiment provides a compound of Formula (XIa) or (XIb), wherein $R^6$ is not hydrogen.

Another embodiment provides a compound of Formula (XIa) or (XIb), wherein $R^6$ is chosen from optionally substituted $C_1$-$C_6$ alkyl, optionally substituted $C_1$-$C_6$ alkoxy, optionally substituted $C_3$-$C_7$ carbocyclyl, optionally substituted $C_3$-$C_7$ carbocyclyloxy, optionally substituted $C_4$-$C_{12}$ carbocyclylalkyl, optionally substituted $C_4$-$C_{12}$ carbocyclylalkoxy, optionally substituted $C_1$-$C_6$ alkynyl, optionally substituted $C_1$-$C_6$ alkenyl, optionally substituted $C_6$-$C_{10}$ aryl, optionally substituted $C_6$-$C_{10}$ aryloxy, optionally substituted $C_6$-$C_{10}$ aryl-S—, optionally substituted $C_7$-$C_{14}$ aralkoxy, optionally substituted heteroaryl, and optionally substituted heteroaryloxy.

Another embodiment provides a compound of Formula (XIa) or (XIb), wherein $R^6$ is chosen from optionally substituted $C_1$-$C_6$ alkyl. Another embodiment provides a compound of Formula (XIa) or (XIb), wherein $R^6$ is chosen from optionally substituted $C_1$-$C_6$ alkoxy. Another embodiment provides a compound of Formula (XIa) or (XIb), wherein $R^6$ is chosen from optionally substituted $C_3$-$C_7$ carbocyclyl. Another embodiment provides a compound of Formula (XIa) or (XIb), wherein $R^6$ is chosen from optionally substituted $C_3$-$C_7$ carbocyclyloxy. Another embodiment provides a compound of Formula (XIa) or (XIb), wherein $R^6$ is chosen from optionally substituted $C_4$-$C_{12}$ carbocyclylalkyl. Another embodiment provides a compound of Formula (XIa) or (XIb), wherein $R^6$ is chosen from optionally substituted $C_4$-$C_{12}$ carbocyclylalkoxy. Another embodiment provides a compound of Formula (XIa) or (XIb), wherein $R^6$ is chosen from optionally substituted $C_1$-$C_6$ alkynyl. Another embodiment provides a compound of Formula (XIa) or (XIb), wherein $R^6$ is chosen from optionally substituted $C_1$-$C_6$ alkenyl. Another embodiment provides a compound of Formula (XIa) or (XIb), wherein $R^6$ is chosen from optionally substituted $C_6$-$C_{10}$ aryl. Another embodiment provides a compound of Formula (XIa) or (XIb), wherein $R^6$ is chosen from optionally substituted $C_6$-$C_{10}$ aryloxy. Another embodiment provides a compound of Formula (XIa) or (XIb), wherein $R^6$ is chosen from optionally substituted $C_6$-$C_{10}$ aryl-S—. Another embodiment provides a compound of Formula (XIa) or (XIb), wherein $R^6$ is chosen from optionally substituted $C_7$-$C_{14}$ aralkoxy. Another embodiment provides a compound of Formula (XIa) or (XIb), wherein $R^6$ is chosen from optionally substituted heteroaryl. Another embodiment provides a compound of Formula (XIa) or (XIb), wherein $R^6$ is chosen from optionally substituted heteroaryloxy.

One embodiment provides a compound, or pharmaceutically acceptable salt thereof, chosen from:

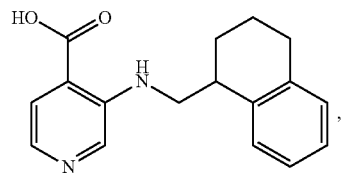

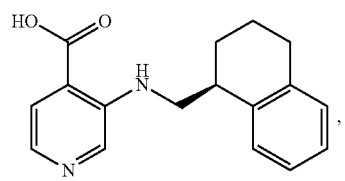

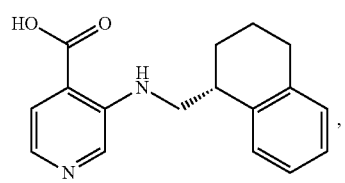

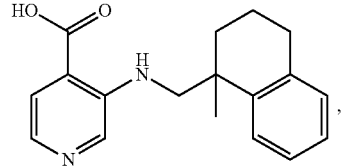

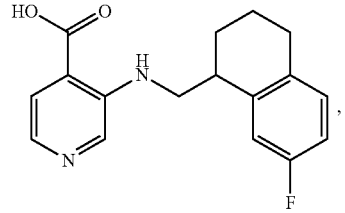

-continued

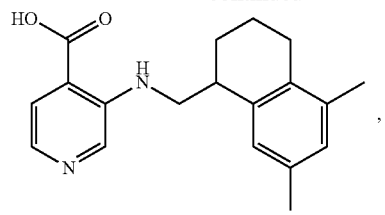

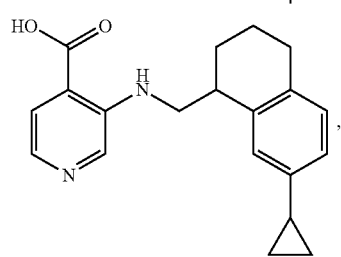

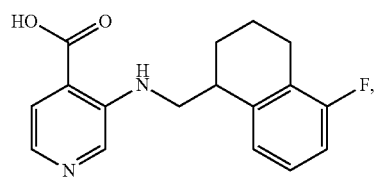

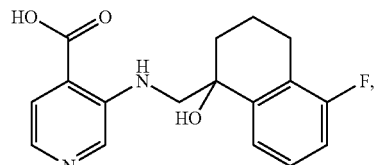

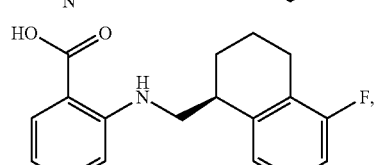

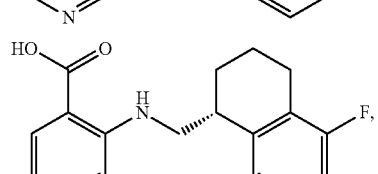

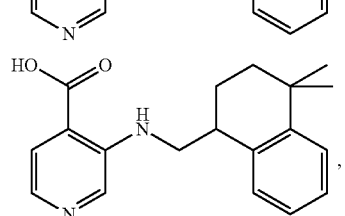

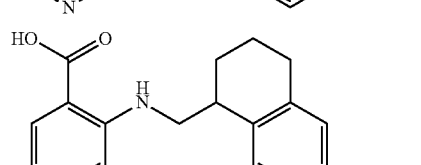

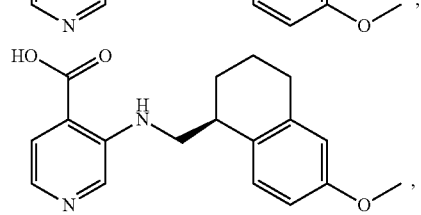

-continued
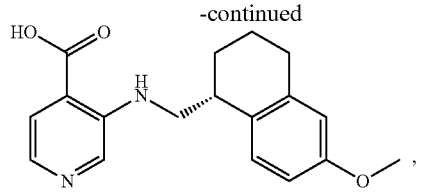
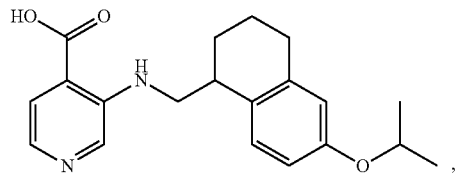
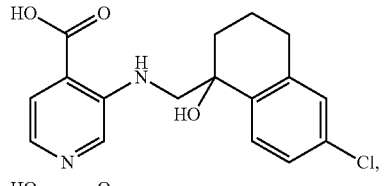
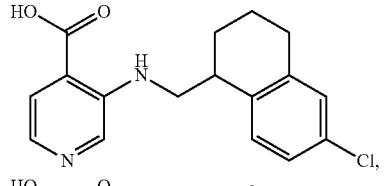
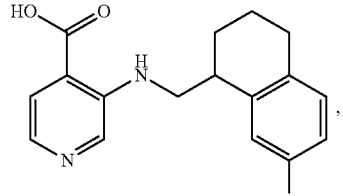
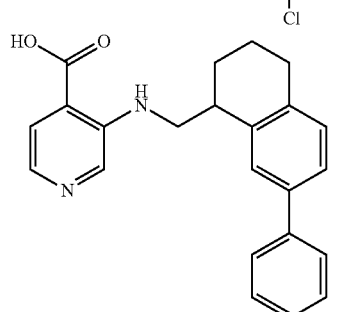
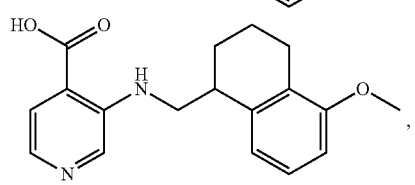
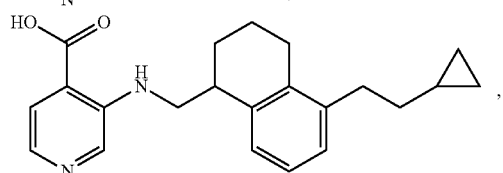
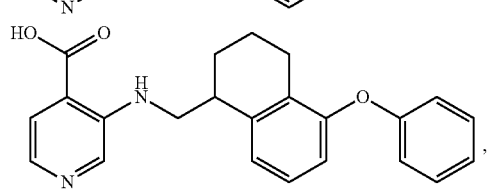
-continued
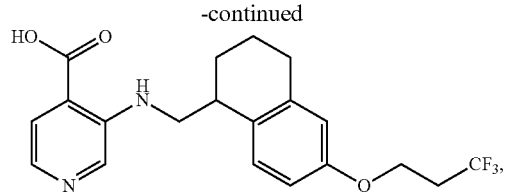
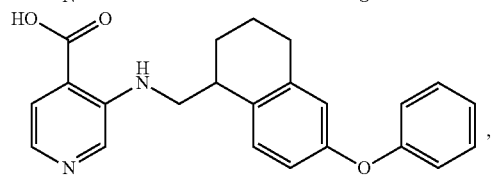
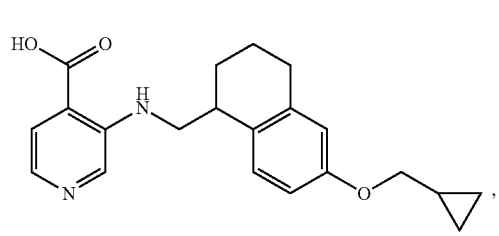
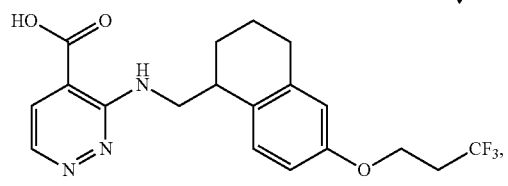
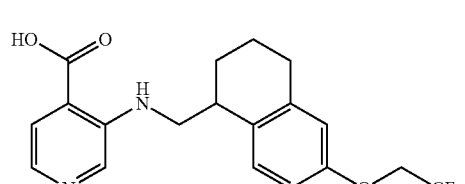
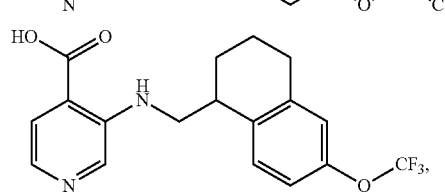
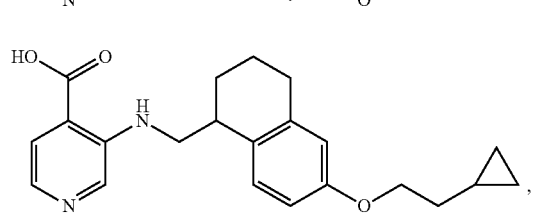
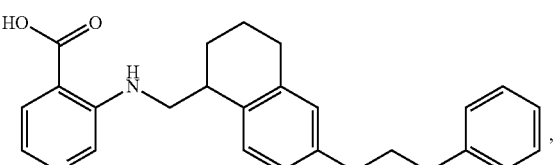
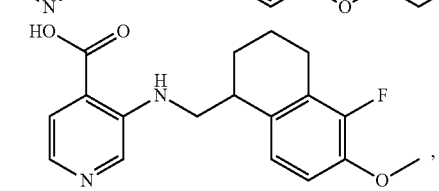

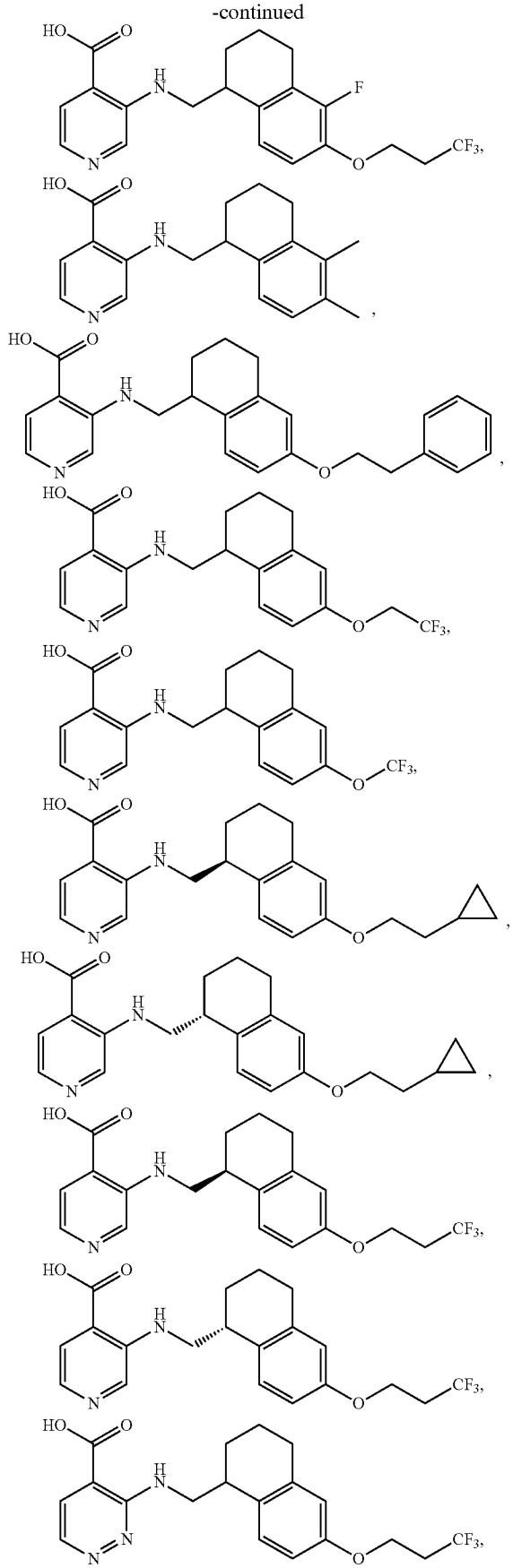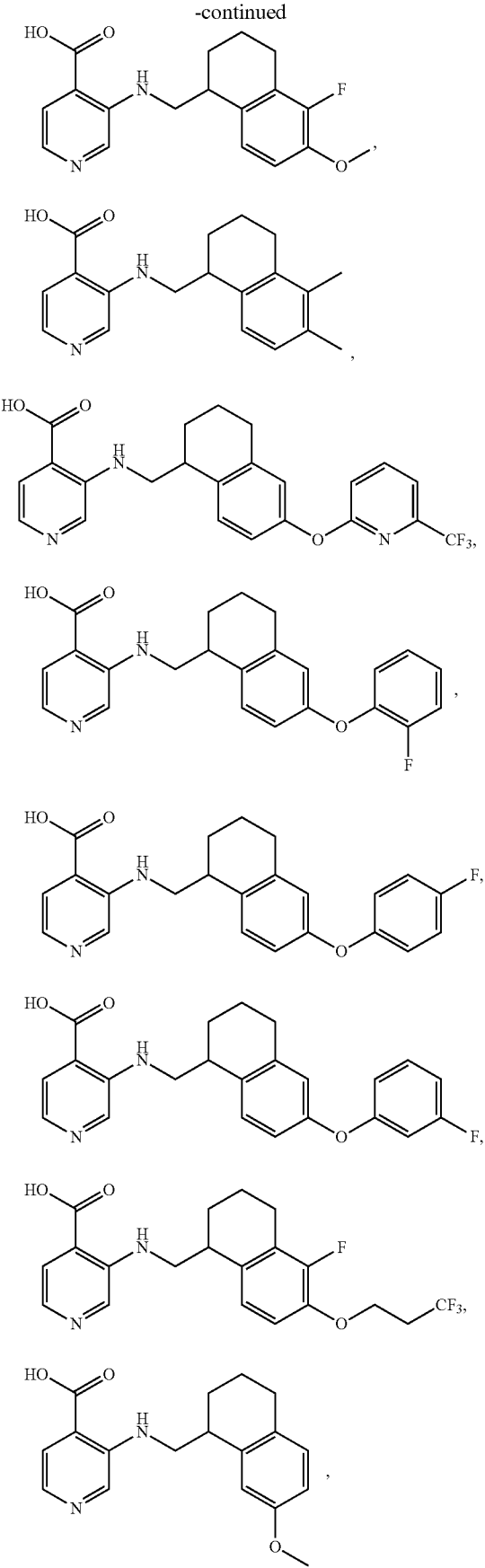

One embodiment provides a compound, or pharmaceutically acceptable salt thereof, chosen from:

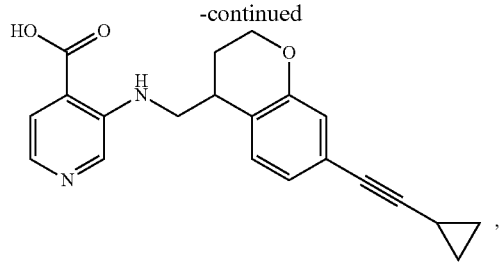
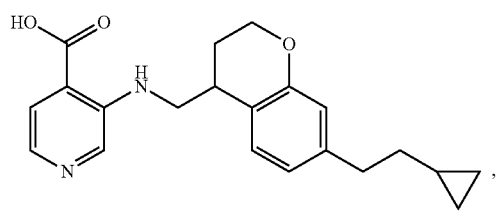
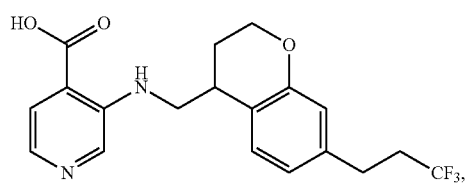
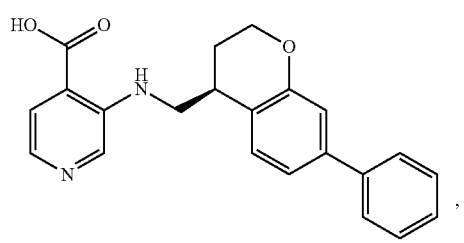
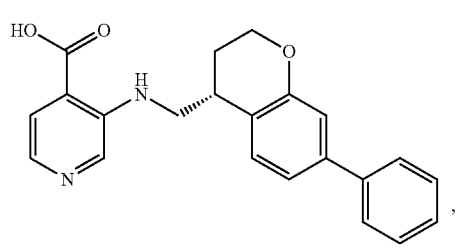
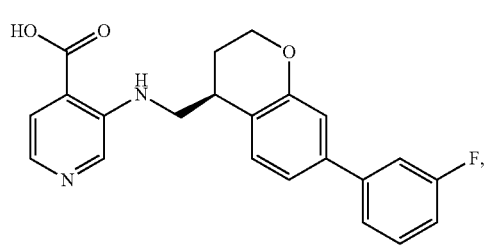
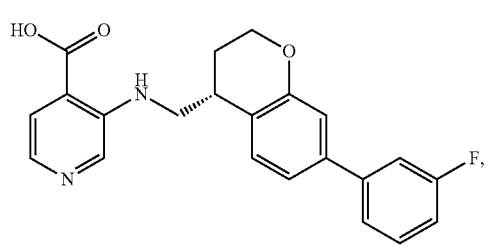
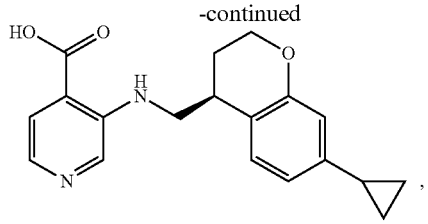
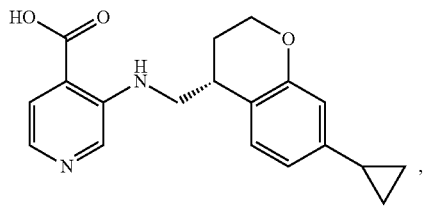
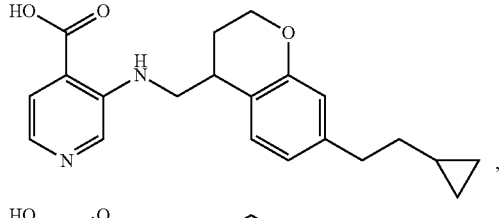
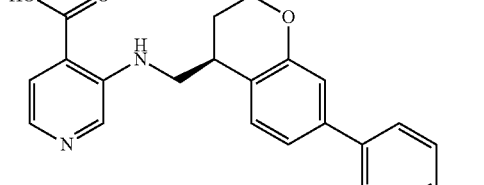
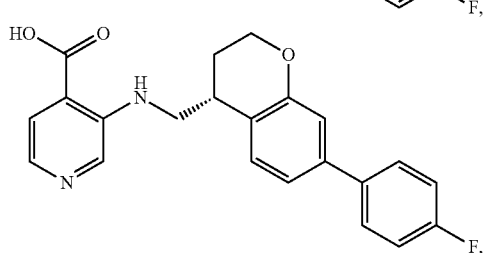
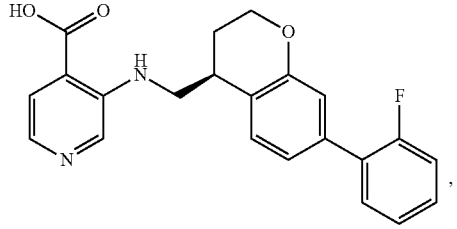
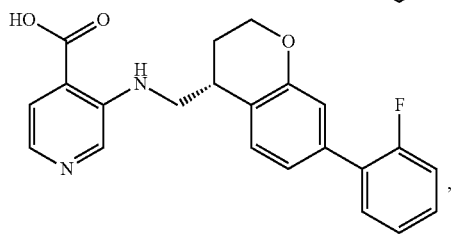
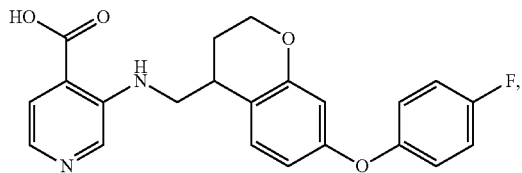

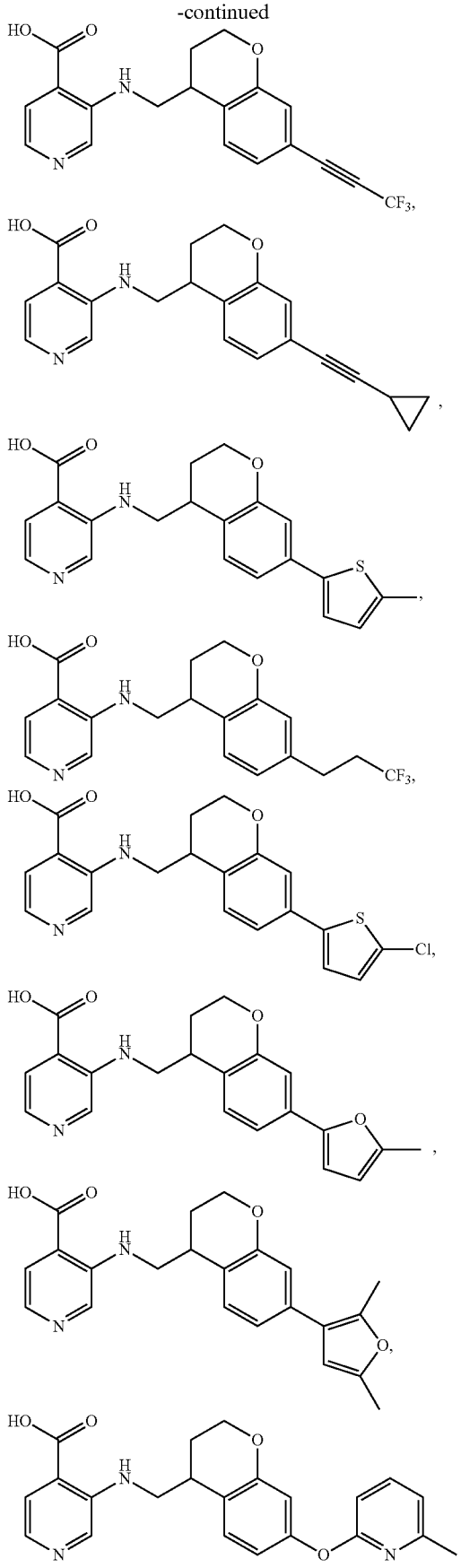
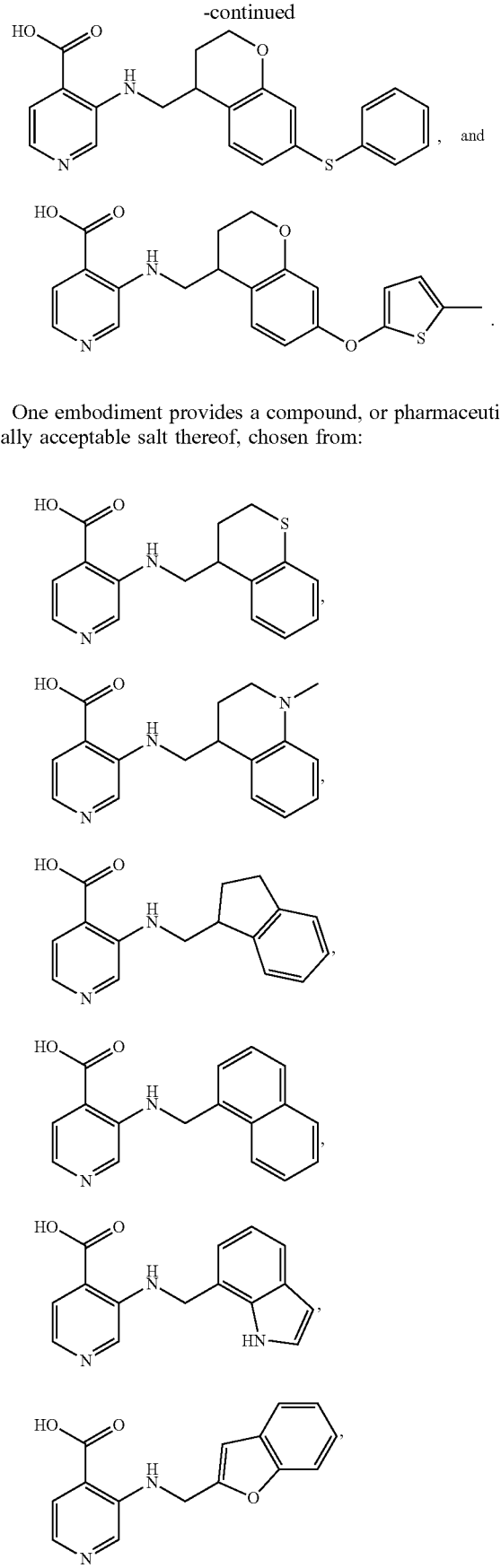
One embodiment provides a compound, or pharmaceutically acceptable salt thereof, chosen from:

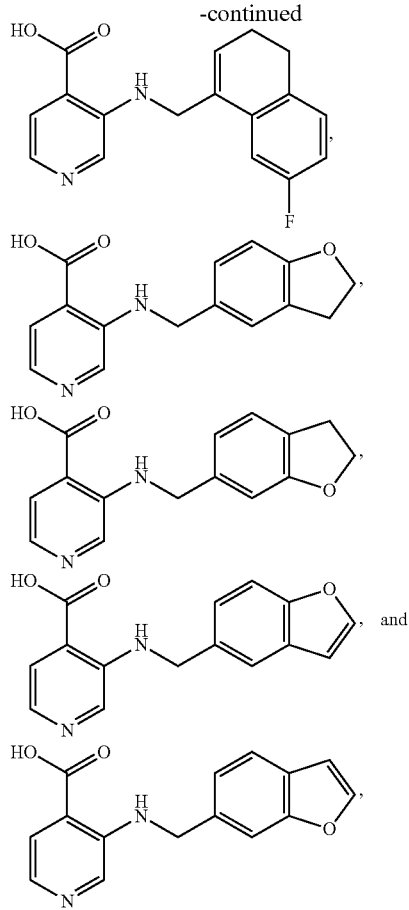
One embodiment provides a compound, or pharmaceutically acceptable salt thereof, chosen from:
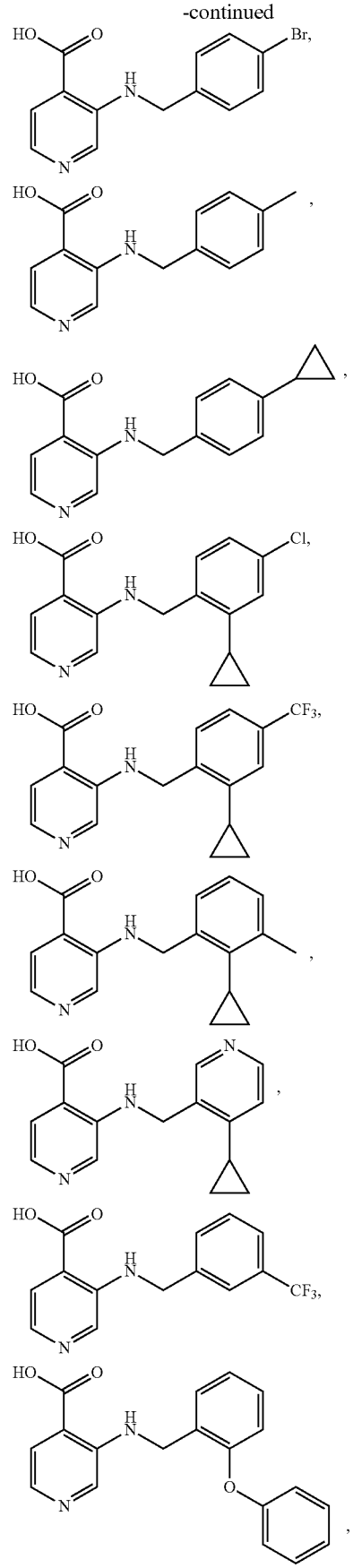

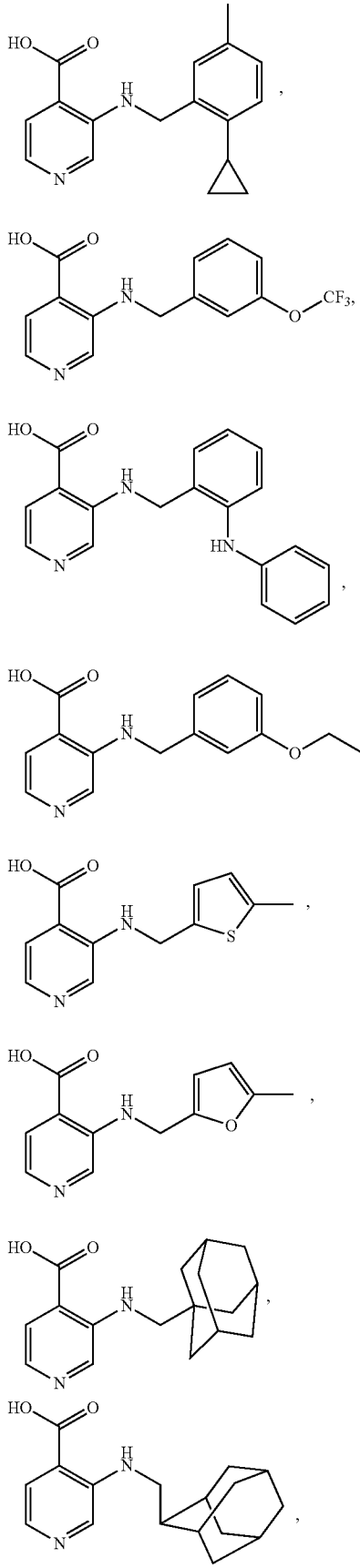
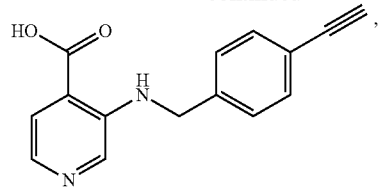
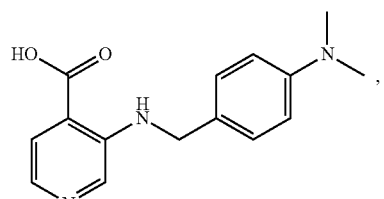
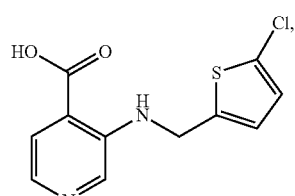
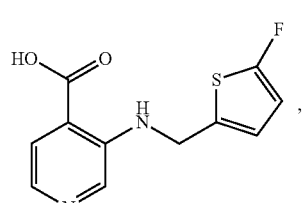
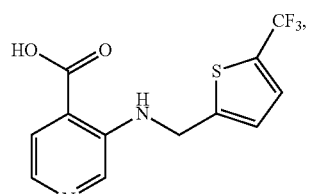
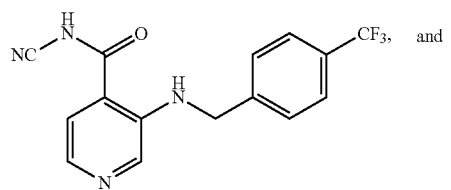
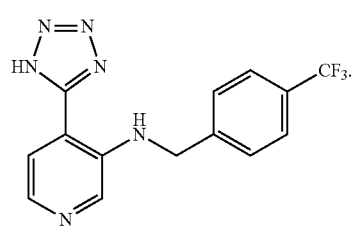
In some embodiments, the substituted aminopyridine or aminopyridazine derivative compound as described herein, or a carboxylic acid ester, or carboxylic acid bioisostere thereof, has the structure provided in Table 1.

TABLE 1

| Chemical Synthesis Example | Structure | Name |
|---|---|---|
| 1 | 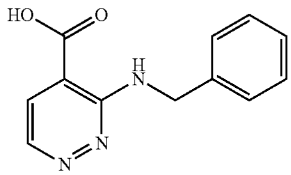 [SMILES: O=C(O)c1ccnnc1NCc1ccccc1] | 3-(benzylamino)pyridazine-4-carboxylic acid |
| 2 | 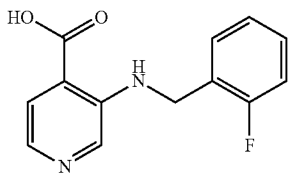 [SMILES: O=C(O)c1ccncc1NCc1ccccc1F] | 3-[(2-fluorobenzyl)amino]pyridine-4-carboxylic acid |
| 3 | 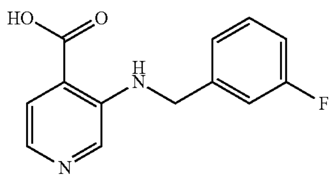 [SMILES: O=C(O)c1ccncc1NCc1cccc(F)c1] | 3-[(3-fluorobenzyl)amino]pyridine-4-carboxylic acid |
| 4 | 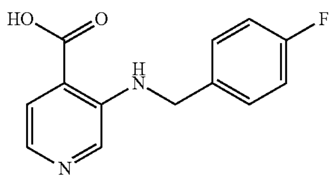 [SMILES: O=C(O)c1ccncc1NCc1ccc(F)cc1] | 3-[(4-fluorobenzyl)amino]pyridine-4-carboxylic acid |
| 5 | 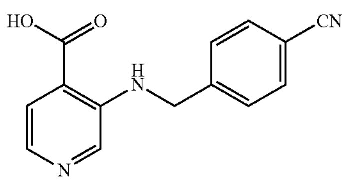 [SMILES: N#Cc1ccc(CNc2cnccc2C(=O)O)cc1] | 3-[(4-cyanobenzyl)amino]pyridine-4-carboxylic acid |
| 6 | 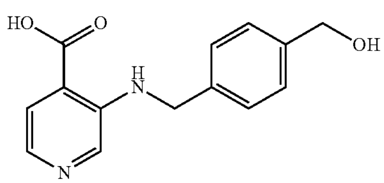 [SMILES: O=C(O)c1ccncc1NCc1ccc(CO)cc1] | 3-{[4-hydroxymethyl)benzyl]amino}pyridine-4-carboxylic acid |
| 7 | 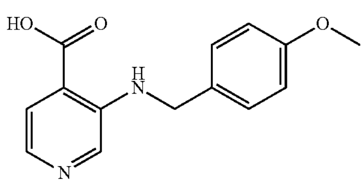 [SMILES: COc1ccc(CNc2cnccc2C(=O)O)cc1] | 3-[(4-methoxybenzyl)amino]pyridine-4-carboxylic acid |
| 8 | 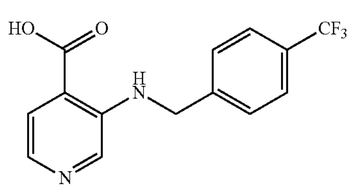 [SMILES: O=C(O)c1ccncc1NCc1ccc(C(F)(F)F)cc1] | 3-{[4-(trifluoromethyl)benzyl]amino}pyridine-4-carboxylic acid |

TABLE 1-continued

| Chemical Synthesis Example | Structure | Name |
|---|---|---|
| 9 | 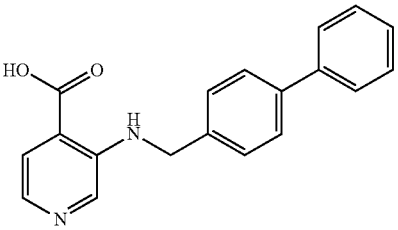 [SMILES: O=C(O)c1ccncc1NCc1ccc(-c2ccccc2)cc1] | 3-[(biphenyl-4-ylmethyl)amino]pyridine-4-carboxylic acid |
| 10 | 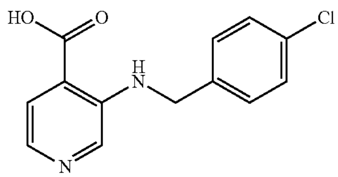 | 3-[(4-chlorobenzyl)amino]pyridine-4-carboxylic acid |
| 11 | 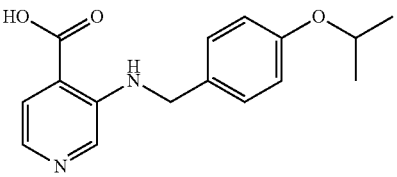 [SMILES: CC(C)Oc1ccc(CNc2cnccc2C(=O)O)cc1] | 3-{[4-(propan-2-yloxy)benzyl]amino}pyridine-4-carboxylic acid |
| 12 | 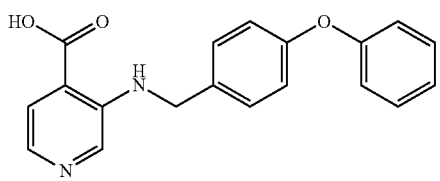 [SMILES: O=C(O)c1ccncc1NCc1ccc(Oc2ccccc2)cc1] | 3-[(4-phenoxybenzyl)amino]pyridine-4-carboxylic acid |
| 13 | 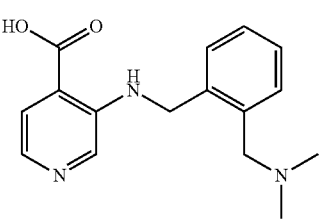 | 3-({2-[(dimethylamino)methyl]benzyl}amino)pyridine-4-carboxylic acid |
| 14 | 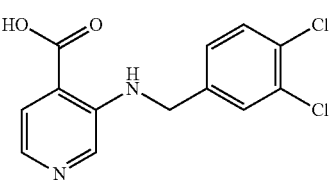 [SMILES: O=C(O)c1ccncc1NCc1ccc(Cl)c(Cl)c1] | 3-[(3,4-dichlorobenzyl)amino]pyridine-4-carboxylic acid |
| 15 | 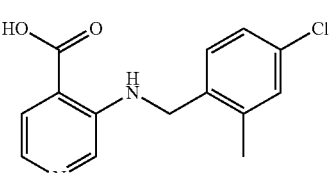 | 3-[(4-chloro-2-methylbenzyl)amino]pyridine-4-carboxylic acid |
| 16 | 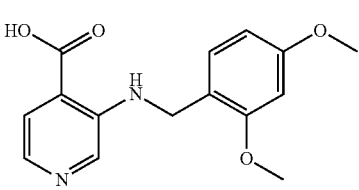 [SMILES: COc1ccc(CNc2cnccc2C(=O)O)c(OC)c1] | 3-[(2,4-dimethyoxybenzyl)amino]pyridine-4-carboxylic acid |

TABLE 1-continued

| Chemical Synthesis Example | Structure | Name |
|---|---|---|
| 17 | 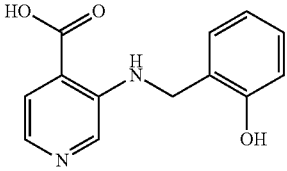 | 3-[(2-hydroxybenzyl)amino]pyridine-4-carboxylic acid |
| 18 | 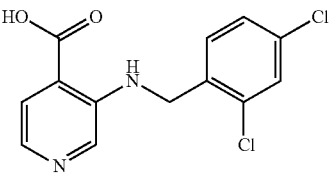 [SMILES: O=C(O)c1ccncc1NCc1ccc(Cl)cc1Cl] | 3-[(2,4-dichlorobenzyl)amino]pyridine-4-carboxylic acid |
| 19 | 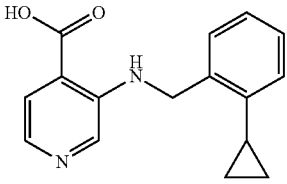 [SMILES: O=C(O)c1ccncc1NCc1ccccc1C1CC1] | 3-[(2-cyclopropylbenzyl)amino]pyridine-4-carboxylic acid |
| 20 | 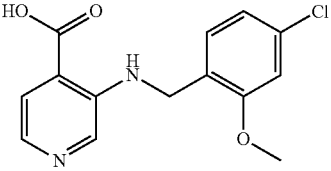 [SMILES: COc1cc(Cl)ccc1CNc1cnccc1C(=O)O] | 3-[(4-chloro-2-methoxybenzyl)amino]pyridine-4-carboxylic acid |
| 21 | 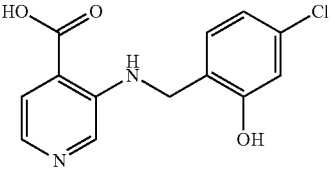 [SMILES: O=C(O)c1ccncc1NCc1ccc(Cl)cc1O] | 3-[(4-chloro-2-hydroxybenzyl)amino]pyridine-4-carboxylic acid |
| 22 | 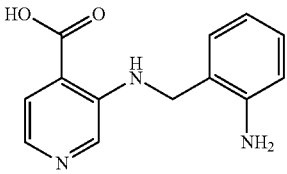 [SMILES: Nc1ccccc1CNc1cnccc1C(=O)O] | 3-[(2-aminobenzyl)amino]pyridine-4-carboxylic acid |
| 23 | 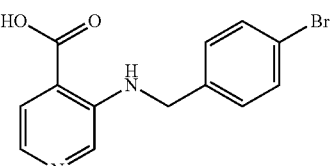 | 3-[(4-bromobenzyl)amino]pyridine-4-carboxylic acid |
| 24 | 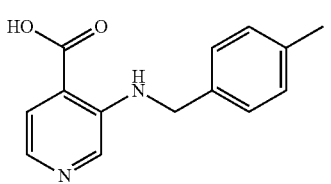 [SMILES: Cc1ccc(CNc2cnccc2C(=O)O)cc1] | 3-[(4-methylbenzyl)amino]pyridine-4-carboxylic acid |

TABLE 1-continued

| Chemical Synthesis Example | Structure | Name |
|---|---|---|
| 25 | 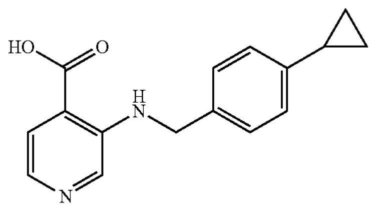 [SMILES: O=C(O)c1ccncc1NCc1ccc(C2CC2)cc1] | 3-[(4-cyclopropylbenzyl)amino]pyridine-4-carboxylic acid |
| 26 | 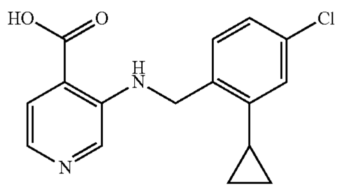 [SMILES: O=C(O)c1ccncc1NCc1ccc(Cl)cc1C1CC1] | 3-[(4-chloro-2-cyclopropylbenzyl)amino]pyridine-4-carboxylic acid |
| 27 | 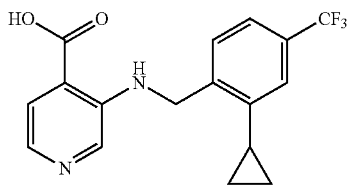 [SMILES: O=C(O)c1ccncc1NCc1ccc(C(F)(F)F)cc1C1CC1] | 3-{[2-cyclopropyl-4-(trifluoromethl)benzyl]amino}pyridine-4-carboxylic acid |
| 28 | 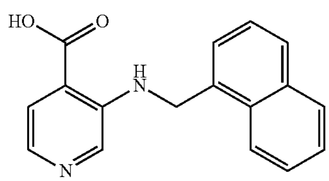 [SMILES: O=C(O)c1ccncc1NCc1cccc2ccccc12] | 3-[(naphthalene-1-ylmethyl)amino]pyridine-4-carboxylic acid |
| 29 | 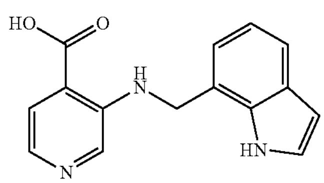 [SMILES: O=C(O)c1ccncc1NCc1cccc2cc[nH]c12] | 3-[(1H-indol-7-ylmethyl)amino]pyridine-4-carboxylic acid |
| 30 | 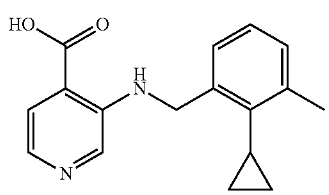 [SMILES: Cc1cccc(CNc2cnccc2C(=O)O)c1C1CC1] | 3-[(2-cyclopropyl-3-methylbenzyl)amino]pyridine-4-carboxylic acid |
| 31 | 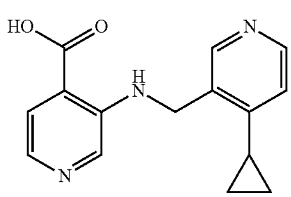 [SMILES: O=C(O)c1ccncc1NCc1cnccc1C1CC1] | 3-{[(4-cyclopropylpyridin-3-yl)-methyl]amino}pyridine-4-carboxylic acid |
| 32 | 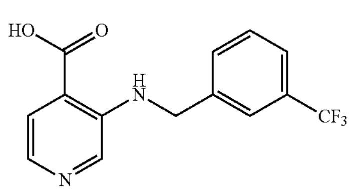 [SMILES: O=C(O)c1ccncc1NCc1cccc(C(F)(F)F)c1] | 3-{[3-(trifluoromethyl)benzyl]amino}pyridine-4-carboxylic acid |

TABLE 1-continued

| Chemical Synthesis Example | Structure | Name |
|---|---|---|
| 33 | 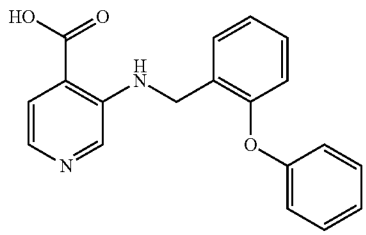 [SMILES: O=C(O)c1ccncc1NCc1ccccc1Oc1ccccc1] | 3-[(2-phenoxybenzyl)amino]pyridine-4-carboxylic acid |
| 34 | 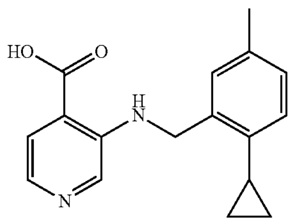 [SMILES: Cc1ccc(C2CC2)c(CNc2cnccc2C(=O)O)c1] | 3-[(2-cyclopropyl-5-methylbenzyl)amino]pyridine-4-carboxylic acid |
| 35 | 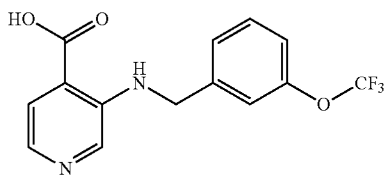 [SMILES: O=C(O)c1ccncc1NCc1cccc(OC(F)(F)F)c1] | 3-{[3-(trifluoromethoxy)benzyl]amino}pyridine-4-carboxylic acid |
| 36 | 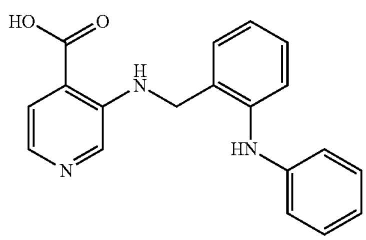 [SMILES: O=C(O)c1ccncc1NCc1ccccc1Nc1ccccc1] | 3-{[2-(phenylaminol)benzyl]amino}pyridine-4-carboxylic acid |
| 37 | 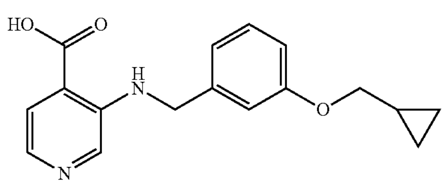 [SMILES: O=C(O)c1ccncc1NCc1cccc(OCC2CC2)c1] | 3-{[3-(cyclopropylmethoxy)benzyl]amino}pyridine-4-carboxylic acid |
| 38 | 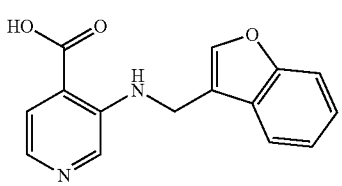 [SMILES: O=C(O)c1ccncc1NCc1coc2ccccc12] | 3-[(1-benzofuran-3-ylmethyl)amino]pyridine-4-carboxylic acid |
| 39 | 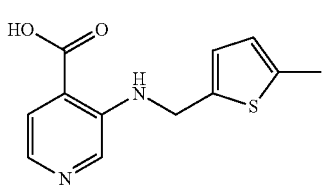 [SMILES: Cc1ccc(CNc2cnccc2C(=O)O)s1] | 3-{[(5-methylthiophen-2-yl)methyl]amino}pyridine-4-carboxylic acid |

TABLE 1-continued

| Chemical Synthesis Example | Structure | Name |
|---|---|---|
| 40 | 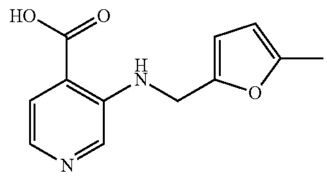 | 3-{[(5-methylfuran-2-yl)methyl]amino}pyridine-4-carboxylic acid |
| 41 | 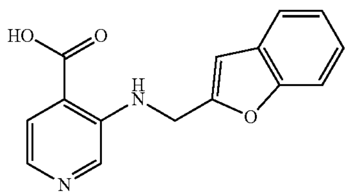 [SMILES: O=C(O)c1ccncc1NCc1cc2ccccc2o1] | 3-[(1-benzofuran-2-ylmethyl)amino]pyridine-4-carboxylic acid |
| 42 | 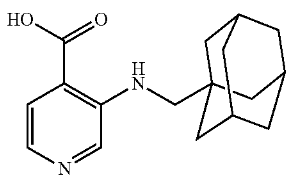 [SMILES: O=C(O)c1ccncc1NCC12CC3CC(CC(C3)C1)C2] | 3-[(adamantan-1-ylmethyl)amino]pyridine-4-carboxylic acid |
| 43 | 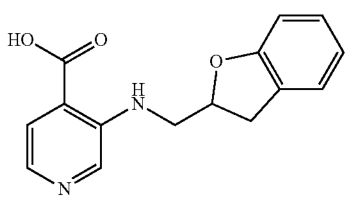 [SMILES: O=C(O)c1ccncc1NCC1Cc2ccccc2O1] | 3-[(2,3-dihydro-1-benzofuran-2-ylmethyl)amino]pyridine-4-carboxylic acid |
| 44 | 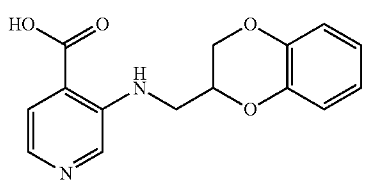 [SMILES: O=C(O)c1ccncc1NCC1COc2ccccc2O1] | 3-[(2,3-dihydro-1,4-benzodioxin-2-yl-methyl)-amino]pyridine-4-carboxylic acid |
| 45 | 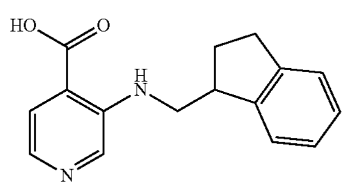 [SMILES: O=C(O)c1ccncc1NCC1CCc2ccccc21] | 3-[(2,3-dihydro-1H-inden-1-yl-methylbenzyl)-amino]-pyridine-4-carboxylic acid |
| 46 | 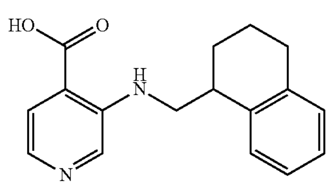 | 3-[(1,2,3,4-tetrahydronaphthalen-1-yl-methyl)amino]-pyridine-4-carboxylic acid |
| 47 | 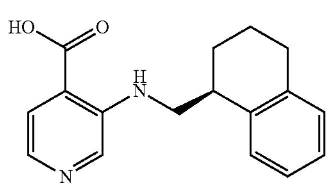 [SMILES: O=C(O)c1ccncc1NC[C@H]1CCCc2ccccc21] | 3-{[(1S)-1,2,3,4-tetrahydronaphthalen-1-yl-methyl]amino}-pyridine-4-carboxylic acid |

TABLE 1-continued

| Chemical Synthesis Example | Structure | Name |
|---|---|---|
| 48 | 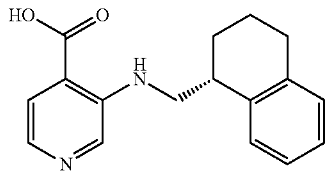 [SMILES: O=C(O)c1ccncc1NC[C@@H]1CCCc2ccccc21] | 3-{[(1R)-1,2,3,4-tetrahydronaphthalen-1-yl-methyl]-amino}pyridine-4-carboxylic acid |
| 49 | 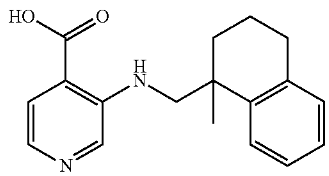 [SMILES: CC1(CNc2cnccc2C(=O)O)CCCc2ccccc21] | 3-{[(1-methyl-1,2,3,4-tetrahydronaphthalen-1-yl)methyl]-amino}pyridine-4-carboxylic acid |
| 50 | 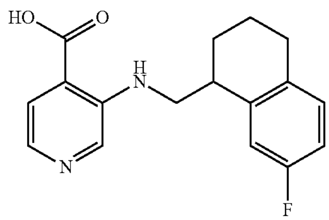 [SMILES: O=C(O)c1ccncc1NCC1CCCc2ccc(F)cc21] | 3-{[(7-fluoro-1,2,3,4-tetrahydronaphthalen-1-yl)methyl]amino}pyridine-4-carboxylic acid |
| 51 | 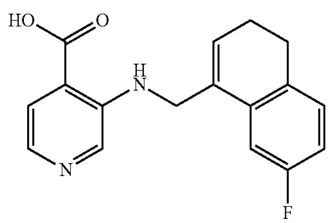 | 3-{[(7-fluoro-3,4-dihydronaphthalen-1-yl)methyl]-amino}pyridine-4-carboxylic acid |
| 52 | 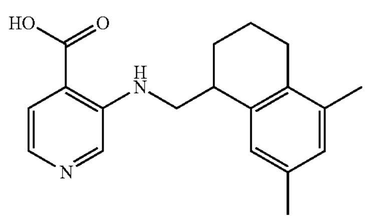 [SMILES: Cc1cc(C)c2c(c1)C(CNc1cnccc1C(=O)O)CCC2] | 3-{[(5,7-dimethyl-1,2,3,4-tetrahydronaphthalen-1-yl)-methyl]amino}pyridine-4-carboxylic acid |
| 53 | 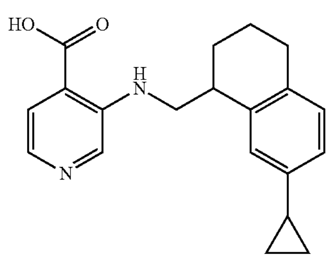 [SMILES: O=C(O)c1ccncc1NCC1CCCc2ccc(C3CC3)cc21] | 3-{[(7-cyclopropyl-1,2,3,4-tetrahydronaphthalen-1-yl)-methyl]amino}pyridine-4-carboxylic acid |
| 54 | 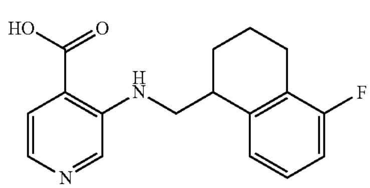 [SMILES: O=C(O)c1ccncc1NCC1CCCc2c(F)cccc21] | 3-{[(5-fluoro-1,2,3,4-tetrahydronaphthalen-1-yl)-methyl]amino}pyridine-4-carboxylic acid |

TABLE 1-continued

| Chemical Synthesis Example | Structure | Name |
|---|---|---|
| 55 | 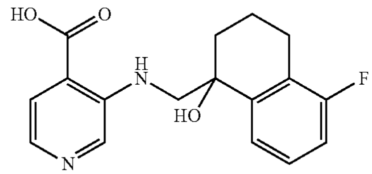 [SMILES: O=C(O)c1ccncc1NCC1(O)CCCc2c(F)cccc21] | 3-{[(5-fluoro-1-hydroxy-1,2,3,4-tetrahydronaphthalen-1-yl)methyl]amino}pyridine-4-carboxylic acid |
| 56 | 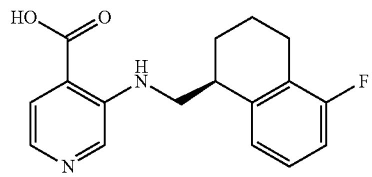 [SMILES: O=C(O)c1ccncc1NC[C@H]1CCCc2c(F)cccc21] | 3-({[(1S)-5-fluoro-1,2,3,4-tetrahydronaphthalen-1-yl]-methyl}amino)pyridine-4-carboxylic acid |
| 57 | 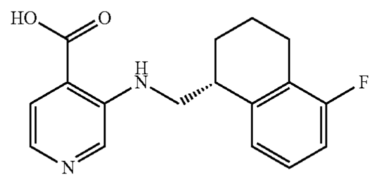 | 3-({[(1R)-5-fluoro-1,2,3,4-tetrahydronaphthalen-1-yl]-methyl}amino)pyridine-4-carboxylic acid |
| 58 | 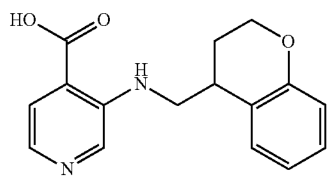 | 3-[(3,4-dihydro-2H-chromen-4-ylmethyl)amino]pyridine-4-carboxylic acid |
| 59 | 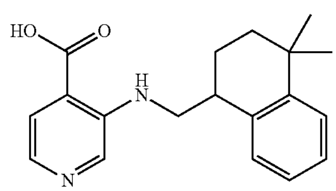 [SMILES: CC1(C)CCC(CNc2cnccc2C(=O)O)c2ccccc21] | 3-{[(4,4-dimethyl-1,2,3,4-tetrahydronaphthalen-1-yl)-methyl]amino}pyridine-4-carboxylic acid |
| 60 | 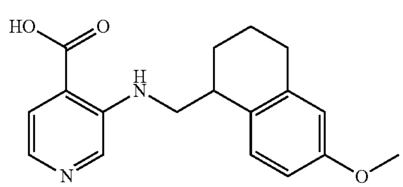 | 3-{[(6-methoxy-1,2,3,4-tetrahydronaphthalen-1-yl)-methyl]amino}pyridine-4-carboxylic acid |
| 61 | 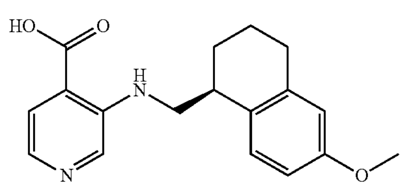 [SMILES: COc1ccc2c(c1)CCC[C@@H]2CNc1cnccc1C(=O)O] | 3-({[(1S)-6-methoxy-1,2,3,4-tetrahydronaphthalen-1-yl]-methyl}amino)pyridine-4-carboxylic acid |
| 62 | 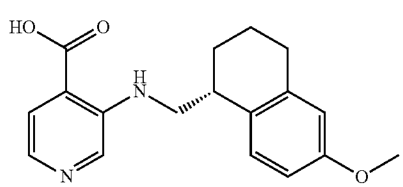 | 3-({[(1R)-6-methoxy-1,2,3,4-tetrahydronaphthalen-1-yl]-methyl}amino)pyridine-4-carboxylic acid |

TABLE 1-continued

| Chemical Synthesis Example | Structure | Name |
|---|---|---|
| 63 | 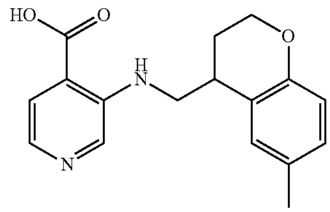 [SMILES: Cc1ccc2c(c1)C(CNc1cnccc1C(=O)O)CCO2] | 3-{[(6-methyl-3,4-dihydro-2H-chromen-4-yl)methyl]-amino}pyridine-4-carboxylic acid |
| 64 | 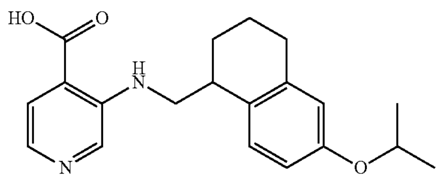 [SMILES: CC(C)Oc1ccc2c(c1)CCCC2CNc1cnccc1C(=O)O] | 3-({[(6-(propan-2-yloxy)-1,2,3,4-tetrahydronaphthalen-1-yl]methyl}amino)pyridine-4-carboxylic acid |
| 65 | 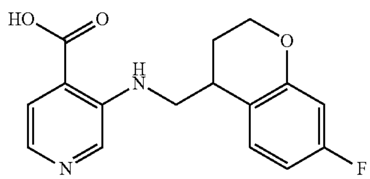 [SMILES: O=C(O)c1ccncc1NCC1CCOc2cc(F)ccc21] | 3-{[(7-fluoro-3,4-dihydro-2H-chromen-4-yl)methyl]-amino}pyridine-4-carboxylic acid |
| 66 | 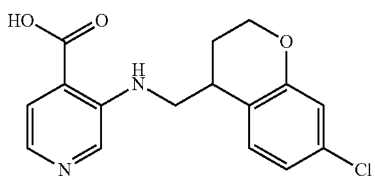 [SMILES: O=C(O)c1ccncc1NCC1CCOc2cc(Cl)ccc21] | 3-{[(7-chloro-3,4-dihydro-2H-chromen-4-yl)methyl]-amino}pyridine-4-carboxylic acid |
| 67 | 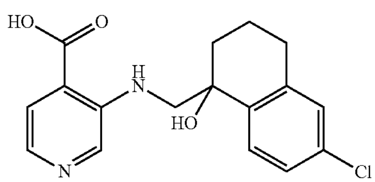 [SMILES: O=C(O)c1ccncc1NCC1(O)CCCc2cc(Cl)ccc21] | 3-{[(6-chloro-1-hydroxy-1,2,3,4-tetrahydronaphthalen-1-yl)methyl]amino}pyridine-4-carboxylic acid |
| 68 | 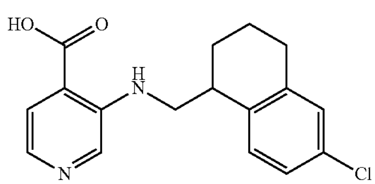 [SMILES: O=C(O)c1ccncc1NCC1CCCc2cc(Cl)ccc21] | 3-{[(6-chloro-1,2,3,4-tetrahydronaphthalen-1-yl)methyl]-amino}pyridine-4-carboxylic acid |
| 69 | 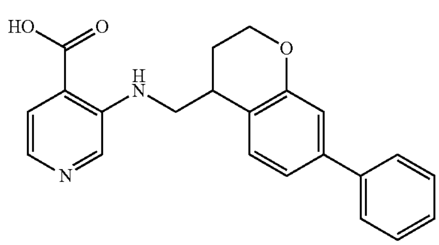 [SMILES: O=C(O)c1ccncc1NCC1CCOc2cc(-c3ccccc3)ccc21] | 3-{[(7-phenyl-3,4-dihydro-2H-chromen-4-yl)methyl]-amino}pyridine-4-carboxylic acid |
| 70 | 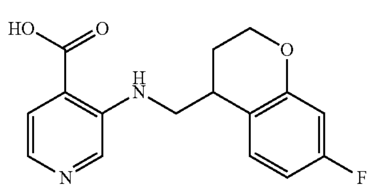 [SMILES: O=C(O)c1ccncc1NCC1CCOc2cc(F)ccc21] | 3-{[(7-fluoro-3,4-dihydro-2H-chromen-4-yl)methyl]-amino}pyridine-4-carboxylic acid |

TABLE 1-continued

| Chemical Synthesis Example | Structure | Name |
|---|---|---|
| 71 | 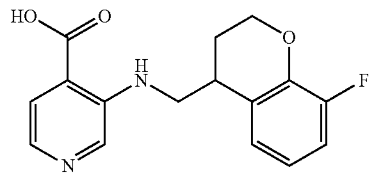 | 3-{[(8-fluoro-3,4-dihydro-2H-chromen-4-yl)methyl]-amino}pyridine-4-carboxylic acid |
| 72 | 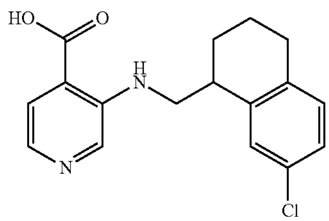 [SMILES: O=C(O)c1ccncc1NCC1CCCc2ccc(Cl)cc21] | 3-{[(7-chloro-1,2,3,4-tetrahydronaphthalen-1-yl)methyl]-amino}pyridine-4-carboxylic acid |
| 73 | 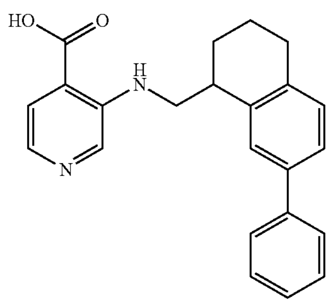 [SMILES: O=C(O)c1ccncc1NCC1CCCc2ccc(-c3ccccc3)cc21] | 3-{[(7-phenyl-1,2,3,4-tetrahydronaphthalen-1-yl)methyl]-amino}pyridine-4-carboxylic acid |
| 74 | 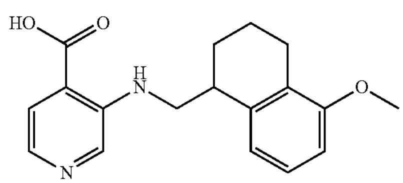 [SMILES: COc1cccc2c1CCCC2CNc1cnccc1C(=O)O] | 3-{[(5-methoxy-1,2,3,4-tetrahydronaphthalen-1-yl)-methyl]amino}pyridine-4-carboxylic acid |
| 75 | 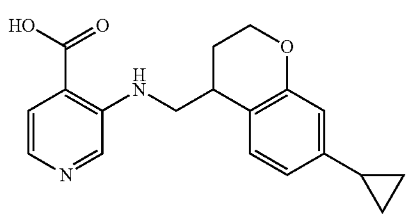 [SMILES: O=C(O)c1ccncc1NCC1CCOc2cc(C3CC3)ccc21] | 3-{[(7-cyclopropyl-3,4-dihydro-2H-chromen-4-yl)-methyl]amino}pyridine-4-carboxylic acid |
| 76 | 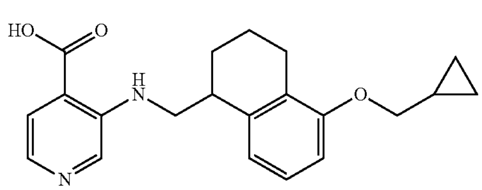 [SMILES: O=C(O)c1ccncc1NCC1CCCc2c(OCC3CC3)cccc21] | 3-({[(5-(cyclopropylmethoxy)-1,2,3,4-tetrahydronaphthalen-1-yl]methyl}amino)pyridine-4-carboxylic acid |
| 77 | 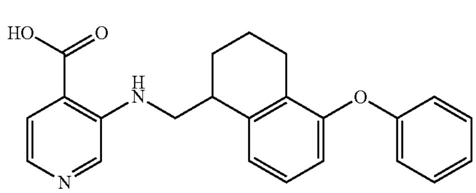 [SMILES: O=C(O)c1ccncc1NCC1CCCc2c(Oc3ccccc3)cccc21] | 3-{[(5-phenoxy-1,2,3,4-tetrahydronaphthalen-1-yl)-methyl]amino}pyridine-4-carboxylic acid |

TABLE 1-continued

| Chemical Synthesis Example | Structure | Name |
|---|---|---|
| 78 | 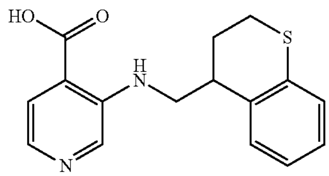 | 3-[(3,4-dihydro-2H-thiochromen-4-yl-methyl)amino]pyridine-4-carboxylic acid |
| 79 | 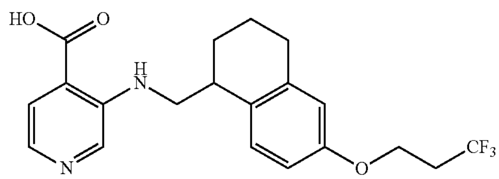 [SMILES: O=C(O)c1ccncc1NCC1CCCc2cc(OCCC(F)(F)F)ccc21] | 3-({[(6-(3,3,3-trifluoropropoxy)-1,2,3,4-tetrahydronaphthalen-1-yl]methyl}amino)pyridine-4-carboxylic acid |
| 80 | 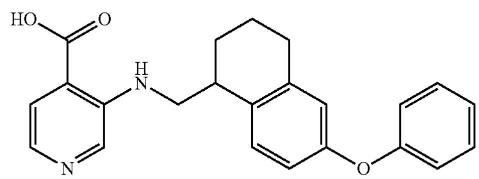 [SMILES: O=C(O)c1ccncc1NCC1CCCc2cc(Oc3ccccc3)ccc21] | 3-{[(5-phenoxy-1,2,3,4-tetrahydronaphthalen-1-yl)-methyl]amino}pyridine-4-carboxylic acid |
| 81 | 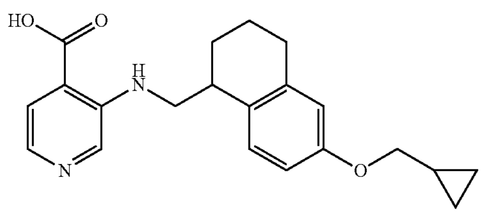 [SMILES: O=C(O)c1ccncc1NCC1CCCc2cc(OCC3CC3)ccc21] | 3-({[(6-(cyclopropylmethoxy)-1,2,3,4-tetrahydro-naphthalen-1-yl]methyl}amino)pyridine-4-carboxylic acid |
| 82 | 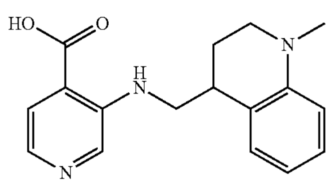 [SMILES: CN1CCC(CNc2cnccc2C(=O)O)c2ccccc21] | 3{[(1-methyl-1,2,3,4-tetrahydroquinolin-4-yl)methyl]-amino}pyridine-4-carboxylic acid |
| 83 | 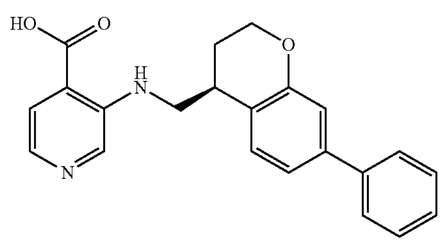 [SMILES: O=C(O)c1ccncc1NC[C@H]1CCOc2cc(-c3ccccc3)ccc21] | 3-({[(4S)-7-phenyl-3,4-dihydro-2H-chromen-4-yl]-methyl}amino)pyridine-4-carboxylic acid |
| 84 | 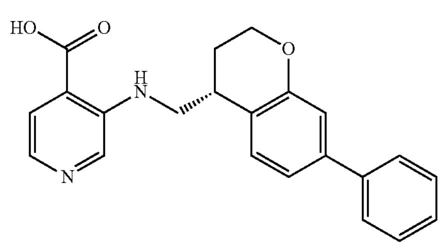 [SMILES: O=C(O)c1ccncc1NC[C@@H]1CCOc2cc(-c3ccccc3)ccc21] | 3-({[(4R)-7-phenyl-3,4-dihydro-2H-chromen-4-yl]-methyl}amino)pyridine-4-carboxylic acid |

TABLE 1-continued

| Chemical Synthesis Example | Structure | Name |
|---|---|---|
| 85 | 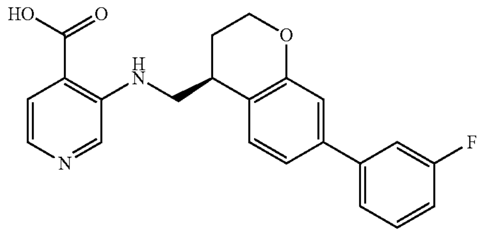 [SMILES: O=C(O)c1ccncc1NC[C@H]1CCOc2cc(-c3cccc(F)c3)ccc21] | 3-({[(4S)-7-(3-fluorophenyl)-3,4-dihydro-2H-chromen-4-yl]-methyl}amino)pyridine-4-carboxylic acid |
| 86 | 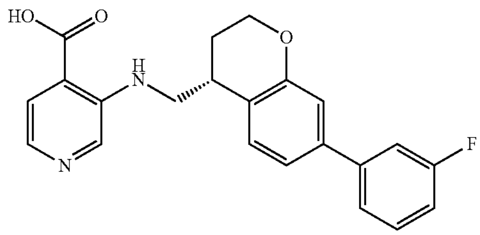 [SMILES: O=C(O)c1ccncc1NC[C@@H]1CCOc2cc(-c3cccc(F)c3)ccc21] | 3-({[(4R)-7-(3-fluorophenyl)-3,4-dihydro-2H-chromen-4-yl]methyl}amino)pyridine-4-carboxylic acid |
| 87 | 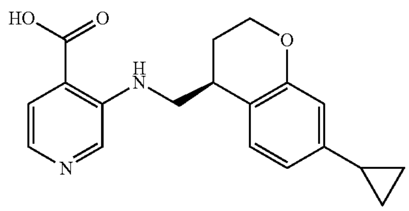 [SMILES: O=C(O)c1ccncc1NC[C@H]1CCOc2cc(C3CC3)ccc21] | 3-({[(4S)-7-cyclopropyl-3,4-dihydro-2H-chromen-4-yl]-methyl}amino)pyridine-4-carboxylic acid |
| 88 | 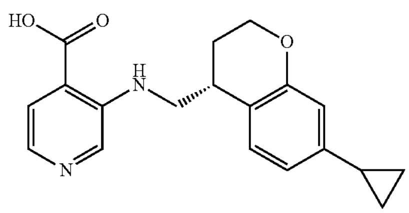 [SMILES: O=C(O)c1ccncc1NC[C@@H]1CCOc2cc(C3CC3)ccc21] | 3-({[(4R)-7-cyclopropyl-3,4-dihydro-2H-chromen-4-yl]-methyl}amino)pyridine-4-carboxylic acid |
| 89 | 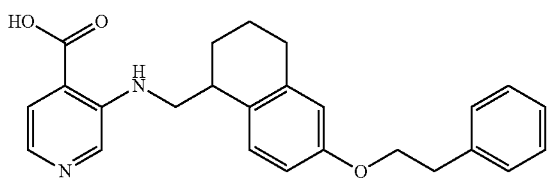 [SMILES: O=C(O)c1ccncc1NCC1CCCc2cc(OCCc3ccccc3)ccc21] | 3-({[6-(2-phenylethoxy)-1,2,3,4-tetrahydronaphthalen-1-yl]methyl}amino)pyridine-4-carboxylic acid |
| 90 | 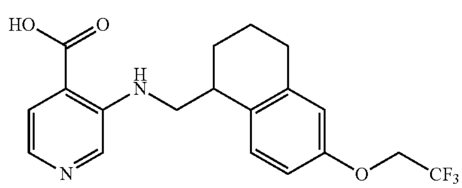 [SMILES: O=C(O)c1ccncc1NCC1CCCc2cc(OCC(F)(F)F)ccc21] | 3-({[6-(2,2,2-trifluoroethoxy)-1,2,3,4-tetrahydronaphthalen-1-yl]methyl}amino)pyridine-4-carboxylic acid |
| 91 | 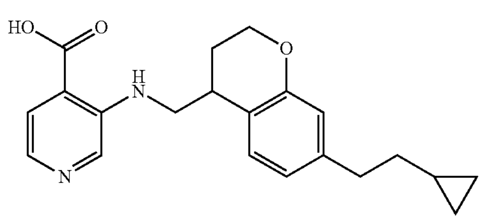 | 3-({[7-(2-cyclopropylethyl)-3,4-dihydro-2H-chromen-4-yl]-methyl}amino)pyridine-4-carboxylic acid |

TABLE 1-continued

| Chemical Synthesis Example | Structure | Name |
|---|---|---|
| 92 | 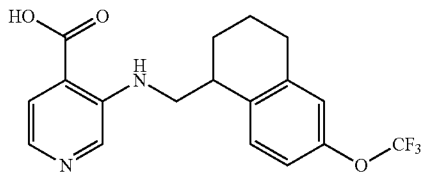 [SMILES: O=C(O)c1ccncc1NCC1CCCc2cc(OC(F)(F)F)ccc21] | 3-({[6-(trifluoromethoxy)-1,2,3,4-tetrahydronaphthalen-1-yl]methyl}amino)pyridine-4-carboxylic acid |
| 93 | 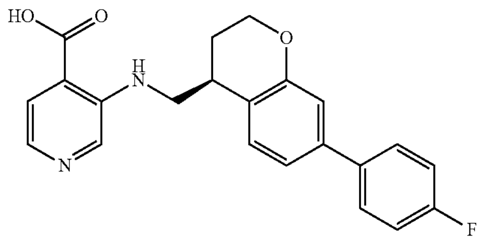 [SMILES: O=C(O)c1ccncc1NC[C@H]1CCOc2cc(-c3ccc(F)cc3)ccc21] | 3-({[(4S)-7-(4-fluorophenyl)-3,4-dihydro-2H-chromen-4-yl]methyl}amino)pyridine-4-carboxylic acid |
| 94 | 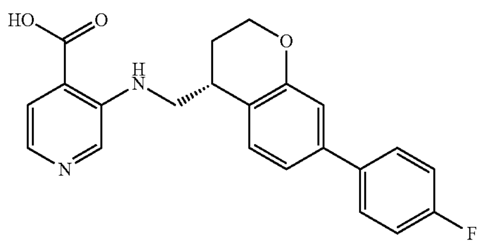 [SMILES: O=C(O)c1ccncc1NC[C@@H]1CCOc2cc(-c3ccc(F)cc3)ccc21] | 3-({[(4R)-7-(4-fluorophenyl)-3,4-dihydro-2H-chromen-4-yl]methyl}amino)pyridine-4-carboxylic acid |
| 95 | 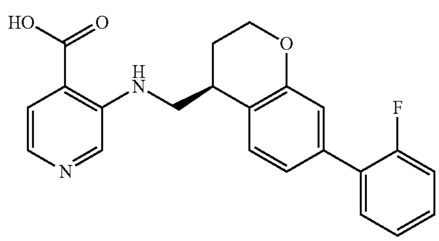 [SMILES: O=C(O)c1ccncc1NC[C@H]1CCOc2cc(-c3ccccc3F)ccc21] | 3-({[(4S)-7-(2-fluorophenyl)-3,4-dihydro-2H-chromen-4-yl]methyl}amino)pyridine-4-carboxylic acid |
| 96 | 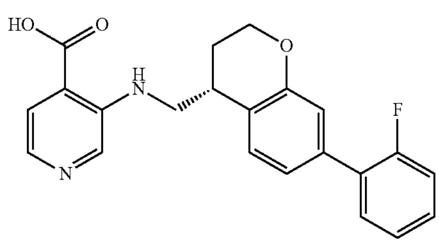 [SMILES: O=C(O)c1ccncc1NC[C@@H]1CCOc2cc(-c3ccccc3F)ccc21] | 3-({[(4R)-7-(2-fluorophenyl)-3,4-dihydro-2H-chromen-4-yl]methyl}amino)pyridine-4-carboxylic acid |
| 97 | 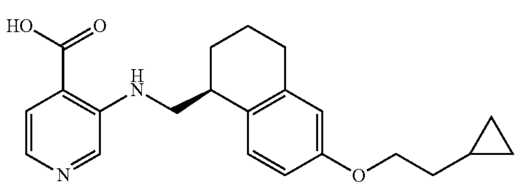 [SMILES: O=C(O)c1ccncc1NC[C@H]1CCCc2cc(OCCC3CC3)ccc21] | 3-({[(1S)-6-(2-cyclopropylethoxy)-1,2,3,4-tetrahydronaphthalen-1-yl]methyl}amino)pyridine-4-carboxylic acid |
| 98 | 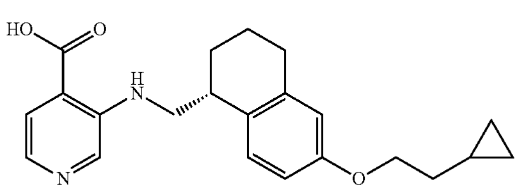 [SMILES: O=C(O)c1ccncc1NC[C@@H]1CCCc2cc(OCCC3CC3)ccc21] | 3-({[(1R)-6-(2-cyclopropylethoxy)-1,2,3,4-tetrahydronaphthalen-1-yl]methyl}amino)pyridine-4-carboxylic acid |

TABLE 1-continued

| Chemical Synthesis Example | Structure | Name |
|---|---|---|
| 99 | 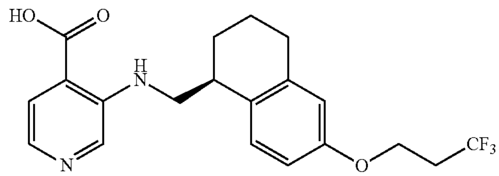 [SMILES: O=C(O)c1ccncc1NC[C@H]1CCCc2cc(OCCC(F)(F)F)ccc21] | 3-({[(1S)-6-(3,3,3-trifluoropropoxy)-1,2,3,4-tetrahydronaphthalen-1-yl]methyl}amino)pyridine-4-carboxylic acid |
| 100 | 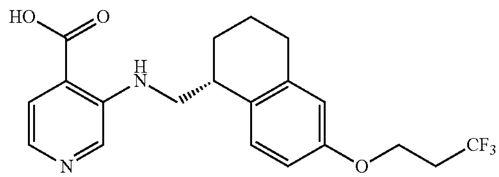 [SMILES: O=C(O)c1ccncc1NC[C@@H]1CCCc2cc(OCCC(F)(F)F)ccc21] | 3-({[(1R)-6-(3,3,3-trifluoropropoxy)-1,2,3,4-tetrahydronaphthalen-1-yl]methyl}amino)pyridine-4-carboxylic acid |
| 101 | 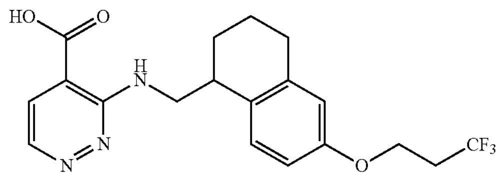 [SMILES: O=C(O)c1ccnnc1NCC1CCCc2cc(OCCC(F)(F)F)ccc21] | 3-({[6-(3,3,3-trifluoropropoxy)-1,2,3,4-tetrahydronaphthalen-1-yl]methyl}amino)pyridazine-4-carboxylic acid |
| 102 | 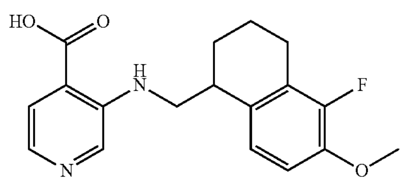 [SMILES: COc1ccc2c(c1F)CCCC2CNc1cnccc1C(=O)O] | 3-{[(5-fluoro-6-methoxy-1,2,3,4-tetrahydronaphthalen-1-yl)methyl]amino}pyridine-4-carboxylic acid |
| 103 | 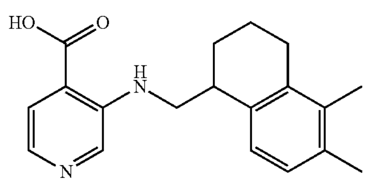 [SMILES: Cc1ccc2c(c1C)CCCC2CNc1cnccc1C(=O)O] | 3-{[(5,6-dimethyl-1,2,3,4-tetrahydronaphthalen-1-yl)-methyl]amino}pyridine-4-carboxylic acid |
| 104 | 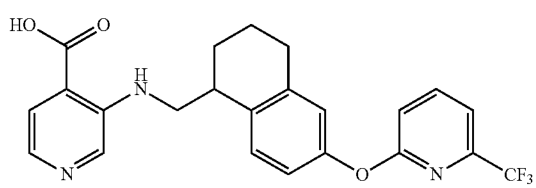 [SMILES: O=C(O)c1ccncc1NCC1CCCc2cc(Oc3cccc(C(F)(F)F)n3)ccc21] | 3-{[(6-{[6-(trifluoromethyl)pyridin-2-yl]oxy}-1,2,3,4-tetrahydronaphthalen-1-yl)methyl]amino}pyridine-4-carboxylic acid |

In some embodiments, the substituted aminopyridine or aminopyridazine derivative compound as described herein, or a carboxylic acid ester, or carboxylic acid bioisostere thereof, has the structure provided in Table 2.

TABLE 2

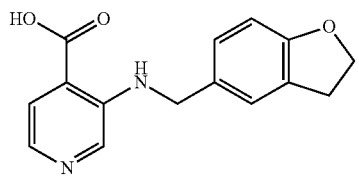

3-[2,3-dihydro-1-benzofuran-5-ylmethyl) amino]pyridine-4-carboxylic acid

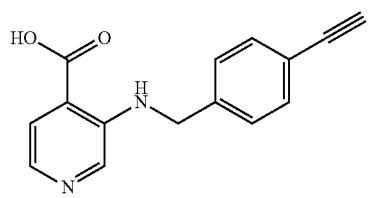

3-[4-ethylnylbenzyl)amino]pyridine-4-carboxylic acid

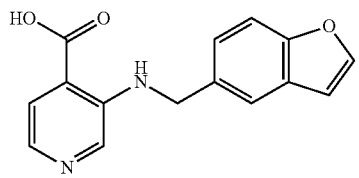

3-[(1-benzofuran-5-ylmethyl)amino] pyridine-4-carboxylic acid

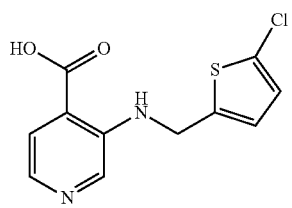

5-{[(5-chlorothiophen-2-yl)methyl] amino}pyridine-4-carboxylic acid

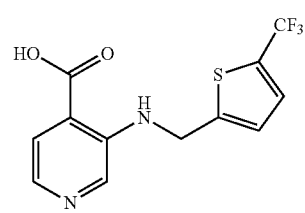

5-{[(5-trifluoromethylthiophen-2-yl) methyl]amino}pyridine-4-carboxylic acid

TABLE 2-continued

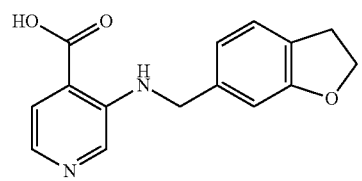

3-[2,3-dihydro-1-benzofuran-6-ylmethyl) amino]pyridine-4-carboxylic acid

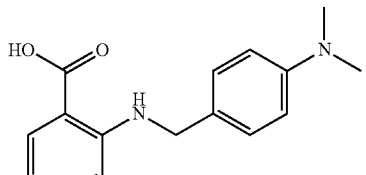

3-{[4-(dimethylamino)benzyl]amino} pyridine-4-carboxylic acid

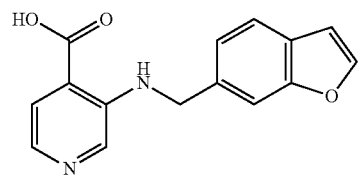

3-[(1-benzofuran-6-ylmethyl)amino] pyridine-4-carboxylic acid

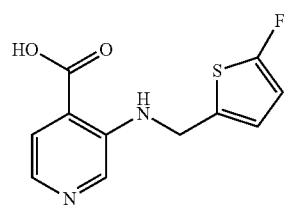

5-{[(5-fluorothiophen-2-yl)methyl] amino}pyridine-4-carboxylic acid

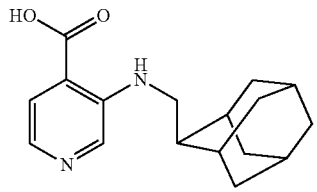

3-[(adamantan-2-ylmethyl)amino] pyridine-4-carboxylic acid

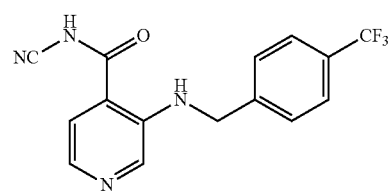

N-cyano-3-(4-(trifluoromethyl) benzylamino)isonicotinamide

TABLE 2-continued

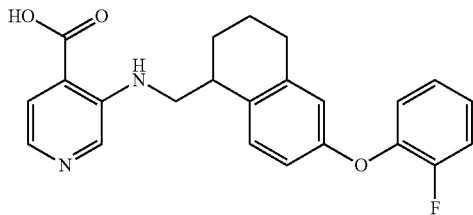

3-({[6-(2-fluorophenoxy)-1,2,3,4-
tetrahydronaphthalen-1-yl]methyl}
amino)pyridine-4-carboxylic acid

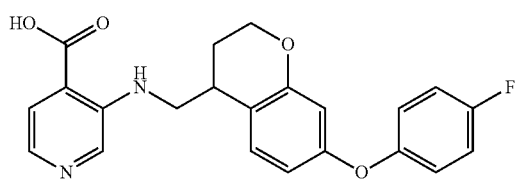

3-({[7-(4-fluorophenoxy)-3,4-dihydro-2H-1-
benzopyran-4-yl]methyl}amino)pyridine-
4-carboxylic acid

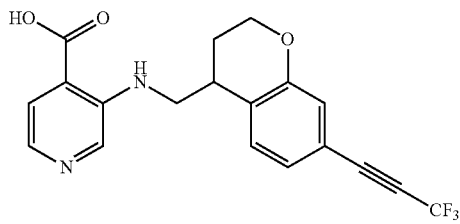

3-({[7-(trifluoroprop-1-yn-1-yl)-3,4-dihydro-
2H-1-benzopyran-4-yl]methyl}amino)
pyridine-4-carboxylic acid

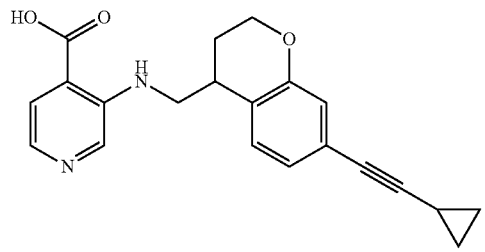

3-({[7-(2-cyclopropylethynyl)-3,4-dihydro-
2H-1-benzopyran-4-yl]methyl}amino)
pyridine-4-carboxylic acid

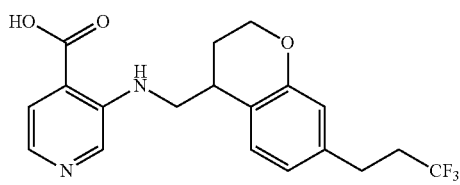

3-({[7-(3,3,3-trifluoropropyl)-3,4-dihydro-
2H-1-benzopyran-4-yl]methyl}amino)
pyridine-4-carboxylic acid

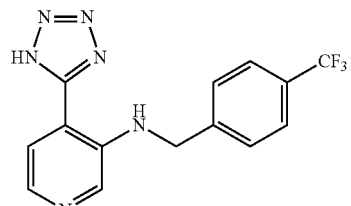

4-(1H-tetrazol-5-yl)-N-(4-(trifluoromethyl)
benzyl)pyridin-3-amine

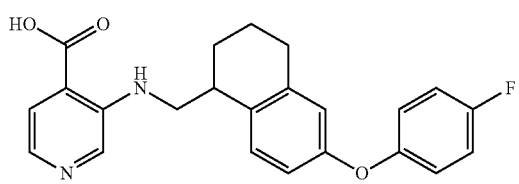

3-({[6-(3-fluorophenoxy)-1,2,3,4-
tetrahydronaphthalen-1-yl]methyl}
amino)pyridine-4-carboxylic acid

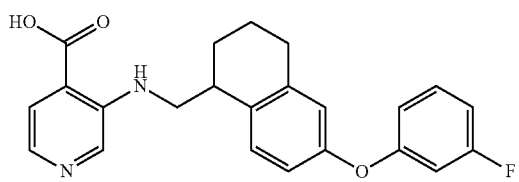

3-({[6-(3-fluorophenoxy)-1,2,3,4-
tetrahydronaphthalen-1-yl]methyl}
amino)pyridine-4-carboxylic acid

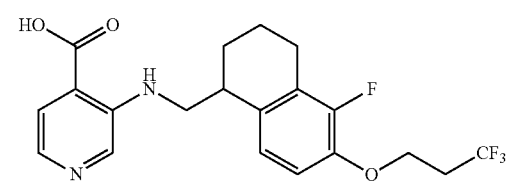

3-({[5-fluoro-6-(3,3,3-trifluoropropoxy)-
1,2,3,4-tetrahydronaphthalen-1-yl]methyl}
amino)pyridine-4-carboxylic acid

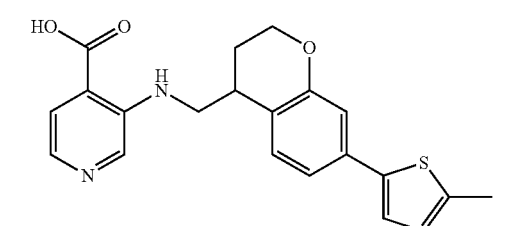

3-({[7-(5-methylthiophen-2-yl)-3,4-dihydro-2H-
1-benzopyran-4-yl]methyl}amino)pyridine-
4-carboxylic acid TABLE 2-continued

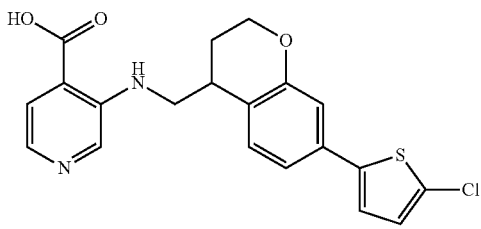

3-({[7-(5-chlorothiophen-2-yl)-3,4-dihydro-2H-
1-benzopyran-4-yl]methyl}amino)pyridine-
4-carboxylic acid

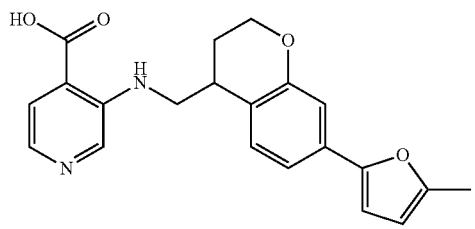

3-({[7-(furan-2-yl)-3,4-dihydro-2H-1-
benzopyran-4-yl]methyl}amino)pyridine-
4-carboxylic acid

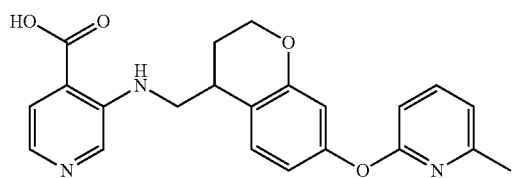

3-[({6-[(6-methylpyridin-2-yl)oxy]-1,2,3,4-
tetrahydronaphthalen-1-yl}methyl)amino]
pyridine-4-carboxylic acid

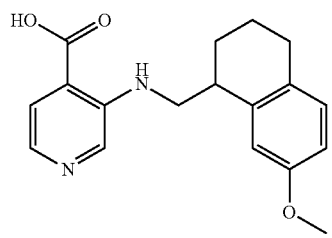

3-{[(7-methoxy-1,2,3,4-
tetrahydronaphthalen-1-yl)methyl]
amino}pyridine-4-carboxylic acid

3-{[(6-ethoxy-1,2,3,4-
tetrahydronaphthalene-1-yl)methyl]
amino}pyridine-4-carboxylic acid

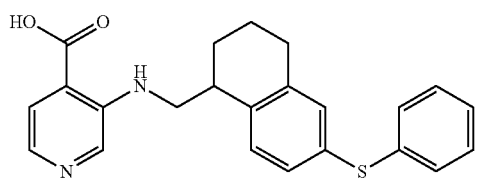

3-({[6-(phenylsulfanyl)-1,2,3,4-
tetrahydronaphthalen-1-yl]methyl}
amino)pyridine-4-carboxylic acid

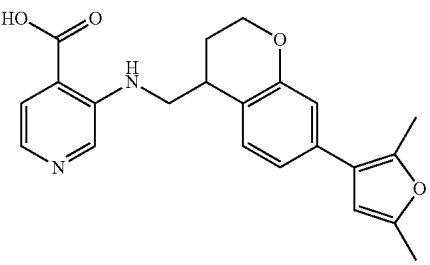

3-({[7-(2,5-dimethylfuran-3-yl)-3,4-dihydro-
2H-1-benzopyran-4-yl]methyl}amino)
pyridine-4-carboxylic acid

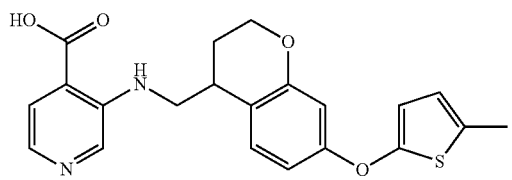

3-[({6-[(5-methylthiophen-2-yl)oxy]-1,2,3,4-
tetrahydronaphthalen-1-yl}methyl)amino]
pyridine-4-carboxylic acid

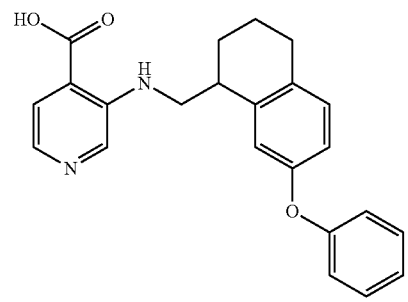

3-{[(7-phenoxy-1,2,3,4-
tetrahydronaphthalen-1-yl)methyl]
amino}pyridine-4-carboxylic acid

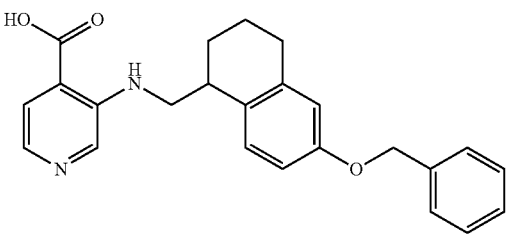

3-{[(6-benzyloxy-1,2,3,4-
tetrahydronaphthalen-1-yl)methyl]
amino}pyridine-4-carboxylic acid TABLE 2-continued

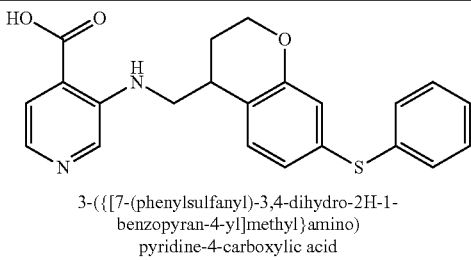

3-({[7-(phenylsulfanyl)-3,4-dihydro-2H-1-benzopyran-4-yl]methyl}amino)pyridine-4-carboxylic acid Preparation of the Substituted Pyridine and Pyridazine Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, SYNTHETIC ORGANIC CHEM., John Wiley & Sons, Inc., New York; Sandler et al., ORGANIC FUNCTIONAL GROUP PREPARATIONS, 2nd Ed., Academic Press, New York, 1983; House, MODERN SYNTHETIC REACTIONS, 2nd Ed., W. A. Benjamin, Inc. Menlo Park, Calif. 1972; Gilchrist, HETEROCYCLIC CHEM., 2nd Ed., John Wiley & Sons, New York, 1992; March, ADVANCED ORGANIC CHEMISTRY: REACTIONS, MECHANISMS & STRUCTURE, 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop & Penzlin, ORGANIC SYNTHESIS: CONCEPTS, METHODS, STARTING MATERIALS, Second, Revised and Enlarged Edition (1994) John Wiley & Sons ISBN: 3-527-29074-5; Hoffman, ORGANIC CHEM., AN INTERMEDIATE TEXT (1996) Oxford Univ. Press, ISBN 0-19-509618-5; Larock, R. C. COMPREHENSIVE ORGANIC TRANSFORMATIONS: A GUIDE TO FUNCTIONAL GROUP PREPARATIONS, 2nd Edition (1999) Wiley-VCH, ISBN: 0-471-19031-4; Otera (editor) MODERN CARBONYL CHEM. (2000) Wiley-VCH, ISBN: 3-527-29871-1; Patai, PATAI'S 1992 GUIDE TO THE CHEM. OF FUNCTIONAL GROUPS (1992) Interscience ISBN: 0-471-93022-9; Solomons, ORGANIC CHEM. 7th Edition (2000) John Wiley & Sons, ISBN: 0-471-19095-0; Stowell, INTERMEDIATE ORGANIC CHEM. 2nd Edition (1993) Wiley-Interscience, ISBN: 0-471-57456-2; INDUSTRIAL ORGANIC CHEMICALS: STARTING MATERIALS AND INTERMEDIATES: AN ULLMANN'S ENCYCLO. (1999) John Wiley & Sons, ISBN: 3-527-29645-X, in 8 volumes; ORGANIC REACTIONS (1942-2000) John Wiley & Sons, in over 55 volumes; and CHEM. OF FUNCTIONAL GROUPS, John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted amidopyridine and amindopyridazine derivative compounds described herein is Stahl & Wermuth, HANDBOOK OF PHARMACEUTICAL SALTS, Verlag Helvetica Chimica Acta, Zurich, 2002.

The substituted pyridine and pyridazine derivative compounds are prepared by the general synthetic routes described below in Schemes 1-5.

Scheme 1

X = halo
A = CH, N

Referring to Scheme 1, compound A and an amine compound B are mixed and treated under a variety of conditions to form compound C. For example, the mixture of compound A and an amine B can be subjected to microwave irradiation in an appropriate solvent, at temperatures ranging from 120° C. to 172° C. The ester compound E can be prepared from compound C and an alcohol D using a coupling reagent, such as HATU, in the presence of a base.

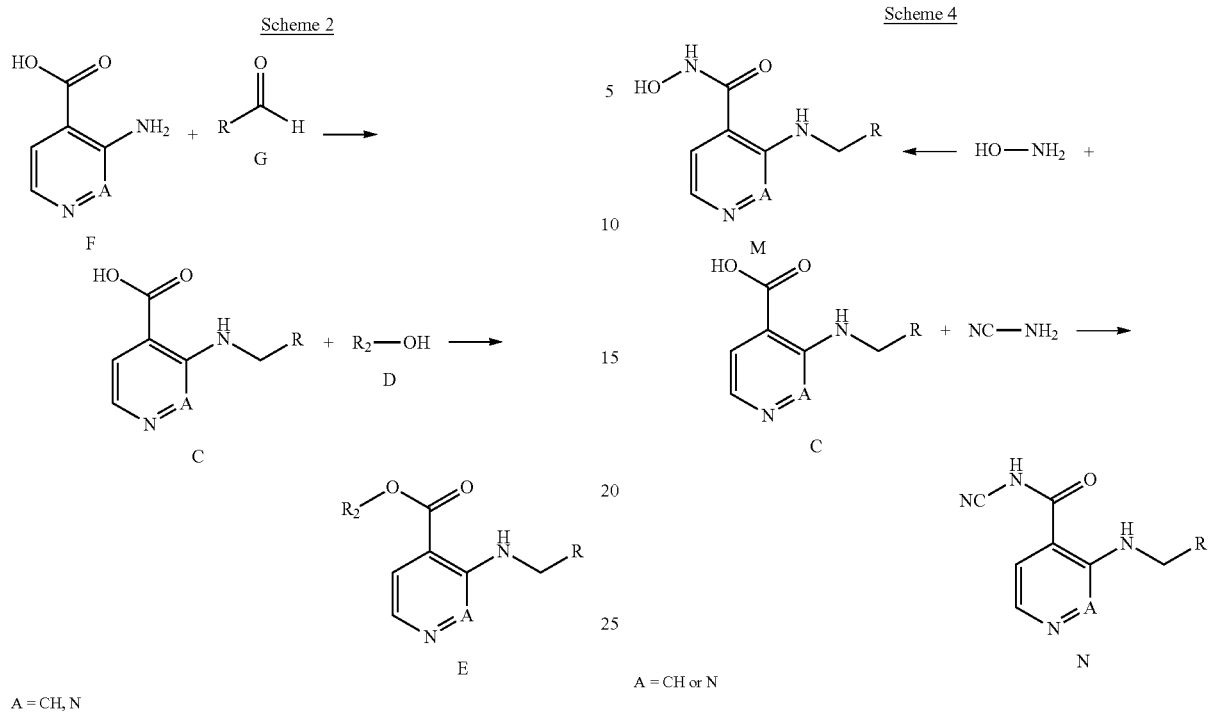

Scheme 2

A = CH, N

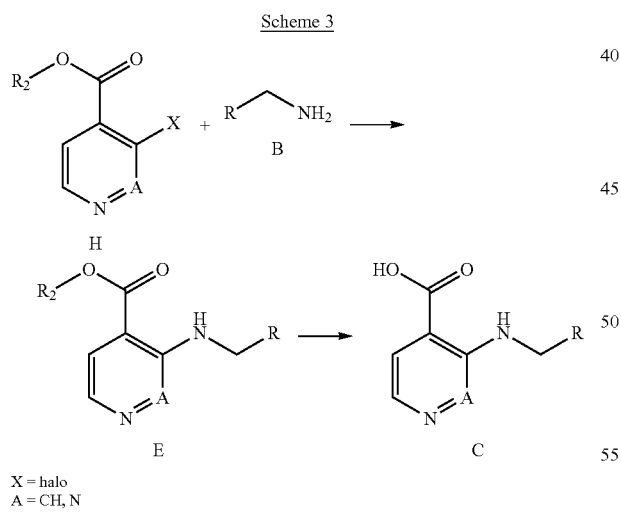

Scheme 3

X = halo
A = CH, N

Referring to Scheme 2, compound F and an aldehyde compound G are mixed and treated under reductive amination conditions to form compound C. The ester compound E can be prepared from compound C and an alcohol D using a coupling reagent, such as HATU, in the presence of a base.

Referring to Scheme 3, compound H and an amine compound B are mixed and treated under a variety of conditions to form compound E. For example, the mixture of compound H and an amine B can be subjected to a Buchwald reaction under microwave irradiation in an appropriate solvent, at temperatures ranging from 100° C. to 120° C. The ester compound E can be hydrolyzed to give compound C, using basic conditions such as 1N aq. NaOH.

Scheme 4

A = CH or N

Referring to Scheme 4, compound C can be used to prepare hydroxamic acid derivatives such as compound M. Treatment of compound C with hydroxylamine hydrochloride in the presence of an acid coupling reagent, such as HATU, in a solvent, such as DMF, for 1 to 24 hours provides compound M. Compound C can also be used to prepare N-acylcyanamides such as compound N. Treatment of compound C with cyanamide in the presence of an acid coupling reagent, such as HATU, in a solvent, such as DMF, for 1 to 24 hours provides compound N.

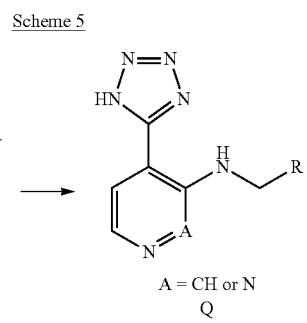

Scheme 5

A = CH or N
P

A = CH or N
Q

Referring to Scheme 5, compound P can be used to prepare tetrazole derivatives such as compound Q. Treatment of compound P with sodium azide and ammonium chloride in DMF followed by heating to 90° C. for 2 to 24 hours provides the desired tetrazole derivative Q.

In each of the above reaction procedures or schemes, the various substituents may be selected from among the various substituents otherwise taught herein.

Pharmaceutical Compositions

In certain embodiments, a substituted amidopyridine or amidopyridazine derivative compound as described by Formulas (I), (III), (V), (XI), (XIa), (XIb), (XIII), or (XV) is administered as a pure chemical. In other embodiments, the substituted amidopyridine or amidopyridazine derivative compound as described by Formulas (I), (III), (V), (XI), (XIa), (XIb), (XIII), or (XV) is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in REMINGTON: SCIENCE & PRACTICE OF PHARMACY (Gennaro, 21st Ed. Mack Pub. Co., Easton, Pa. (2005)), the disclosure of which is hereby incorporated herein by reference, in its entirety.

Accordingly, provided herein is a pharmaceutical composition comprising at least one substituted amidopyridine or amidopyridazine derivative compound, or a stereoisomer, prodrug, pharmaceutically acceptable salt, hydrate, solvate, or N-oxide thereof, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formulas (I), (III), (V), (XI), (XIa), (XIb), (XIII), or (XV), or a tautomer, stereoisomer, geometric isomer, N-oxide, or pharmaceutically acceptable salt thereof.

In certain embodiments, the substituted amidopyridine or amidopyridazine derivative compound as described by Formulas (I), (III), (V), (XI), (XIa), (XIb), (XIII), or (XV) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. See, e.g., REMINGTON: SCIENCE & PRACTICE OF PHARMACY (Gennaro, 21st Ed. Mack Pub. Co., Easton, Pa. (2005).

The dose of the composition comprising at least one substituted amidopyridine or amidopyridazine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenyosyl methionine (SAM) to histones. Histone methylation is known to participate in a diverse range of biological processes including heterochromatin formation, X-chromosome inactivation, and transcriptional regulation. Lachner et al., (2003) J. Cell Sci. 116:2117-2124; Margueron et al., (2005) Curr. Opin. Genet. Dev. 15:163-176.

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri-and di-methylated H3-K9, while increasing levels of mono-methylated H3-K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and α-ketoglutarate, wherein oxidative decarboxylation of α-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPARγ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al. (2006) Nature Reviews/Genetics 7:715-727. The JARID1 family contains several conserved domains: JmjN, ARID, JmjC, PHD and a C5HC2 zing finger.

JARID1A, also called KDM5A or RBP2, was initially found as a binding partner of retinoblastoma (Rb) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1 (Lin et al. P.N.A.S. Aug. 16, 2011, 108(33):13379-86; doi: 10.1073/pnas.1110104108) and the authors of the study concluded that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as BRCA1, CAV1 and 14-3-3σ, and knockdown of JARID1B was found to increase the levels of tri-methylated H3K4 at these genes.

In an additional embodiment is the method for inhibiting a histone-demethylase enzyme, wherein the histone-demethylase enzyme comprises a JmjC domain. In an additional embodiment is the method for inhibiting a histone-demethylase enzyme, wherein the histone-demethylase enzyme is selected from JARID1A, JARID1B, or JMJD2C.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of a demethylase comprising a JmjC domain (e.g., a histone demethylase such as a JHDM protein(s)).

In a further embodiment is the method for treating cancer in a subject wherein the cancer is selected from prostate cancer, breast cancer, bladder cancer, lung cancer or melanoma.

In an additional embodiment is a method for inhibiting the growth of a tumor comprising administering a composition comprising a compound of Formula (I), (III), (V), (XI), (XIa), (XIb), (XIII), or (XV), or a pharmaceutically acceptable salt thereof, wherein the tumor is characterized by a loss of retinoblastoma gene (RB1) function.

In an additional embodiment is a method for inhibiting the growth of a tumor comprising administering a composition comprising a compound of Formula (I), (III), (V), (XI), (XIa), (XIb), (XIII), or (XV), or a pharmaceutically acceptable salt thereof, wherein the tumor is characterized by a loss of multiple endocrine neoplasia type 1 gene (Men1) function.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1: 3-(benzylamino)pyridazine-4-carboxylic acid

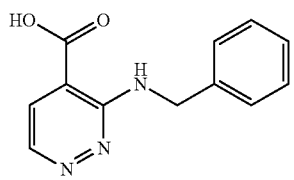 [SMILES: O=C(O)c1ccnnc1NCc1ccccc1]

3-Aminopyridazine-4-carboxylic acid (200 mg, 1.43 mmol) and benzaldehyde (0.18 mL, 1.73 mmol) were stirred in DMF (3 mL) at 90° C. for four days. The reaction mixture was allowed to cool to room temperature ("rt") and sodium triacetoborohydride (605 mg, 2.86 mmol) was added. The reaction was stirred for 16 hr. The reaction was quenched with water and extracted with EtOAc. The extracts were dried (Na$_2$SO$_4$) and concentrated. The residue was purified by column chromatography (0-20% MeOH/DCM). The relevant fractions were concentrated to give 6.3 mg (4%) of the title compound. $^1$H NMR (500 MHz, DMSO-d$_6$): δ 8.51 (d, 1H, 5 Hz), 7.63 (d, 1H, J=5.0 Hz), 7.30-7.39 (m, 4H), 7.22-7.25 (m, 1H), 4.72 (br s, 2H). [M+H] calc'd for C$_{12}$H$_{11}$N$_3$O$_2$, 230; found 230.

Example 2: 3-[(2-fluorobenzyl)amino]pyridine-4-carboxylic acid

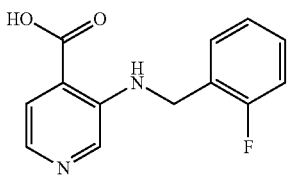 [SMILES: O=C(O)c1ccncc1NCc1ccccc1F]

3-Fluoroisonicotinic acid (100 mg, 0.71 mmol) and 2-fluorobenzylamine (308 μL, 2.84 mmol) were combined in ACN (3 mL) and the solution was stirred at 158° C. in a microwave for 1 hr. The solution was concentrated in vacuo and purified by silica gel chromatography (10% to 20% MeOH/DCM). The semi-pure fractions were concentrated and then taken up in water to give a white precipitate, which was collected by filtration and dried under vacuum to give 18 mg (10%) of the title compound. $^1$H NMR (500 MHz, DMSO-d$_6$): δ 8.18 (s, 1H), 7.99 (br s, 1H), 7.84 (d, 1H, J=5.0 Hz), 7.58 (d, 1H, J=5.0 Hz), 7.31-7.41 (m, 2H), 7.15-7.23 (m, 2H), 4.62 (s, 2H). [M+H] calc'd for C$_{13}$H$_{11}$FN$_2$O$_2$, 247; found 247.

Example 3: 3-[(3-fluorobenzyl)amino]pyridine-4-carboxylic acid

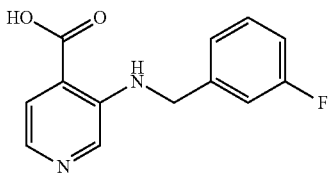

3-Fluoroisonicotinic acid (100 mg, 0.71 mmol) and 3-fluorobenzylamine (308 μL, 2.84 mmol) were combined in DMA (3 mL) and the solution was stirred at 168° C. in a microwave for 90 min. The solution was concentrated in vacuo and purified through a short plug of silica gel chromatography (20% MeOH/DCM). The semi-pure fractions were concentrated and then taken up in water to give a white precipitate, which was collected by filtration and dried under vacuum to give 58 mg (33%) of the title compound. $^1$H NMR (500 MHz, DMSO-d$_6$): δ 8.18 (s, 1H), 7.99 (br s, 1H), 7.84 (d, 1H, J=5.0 Hz), 7.58 (d, 1H, J=5.0 Hz), 7.31-7.41 (m, 2H), 7.15-7.23 (m, 2H), 4.62 (s, 2H). [M+H] calc'd for C$_{13}$H$_{11}$FN$_2$O$_2$, 247; found 247.

Example 4: 3-[(4-fluorobenzyl)amino]pyridine-4-carboxylic acid

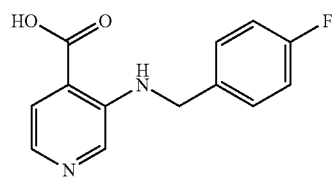

The title compound was prepared in 55% yield from 4-fluorobenzylamine and 4-fluoroisonicotinic acid according to the procedure for the preparation of Example 3. $^1$H NMR (500 MHz, DMSO-d$_6$): δ 13.45 (br s, 1H), 8.11 (s, 1H), 8.03 (br s, 1H), 7.83 (d, 1H, J=5.0 Hz), 7.58 (d, 1H, J=5.0 Hz), 7.36-7.42 (m, 1H), 7.16-7.23 (m, 2H), 7.05-7.11 (m, 1H), 4.60 (s, 2H). [M+H] calc'd for C$_{13}$H$_{11}$FN$_2$O$_2$, 247; found 247.

Preparation 4A: methyl 3-[(4-fluorobenzyl)amino]pyridine-4-carboxylate

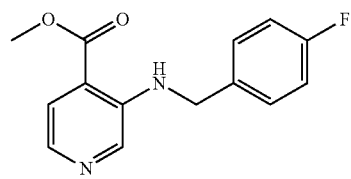 [SMILES: COC(=O)c1ccncc1NCc1ccc(F)cc1]

Methyl 3-bromoisonicotinate (220 mg, 1.02 mmol), 4-fluorobenzylamine (132 μL, 1.22 mmol), tris(dibenzylideneacetone)dipalladium(0) (47 mg, 0.051 mmol), Xantphos (89 mg, 0.153 mmol), and cesium carbonate (500 mg, 1.53 mmol) were combined in dioxane (4 mL) under N$_2$ in a sealed microwave tube. The reaction mixture was heated at 116° C. in a microwave for 1 hr. The mixture was then filtered, washing with DCM, to remove solids. The solution was concentrated in vacuo and purified by silica gel chromatography (20-50% EtOAc/hexanes) to give 228 mg (88%) of the title compound as a white solid. $^1$H NMR (400 MHz, CDCl$_3$): δ 8.18 (s, 1H), 7.93 (d, 1H, J=5.0 Hz), 7.79 (br s, 1H), 7.63 (d, 1H, J=5.0 Hz), 7.27-7.34 (m, 2H), 7.03 (t, 2H, J=8.6 Hz), 4.47 (d, 2H, J=5.6 Hz), 3.89 (s, 3H). [M+H] calc'd for C$_{14}$H$_{13}$FN$_2$O$_2$, 261; found 261.

Example 5: 3-[(4-cyanobenzyl)amino]pyridine-4-carboxylic acid

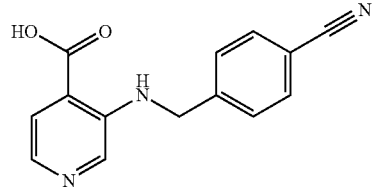 [SMILES: N#Cc1ccc(CNc2cnccc2C(=O)O)cc1]

3-Fluoroisonicotinic acid (100 mg, 0.71 mmol), 4-(aminomethyl)-benzonitrile hydrochloride (240 mg, 1.42 mmol), and DIEA (250 µL, 1.42 mmol) were combined in DMA (2 mL) and the reaction mixture was stirred at 166° C. in a microwave for 90 min. The solution was concentrated in vacuo and purified by silica gel chromatography (10-20% MeOH/DCM). The semi-pure fractions were concentrated and then taken up in water to give a pale yellow precipitate, which was collected by filtration and dried under vacuum to give 32 mg (18%) of the title compound. $^1$H NMR (500 MHz, DMSO-d$_6$): δ 8.10 (br s, 1H), 8.04 (s, 1H), 7.83 (d, 1H, J=5.0 Hz), 7.81 (d, 2H, J=8.0 Hz), 7.58 (d, 1H, J=5.0 Hz), 7.54 (d, 2H, J=8.0 Hz), 4.69 (s, 2H). [M+H] calc'd for C$_{14}$H$_{11}$N$_3$O$_2$, 254; found 254.

Preparation 5A: methyl 3-[(4-cyanobenzyl)amino]pyridine-4-carboxylate

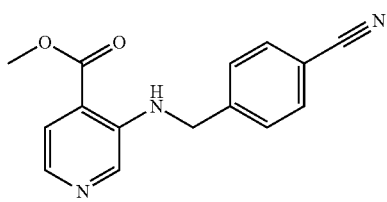 [SMILES: COC(=O)c1ccncc1NCc1ccc(C#N)cc1]

The title compound was prepared in 4% yield from 4-(aminomethyl)-benzonitrile hydrochloride and methyl 3-bromoisonicotinate according to the procedure for Preparation 4A. $^1$H NMR (500 MHz, CDCl$_3$): δ 8.07 (s, 1H), 7.97 (d, 2H, J=5.0 Hz), 7.63-7.70 (m, 3H), 7.46 (d, 2H, J=8.3 Hz), 4.61 (d, 2H, J=6.1 Hz), 3.94 (s, 3H). [M+H] calc'd for C$_{15}$H$_{13}$N$_3$O$_2$, 268; found 268.

Example 6: 3-{[4-hydroxymethyl)benzyl]amino}pyridine-4-carboxylic acid

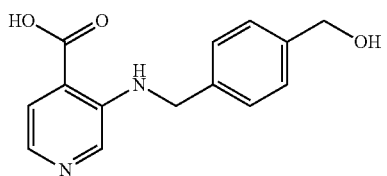 [SMILES: O=C(O)c1ccncc1NCc1ccc(CO)cc1]

The title compound was prepared in 9% yield from (4-aminomethyl)benzyl alcohol hydrochloride and 3-fluoroisonicotinic acid according to the procedure for the preparation of Example 5. $^1$H NMR (400 MHz, DMSO-d$_6$): δ 8.12 (s, 1H), 7.81 (d, 1H, J=5.0 Hz), 7.56 (d, 1H, J=5.0 Hz), 7.26-7.34 (m, 4H), 5.13 (t, 1H, J=1.6 Hz), 4.53 (s, 2H), 4.46 (d, 2H, J=5.2 Hz). [M+H] calc'd for C$_{14}$H$_{14}$N$_2$O$_3$, 259; found 259.

Example 7: 3-[(4-methoxybenzyl)amino]pyridine-4-carboxylic acid

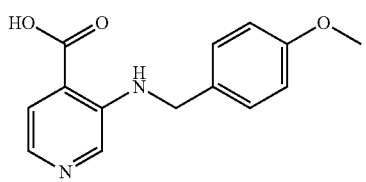 [SMILES: COc1ccc(CNc2cnccc2C(=O)O)cc1]

The title compound was prepared in 26% yield from 4-methoxybenzylamine and 3-fluoroisonicotinic acid according to the procedure for the preparation of Example 3. $^1$H NMR (400 MHz, DMSO-d$_6$): δ 8.17 (s, 1H), 7.81 (d, 1H, J=5.0 Hz), 7.56 (d, 1H, J=5.0 Hz), 7.29 (d, 2H, J=8.5 Hz), 6.91 (d, 2H, J=8.5 Hz), 4.47 (s, 2H), 3.73 (s, 3H). [M+H] calc'd for C$_{14}$H$_{14}$N$_2$O$_3$, 259; found 259.

Example 8: 3-{[4-(trifluoromethyl)benzyl]amino}pyridine-4-carboxylic acid

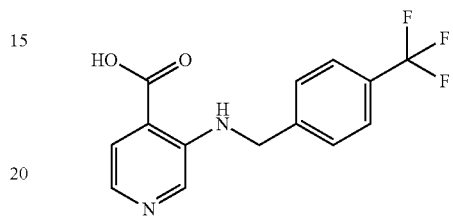

The title compound was prepared in 28% yield from 4-(trifluoromethyl)-benzylamine and 3-fluoroisonicotinic acid according to the procedure for the preparation of Example 3. $^1$H NMR (400 MHz, DMSO-d$_6$): δ 8.10 (br s, 1H), 8.04 (s, 1H), 7.83 (d, 1H, J=5.0 Hz), 7.81 (d, 2H, J=8.0 Hz), 7.58 (d, 1H, J=5.0 Hz), 7.54 (d, 2H, J=8.0 Hz), 4.69 (s, 2H). [M+H] calc'd for C$_{14}$H$_{11}$F$_3$N$_2$O$_2$, 297; found 297.

Preparation 8A: methyl 3-{[4-(trifluoromethyl)benzyl]amino}pyridine-4-carboxylate

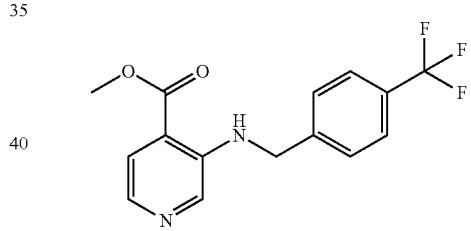

The title compound was prepared in 40% yield from 4-(trifluoromethyl)benzylamine and methyl 3-bromoisonicotinate according to the procedure for Preparation 4A. $^1$H NMR (400 MHz, CDCl$_3$): δ 8.12 (s, 1H), 7.95 (d, 1H, J=5.0 Hz), 7.93 (br s, 1H), 7.65 (d, 1H, J=5.0 Hz), 7.60 (d, 2H, J=8.1 Hz), 7.47 (d, 2H, J=8.1 Hz), 4.58 (d, 2H, J=5.9 Hz) 3.91 (s, 3H). [M+H] calc'd for C$_{15}$H$_{13}$F$_3$N$_2$O$_2$, 311; found 311.

Example 9: 3-[(biphenyl-4-ylmethyl)amino]pyridine-4-carboxylic acid

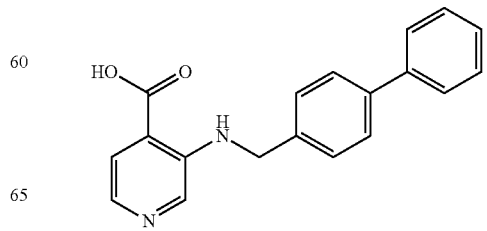

The title compound was prepared in 36% yield from 4-phenylbenzylamine and 3-fluoroisonicotinic acid according to the procedure for the preparation of Example 3. $^1$H NMR (400 MHz, DMSO-$d_6$): δ 13.55 (br s, 1H), 8.17 (s, 1H), 7.83 (d, 1H, J=5.0 Hz), 7.71 (m, 4H), 7.58 (d, 1H, J=5.0 Hz), 7.32-7.48 (m, 5H), 4.62 (s, 2H). [M+H] calc'd for $C_{19}H_{16}N_2O_2$, 305; found 305.

Example 10: 3-[(4-chlorobenzyl)amino]pyridine-4-carboxylic acid

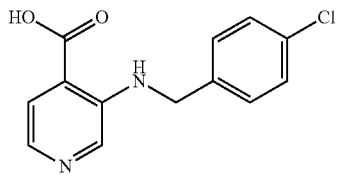 [SMILES: O=C(O)c1ccncc1NCc1ccc(Cl)cc1]

The title compound was prepared in 32% yield from 4-chlorobenzylamine and 3-fluoroisonicotinic acid according to the procedure for the preparation of Example 3. $^1$H NMR (400 MHz, DMSO-$d_6$): δ 13.45 (br s, 1H), 8.04 (s, 1H), 7.76 (d, 1H, J=5.0 Hz), 7.51 (d, 1H, J=5.0 Hz), 7.29-7.36 (m, 4H), 4.51 (s, 2H). [M+H] calc'd for $C_{13}H_{11}ClN_2O_2$, 263, 265; found 263, 265.

Preparation 10A: methyl 3-[(4-chlorobenzyl)amino]pyridine-4-carboxylate

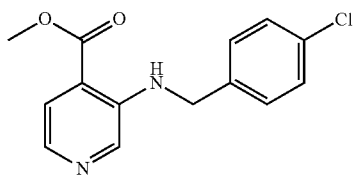 [SMILES: COC(=O)c1ccncc1NCc1ccc(Cl)cc1]

The title compound was prepared in 72% yield from 4-chlorobenzylamine and methyl 3-bromoisonicotinate according to the procedure for Preparation 4A. $^1$H NMR (400 MHz, CDCl$_3$): δ 8.14 (s, 1H), 7.94 (d, 1H, J=5.0 Hz), 7.82 (br s, 1H), 7.62 (d, 1H, J=5.0 Hz), 7.24-7.32 (m, 4H), 4.47 (d, 2H, J=5.7 Hz), 3.89 (s, 3H). [M+H] calc'd for $C_{14}H_{13}ClN_2O_2$, 277, 279; found 277, 279.

Example 11: 3-{[4-(propan-2-yloxy)benzyl]amino}pyridine-4-carboxylic acid

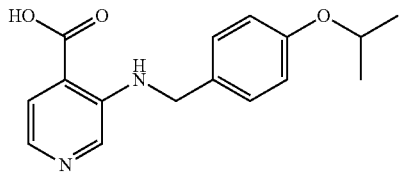 [SMILES: CC(C)Oc1ccc(CNc2cnccc2C(=O)O)cc1]

The title compound was prepared in 28% yield from 1-(4-isopropoxyphenyl)-methanamine and 3-fluoroisonicotinic acid according to the procedure for the preparation of Example 3. $^1$H NMR (400 MHz, DMSO-$d_6$): δ 8.12 (s, 1H), 7.80 (d, 1H, J=5.0 Hz), 7.56 (d, 1H, J=5.0 Hz), 7.28 (d, 2H, J=8.0 Hz), 7.21 (d, 2H, J=8.0 Hz), 4.49 (s, 2H), 2.82-2.89 (m, 1H), 1.19 (d, 6H, J=4.5 Hz). [M+H] calc'd for $C_{16}H_{18}N_2O_3$, 287; found 287.

Example 12: 3-[(4-phenoxybenzyl)amino]pyridine-4-carboxylic acid

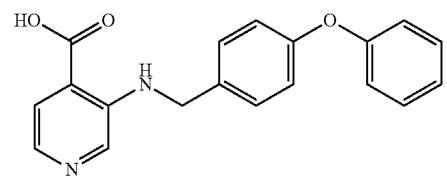 [SMILES: O=C(O)c1ccncc1NCc1ccc(Oc2ccccc2)cc1]

The title compound was prepared in 36% yield from 4-phenoxybenzylamine and 3-fluoroisonicotinic acid according to the procedure for the preparation of Example 3. $^1$H NMR (400 MHz, DMSO-$d_6$): δ 13.42 (br s, 1H), 8.18 (s, 1H), 7.83 (d, 1H, J=5.0 Hz), 7.57 (d, 1H, J=5.0 Hz), 7.35-7.40 (m, 4H), 7.13 (t, 1H, J=7.2), 6.97-7.02 (m, 4H), 4.55 (s, 2H). [M+H] calc'd for $C_{19}H_{16}N_2O_3$, 321; found 321.

Preparation 13A: methyl 3-({2-[(dimethylamino)methyl]benzyl}amino)pyridine-4-carboxylate

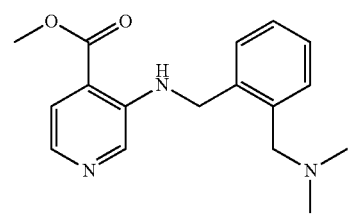

The title compound was prepared in 65% yield from N-[2-(aminomethyl)benzyl]-N,N-dimethylamine and methyl 3-bromoisonicotinate according to the procedure for Preparation 4A. $^1$H NMR (400 MHz, CDCl$_3$): δ 8.27 (s, 1H), 7.88 (d, 1H, J=5.1 Hz), 7.82 (br s, 1H), 7.61 (d, 1H, J=5.1 Hz), 7.20-7.36 (m, 4H), 4.68 (d, 2H, J=5.8 Hz), 3.87 (s, 3H), 3.46 (s, 2H), 2.22 (s, 6H). [M+H] calc'd for $C_{17}H_{21}N_3O_2$, 300; found 300.

Example 13: 3-({2-[(dimethylamino)methyl]benzyl}amino)pyridine-4-carboxylic acid, formic acid salt

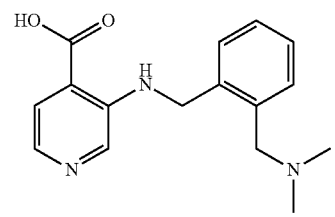 [SMILES: CN(C)Cc1ccccc1CNc1cnccc1C(=O)O]

Preparation 13A (338 mg, 1.13 mmol) was stirred in MeOH (5 mL) with 1N NaOH (2 mL) at 40° C. for 2 hr. The solution was concentrated and purified by prep-HPLC (0-20% ACN/water with 0.1% formic acid) to give 260 mg (70%) of the title compound as a white solid. $^1$H NMR (400 MHz, DMSO-d$_6$): δ 8.26 (br s, 1H), 8.12 (br s, 1H), 7.88 (br s, 1H), 7.80 (d, 1H, J=5.0 Hz), 7.39-7.57 (m, 4H), 4.61 (s, 2H), 4.44 (s, 2H), 2.85 (s, 6H). [M+H] calc'd for C$_{16}$H$_{19}$N$_3$O$_2$, 286; found 286.

Example 14: 3-[(3,4-dichlorobenzyl)amino]pyridine-4-carboxylic acid

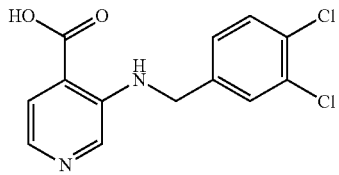 [SMILES: O=C(O)c1ccncc1NCc1ccc(Cl)c(Cl)c1]

The title compound was prepared in 37% yield from 3,4-dichlorobenzylamine and 3-fluoroisonicotinic acid according to the procedure for the preparation of Example 3. $^1$H NMR (400 MHz, DMSO-d$_6$): δ 13.48 (br s, 1H), 8.10 (s, 1H), 7.84 (d, 1H, J=5.0 Hz), 7.57-7.65 (m, 3H), 7.35 (dd, 1H, J=8.3, 1.9 Hz), 4.59 (s, 2H). [M+H] calc'd for C$_{13}$H$_{10}$Cl$_2$N$_2$O$_2$, 297, 299; found 297, 299.

Preparation 14A: methyl 3-[(3,4-dichlorobenzyl)amino]pyridine-4-carboxylate

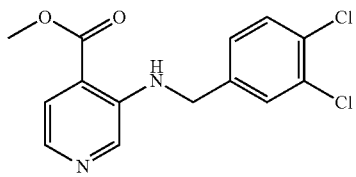 [SMILES: COC(=O)c1ccncc1NCc1ccc(Cl)c(Cl)c1]

The title compound was prepared in 73% yield from 3,4-dichlorobenzylamine and methyl 3-bromoisonicotinate according to the procedure for Preparation 4A. $^1$H NMR (400 MHz, CDCl$_3$): δ 8.10 (s, 1H), 7.95 (d, 1H, J=5.1 Hz), 7.87 (br s, 1H), 7.65 (d, 1H, J=5.1 Hz), 7.42 (d, 1H, J=8.7 Hz), 7.39 (s, 1H), 7.18 (dd, 1H, J=8.2 Hz), 4.48 (d, 2H, J=6.0 Hz), 3.91 (s, 3H). [M+H] calc'd for C$_{14}$H$_{12}$Cl$_2$N$_2$O$_2$, 311, 313; found 311, 313.

Example 15: 3-[(4-chloro-2-methylbenzyl)amino]pyridine-4-carboxylic acid

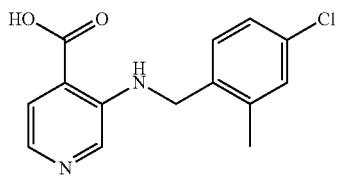 [SMILES: Cc1cc(Cl)ccc1CNc1cnccc1C(=O)O]

The title compound was prepared in 45% yield from 4-chloro-2-methylbenzylamine and 3-fluoroisonicotinic acid according to the procedure for the preparation of Example 3. $^1$H NMR (400 MHz, DMSO-d$_6$): δ 13.50 (br s, 1H), 8.10 (s, 1H), 7.85 (d, 1H, J=5.0 Hz), 7.61 (br s, 1H), 7.59 (d, 1H, J=5.0 Hz), 7.31 (s, 1H), 7.19-7.25 (m, 2H), 4.52 (s, 2H), 2.34 (s, 3H). [M+H] calc'd for C$_{14}$H$_{13}$ClN$_2$O$_2$, 277, 279; found 277, 279.

Example 16: 3-[(2,4-dimethyoxybenzyl)amino]pyridine-4-carboxylic acid

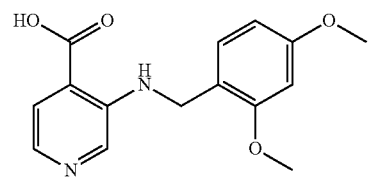 [SMILES: COc1ccc(CNc2cnccc2C(=O)O)c(OC)c1]

The title compound was prepared in 61% yield from 2,4-dimethoxybenzylamine and 3-fluoroisonicotinic acid according to the procedure for the preparation of Example 3. $^1$H NMR (400 MHz, DMSO-d$_6$): δ 13.41 (br s, 1H), 8.20 (s, 1H), 7.80 (d, 1H, J=5.0 Hz), 7.54 (d, 1H, J=5.0 Hz), 7.18 (d, 1H, J=8.3 Hz), 6.59 (d, 1H, J=2.4 Hz), 6.48 (dd, 1H, J=8.3, 2.4 Hz), 4.40 (s, 2H), 382 (s, 3H), 3.74 (s, 3H). [M+H] calc'd for C$_{15}$H$_{16}$N$_2$O$_4$, 259; found 259.

Example 17: 3-[(2-hydroxybenzyl)amino]pyridine-4-carboxylic acid

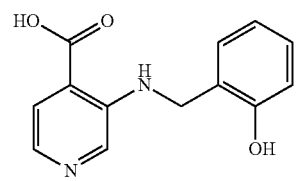 [SMILES: O=C(O)c1ccncc1NCc1ccccc1O]

The title compound was prepared in 2% yield from 2-(aminomethyl)phenol and 3-fluoroisonicotinic acid according to the procedure for the preparation of Example 3. $^1$H NMR (400 MHz, DMSO-d$_6$): δ 13.30 (br s, 1H), 9.67 (s, 1H), 8.20 (s, 1H), 7.79 (d, 1H, J=4.9 Hz), 7.54 (d, 1H, J=4.9 Hz), 7.20 (d, 1H, J=7.0 Hz), 7.09 (t, 1H, J=7.6 Hz), 6.84 (d, 1H, J=8.1), 6.84 (dd, 1H, J=7.4 Hz), 4.44 (s, 2H). [M+H] calc'd for C$_{13}$H$_{12}$N$_2$O$_3$, 245; found 245.

Example 18: 3-[(2,4-dichlorobenzyl)amino]pyridine-4-carboxylic acid

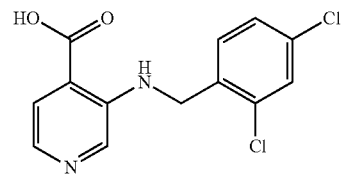 [SMILES: O=C(O)c1ccncc1NCc1ccc(Cl)cc1Cl]

The title compound was prepared in 42% yield from 2,4-dichlorobenzylamine and 3-fluoroisonicotinic acid according to the procedure for the preparation of Example 3. $^1$H NMR (400 MHz, DMSO-d$_6$): δ 13.49 (br s, 1H), 8.04 (s, 1H), 7.87 (d, 1H, J=5.0 Hz), 7.66 (s, 1H), 7.59 (d, 1H, J=5.0

Hz), 7.38-7.42 (m, 2H), 4.63 (s, 2H). [M+H] calc'd for $C_{13}H_{10}Cl_2N_2O_2$, 297, 299; found 297, 299.

Preparation 19A: 3-[(2-bromobenzyl)amino]pyridine-4-carboxylic acid

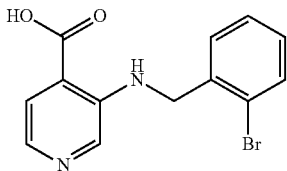 [SMILES: O=C(O)c1ccncc1NCc1ccccc1Br]

The title compound was prepared in 33% yield from 2-bromobenzylamine and 3-fluoroisonicotinic acid according to the procedure for the preparation of Example 3. [M+H] calc'd for $C_{13}H_{11}BrN_2O_2$, 307, 309; found 307, 309.

Preparation 19B: methyl 3-[(2-bromobenzyl)amino]pyridine-4-carboxylate

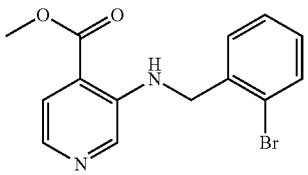 [SMILES: COC(=O)c1ccncc1NCc1ccccc1Br]

Preparation 19A (202 mg, 0.66 mmol) was stirred in DMF (5 mL) with MeOH (0.5 mL). Triethylamine (120 µL, 0.86 mmol) and then HATU (300 mg, 0.79 mmol) were added, and the reaction stirred for 1 hr. The solution was concentrated and purified by silica gel chromatography (20%-80% EtOAc/hexanes) to give 128 mg (60%) of the title compound as a white solid. $^1$H NMR (400 MHz, CDCl$_3$): δ 8.21 (s, 1H), 7.94 (d, 1H, J=5.0 Hz), 7.91 (br s, 1H), 7.65 (d, 1H, J=5.0 Hz), 7.59 (dd, 1H, J=7.9, 1.0 Hz), 7.24-7.35 (m, 2H), 7.14 (td, 1H, J=7.8, 1.6 Hz), 4.59 (d, 2H, J=6.1 Hz), 3.92 (s, 3H). [M+H] calc'd for $C_{14}H_{13}BrN_2O_2$, 321, 323; found 321, 323.

Preparation 19C: methyl 3-[(2-cyclopropylbenzyl)amino]pyridine-4-carboxylate

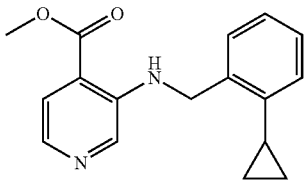 [SMILES: COC(=O)c1ccncc1NCc1ccccc1C1CC1]

Potassium phosphate (119 mg, 0.56 mmol), palladium acetate (4.2 mg, 0.019 mmol) and tricyclohexylphosphine (10.4 mg, 0.037 mmol) were combined in toluene (3 mL) with water (0.15 mL) under N$_2$. Preparation 19B (120 mg, 0.37 mmol) and cyclopropylboronic acid (48 mg, 0.56 mmol) were added, and the reaction stirred at 142° C. in a microwave for 1 hr. The reaction mixture was diluted with DCM, dried (MgSO$_4$) and concentrated in vacuo. Purification by silica gel chromatography (20-60% EtOAc/DCM) gave 88 mg (84%) of the title compound as a white solid. $^1$H NMR (400 MHz, CDCl$_3$): δ 8.22 (s, 1H), 7.91 (d, 1H, J=5.0 Hz), 7.73 (br s, 1H), 7.63 (d, 1H, J=5.0 Hz), 7.13-7.31 (m, 3H), 7.07 (d, 1H, J=7.7 Hz), 4.67 (d, 2H, J=5.6 Hz), 3.87 (s, 3H), 1.92-1.97 (m, 1H), 0.93-0.98 (m, 2H), 0.69-0.74 (m, 2H). [M+H] calc'd for $C_{17}H_{18}N_2O_2$, 283; found 283.

Example 19: 3-[(2-cyclopropylbenzyl)amino]pyridine-4-carboxylic acid

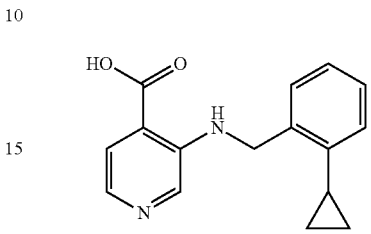

The title compound was prepared in 46% yield from Preparation 19C according to the general hydrolysis procedure outlined for Example 13. $^1$H NMR (400 MHz, DMSO-d$_6$): δ 13.42 (br s, 1H), 8.17 (s, 1H), 7.84 (d, 1H, J=5.0 Hz), 7.61 (br s, 1H), 7.58 (d, 1H, J=5.0 Hz), 7.12-7.27 (m, 3H), 7.04 (d, 1H, J=7.1 Hz), 4.70 (s, 2H), 1.99-2.09 (m, 1H), 0.90-0.96 (m, 2H), 0.65-0.69 (m, 2H). [M+H] calc'd for $C_{16}H_{16}N_2O_2$, 269; found 269.

Example 20: 3-[(4-chloro-2-methoxybenzyl)amino]pyridine-4-carboxylic acid

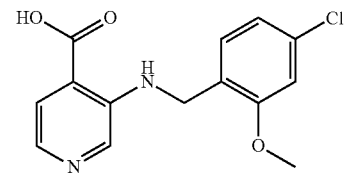 [SMILES: COc1cc(Cl)ccc1CNc1cnccc1C(=O)O]

The title compound was prepared in 35% yield from 4-chloro-2-methoxy-benzylamine and 3-fluoroisonicotinic acid according to the procedure for the preparation of Example 3. $^1$H NMR (400 MHz, DMSO-d$_6$): δ 13.49 (br s, 1H), 8.10 (s, 1H), 8.00 (br s, 1H), 7.81 (d, 1H, J=5.0 Hz), 7.56 (d, 1H, J=5.0 Hz), 7.24 (d, 1H, J=8.1 Hz), 7.11 (d, 1H, J=1.9 Hz), 6.96 (dd, 1H, J=8.0, 1.9 Hz), 4.47 (s, 2H), 3.87 (s, 3H). [M+H] calc'd for $C_{14}H_{13}ClN_2O_3$, 293, 295; found 293, 295.

Example 21: 3-[(4-chloro-2-hydroxybenzyl)amino]pyridine-4-carboxylic acid

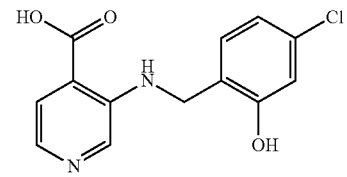 [SMILES: O=C(O)c1ccncc1NCc1ccc(Cl)cc1O]

Example 20 (50 mg, 0.17 mmol) was stirred in DCM (10 mL) at 0° C. BBr$_3$ (0.51 mL, 1.0 M, 0.51 mmol) was added, and the reaction stirred for 2 hr while warming to rt. The solution was poured over a mixture of 1N NaOH (10 mL) and MeOH (10 mL), and the solution was concentrated in vacuo. Purification by prep-HPLC (5-95% ACN/water with 0.05% formic acid) gave 8 mg (17%) of the title compound as a pale yellow solid. $^1$H NMR (400 MHz, DMSO-d$_6$): δ 10.29 (br s, 1H), 8.16 (br s, 1H), 8.09 (br s, 1H), 7.79 (br s, 1H), 7.56 (br s, 1H), 7.19 (d, 1H, J=8.1 Hz), 6.87 (d, 1H, J=2.0 Hz), 6.80 (dd, 1H, J=8.1, 2.0 Hz) 4.40 (s, 2H). [M+H] calc'd for C$_{13}$H$_{11}$ClN$_2$O$_3$, 279, 281; found 279, 281.

Example 22: 3-[(2-aminobenzyl)amino]pyridine-4-carboxylic acid

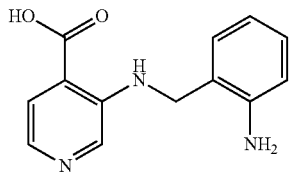 [SMILES: Nc1ccccc1CNc1cnccc1C(=O)O]

The title compound was prepared in 9% yield from 2-aminobenzylamine and 3-fluoroisonicotinic acid according to the procedure for the preparation of Example 3. $^1$H NMR (400 MHz, DMSO-d$_6$): δ 8.16 (s, 1H), 7.82 (d, 1H, J=5.0 Hz), 7.56 (d, 1H, J=5.0 Hz), 7.05 (d, 1H, J=7.5 Hz), 6.97 (td, 1H, J=7.8, 1.4 Hz), 6.66 (d, 1H, J=7.9 Hz), 6.52 (td, 1H, J=7.4, 1.0 Hz), 4.35 (s, 2H). [M+H] calc'd for C$_{13}$H$_{13}$N$_3$O$_2$, 244; found 244.

Example 23: 3-[(4-bromobenzyl)amino]pyridine-4-carboxylic acid

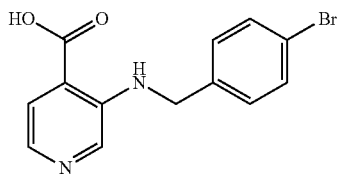 [SMILES: O=C(O)c1ccncc1NCc1ccc(Br)cc1]

The title compound was prepared in 39% yield from 4-bromobenzylamine and 3-fluoroisonicotinic acid according to the procedure for the preparation of Example 3. $^1$H NMR (400 MHz, DMSO-d$_6$): δ 13.55 (br s, 1H), 8.08 (s, 1H), 7.82 (d, 1H, J=5.0 Hz), 7.52-7.58 (m, 3H), 7.32 (d, 2H, J=8.3 Hz), 4.55 (s, 2H). [M+H] calc'd for C$_{13}$H$_{11}$BrN$_2$O$_2$, 307, 309; found 307, 309.

Example 24: 3-[(4-methylbenzyl)amino]pyridine-4-carboxylic acid

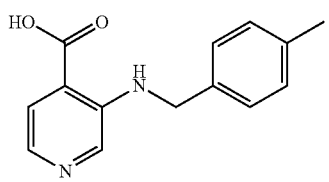

The title compound was prepared in 51% yield from 4-methylbenzylamine and 3-fluoroisonicotinic acid according to the procedure for the preparation of Example 3. $^1$H NMR (400 MHz, DMSO-d$_6$): δ 13.41 (br s, 1H), 8.13 (s, 1H), 7.81 (d, 1H, J=5.0 Hz), 7.56 (d, 1H, J=5.0 Hz), 7.25 (d, 2H, J=7.9 Hz), 7.15 (d, 2H, J=7.8 Hz), 4.50 (s, 2H), 2.28 (s, 3H). [M+H] calc'd for C$_{14}$H$_{14}$N$_2$O$_2$, 243; found 243.

Preparation 25A: methyl 3-[(4-bromobenzyl)amino]pyridine-4-carboxylate

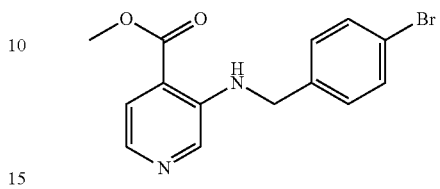

The title compound was prepared in 87% yield from Example 23 according to the procedure for Preparation 19B. $^1$H NMR (400 MHz, DMSO-d$_6$): δ 13.47 (br s, 1H), 8.14 (s, 1H), 7.81 (d, 1H, J=5.0 Hz), 7.56 (d, 1H, J=5.0 Hz), 7.23 (d, 2H, J=8.0 Hz), 7.04 (d, 2H, J=8.0 Hz), 4.49 (s, 2H), 1.86-1.91 (m, 1H), 0.89-0.94 (m, 2H), 0.60-0.65 (m, 2H). [M+H] calc'd for C$_{16}$H$_{16}$N$_2$O$_2$, 269; found 269.

Preparation 25B: methyl 3-[(4-cyclopropylbenzyl)amino]pyridine-4-carboxylate

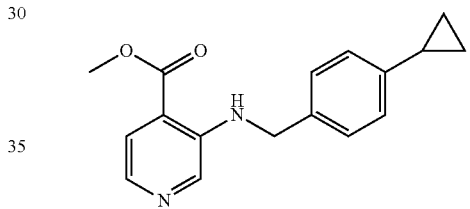

The title compound was prepared in 82% yield from Preparation 25A according to the general procedure for Preparation 19C. $^1$H NMR (400 MHz, CDCl$_3$): δ 8.21 (s, 1H), 7.91 (d, 1H, J=5.0 Hz), 7.75 (br s, 1H), 7.62 (d, 1H, J=5.0 Hz), 7.23 (d, 2H, J=8.2 Hz), 7.04 (d, 2H, J=8.2 Hz), 4.46 (d, 2H, J=5.6 Hz), 3.89 (s, 3H), 1.84-1.91 (m, 1H), 0.92-0.98 (m, 2H), 0.64-0.70 (m, 2H). [M+H] calc'd for C$_{17}$H$_{18}$N$_2$O$_2$, 283; found 283.

Example 25: 3-[(4-cyclopropylbenzyl)amino]pyridine-4-carboxylic acid

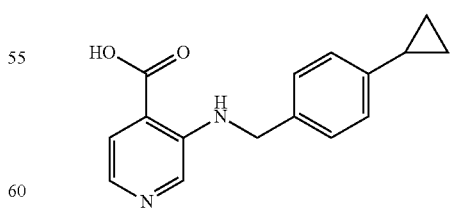

The title compound was prepared in 35% yield from Preparation 25B according to the general hydrolysis procedure outlined for Example 13. $^1$H NMR (400 MHz, DMSO-d$_6$): δ 13.47 (br s, 1H), 8.14 (s, 1H), 7.81 (d, 1H, J=5.0 Hz), 7.56 (d, 1H, J=5.0 Hz), 7.23 (d, 2H, J=8.0 Hz), 7.04 (d, 2H, J=8.0 Hz), 4.49 (s, 2H), 1.86-1.91 (m, 1H), 0.89-0.94 (m, 2H), 0.60-0.65 (m, 2H). [M+H] calc'd for $C_{16}H_{16}N_2O_2$, 269; found 269.

Preparation 26A:
4-chloro-2-cyclopropyl-benzonitrile

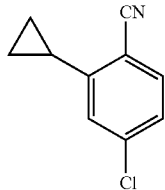 [SMILES: N#Cc1ccc(Cl)cc1C1CC1]

The title compound was prepared in 82% yield from 2-bromo-4-chloro-benzonitrile according to the general procedure for Preparation 19C. $^1$H NMR (400 MHz, CDCl$_3$): δ 0.79-0.84 (2H, m), 1.16-1.21 (2H, m), 2.25-2.29 (1H, m), 6.91 (1H, d, J=2.0 Hz), 7.21 (1H, dd, J=2.0, 8.4 Hz), 7.51 (1H, d, J=8.4 Hz).

Preparation 26B:
4-chloro-2-cyclopropyl-benzylamine

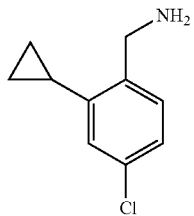 [SMILES: NCc1ccc(Cl)cc1C1CC1]

To a solution Preparation 26A (1.0 g, 5.7 mmol) in THF (20 mL) was added LiAlH$_4$ (11.3 mL, 1.0 M) at rt, and the reaction was stirred for 2 h. The reaction mixture was cooled to 0° C. and slowly diluted with water (0.5 mL), 15% NaOH (0.5 mL), and water (1.5 mL). The reaction was filtered through Celite and concentrated to give 900 mg (71%) of the crude title compound as a yellow oil. $^1$H NMR (400 MHz, CDCl$_3$): δ 0.66-0.70 (2H, m), 0.95-1.00 (2H, m), 1.93-1.97 (1H, m), 6.95 (1H, d, J=2.0 Hz), 7.14 (1H, dd, J=2.0, 8.4 Hz), 7.24 (1H, d, J=8.4 Hz).

Example 26: 3-[(4-chloro-2-cyclopropylbenzylbenzyl)amino]pyridine-4-carboxylic acid

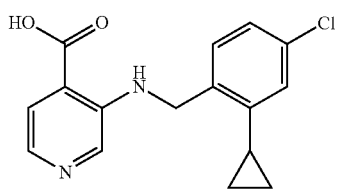 [SMILES: O=C(O)c1ccncc1NCc1ccc(Cl)cc1C1CC1]

The title compound was prepared in 3% yield from Preparation 26B and 3-fluoroisonicotinic acid according to the procedure for the preparation of Example 3. $^1$H NMR (400 MHz, DMSO-d$_6$): δ 0.71-0.75 (2H, m), 0.93-0.98 (2H, m), 2.02-2.09 (1H, m), 4.70 (2H, s), 7.06 (1H, s), 7.19-7.27 (2H, m), 7.60 (1H, d, J=4.8 Hz), 7.85-7.90 (2H, m), 8.13 (1H, s). [M+H] Calc'd for $C_{16}H_{15}ClN_2O_2$, 303; found, 303.

Preparation 26C: methyl 3-[(4-chloro-2-cyclopropylbenzyl)amino]pyridine-4-carboxylate

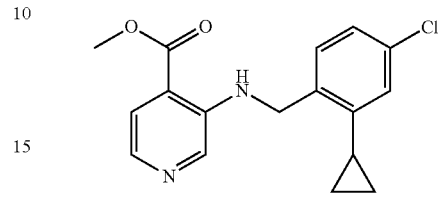

To a solution of Example 26 (15 mg, 0.05 mmol) in MeOH (10 mL) was added thionyl chloride (1 mL) at rt. The reaction was stirred at reflux for 2 days. The solution was concentrated and purified by prep-HPLC to give 5 mg (31%) of the title compound as a yellow solid. $^1$H NMR (400 MHz, CD$_3$OD): δ 0.70-0.73 (2H, m), 1.0-1.04 (2H, m), 2.0-2.04 (1H, m), 3.96 (2H, s), 4.74 (3H, s), 7.08 (1H, d, J=1.6 Hz), 7.14 (1H, dd, J=2.0, 8.4 Hz), 7.25 (1H, d, J=8.0 Hz), 7.91 (1H, d, J=4.0 Hz), 8.05 (1H, d, J=5.6 Hz), 8.13 (1H, s). [M+H] Calc'd for $C_{17}H_{17}ClN_2O_2$, 317; found, 317.

Preparation 27A:
2-cyclopropyl-4-(trifluoromethyl)-benzonitrile

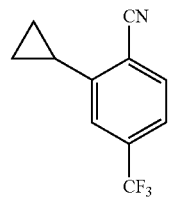 [SMILES: N#Cc1ccc(C(F)(F)F)cc1C1CC1]

The title compound was prepared in 71% yield from 2-bromo-4-(trifluoromethyl)-benzonitrile according to the general procedure for Preparation 19C. [M+H] Calc'd for $C_{11}H_8F_3N$, 212; found, 212.

Preparation 27B:
2-cyclopropyl-4-(trifluoromethyl)-benzylamine

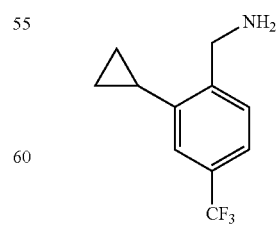

The title compound was prepared in 80% yield from Preparation 27A according to the general procedure for Preparation 26B.

Example 27: 3-{[2-cyclopropyl-4-(trifluoromethyl)benzyl]amino}pyridine-4-carboxylic acid

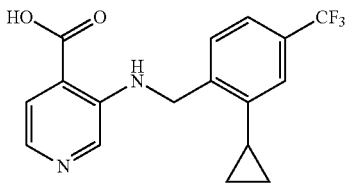

The title compound was prepared in 2% yield from Preparation 27B and 3-fluoroisonicotinic acid according to the procedure for the preparation of Example 3. $^1$H NMR (400 MHz, DMSO-d$_6$): δ 0.75-0.79 (2H, m), 0.98-1.03 (2H, m), 2.11-2.15 (1H, m), 4.83 (2H, s), 7.33 (1H, s), 7.43 (1H, d, J=8.0 Hz), 7.51 (1H, d, J=8.0 Hz), 7.65 (1H, d, J=5.2 Hz), 7.87 (1H, d, J=4.0 Hz), 8.04-8.08 (2H, m). [M+H] Calc'd for C$_{17}$H$_{15}$F$_3$N$_2$O$_2$, 337; found, 337.

Example 28: 3-[(naphthalene-1-ylmethyl)amino]pyridine-4-carboxylic acid

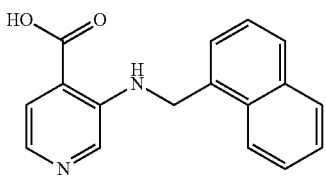 [SMILES: O=C(O)c1ccncc1NCc1cccc2ccccc12]

The title compound was prepared in 66% yield from 1-naphthylmethylamine and 3-fluoroisonicotinic acid according to the procedure for the preparation of Example 3. $^1$H NMR (400 MHz, DMSO-d$_6$): δ 13.39 (br s, 1H), 8.25 (s, 1H), 8.15 (d, 1H, J=7.9 Hz), 7.98 (d, 1H, J=7.5 Hz), 7.84-7.89 (m, 2H), 7.45-7.62 (m, 5H), 5.03 (s, 2H). [M+H] calc'd for C$_{17}$H$_{14}$N$_2$O$_2$, 279; found 279.

Preparation 29A: 1-{[2-(trimethylsilyl)ethoxy]methyl}-1H-indole-7-carbonitrile

7-Cyanoindole (1.0 g, 7.0 mmol) was stirred in DMF (10 mL) at 0° C. Sodium hydride (60%, 310 mg, 7.7 mmol) was added, and the reaction stirred 30 min at rt. SEM-chloride was added, and the reaction stirred 16 hr. The solution was concentrated in vacuo and purified by silica gel chromatography (10%-40% EtOAc/hexanes) to give 1.5 g (78%) of the title compound as a clear oil. $^1$H NMR (400 MHz, CDCl$_3$): δ 7.85 (dd, 1H, J=7.9, 0.9 Hz), 7.56 (d, 1H, J=7.5 Hz), 7.26 (d, 1H, J=6.3 Hz), 7.17 (t, 1H, J=7.7 Hz), 6.62 (d, 1H, J=3.3 Hz), 5.79 (s, 2H), 3.58 (t, 2H, J=8.1 Hz), 0.92 (t, 2H, J=8.2 Hz), -0.05 (s, 9H). [M+H] calc'd for C$_{15}$H$_{20}$N$_2$OSi, 273; found 273.

Preparation 29B: (1-{[2-(trimethylsilyl)ethoxy]methyl}-1H-indol-7-yl)methanamine

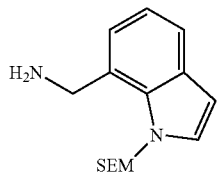

Hydrogenation of Preparation 29A (1.5 g, 5.5 mmol) was carried out with Raney nickel in MeOH under a balloon of hydrogen for 16 hr. The reaction was filtered and concentrated. Purification by silica gel chromatography (1-10% MeOH/DCM) gave 1.02 g (67%) of the title compound as a clear oil. $^1$H NMR (400 MHz, CDCl$_3$): δ 7.56 (d, 1H, J=7.4 Hz), 7.08-7.15 (m, 3H), 6.51 (d, 1H, J=3.2 Hz), 5.73 (s, 2H), 4.28 (s, 2H), 3.48 (t, 2H, J=8.2 Hz), 1.73 (br s, 2H), 0.88 (t, 2H, J=8.2 Hz), -0.05 (s, 9H). [M+H] calc'd for C$_{15}$H$_{24}$N$_2$OSi, 277; found 277.

Preparation 29C: methyl 3-{[(1-{[2-(trimethylsilyl)ethoxy]methyl}-1H-indol-7-yl)methyl]amino}pyridine-4-carboxylate

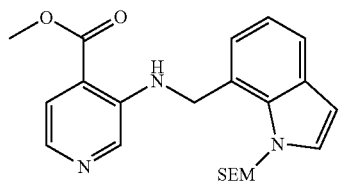 [SMILES: COC(=O)c1ccncc1NCc1cccc2ccn(COCC[Si](C)(C)C)c12]

The title compound was prepared in 66% yield from Preparation 29B and methyl-3-bromoisonicotinate according to the procedure for Preparation 4A. [M+H] calc'd for C$_{22}$H$_{29}$N$_3$O$_3$Si, 412; found 412.

Preparation 29D: 3-{[(1-{[2-(trimethylsilyl)ethoxy]methyl}-1H-indol-7-yl)methyl]amino}pyridine-4-carboxylic acid

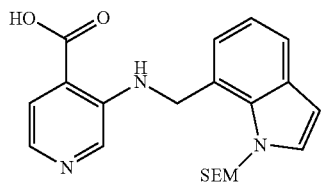 [SMILES: C[Si](C)(C)CCOCn1ccc2cccc(CNc3cnccc3C(=O)O)c21]

The title compound was prepared in 85% yield from Preparation 29C according to the general hydrolysis procedure outlined for Example 13. $^1$H NMR (400 MHz, DMSO-d$_6$): δ 13.53 (br s, 1H), 8.31 (s, 1H), 7.97 (d, 1H, J=5.0 Hz), 7.89 (br s, 1H), 7.59-7.71 (m, 3H), 7.11-7.21 (m, 2H), 6.61 (d, 1H, J=3.2 Hz), 5.65 (s, 2H), 5.08 (s, 2H), 3.53 (t, 2H, J=8.1 Hz), 0.91 (t, 2H, J=8.1 Hz), -0.01 (s, 9H). [M+H] calc'd for C$_{21}$H$_{27}$N$_3$O$_3$Si, 398; found 398.

Example 29: 3-[(1H-indol-7-ylmethyl)amino]pyridine-4-carboxylic acid

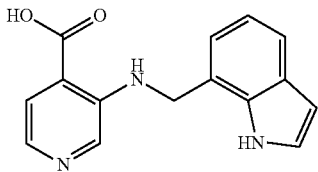 [SMILES: O=C(O)c1ccncc1NCc1cccc2cc[nH]c12]

Preparation 29C (200 mg, 0.5 mmol) was stirred in THF (10 mL). TBAF (1N, 2.0 mL, 2.0 mmol) was added, and the reaction stirred at 68° C. for 16 h. The solution was concentrated and purified by prep-HPLC (5-95% ACN/water with 0.1% formic acid) to give 38 mg (28%) of the title compound as a white solid. $^1$H NMR (400 MHz, DMSO-$d_6$): δ 13.34 (br s, 1H), 11.27 (s, 1H), 8.27 (s, 1H), 7.98 (br s, 1H), 7.82 (d, 1H, J=5.0 Hz), 7.56 (d, 1H, J=5.0 Hz), 7.48 (d, 1H, J=7.8 Hz), 7.39 (t, 1H, J=2.8 Hz), 7.08 (d, 1H, J=7.0 Hz), 6.97 (t, 1H, J=7.5 Hz), 6.47 (dd, 1H, J=2.9, 1.8 Hz), 4.78 (s, 2H). [M+H] calc'd for $C_{15}H_{13}N_3O_2$, 268; found 268.

Preparation 30A: 2-cyclopropyl-3-methyl-benzonitrile

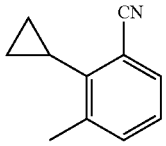

The title compound was prepared in 50% yield from 2-bromo-3-methyl-benzonitrile according to the general procedure for Preparation 19C. $^1$H NMR (400 MHz, CDCl$_3$): δ 0.78-0.84 (2H, m), 1.14-1.21 (2H, m), 1.89-1.95 (1H, m), 2.47 (3H, s), 7.21 (1H, t, J=10.0 Hz), 7.35 (1H, d, J=10.0 Hz), 7.46 (1H, d, J=9.6 Hz).

Preparation 30B: 2-cyclopropyl-3-methyl-benzylamine

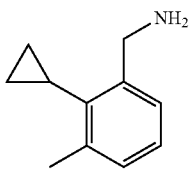

The title compound was prepared in 89% yield from Preparation 30A according to the general procedure for Preparation 26B. $^1$H NMR (400 MHz, CDCl$_3$): δ 0.57-0.62 (2H, m), 1.04-1.10 (2H, m), 1.73-1.79 (1H, m), 2.45 (3H, s), 4.09 (2H, s), 7.05-7.08 (1H, m), 7.12-7.19 (2H, m).

Example 30: 3-[(2-cyclopropyl-3-methylbenzyl)amino]pyridine-4-carboxylic acid

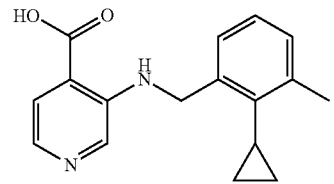 [SMILES: Cc1cccc(CNc2cnccc2C(=O)O)c1C1CC1]

The title compound was prepared in 17% yield from Preparation 30B and 3-fluoroisonicotinic acid according to the procedure for the preparation of Example 3. $^1$H NMR (300 MHz, DMSO-$d_6$): δ 0.56-0.58 (2H, m), 1.00-1.03 (2H, m), 1.78-1.82 (1H, m), 2.36 (3H, s), 4.71 (2H, s), 7.07-7.11 (3H, m), 7.57 (1H, d, J=5.1 Hz), 7.81 (1H, d, J=5.1 Hz), 8.12 (1H, s). [M+H] Calc'd for $C_{17}H_{18}N_2O_2$, 283; found, 283.

Preparation 30C: methyl 3-[(2-cyclopropyl-3-methylbenzyl)amino]pyridine-4-carboxylate

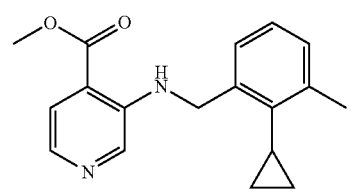

The title compound was prepared in 51% yield from Example 30 according to the procedure for Preparation 26C. $^1$H NMR (300 MHz, DMSO-$d_6$): δ 0.56-0.58 (2H, m), 1.01-1.05 (2H, m), 1.80-1.85 (1H, m), 2.40 (3H, s), 3.87 (3H, s), 4.75 (2H, s), 7.07-7.11 (3H, m), 7.75 (1H, d, J=5.7 Hz), 7.907.94 (2H, m), 8.20 (1H, s). [M+H] Calc'd for $C_{17}H_{18}N_2O_2$, 283; found, 283.

Preparation 31A: 4-cyclopropyl-3-cyano-pyridine

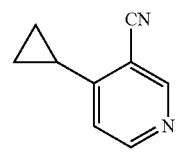 [SMILES: N#Cc1cnccc1C1CC1]

The title compound was prepared in 72% yield from 4-chloro-3-cyano-pyridine according to the general procedure for Preparation 19C. $^1$H NMR (400 MHz, CDCl$_3$): δ 0.92-0.96 (2H, m), 1.29-1.34 (2H, m), 2.26-2.32 (1H, m), 6.77 (1H, t, J=5.6 Hz), 8.58 (1H, d, J=5.6 Hz), 8.74 (1H, s).

Preparation 31B: (4-cyclopropylpyridin-3-yl)-methylamine

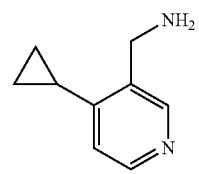 [SMILES: NCc1cnccc1C1CC1]

The title compound was prepared in 91% yield from Preparation 31A according to the general procedure for Preparation 26B.

Example 31: 3-{[(4-cyclopropylpyridin-3-yl)-methyl]amino}pyridine-4-carboxylic acid

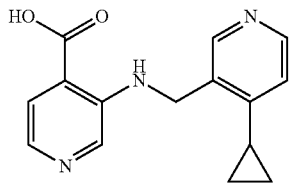

The title compound was prepared in 8% yield from Preparation 31B and 3-fluoroisonicotinic acid according to the procedure for the preparation of Example 3. ¹H NMR (400 MHz, CD₃OD): δ 1.20-1.23 (2H, m), 1.47-1.50 (2H, m), 2.37-2.39 (1H, m), 4.92 (2H, s), 7.53 (1H, d, J=6.4 Hz), 8.06 (1H, d, J=5.6 Hz), 8.23 (1H, d, J=5.6 Hz), 8.31 (1H, s), 8.58-8.59 (2H, m). [M+H] Calc'd for $C_{15}H_{15}N_3O_2$, 270; found, 270.

Example 32: 3-{[3-(trifluoromethyl)benzyl]amino}pyridine-4-carboxylic acid

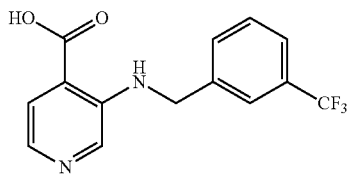

The title compound was prepared in 39% yield from 3-trifluoromethyl-benzylamine and 3-fluoroisonicotinic acid according to the procedure for the preparation of Example 3. ¹H NMR (400 MHz, DMSO-d₆): δ 13.47 (br s, 1H), 8.12 (s, 1H), 7.83 (d, 1H, J=5.0 Hz), 7.74 (s, 1H), 7.57-7.69 (m, 4H), 4.67 (s, 2H). [M+H] calc'd for $C_{14}H_{11}F_3N_2O_2$, 297; found 297.

Preparation 32A: methyl 3-{[3-(trifluoromethyl)benzyl]amino}pyridine-4-carboxylate

The title compound was prepared in 70% yield from Example 32 according to the procedure for Preparation 19B. ¹H NMR (400 MHz, CDCl₃): δ 8.15 (s, 1H), 7.88-7.97 (m, 2H), 7.67 (br s, 1H), 7.61 (s, 1H), 7.45-7.57 (m, 3H), 4.59 (d, 2H, J=5.9 Hz), 3.92 (s, 3H). [M+H] calc'd for $C_{15}H_{13}F_3N_2O_2$, 311; found 311.

Example 33A: 2-phenoxy-benzonitrile

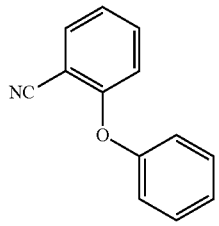 [SMILES: N#Cc1ccccc1Oc1ccccc1]

To a suspension of 2-fluorobenzonitrile (10.0 g, 82.6 mmol) and phenol (7.7 g, 5.1 mmol) in DMF (80 mL) was added K₂CO₃ (22.8 g, 165 mmol) at rt. The reaction was stirred at 130° C. for 10 hr. The reaction mixture was diluted with water, extracted with EtAOAc (100 mL×3), washed with brine (100 mL), dried (Na₂SO₄), and concentrated to give 15.0 g, (93%) of the title compound as a yellow oil. ¹H NMR (400 MHz, CDCl₃): δ 6.85 (1H, d, J=8.4 Hz), 7.07-7.14 (3H, m), 7.22 (1H, t, J=7.2 Hz), 7.40 (2H, t, J=8.0 Hz), 7.47 (1H, td, J=2.0, 8.4 Hz), 7.65 (1H, dd, J=1.2, 8.0 Hz).

Preparation 33B: 2-phenoxybenzylamine

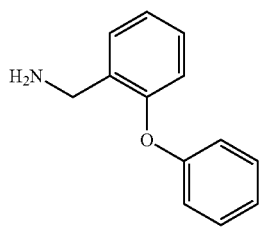 [SMILES: NCc1ccccc1Oc1ccccc1]

The title compound was prepared in 98% yield from Preparation 33A according to the general procedure for Preparation 26B.

Example 33: 3-[(2-phenoxybenzyl)amino]pyridine-4-carboxylic acid

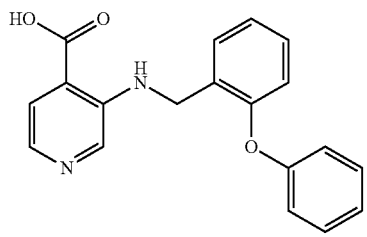 [SMILES: O=C(O)c1ccncc1NCc1ccccc1Oc1ccccc1]

The title compound was prepared in 12% yield from Preparation 33B and 3-fluoroisonicotinic acid according to the procedure for the preparation of Example 3. ¹H NMR (300 MHz, DMSO-d₆): δ 4.57 (2H, s), 6.87 (1H, d, J=8.1 Hz), 6.98 (2H, d, J=7.8 Hz), 7.12 (2H, d, J=7.8 Hz), 7.27 (1H, t, J=7.5 Hz), 7.36-7.46 (3H, m), 7.55 (1H, d, J=5.1 Hz), 7.81 (1H, d, J=5.1 Hz), 7.95 (1H, br s), 8.18 (1H, s). [M+H] Calc'd for C$_{19}$H$_{16}$N$_2$O$_3$, 321; found, 321.

Preparation 34A:
2-cyclopropyl-5-methyl-benzonitrile

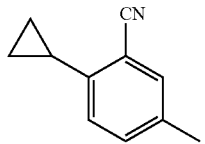

The title compound was prepared in 75% yield from 2-bromo-5-methyl-benzonitrile according to the general procedure for Preparation 19C. $^1$H NMR (400 MHz, CDCl$_3$): δ 0.73-0.77 (2H, m), 1.07-1.12 (2H, m), 2.21-2.25 (1H, m), 2.35 (3H, s), 6.83 (1H, d, J=8.0 Hz), 7.25-7.28 (1H, m), 7.38 (1H, dd, J=0.8, 1.6 Hz).

Preparation 34B:
2-cyclopropyl-5-methyl-benzylamine

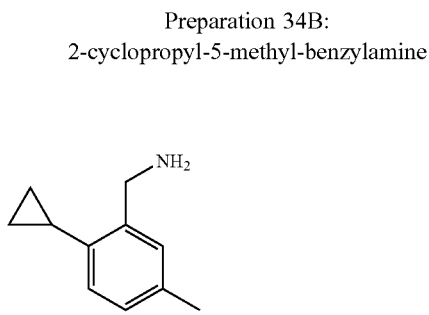

The title compound was prepared in 81% yield from Preparation 34A according to the general procedure for Preparation 26B.

Example 34: 3-[(2-cyclopropyl-5-methylbenzyl)amino]pyridine-4-carboxylic acid

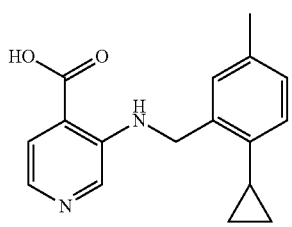 [SMILES: Cc1ccc(C2CC2)c(CNc2cnccc2C(=O)O)c1]

The title compound was prepared in 19% yield from Preparation 34B and 3-fluoroisonicotinic acid according to the procedure for the preparation of Example 3. $^1$H NMR (300 MHz, DMSO-d$_6$): δ 0.59-0.64 (2H, m), 0.86-0.92 (2H, m), 1.95-1.99 (1H, m), 2.22 (3H, s), 4.64 (2H, s), 6.93 (1H, d, J=7.8 Hz), 7.01 (1H, d, J=7.8 Hz), 7.09 (1H, s), 7.58 (1H, d, J=5.1 Hz), 7.84 (1H, d, J=5.1 Hz), 8.20 (1H, s). [M+H] Calc'd for C$_{17}$H$_{18}$N$_2$O$_2$, 283; found, 283.

Example 35: 3-{[3-(trifluoromethoxy)benzyl]amino}pyridine-4-carboxylic acid

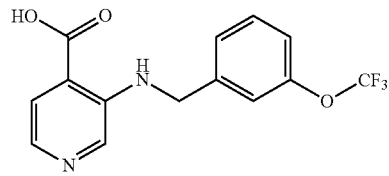 [SMILES: O=C(O)c1ccncc1NCc1cccc(OC(F)(F)F)c1]

The title compound was prepared in 4% yield from 3-trifluoromethoxy-benzylamine and 3-fluoroisonicotinic acid according to the procedure for the preparation of Example 3. $^1$H NMR (400 MHz, DMSO-d$_6$): δ 13.47 (br s, 1H), 8.11 (br s, 1H), 7.84 (br s, 1H), 7.59 (s, 1H), 7.24-7.51 (m, 4H), 4.64 (s, 2H). [M+H] calc'd for C$_{14}$H$_{11}$F$_3$N$_2$O$_3$, 313; found 313.

Example 36A: 2-(phenylamino)benzonitrile

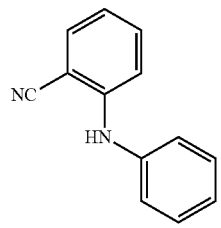 [SMILES: N#Cc1ccccc1Nc1ccccc1]

To a suspension of 2-bromobenzonitrile (1.5 g, 8.2 mmol), aniline (1.1 g, 12.4 mmol), Xantphos (0.7 g, 1.2 mmol) and cesium carbonate (5.4 g, 16.5 mmol) in dioxane (50 mL) was added Pd$_2$dba$_3$ (375 mg, 0.4 mmol) at rt under N$_2$. The reaction was stirred at 90° C. for 8 hr. The reaction mixture was filtered and concentrated. Purification by silica gel chromatography (PE:EtOAc=200:1) gave 1.3 g (81%) of the title compound as a yellow oil. $^1$H NMR (300 MHz, CDCl$_3$): δ 6.36 (1H, br s), 6.86 (1H, td, J=0.9, 7.8 Hz), 7.13-7.18 (4H, m), 7.36-7.41 (3H, m), 7.51 (1H, dd, J=1.8, 7.8 Hz).

Preparation 36B: 2-(phenylamino)benzylamine

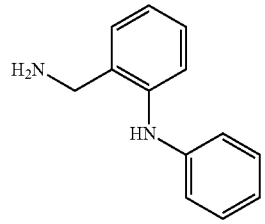 [SMILES: NCc1ccccc1Nc1ccccc1]

The title compound was prepared in 98% yield from Preparation 36A according to the general procedure for Preparation 26B.

Example 36: 3-{[2-(phenylamino)benzyl]amino}pyridine-4-carboxylic acid

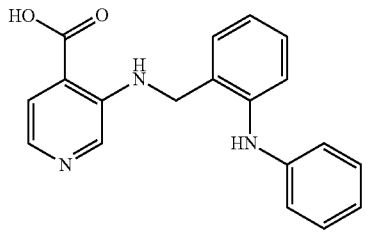 [SMILES: O=C(O)c1ccncc1NCc1ccccc1Nc1ccccc1]

The title compound was prepared in 11% yield from Preparation 36B and 3-fluoroisonicotinic acid according to the procedure for the preparation of Example 3. $^1$H NMR (400 MHz, DMSO-d$_6$): δ 4.53 (2H, s), 6.79 (1H, t, J=7.2 Hz), 6.90 (2H, d, J=8.0 Hz), 6.96 (1H, td, J=1.6, 8.0 Hz), 7.17-7.23 (4H, m), 7.29 (1H, d, J=7.6 Hz), 7.55 (1H, d, J=6.0 Hz), 7.59 (1H, s), 7.81 (1H, d, J=4.8 Hz), 8.08 (1H, s). [M+H] Calc'd for C$_{19}$H$_{17}$N$_3$O$_2$, 320; found, 320.

Example 37: 3-{[3-(cyclopropylmethoxy)benzyl]amino}pyridine-4-carboxylic acid

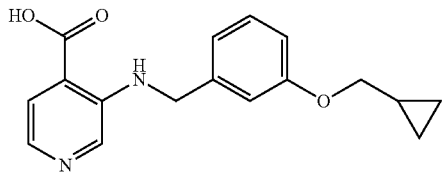 [SMILES: O=C(O)c1ccncc1NCc1cccc(OCC2CC2)c1]

The title compound was prepared in 7% yield from 3-cyclopropylmethoxy-benzylamine hydrochloride and 3-fluoroisonicotinic acid according to the procedure for the preparation of Example 5. $^1$H NMR (400 MHz, DMSO-d$_6$): δ 8.07 (s, 1H), 7.79 (d, 1H, J=5.0 Hz), 7.57 (d, 1H, J=5.0 Hz), 7.23 (t, 1H, J=8.0 Hz), 6.89-6.95 (m, 2H), 6.79 (d, 1H, J=7.6 Hz), 4.49 (s, 2H), 3.78 (d, 2H, J=6.9 Hz), 1.15-1.21 (m, 1H), 0.51-0.57 (m, 2H), 0.27-0.32 (m, 2H). [M+H] calc'd for C$_{17}$H$_{18}$N$_2$O$_3$, 299; found 299.

Example 38: 3-[(1-benzofuran-3-ylmethyl)amino]pyridine-4-carboxylic acid

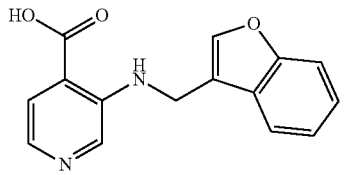 [SMILES: O=C(O)c1ccncc1NCc1coc2ccccc12]

The title compound was prepared in 8% yield from (1-benzofuran-3-yl)methylamine hydrochloride and 3-fluoroisonicotinic acid according to the procedure for the preparation of Example 5. $^1$H NMR (400 MHz, DMSO-d$_6$): δ 13.39 (br s, 1H), 8.33 (s, 1H), 7.97 (s, 1H), 7.77 (d, 1H, J=5.0 Hz), 7.68 (br s, 1H), 7.57 (d, 1H, J=7.6 Hz), 7.48-7.52 (m, 2H), 7.17-7.28 (m, 2H), 4.64 (s, 2H). [M+H] calc'd for C$_{15}$H$_{12}$N$_2$O$_3$, 267; found 267.

Example 39: 3-{[(5-methylthiophen-2-yl)methyl]amino}pyridine-4-carboxylic acid

The title compound was prepared in 7% yield from 5-methylthiophen-2-ylmethylamine and 3-fluoroisonicotinic acid according to the procedure for the preparation of Example 3. $^1$H NMR (400 MHz, DMSO-d$_6$): δ 8.27 (br s, 1H), 7.84 (br s, 1H), 7.57 (d, 1H, J=4.8 Hz), 6.87 (d, 1H, 3.2 Hz), 6.65 (d, 1H, J=2.3 Hz), 4.65 (s, 2H), 2.38 (s, 3H). [M+H] calc'd for C$_{12}$H$_{12}$N$_2$O$_2$S, 249; found 249.

Example 40: 3-{[(5-methylfuran-2-yl)methyl]amino}pyridine-4-carboxylic acid

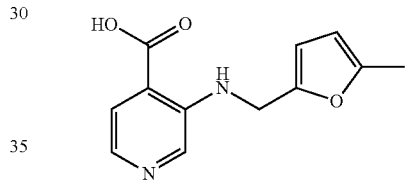

The title compound was prepared in 34% yield from 5-methylfurfurylamine and 3-fluoroisonicotinic acid according to the procedure for the preparation of Example 3. $^1$H NMR (400 MHz, DMSO-d$_6$): δ 13.45 (br s, 1H), 8.35 (s, 1H), 7.86 (d, 1H, J=5.0 Hz), 7.77 (br s, 1H), 7.57 (d, 1H, J=5.0 Hz), 6.24 (d, 1H, J=2.9 Hz), 6.00 (d, 1H, J=2.0 Hz), 4.50 (s, 2H), 2.23 (s, 3H). [M+H] calc'd for C$_{12}$H$_{12}$N$_2$O$_3$, 233; found 233.

Preparation 40A: methyl 3-{[(5-methylfuran-2-yl)methyl]amino}pyridine-4-carboxylate

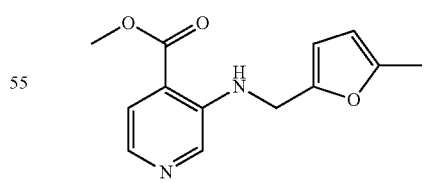

The title compound was prepared in 71% yield from Example 40 according to the procedure for Preparation 19B. $^1$H NMR (400 MHz, CDCl$_3$): δ 8.34 (s, 1H), 7.94 (d, 1H, J=5.1 Hz), 7.8 (br s, 1H), 7.63 (dd, 1H, J=5.1, 0.3 Hz), 6.15 (d, 1H, J=3.0 Hz), 5.89-5.91 (m, 1H), 4.43 (d, 2H, J=5.7 Hz), 3.89 (s, 3H), 2.38 (s, 3H). [M+H] calc'd for C$_{13}$H$_{14}$N$_2$O$_3$, 247; found 247.

Example 41: 3-[(1-benzofuran-2-ylmethyl)amino]pyridine-4-carboxylic acid

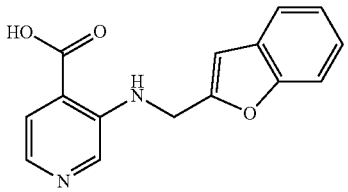

The title compound was prepared in 3% yield from (1-benzofuran-2-ylmethyl)amine hydrochloride and 3-fluoroisonicotinic acid according to the procedure for the preparation of Example 5. $^1$H NMR (400 MHz, DMSO-$d_6$): δ 13.44 (br s, 1H), 8.39 (s, 1H), 7.97 (br s, 1H), 7.87 (d, 1H, J=5.0 Hz), 7.52-7.60 (m, 3H), 7.19-7.29 (m, 2H), 6.81 (s, 1H), 4.79 (s, 2H). [M+H] calc'd for $C_{15}H_{12}N_2O_3$, 269; found 269.

Example 42: 3-[(adamantan-1-ylmethyl)amino]pyridine-4-carboxylic acid

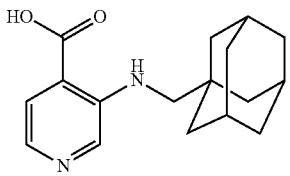 [SMILES: O=C(O)c1ccncc1NCC12CC3CC(CC(C3)C1)C2]

The title compound was prepared in 38% yield from 1-adamanteanemethylamine and 3-fluoroisonicotinic acid according to the procedure for the preparation of Example 3. $^1$H NMR (400 MHz, DMSO-$d_6$): δ 13.31 (br s, 1H), 8.28 (s, 1H), 7.77 (d, 1H, J=5.0 Hz), 7.54 (d, 1H, J=5.0 Hz), 2.99 (s, 2H), 1.95-2.00 (m, 3H), 1.56-1.72 (m, 12H). [M+H] calc'd for $C_{17}H_{22}N_2O_2$, 287; found 287.

Preparation 42A: methyl 3-[(adamantan-1-ylmethyl)amino]pyridine-4-carboxylate

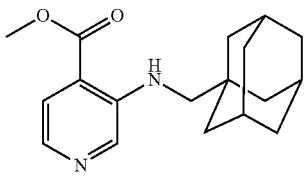 [SMILES: COC(=O)c1ccncc1NCC12CC3CC(CC(C3)C1)C2]

The title compound was prepared in 42% yield from Example 42 according to the procedure for Preparation 19B. $^1$H NMR (400 MHz, CDCl$_3$): δ 8.26 (s, 1H), 7.85 (d, 1H, J=5.0 Hz), 7.60 (d, 1H, J=5.0 Hz), 7.55 (br s, 1H), 3.90 (s, 3H), 2.97 (d, 2H, J=5.6 Hz), 2.00-2.05 (m, 3H), 1.62-1.74 (m, 12H). [M+H] calc'd for $C_{18}H_{24}N_2O_2$, 301; found 301.

Example 43: 3-[(2,3-dihydro-1-benzofuran-2-ylmethyl)amino]pyridine-4-carboxylic acid

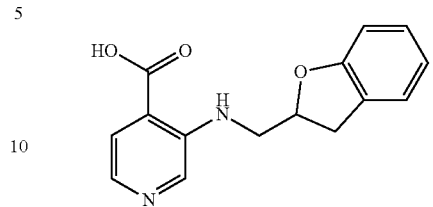

The title compound was prepared in 18% yield from (2,3-dihyro-1-benzofuran-2-yl) methylamine hydrochloride and 3-fluoroisonicotinic acid according to the procedure for the preparation of Example 5. $^1$H NMR (400 MHz, DMSO-$d_6$): δ 13.41 (br s, 1H), 8.29 (s, 1H), 7.78 (d, 1H, J=5.0 Hz), 7.75 (br s, 1H), 7.48 (d, 1H, J=5.0 Hz), 7.15 (d, 1H, J=7.2 Hz), 7.01 (t, 1H, J=7.7 Hz), 6.75 (t, 1H, J=7.4 Hz), 6.67 (d, 1H, J=7.9 Hz), 4.95-4.99 (m, 1H), 3.24-3.64 (m, 3H), 2.88-2.95 (m, 1H). [M+H] calc'd for $C_{15}H_{14}N_2O_3$, 271; found 271.

Example 44: 3-[(2,3-dihydro-1,4-benzodioxin-2-ylmethyl)amino]pyridine-4-carboxylic acid

The title compound was prepared in 6% yield from 2,3-dihydro-1,4-benzodioxin-2-ylmethylamine and 3-fluoroisonicotinic acid according to the procedure for the preparation of Example 3. $^1$H NMR (400 MHz, DMSO-$d_6$): δ 13.43 (br s, 1H), 8.37 (s, 1H), 7.87 (d, 1H, J=5.0 Hz), 7.77 (br s, 1H), 7.57 (d, 1H, J=5.0 Hz), 6.80-6.90 (m, 4H), 4.37-4.48 (m, 2H), 4.02-4.07 (m, 1H), 3.55-3.75 (m, 2H). [M+H] calc'd for $C_{15}H_{14}N_2O_4$, 287; found 287.

Example 45: 3-[(2,3-dihydro-1H-inden-1-ylmethylbenzyl)amino]pyridine-4-carboxylic acid

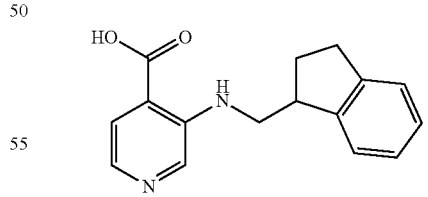

The title compound was prepared in 19% yield from 1-aminomethylindane hydrochloride and 3-fluoroisonicotinic acid according to the procedure for the preparation of Example 5. $^1$H NMR (400 MHz, DMSO-$d_6$): δ 13.38 (br s, 1H), 8.35 (s, 1H), 7.84 (d, 1H, J=5.0 Hz), 7.55 (d, 1H, J=5.0 Hz), 7.35 (t, 1H, J=4.1 Hz), 7.14-7.26 (m, 3H), 3.62-3.67 (m, 1H), 3.36-3.49 (m, 2H), 2.69-3.02 (m, 2H), 2.21-2.28 (m, 1H), 1.80-1.89 (m, 1H). [M+H] calc'd for $C_{16}H_{16}N_2O_2$, 269; found 269.

Preparation 46A: methyl 3-[(1,2,3,4-tetrahydronaphthalen-1-yl-methyl)amino]pyridine-4-carboxylate

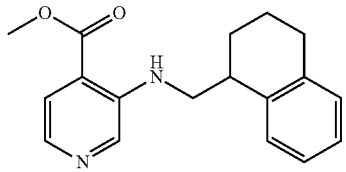 [SMILES: COC(=O)c1ccncc1NCC1CCCc2ccccc21]

Methyl 3-bromoisonicotinate (1.34 g, 6.2 mmol) 1,2,3,4-tetrahydro-1-naphthalene-methanamine (1.0 g, 6.62 mmol), and cesium carbonate (3.0 g, 9.43 mmol) were combined in dioxane (12 mL) under $N_2$ in a microwave vial. $Pd_2dba_3$ (284 mg, 0.31 mmol) and Xantphos (538 mg, 0.93 mmol) were added, and the reaction stirred at 128° C. in the microwave for 90 min. The reaction was filtered, washing with acetone, and concentrated in vacuo. Purification by silica gel chromatography (20-80% EtOAc/hexanes) gave 826 (45%) of the title compound as a light orange solid. $^1$H NMR (400 MHz, CDCl$_3$): δ 8.32 (s, 1H), 7.91 (d, 1H, J=5.1 Hz), 7.64 (d, 1H, J=5.0 Hz), 7.59 (s, 1H), 7.24 (d, 1H, J=4.9 Hz), 7.11-7.19 (m, 3H), 3.89 (s, 3H), 3.56-3.63 (m, 1H), 3.39-3.47 (m, 1H), 3.18-3.21 (s, 1H), 2.78-2.84 (m, 2H), 1.77-1.97 (m, 4H). [M+H] calc'd for $C_{18}H_{20}N_2O_2$, 297; found 297.

Example 46: 3-[(1,2,3,4-tetrahydronaphthalen-1-ylmethyl)amino]pyridine-4-carboxylic acid

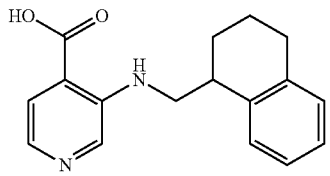

Preparation 46A (40 mg, 0.13 mmol) was stirred in MeOH (3 mL) with 1N NaOH (1 mL) at 50° C. for 1 hr. The solution was cooled to rt, neutralized with HOAc, and concentrated in vacuo. The residue was precipitated with water and the resulting solid was collected by filtration. The solid was washed with MeOH and dried in vacuo to yield 28 mg (74%) of the title compound as a white solid. $^1$H NMR (400 MHz, DMSO-d$_6$): δ 13.32 (br s, 1H), 8.34 (s, 1H), 7.82 (d, 1H, J=5.0 Hz), 7.56 (d, 1H, J=5.0 Hz), 7.31 (t, 1H, J=4.3 Hz), 7.08-7.13 (m, 3H), 3.41-3.60 (m, 2H), 3.08-3.11 (m, 1H), 2.70-2.76 (m, 2H), 1.65-1.89 (m, 4H). [M+H] calc'd for $C_{17}H_{18}N_2O_2$, 283; found 283.

Preparation 47A and Preparation 48A: methyl 3-{[(1S)-1,2,3,4-tetrahydronaphthalen-1-yl-methyl]amino}pyridine-4-carboxylate; methyl 3-{[(1R)-1,2,3,4-tetrahydronaphthalen-1-yl-methyl]amino}pyridine-4-carboxylate

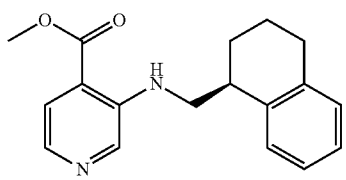

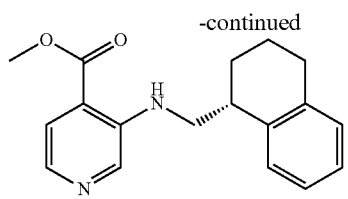

Preparation 46A (94 mg) was separated by chiral HPLC (Column: Chiralcel OD-H, 250 mm*4.6 mm 5 μm; Mobile phase: Hex:IPA=80:20; F: 1.0 mL/min; W: 230 nm; T=30° C.) to give to give the two enantiomers: 35 mg (33%) of the first isomer eluted at 4.93 min, and 35 mg (33%) of the second isomer eluted at 5.38 min.

Example 47 and Example 48: 3-{[(1S)-1,2,3,4-tetrahydronaphthalen-1-ylmethyl]amino}-pyridine-4-carboxylic acid; 3-{[(1R)-1,2,3,4-tetrahydronaphthalen-1-ylmethyl]amino}pyridine-4-carboxylic acid

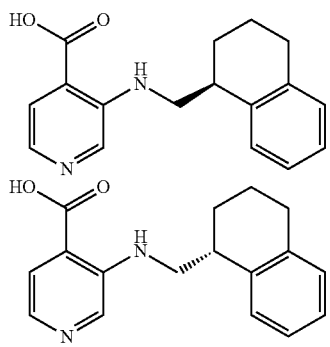

To a solution of the ester from Preparation 46A or 47A (35 mg, 0.12 mmol) in THF (5 mL) and water (5 mL) was added lithium hydroxide monohydrate (10 mg, 0.24 mmol), and the reaction stirred for 3 hr at rt. The solution was concentrated in vacuo to remove THF, and then acidified to pH 5 with 0.5 N HCl. The resulting precipitate was collected by filtration and dried under vacuum to give 20 mg (61%) of the title compound as a white solid. NMR and MS for each of the title compounds matched Example 46.

Example 49: 3-{[(1-methyl-1,2,3,4-tetrahydronaphthalen-1-yl)methyl]amino}pyridine-4-carboxylic acid

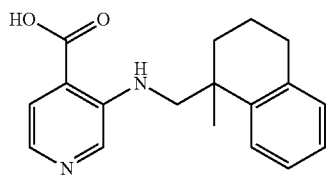 [SMILES: CC1(CNc2cnccc2C(=O)O)CCCc2ccccc21]

The title compound was prepared in 8% yield from 1-(1-methyl-1,2,3,4-tetrahydronaphthalen-1-yl)methanamine hydrochloride and 3-fluoroisonicotinic acid according to the procedure for the preparation of Example 5. $^1$H NMR (400 MHz, DMSO-d$_6$): δ 13.24 (br s, 1H), 8.31 (s, 1H), 7.78 (d, 1H, J=5.0 Hz), 7.48 (d, 1H, J=5.0 Hz), 7.45 (br s, 1H), 7.42 (d, 1H, J=7.3 Hz), 7.05-7.15 (m, 3H), 3.44-3.57 (m, 2H), 2.72 (t, 2H, J=6.4 Hz), 1.59-1.92 (m, 4H), 1.32 (s, 3H). [M+H] calc'd for $C_{18}H_{20}N_2O_2$, 297; found 297.

Preparation 50A:
1-(7-fluoro-1,2,3,4-tetrahydronaphthalen-1 yl)methanamine

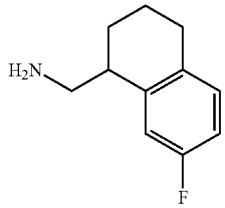 [SMILES: NCC1CCCc2ccc(F)cc21]

To a solution of 7-fluoro-1-tetralone (2.0 g, 12.2 mmol) and $ZnI_2$ (20 mg) in toluene (20 mL) was added TMS-CN (3.27 mL, 26.1 mmol) at rt. The mixture was heated at 60° C. overnight and then was cooled to rt and diluted with THF (20 mL). This was slowly added to a solution of lithium aluminum hydride (930 mg, 24.5 mmol) in THF (10 mL) at rt, and the reaction mixture was heated to 40° C. for 4 hr. The reaction was quenched with the addition of EtOAc (10 mL) at rt and was stirred for 30 min. Water (1 mL) and aqueous 1 N NaOH (1 mL) were added, and the mixture stirred 30 min. The mixture was dried ($Na_2SO_4$), filtered, and concentrated to give crude intermediate (2.3 g, 97%) as a yellow oil.

To a solution of the intermediate (2.3 g, 11.8 mmol) in toluene (30 mL) was added HCl/dioxane (10 mL, 4.0 M), and the reaction stirred at reflux overnight. The reaction was cooled to rt and concentrated in vacuo.

Hydrogenation of the resulting intermediated was carried out in the presence of Raney Nickel (750 mg) in 2:1 MeOH/HOAc under 50 psi of $H_2$ for 6 hr. The reaction was filtered through Celite and concentrated in vacuo. Purification by silica gel chromatography (5-20% MeOH/DCM with 0.5% $Et_3N$) gave 1.2 g (57%) of the title compound as a white solid. [M+H] calc'd for $C_{11}H_{14}FN$, 180; found 180. The presence of unreduced material was also detected.

Example 50: 3-{[(7-fluoro-1,2,3,4-tetrahydronaphthalen-1-yl)methyl]amino}pyridine-4-carboxylic acid

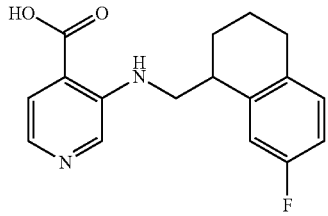

The title compound was prepared in 4% yield from Preparation 50A and 3-fluoroisonicotinic acid according to the procedure for the preparation of Example 3. $^1$H NMR (400 MHz, DMSO-$d_6$): δ 13.37 (br s, 1H), 8.39 (s, 1H), 7.84 (d, 1H, J=5.0 Hz), 7.56 (d, 1H, J=5.0 Hz), 7.10-7.23 (m, 2H), 6.92-7.00 (m, 2H), 3.43-3.65 (m, 2H), 3.10-3.14 (m, 1H), 2.64-2.72 (m, 2H), 1.65-1.87 (m, 4H). [M+H] calc'd for $C_{17}H_{17}FN_2O_2$, 301; found 301.

Example 51: 3-{[(7-fluoro-3,4-dihydronaphthalen-1-yl)methyl]amino}pyridine-4-carboxylic acid

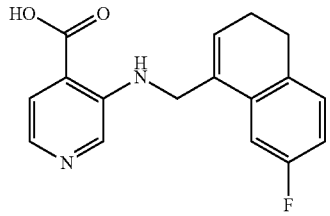

The title compound was isolated in 4% yield as a side-product in the preparation of Example 50, due to incomplete reduction in the hydrogenation step for Preparation 50A. $^1$H NMR (400 MHz, DMSO-$d_6$): δ 13.35 (br s, 1H), 8.27 (s, 1H), 7.84 (d, 1H, J=5.0 Hz), 7.79 (br s, 1H), 7.56 (d, 1H, J=5.0 Hz), 7.19-7.23 (m, 2H), 6.97-7.01 (m, 1H), 6.15 (t, 1H, J=4. Hz), 4.37 (s, 2H), 2.64-2.69 (m, 2H), 2.23-2.28 (m, 2H). [M+H] calc'd for $C_{17}H_{15}FN_2O_2$, 299; found 299.

Preparation 52A:
1-(5,7-dimethyl-1,2,3,4-tetrahydronaphthalen-1 yl)methanamine

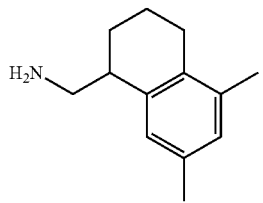

TMS-cyanide (8.52 mL, 68.1 mmol) was added to a solution of 5,7-dimethyl-1-tetralone (2.5 g, 14.4 mmol) in toluene (20 mL). A trace amount (~20 mg) of zinc iodide was added, and the reaction was stirred at 60° C. for 16 hr. The solution was cooled to rt and diluted with THF (10 mL). This was added to a mixture of lithium aluminum hydride (1.09 g, 28.7 mmol) in THF (20 mL), and the reaction mixture was heated at 42° C. for 4 hr. The reaction was cooled to rt. EtOAc (5 mL) was slowly added, and the reaction stirred 30 min. Water (1 mL) and then 2N NaOH (1 mL) were slowly added, and the reaction stirred 1 hr. The reaction mixture was diluted with EtOAc (50 mL), dried (MgSO$_4$), and filtered through Celite.

The crude intermediate was taken up in toluene (30 mL). 4N HCl in dioxane (10 mL) was added, and the reaction was heated at reflux under a Dean-Stark condenser for 8 hr. The solution was concentrated in vacuo.

Hydrogenation of this crude intermediate was carried out in the presence of 10% Pd/C in 3:1 MeOH:HOAc under 50 psi of $H_2$ for 16 hr. The reaction was filtered through Celite and concentrated in vacuo. Purification by silica gel chromatography (5%-20% MeOH/DCM with 0.5% Et$_3$N) gave 1.20 g (44%) of the title compound as a white solid. $^1$H NMR (400 MHz, DMSO-$d_6$): δ 6.87 (s, 1H), 6.83 (s, 1H), 2.96-23.02 (m, 2H), 2.82-2.90 (m, 1H), 2.38-2.52 (m, 2H), 2.21 (s, 3H), 2.12 (s, 3H), 1.67-1.86 (m, 4H). [M+H] calc'd for $C_{13}H_{19}N$, 190; found 190.

Example 52: 3-{[(5,7-dimethyl-1,2,3,4-tetrahydronaphthalen-1-yl)methyl]amino}pyridine-4-carboxylic acid

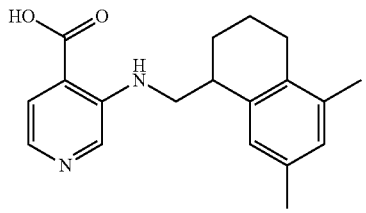 [SMILES: Cc1cc(C)c2c(c1)C(CNc1cnccc1C(=O)O)CCC2]

The title compound was prepared in 8% yield from Preparation 52A and 3-fluoroisonicotinic acid according to the procedure for the preparation of Example 3. $^1$H NMR (400 MHz, DMSO-$d_6$): δ 8.35 (s, 1H), 7.83 (d, 1H, J=5.0 Hz), 7.76 (br s, 1H), 7.57 (d, 1H, J=5.0 Hz), 6.93 (s, 1H), 6.82 (s, 1H), 3.40-3.53 (m, 2H), 2.99-3.05 (m, 1H), 2.56-2.63 (m, 2H), 2.20 (s, 3H), 2.13 (s, 3H), 1.72-1.87 (m, 4H). [M+H] calc'd for $C_{19}H_{22}N_2O_2$, 311; found 311.

Preparation 53A: 7-cyclopropyl-3,4,-dihydronaphthalen-1(2H)-one

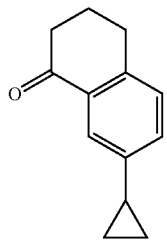 [SMILES: O=C1CCCc2ccc(C3CC3)cc21]

The title compound was prepared in 77% yield from 7-bromo-1-tetralone according to the general procedure for Preparation 19C. $^1$H NMR (400 MHz, CDCl$_3$): δ 7.72 (d, 1H, J=2.0 Hz), 7.21 (dd, 1H, J=7.9, 2.0 Hz), 7.13 (d, 1H, J=7.9 Hz), 2.91 9t, 2H, J=6.1 Hz), 2.63 (t, 2H, J=6.1 Hz), 2.09-2.15 (m, 2H), 1.87-1.93 (m, 1H), 0.93-0.99 (m, 2H), 0.69-0.73 (m, 2H). [M+H] calc'd for $C_{13}H_{14}O$, 187; found 187.

Preparation 53B: 1-(7-cyclopropyl-1,2,3,4-tetrahydronaphthalen-1yl)methanamine

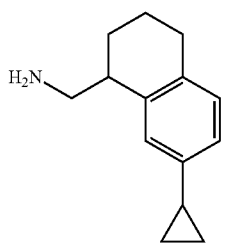 [SMILES: NCC1CCCc2ccc(C3CC3)cc21]

The title compound was prepared in 47% yield from Preparation 53A according to the general procedure for Preparation 52A. $^1$H NMR (400 MHz, CDCl$_3$): δ 9.22 (br s, 2H), 6.94-6.98 (m, 2H), 6.80 (d, 1H, J=7.8 Hz), 3.01-3.22 (m, 3H), 268-2.72 (m, 2H), 1.76-1.91 (m, 5H), 0.88-0.93 (m, 2H), 0.62-0.66 (m, 2H). [M+H] calc'd for $C_{14}H_{19}N$, 202; found 202.

Example 53: 3-{[(7-cyclopropyl-1,2,3,4-tetrahydronaphthalen-1-yl)methyl]amino}pyridine-4-carboxylic acid

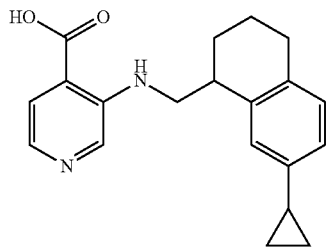 [SMILES: O=C(O)c1ccncc1NCC1CCCc2ccc(C3CC3)cc21]

3-Fluoroisonicotinic acid (295 mg, 2.09 mmol), Preparation 53B (420 mg, 2.09 mmol) and DIEA (364 μL, 2.09 mmol) were combined in DMA (4 mL) and heated at 168° C. in the microwave for 80 min. The reaction was concentrated and purified by prep-HPLC (35-80% ACN/water with 0.1% formic acid) to give 32 mg (5%) of the title compound as a pale yellow solid. $^1$H NMR (400 MHz, DMSO-$d_6$): δ 8.35 (s, 1H), 7.83 (d, 1H, J=5.0 Hz), 7.79 (br s, 1H), 7.47 (d, 1H, J=5.0 Hz), 6.93-6.98 (m, 2H), 6.81 (dd, 1H, J=7.8, 1.4 Hz), 3.39-3.69 (m, 2H), 3.03-3.06 (m, 1H), 2.63-2.69 (m, 2H), 1.63-1.86 (m, 5H), 0.84-0.88 (m, 2H), 0.57-0.62 (m, 2H). [M+H] calc'd for $C_{20}H_{22}N_2O_2$, 323; found 323.

Preparation 54A: 1-(5-fluoro-1,2,3,4-tetrahydronaphthalen-1yl)methanamine

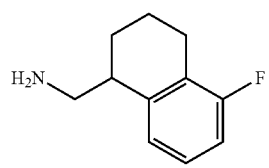 [SMILES: NCC1CCCc2c(F)cccc21]

The title compound was prepared in 37% overall yield from 5-fluoro-1-tetralone according to the procedure for Preparation 50A, except the reduction step ran for 16 hr instead of 6 hr. [M+H] calc'd for $C_{11}H_{14}FN$, 180; found 180.

Example 54: 3-{[(5-fluoro-1,2,3,4-tetrahydronaphthalen-1-yl)methyl]amino}pyridine-4-carboxylic acid

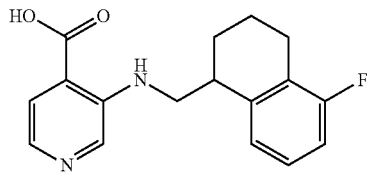

The title compound was prepared in 6% yield from Preparation 54A and 3-fluoroisonicotinic acid according to the procedure for the preparation of Example 53. ¹H NMR (400 MHz, DMSO-d₆): δ 8.32 (s, 1H), 7.89 (br s, 1H), 8.82 (d, 1H, J=5.0 Hz), 7.56 (d, 1H, J=5.0 Hz), 7.15-7.18 (m, 2H), 6.95-7.00 (m, 1H), 3.42-3.61 (m, 2H), 3.12-3.16 (m, 1H), 2.54-2.75 (m, 2H), 1.69-1.88 (m, 4H). [M+H] calc'd for $C_{17}H_{17}FN_2O_2$, 301; found 301.

Example 55: 3-{[(5-fluoro-1-hydroxy-1,2,3,4-tetra-hydronaphthalen-1-yl)methyl]amino}pyridine-4-carboxylic acid

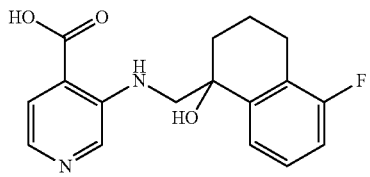

The title compound was isolated in 2% yield as a side-product from the preparation of Example 54. ¹H NMR (400 MHz, DMSO-d₆): δ 8.12-8.31 (m, 2H), 7.47-7.71 (m, 2H), 7.17-7.22 (m, 1H), 6.98-7.03 (m, 1H), 3.35-3.48 (m, 2H), 2.99-3.14 (m, 1H), 2.60-2.74 (m, 2H), 2.08 (br s, 1H), 1.73-1.85 (m, 4H). [M+H] calc'd for $C_{17}H_{17}FN_2O_3$, 317; found 317.

Preparation 56A: methyl 3-{[(5-fluoro-1,2,3,4-tetra-hydronaphthalen-1-yl)methyl]amino}pyridine-4-carboxylate

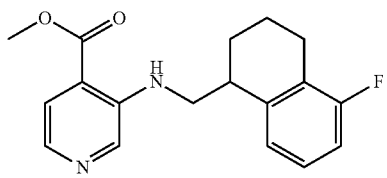 [SMILES: COC(=O)c1ccncc1NCC1CCCc2c(F)cccc21]

To a suspension of Preparation 54A (480 mg, 2.7 mmol) in DMA (5 mL) was added methyl 3-fluoroisonicotinate at rt. The reaction mixture was stirred at 170° C. for 1 hr in a microwave. Concentration in vacuo followed by purification by silica gel chromatography gave 395 mg (47%) of the title compound as a yellow gum. [M+H] calc'd for $C_{18}H_{19}FN_2O_2$, 315; found 315.

Preparation 56B and Preparation 57B: methyl 3-({[(1S)-5-fluoro-1,2,3,4-tetrahydronaphthalen-1-yl]methyl}amino)pyridine-4-carboxylate; methyl 3-({[(1R)-5-fluoro-1,2,3,4-tetrahydronaphthalen-1-yl]methyl}amino)pyridine-4-carboxylate

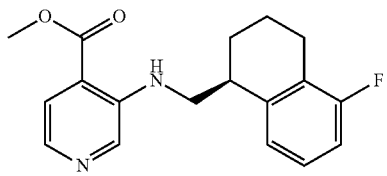

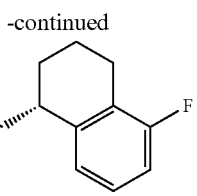

Preparation 56A (395 mg) was separated by chiral HPLC (Column: Chiralcel OJ-H, 250 mm*4.6 mm 5 μm; Mobile phase: Hex:IPA=80:20; F: 1.0 mL/min; W: 230 nm; T=30° C.) to give to give the two enantiomers: 110 mg (27%) of the first isomer eluted at 4.95 min, and 126 mg (31%) of the second isomer eluted at 5.39 min.

Example 56 and Example 57: 3-({[(1S)-5-fluoro-1,2,3,4-tetrahydronaphthalen-1-yl]methyl}-amino)pyridine-4-carboxylic acid; 3-({[(1R)-5-fluoro-1,2,3,4-tetrahydronaphthalen-1-yl]-methyl}amino)pyridine-4-carboxylic acid

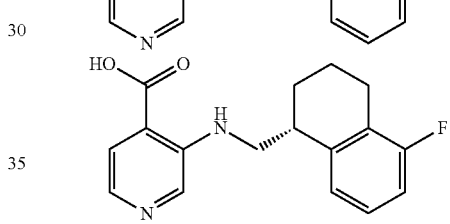

To a solution of Preparation 56B (110 mg, 0.35 mmol) in THF (5 mL) and water (5 mL) was added lithium hydroxide monohydrate (30 mg, 0.7 mmol), and the reaction stirred for 16 h at rt. The solution was concentrated in vacuo to remove THF, and then acidified to pH 3 with 1.0 N HCl. The resulting precipitate was collected by filtration and dried under vacuum to give 88 mg (83%) of Example 56 as a white solid. Example 57 was prepared in 88% yield by the same method. NMR and MS for each of the title compounds matched Example 54.

Example 58: 3-[(3,4-dihydro-2H-chromen-4-ylmethyl)amino]pyridine-4-carboxylic acid

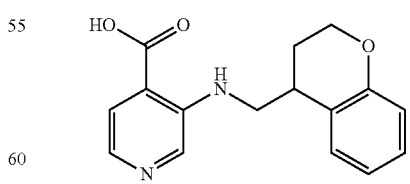

The title compound was prepared in 13% yield from 1-(3,4-dihydro-2H-chromen-4-yl) methanamine and 3-fluoroisonicotinic acid according to the procedure for the preparation of Example 53. ¹H NMR (400 MHz, DMSO-d₆): δ 8.33 (s, 1H), 7.78 (d, 1H, J=5.0 Hz), 7.74 (br s, 1H), 7.50 (d, 1H, J=5.0 Hz), 7.23 (d, 1H, J=7.4 Hz), 7.04 (t, 1H, J=7.1 Hz), 6.78 (t, 1H, J=7.3 Hz), 6.69 (d, 1H, J=8.0 Hz), 4.06-4.17 (m, 2H), 3.59-3.65 (m, 1H), 3.41-3.47 (m, 1H), 3.04-3.09 (m, 1H), 1.79-1.96 (m, 2H). [M+H] calc'd for $C_{16}H_{16}N_2O_3$, 285; found 285.

Example 59: 3-{[(4,4-dimethyl-1,2,3,4-tetrahydronaphthalen-1-yl)methyl]amino}pyridine-4-carboxylic acid

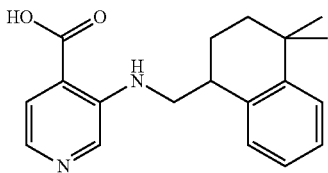 [SMILES: CC1(C)CCC(CNc2cnccc2C(=O)O)c2ccccc21]

The title compound was prepared in 17% yield from 1-(4,4-dimethyl-1,2,3,4-tetrahydronaphthalen-1-yl)methanamine and 3-fluoroisonicotinic acid according to the procedure for the preparation of Example 5. $^1$H NMR (400 MHz, DMSO-$d_6$): δ 13.36 (br s, 1H), 8.37 (s, 1H), 7.83 (d, 1H, J=5.0 Hz), 7.59 (br s, 1H), 7.55 (d, 1H, J=5.0 Hz), 7.38 (d, 1H, J=7.8 Hz), 7.26 (d, 1H, J=6.8 Hz), 7.07-7.19 (m, 2H), 3.47-3.58 (m, 2H), 3.07-3.11 (m, 1H), 1.77-1.90 (m, 3H), 1.51-1.57 (m, 1H), 1.31 (s, 3H), 1.21 (s, 3H). [M+H] calc'd for $C_{19}H_{22}N_2O_2$, 311; found 311.

Preparation 60A: 1-(6-methoxy-1,2,3,4-tetrahydronaphthalen-1 yl)methanamine, hydrochloride

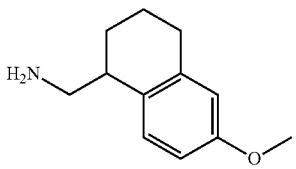

TMS-cyanide (8.52 mL, 68.1 mmol) was added to a solution of 6-methoxy-1-tetralone (6.0 g, 34 mmol) in toluene (50 mL). A trace amount (~20 mg) of zinc iodide was added, and the reaction was stirred at 60° C. for 16 hr. The solution was cooled to rt and diluted with THF (30 mL). This was added to a mixture of lithium aluminum hydride (2.58 g) in THF (50 mL), and the reaction mixture was heated at 42° C. for 2 hr. The reaction was cooled to rt. EtOAc (10 mL) was slowly added, and the reaction stirred 30 min. Water (2 mL) and then 5N NaOH (1 mL) were slowly added, and the reaction stirred 1 hr. The reaction mixture was diluted with EtOAc (100 mL), dried (MgSO$_4$), and filtered through Celite. Purification by silica gel chromatography (10%-20% MeOH/DCM) gave 4.82 g of 1-(aminomethyl)-6-methoxy-1,2,3,4-tetrahydronaphthalen-1-ol as a clear oil.

The intermediate was taken up in toluene (60 mL). 4N HCl in dioxane (20 mL) was added, and the reaction was heated at reflux under a Dean-Stark condenser for 2 hr. The solution was concentrated in vacuo and precipitated from cold EtOAc. The solid was collected by filtration to give 3.76 g of 1-(6-methoxy-3,4-dihydronaphthalen-1yl)methanamine. $^1$H NMR (400 MHz, DMSO-$d_6$): δ 8.30 (br s, 3H), 7.22 (d, 1H, J=8.4 Hz), 6.76-6.83 (m, 2H), 6.05 (t, 1H, J=4.5 Hz), 3.82 (br s, 2H), 3.76 (s, 3H), 2.69 (t, 2H, J=7.9 Hz), 2.22-2.28 (m, 2H). [M+H] calc'd for $C_{12}H_{15}NO$, 190; found 190.

Hydrogenation of 1-(6-methoxy-3,4-dihydronaphthalen-1yl)methanamine was carried out in the presence of 10% Pd/C in 3:1 MeOH:HOAc under 50 psi of H$_2$ for 16 hr. The reaction was filtered through Celite and concentrated in vacuo. Precipitation from EtOAc and collection by filtration gave 3.0 g (39%) of the title compound as a white solid. $^1$H NMR (400 MHz, DMSO-$d_6$): δ 7.88 (br s, 3H), 7.16 (d, 1H, J=8.5 Hz), 6.73 (dd, 1H, J=8.4, 2.6 Hz), 6.64 (d, 1H, J=2.4 Hz), 3.70 (s, 3H), 2.81-3.09 (m, 3H), 2.63-2.70 (m, 2H), 1.61-1.87 (m, 4H). [M+H] calc'd for $C_{12}H_{17}NO$, 192; found 192.

Example 60: 3-{[(6-methoxy-1,2,3,4-tetrahydronaphthalen-1-yl)methyl]amino}pyridine-4-carboxylic acid

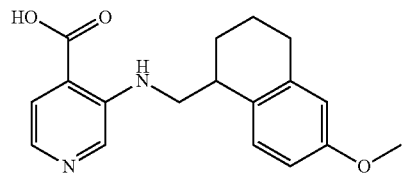 [SMILES: COc1ccc2c(c1)CCCC2CNc1cnccc1C(=O)O]

The title compound was prepared in 15% yield from Preparation 60A and 3-fluoroisonicotinic acid according to the procedure for the preparation of Example 5. $^1$H NMR (400 MHz, DMSO-$d_6$): δ 8.35 (s, 1H), 7.83 (d, 1H, J=5.0 Hz), 7.65 (br s, 1H), 7.56 (d, 1H, J=5.0 Hz), 7.21 (d, 1H, J=8.5 Hz), 6.70 (dd, 1H, J=8.5, 2.6 Hz), 6.65 (d, 1H, J=2.4 Hz), 3.70 (s, 3H), 3.38-3.56 (m, 2H), 3.02-3.06 (m, 1H), 2.67-2.74 (m, 2H), 1.62-1.84 (m, 4H). [M+H] calc'd for $C_{18}H_{20}N_2O_3$, 313; found 313.

Preparation 61A: methyl 3-{[(6-methoxy-1,2,3,4-tetrahydronaphthalen-1-yl)methyl]amino}pyridine-4-carboxylate

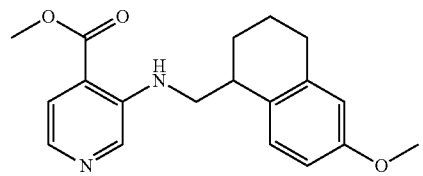

Methyl 3-bromoisonicotinate (930 mg, 4.3 mmol), Preparation 60A (980 mg, 4.3 mmol), and cesium carbonate (3.5 g, 10.8 mmol) were combined in dioxane (12 mL) under N$_2$ in a microwave vial. Pd$_2$dba$_3$ (197 mg, 0.22 mmol) and Xantphos (373 mg, 0.65 mmol) were added, and the reaction stirred at 128° C. in the microwave for 1 hr. As there was very little conversion by HPLC at this point, the reaction was heated an additional 2 hr at 148° C. The reaction was filtered, washing with acetone, and concentrated in vacuo. Purification by silica gel chromatography (20-80% EtOAc/hexanes) gave 256 (18%) of the title compound light yellow oil. $^1$H NMR (400 MHz, CDCl$_3$): δ 8.32 (s, 1H), 7.91 (d, 1H, J=5.2 Hz), 7.62 (dd, 1H, J=5.2, 0.5 Hz), 7.56 (br s, 1H), 7.16 (d, 1H, J=8.5 Hz), 6.74 (dd, 1H, J=8.4, 2.7 Hz), 6.65 (d, 1H, J=2.7 Hz), 3.89 (s, 3H), 3.78 (s, 3H), 3.52-3.58 (m, 1H), 3.37-3.43 (m, 1H), 3.11-3.15 (s, 1H), 2.77-2.82 (m, 2H), 1.76-1.95 (m, 4H). [M+H] calc'd for $C_{19}H_{22}N_2O_3$, 327; found 327.

Preparation 61B and Preparation 62B: methyl 3-({[(1S)-6-methoxy-1,2,3,4-tetrahydronaphthalen-1-yl]methyl}amino)pyridine-4-carboxylate; methyl 3-({[(1R)-6-methoxy-1,2,3,4-tetrahydronaphthalen-1-yl]methyl}amino)pyridine-4-carboxylate

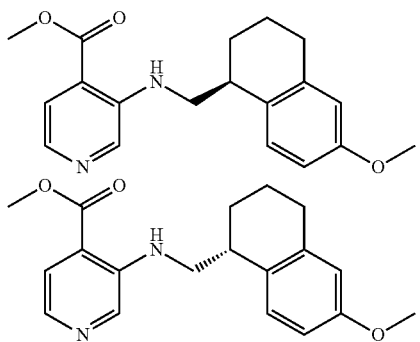

Preparation 61A (240 mg) was separated by chiral HPLC (Column: Chiralcel OJ-H, 250 mm*4.6 mm 5 μm; Mobile phase: Hex:IPA=80:20; F: 1.0 mL/min; W: 230 nm; T=30° C.) to give to give the two enantiomers: 60 mg (25%) of the first isomer eluted at 8.66 and 60 mg (25%) of the second isomer eluted at 10.59 min.

Example 61 and Example 62: 3-({[(1S)-6-methoxy-1,2,3,4-tetrahydronaphthalen-1-yl]methyl}-amino) pyridine-4-carboxylic acid; 3-({[(1R)-6-methoxy-1,2,3,4-tetrahydronaphthalen-1-yl]-methyl}amino) pyridine-4-carboxylic acid

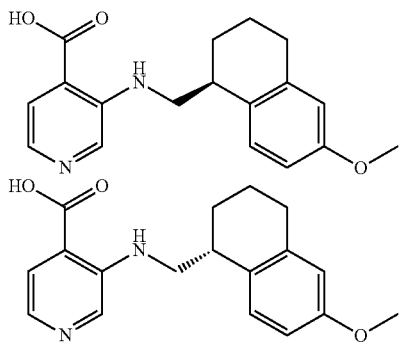

Hydrolysis of each of the pure enantiomers (Preparation 61B and Preparation 62B) were carried out as follows: To the ester (60 mg, 0.18 mmol) in THF (5 mL) and water (5 mL) was added lithium hydroxide monohydrate (15 mg, 0.36 mmol), and the reaction stirred for 3 h at rt. The solution was concentrated in vacuo to remove THF, and then acidified to pH 5 with 0.5 N HCl. The resulting precipitate was collected by filtration and dried under vacuum to give 50 mg (89%) of the title compound as a yellow solid. NMR and MS for each of the title compounds matched Example 60.

Preparation 63A: 1-(6-methyl-3,4-dihydro-2H-chromen-4-yl)methanamine

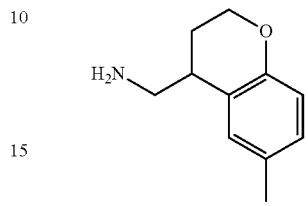

To a solution of 6-methyl-4-chromanone (2.0 g, 12.3 mmol), $ZnI_2$ (20 mg) in toluene (20 mL) was added TMS-CN (3.3 mL, 24.7 mmol) at rt. The solution was heated at 60° C. overnight. The reaction was cooled to rt and diluted with THF (10 mL), and then it was added dropwise to a solution of lithium aluminum hydride (10.3 mL, 2.4 M, 24.7 mmol) at rt. The reaction mixture was heated to 40° C. for 3 hr, and then cooled to rt. EtOAc (10 mL) was added at rt and the reaction stirred for 30 min. Water (2 mL) was added, and then the mixture was dried ($Na_2SO_4$), filtered, and concentrated to give 2.3 g (95%) of the crude intermediate as a yellow oil.

To a solution of the intermediate (1.5 g, 7.8 mmol) in toluene (20 mL) was added 4N HCl/dioxane (10 mL), and the reaction stirred at reflux overnight. The solution was cooled to 0° C. and filtered to give 1-(6-methyl-2H-chromen-4-yl)methanamine hydrochloride (800 mg, 49%) as a yellow solid. $^1$H NMR (300 MHz, $CD_3OD$): δ 2.32 (3H, s), 3.99 (2H, s), 4.76 (2H, d, J=3.0 Hz), 6.01 (1H, t, J=3.0 Hz), 6.75 (1H, d, J=6.3 Hz), 7.04 (1H, d, J=6.3 Hz), 7.08 (1H, s).

To a solution of 1-(6-methyl-2H-chromen-4-yl)methanamine hydrochloride (700 mg, 3.3 mmol) in MeOH (20 mL) and AcOH (2 mL) under $N_2$ was added 10% Pd/C (70 mg) at rt. The suspension was stirred at rt overnight under 50 psi of $H_2$. The reaction was filtered and concentrated. The residue was dissolved in EtOAc and washed with sat. $Na_2CO_3$, and the organics were concentrated to give 400 mg (68%) of the title compound as a yellow oil. $^1$H NMR (300 MHz, $CDCl_3$): δ 1.98-2.09 (2H, m), 2.28 (3H, s), 2.80-2.83 (1H, m), 2.88-2.96 (1H, m), 3.09 (1H, dd, J=4.5, 12.6 Hz), 4.17 (2H, t, J=6.3 Hz), 6.73 (1H, d, J=8.4 Hz), 6.91-6.97 (2H, m).

Example 63: 3-{[(6-methyl-3,4-dihydro-2H-chromen-4-yl)methyl]amino}pyridine-4-carboxylic acid

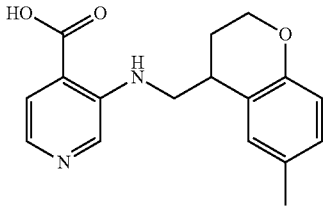 [SMILES: Cc1ccc2c(c1)C(CNc1cnccc1C(=O)O)CCO2]

The title compound was prepared in 15% yield from Preparation 63A and 3-fluoroisonicotinic acid according to the procedure for the preparation of Example 3. $^1$H NMR (400 MHz, DMSO-$d_6$): δ 1.86-1.90 (1H, m), 1.94-1.98 (1H, m), 2.20 (3H, s), 3.07-3.09 (1H, m), 3.47-3.51 (1H, m), 3.66-3.70 (1H, m), 4.13-4.16 (2H, m), 6.65 (1H, d, J=8.4 Hz), 6.90 (1H, t, J=8.4 Hz), 7.10 (1H, s), 7.59 (1H, d, J=4.8 Hz), 7.86 (1H, d, J=4.8 Hz), 8.43 (1H, s). [M+H] Calc'd for $C_{17}H_{18}N_2O_3$, 299; found, 299.

Preparation 64A: 1-[6-(propan-2-yloxy)-1,2,3,4-tetrahydronaphthalen-1yl]methanamine, hydrochloride

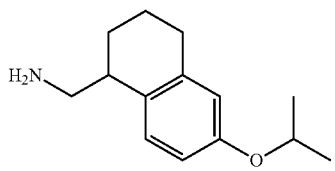 [SMILES: CC(C)Oc1ccc2c(c1)CCCC2CN]

The title compound was prepared in 32% yield from 6-(propan-2yloxy)-1-tetralone according to the general procedure for Preparation 60A. $^1$H NMR (400 MHz, DMSO-$d_6$): δ 7.49 (br s, 3H), 7.13 (d, 1H, J=8.6 H), 6.70 (dd, 1H, J=8.4, 2.6 Hz), 6.61 (d, 1H, J=2.4 Hz), 4.51-4.58 (m, 1H), 2.99-3.08 (m, 2H), 2.82-2.89 (m, 1H), 2.63-2.69 (m, 2H), 1.62-1.82 (m, 4H), 1.23 (d, 6H, J=6.0 Hz). [M+H] calc'd for $C_{14}H_{21}NO$, 220; found 220.

Example 64: 3-({[(6-(propan-2-yloxy)-1,2,3,4-tetrahydronaphthalen-1-yl]methyl}amino)pyridine-4-carboxylic acid

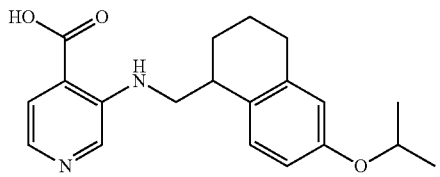

The title compound was prepared in 6% yield from Preparation 64A and 3-fluoroisonicotinic acid according to the procedure for the preparation of Example 5. $^1$H NMR (400 MHz, MeOD): δ 8.14 (s, 1H), 7.84 (d, 1H, J=5.0 Hz), 7.78 (br s, 1H), 7.14 (d, 1H, J=8.5 Hz), 6.61-6.68 (m, 2H), 4.49-4.56 (m, 1H), 3.40-3.57 (m, 2H), 3.07-3.13 (m, 1H), 2.72-2.81 (m, 2H), 1.85-1.94 (m, 3H), 1.71-1.78 (m, 3H), 1.27 (dd, 6H, J=6.0, 1.2 Hz). [M+H] calc'd for $C_{20}H_{24}N_2O_3$, 341; found 341.

Preparation 65A: 1-(6-fluoro-3,4-dihydro-2H-chromen-4-yl)methanamine

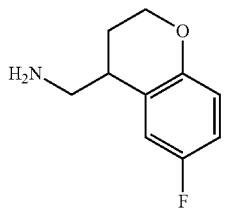 [SMILES: NCC1CCOc2ccc(F)cc21]

To a solution of 6-fluoro-4-chromanone (2.5 g, 15 mmol) and ZnI$_2$ (20 mg) in toluene (30 mL) was added TMS-CN (3.0 g, 30.1 mmol) at rt. The mixture was heated at 60° C. overnight and then was cooled to rt and diluted with THF (20 mL). A solution of lithium aluminum hydride in THF (12.6 mL, 2.4 M, 30.1 mmol) was added dropwise at rt, and the reaction mixture was heated to 40° C. for 4 hr. The reaction was quenched with the addition of EtOAc (10 mL) at rt and was stirred for 30 min. Water (1 mL) and aqueous 1 N NaOH (1 mL) were added, and the mixture was dried (Na$_2$SO$_4$), filtered, and concentrated to give crude intermediate (2.3 g, 80%) as a yellow oil.

To a solution of the intermediate (2.3 g, 12 mmol) in toluene (50 mL) was added 4N HCl/dioxane (20 mL), and the reaction stirred at reflux for 4 hr. The reaction was cooled to rt and filtered to give 1.36 g (63%) of 1-(6-fluoro-2H-chromen-4-yl)methanamine hydrochloride as a white solid. $^1$H NMR (300 MHz, CD$_3$OD): δ 3.97 (2H, s), 4.78-4.80 (2H, m), 6.10 (1H, br s), 6.82-6.87 (1H, m), 6.92-6.96 (1H, m), 7.05-7.09 (1H, m).

To a solution of 1-(6-fluoro-2H-chromen-4-yl)methanamine hydrochloride (1.36 g, 7.6 mmol) in MeOH (20 mL) and AcOH (10 mL) was added Raney Nickel (760 mg) at rt. The suspension was stirred at rt overnight under 50 psi of H$_2$. The reaction mixture was filtered and concentrated. The residue was dissolved in DCM and washed with sat. NaHCO$_3$, dried (Na$_2$SO$_4$), and concentrated to give 490 mg (36%) of the title compound as a green oil. [M+H] calc'd for $C_{10}H_{12}FNO$, 182; found 182.

Example 65: 3-{[(6-fluoro-3,4-dihydro-2H-chromen-4-yl)methyl]amino}pyridine-4-carboxylic acid

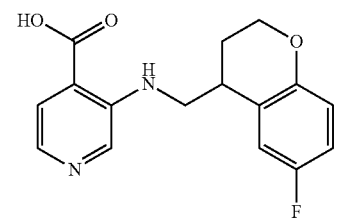 [SMILES: O=C(O)c1ccncc1NCC1CCOc2ccc(F)cc21]

The title compound was prepared in 7% yield from Preparation 65A and 3-fluoroisonicotinic acid according to the procedure for the preparation of Example 3. $^1$H NMR (300 MHz, DMSO-$d_6$): δ 1.17-1.98 (2H, m), 3.12-3.25 (1H, m), 3.38-3.43 (1H, m), 3.70-3.76 (1H, m), 4.12-4.19 (2H, m), 6.75-6.80 (1H, m), 6.91-6.97 (1H, m), 7.17-7.22 (1H, dd, J=3.0 Hz), 7.57 (1H, d, J=4.8 Hz), 7.84 (1H, d, J=5.1 Hz), 8.43 (1H, s). [M+H] Calc'd for $C_{16}H_{15}FN_2O_3$, 302; found, 302.

Preparation 66A: 1-(7-chloro-3,4-dihydro-2H-chromen-4-yl)methanamine, hydrochloride

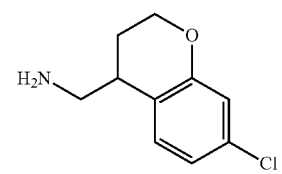 [SMILES: NCC1CCOc2cc(Cl)ccc21]

To a solution of 7-chloro-4-chromanone (5.0 g, 27.4 mmol) and ZnI$_2$ (30 mg) in toluene (50 mL) was added TMS-CN (6.85 mL, 54.8 mmol) at rt. The mixture was heated at 60° C. overnight and then was cooled to rt and diluted with THF (40 mL). This was slowly added to a solution of lithium aluminum hydride (2.08 g, 54.8 mmol) in THF (20 mL) at rt, and the reaction mixture was heated to 42° C. for 4 hr. The reaction was quenched with the addition of EtOAc (10 mL) at rt and was stirred for 30 min. Water (2 mL) and aqueous 1 N NaOH (1 mL) were added, and the mixture stirred 30 min. The mixture was dried (MgSO$_4$), filtered, and concentrated to give crude intermediate (4.8 g, 82%) as a yellow oil.

To a solution of the intermediate (4.8 g, 22.5 mmol) in toluene (60 mL) was added 4N HCl/dioxane (20 mL), and the reaction stirred at reflux 4 hr. The reaction was cooled to rt and concentrated in vacuo. The resulting oily solid was taken up in EtOAc, sonicated, and the solid collected by filtration to give 2.2 g (50%) of 1-(7-chloro-2H-chromen-4-yl)methanamine hydrochloride as white solid. $^1$H NMR (400 MHz, DMSO-d$_6$): δ 8.37 (br s, 3H), 7.37 (d, 1H, J=2.5 Hz), 7.23 (dd, 1H, J=8.6, 2.5 Hz), 6.85 (d, 1H, J=8.6 Hz), 6.10 (s, 1H), 4.80 (t, 2H, J=1.8 Hz), 3.87 (s, 2H). [M+H] calc'd for C$_{10}$H$_{10}$ClNO, 196; found 196.

Hydrogenation of 1-(7-chloro-2H-chromen-4-yl)methanamine hydrochloride (500 mg, 2.6 mmol) was carried out in the presence of Raney Nickel (300 mg) in 2:1 MeOH/HOAc under 50 psi of H$_2$ for 16 hr at 30° C. The reaction was filtered through Celite and concentrated in vacuo. Precipitation from EtOAc and filtration gave 280 mg (56%) of the title compound as a white solid. [M+H] calc'd for C$_{10}$H$_{12}$ClNO, 198; found 198.

Example 66: 3-{[(7-chloro-3,4-dihydro-2H-chromen-4-yl)methyl]amino}pyridine-4-carboxylic acid

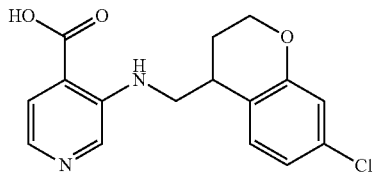

The title compound was prepared in 6% yield from Preparation 66A and 3-fluoroisonicotinic acid according to the procedure for the preparation of Example 5. $^1$H NMR (400 MHz, DMSO-d$_6$): δ 13.38 (br s, 1H), 8.46 (s, 1H), 7.85 (d, 1H, J=5.0 Hz), 7.68 (br s, 1H), 7.57 (d, 1H, J=5.0 Hz), 7.38 (d, 1H, J=2.5 Hz), 7.13 (dd, 1H, J=8.7, 2.6 Hz), 6.79 (d, 1H, J=8.7 Hz), 4.14-4.25 (m, 2H), 3.80-3.76 (m, 1H), 3.49-3.56 (m, 1H), 3.13-3.18 (m, 1H), 1.83-2.02 (m, 2H). [M+H] calc'd for C$_{16}$H$_{15}$ClN$_2$O$_3$, 319; found 319.

Preparation 67A:
1-(6-chloro-1,2,3,4-tetrahydronaphthalen-1 yl)methanamine, hydrochloride

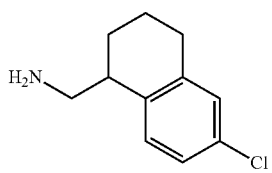 [SMILES: NCC1CCCc2cc(Cl)ccc21]

The title compound was prepared in 55% overall yield from 6-chloro-1-tetralone according to the procedure for Preparation 66A; however, the product was impure and contained significant amounts of over-reduced (de-chlorinated) material, as well as un-reduced (dihydronaphthalene) material. [M+H] calc'd for C$_{10}$H$_{12}$ClNO, 198; found 198.

Example 67: 3-{[(6-chloro-1,2,3,4-tetrahydronaphthalen-1-yl)methyl]amino}pyridine-4-carboxylic acid

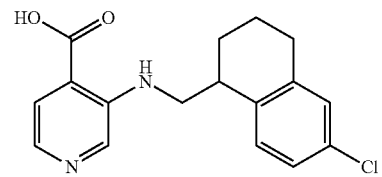 [SMILES: O=C(O)c1ccncc1NCC1CCCc2cc(Cl)ccc21]

The title compound was prepared in 1% yield from Preparation 67A and 3-fluoroisonicotinic acid according to the procedure for the preparation of Example 5. $^1$H NMR (400 MHz, MeOD): 8.08 (s, 1H), 7.77-7.80 (m, 2H), 7.09-7.22 (m, 3H), 3.39-3.54 (m, 2H), 3.12-3.17 (m, 1H), 2.74-2.80 (m, 2H), 1.77-1.97 (m, 4H). [M+H] calc'd for C$_{17}$H$_{17}$ClN$_2$O$_2$, 317; found 317.

Example 68: 3-{[(6-chloro-1-hydroxy-1,2,3,4-tetrahydronaphthalen-1-yl)methyl]amino}pyridine-4-carboxylic acid

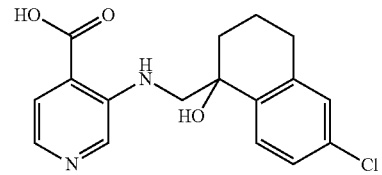 [SMILES: O=C(O)c1ccncc1NCC1(O)CCCc2cc(Cl)ccc21]

The title compound was isolated in <1% yield from the preparation of Example 67. $^1$H NMR (400 MHz, DMSO-d$_6$): δ 13.30 (br s, 1H), 8.26 (s, 1H), 7.84 (br s, 1H), 7.77 (d, 1H, J=5.0 Hz), 7.61 (d, 1H, J=8.4 Hz), 7.52 (d, 1H, J=5.0 Hz), 7.16-7.23 (m, 2H), 5.41 (s, 1H), 3.35-3.55 (m, 2H), 2.73-2.76 (m, 2H), 2.00-2.05 (m, 1H), 1.74-1.82 (m, 3H). [M+H] calc'd for C$_{17}$H$_{17}$ClN$_2$O$_3$, 333; found 333.

Preparation 69A:
1-(7-bromo-2H-chromen-4-yl)methanamine

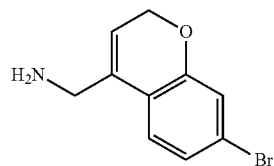

TMS-cyanide (2.2 mL, 17.6 mmol) was added to a solution of 7-bromochroman-4-one (2.0 g, 8.8 mmol) in toluene (20 mL). Zinc iodide (20 mg) was added, and the reaction was stirred at 60° C. for 16 hr. The solution was cooled to rt and diluted with THF (10 mL). This was added to a mixture of lithium aluminum hydride (670 mg, 17.6 mmol) in THF (20 mL), and the reaction mixture was heated at 42° C. for 2 hr. The reaction was cooled to rt. EtOAc (5 mL) was slowly added, and the reaction stirred 30 min. Water (1 mL) and then 5N NaOH (1 mL) were slowly added, and the reaction stirred 1 hr. The reaction mixture was diluted with EtOAc (30 mL), dried (MgSO$_4$), filtered through Celite, and concentrated to give 1.8 g (79%) yellow oil.

The intermediate was taken up in toluene (20 mL). 4N HCl in dioxane (10 mL) was added, and the reaction was heated at reflux under a Dean-Stark condenser for 2 hr. The solution was concentrated in vacuo and taken up in EtOAc. The solid was collected by filtration, and was then dissolved in sat. NaHCO$_3$ and extracted (3×) with EtOAc. Organics were dried (Na$_2$SO$_4$) and concentrated to give 900 mg (54%) of the title compound as a yellow oil. $^1$H NMR (300 MHz, CD$_3$OD): δ 3.98 (2H, s), 4.84-4.87 (2H, m), 6.06 (1H, t, J=3.6 Hz), 7.01 (1H, d, J=1.8 Hz), 7.13 (1H, dd, J=1.8, 8.4 Hz), 7.18 (1H, d, J=8.4 Hz).

Preparation 69B: tert-butyl [(7-bromo-2H-chromen-4-yl)methyl]carbamate

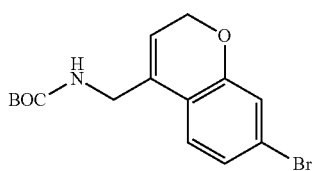 [SMILES: CC(C)(C)OC(=O)NCC1=CCOc2cc(Br)ccc21]

Preparation 69A (900 mg, 3.75 mmol) was dissolved in DCM (60 mL). DIEA (1.65 mL, 9.5 mmol) and then di-tert-butyl dicarbonate (0.99 g, 4.5 mmol) were added, and the reaction stirred at rt for 2 hr. The solution was concentrated and purified by silica gel chromatography (20-80% EtOAc/hexanes to give 886 mg (69%) of the title compound as a yellow foam. $^1$H NMR (400 MHz, CDCl$_3$): δ 6.97-7.03 (m, 3H), 5.72-5.75 (m, 1H), 4.76-4.79 (m, 2H), 4.67 (br s, 1H), 4.08-4.15 (m, 2H), 1.45 (s, 9H). [M+H] calc'd for C$_{15}$H$_{18}$BrNO$_3$, 340, 342; found 340, 342.

Preparation 69C: tert-butyl [(7-phenyl-2H-chromen-4-yl)methyl]carbamate

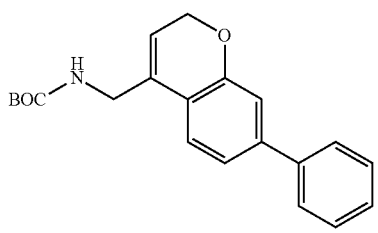 [SMILES: CC(C)(C)OC(=O)NCC1=CCOc2cc(-c3ccccc3)ccc21]

Preparation 69B (820 mg, 2.41 mmol), phenylboronic acid (353 mg, 2.89 mmol), and tetrakis(triphenylphosphine)palladium(0) (417 mg, 0.36 mmol) were combined in dioxane (4 mL) with saturated NaHCO$_3$ (0.5 mL) under N$_2$. The reaction was heated at 122° C. in a microwave for 1 hr. The reaction was diluted with DCM, dried (MgSO$_4$), and concentrated in vacuo. Purification by silica gel chromatography (10-80% EtOAc/hexanes) gave 508 mg (63%) of the title compound as a yellow oil, which slowly solidified overnight. [M+H] calc'd for C$_{21}$H$_{23}$NO$_3$, 338; found 338.

Preparation 69D: 1-(7-phenyl-3,4-dihydro-2H-chromen-4-yl)methanamine

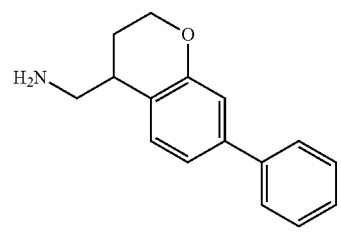 [SMILES: NCC1CCOc2cc(-c3ccccc3)ccc21]

Preparation 69C (508 mg, 1.5 mmol) was stirred in 50% TFA/DCM (6 mL) for 1 hr. The solution was concentrated in vacuo. Hydrogenation was carried out in the presence of 10% Pd/C in 3:1 MeOH:HOAc under 50 psi of H$_2$ for 16 hr. The reaction was filtered through Celite and concentrated in vacuo. Purification by silica gel chromatography (5-15% MeOH/DCM) gave 258 mg (72%) of the title compound as a light yellow oil. $^1$H NMR (400 MHz, MeOD): δ 7.40-7.52 (m, 2H), 7.25-7.33 (m, 2H), 7.16-7.23 (m, 2H), 7.07-7.11 (m, 1H), 6.98 (d, 1H, J=1.6 Hz), 4.11-4.17 (m, 2H), 3.12-3.17 (m, 1H), 3.03-3.09 (m, 2H), 2.05-2.14 (m, 1H), 1.91-1.98 (m, 1H). [M+H] calc'd for C$_{16}$H$_{17}$NO, 240; found 240.

Example 69: 3-{[(7-phenyl-3,4-dihydro-2H-chromen-4-yl)methyl]amino}pyridine-4-carboxylic acid

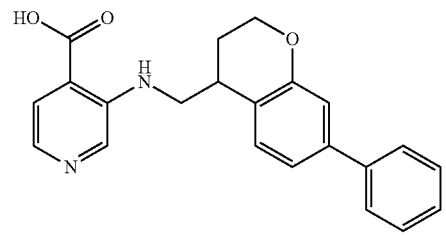

The title compound was prepared in 12% yield from Preparation 69D and 3-fluoroisonicotinic acid according to the procedure for the preparation of Example 53. $^1$H NMR (400 MHz, DMSO-d$_6$): δ 13.38 (br s, 1H), 8.45 (s, 1H), 7.86 (d, 1H, J=5.0 Hz), 7.76 (br s, 1H), 7.57-7.64 (m, 3H), 7.36-7.46 (m, 4H), 7.16 (dd, 1H, J=8.0, 1.8 Hz), 7.05 (d, 1H, J=1.8 Hz), 4.18-4.29 (m, 2H), 3.73-3.77 (m, 1H), 3.52-3.59 (m, 1H), 3.18-3.21 (m, 1H), 1.89-2.07 (m, 2H). [M+H] calc'd for C$_{22}$H$_{20}$N$_2$O$_3$, 361; found 361.

Preparation 70A: 1-(7-fluoro-3,4-dihydro-2H-chromen-4-yl)methanamine

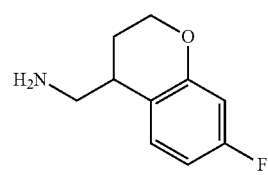 [SMILES: NCC1CCOc2cc(F)ccc21]

The title compound was prepared in 45% overall yield from 7-fluoro-4-chromanone according to the procedure for Preparation 65A. [M+H] calc'd for $C_{10}H_{12}FNO$, 182; found 182.

Example 70: 3-{[(7-fluoro-3,4-dihydro-2H-chromen-4-yl)methyl]amino}pyridine-4-carboxylic acid

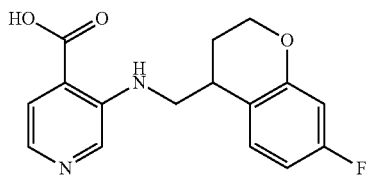

The title compound was prepared in 5% yield from Preparation 70A and 3-fluoroisonicotinic acid according to the procedure for the preparation of Example 3. $^1$H NMR (300 MHz, DMSO-$d_6$): δ 1.89-1.99 (2H, m), 3.10-3.15 (1H, m), 3.47-3.55 (1H, m), 3.65-3.71 (1H, m), 4.17-4.23 (2H, m), 6.60-6.72 (2H, m), 7.31-7.36 (1H, m), 7.59 (1H, d, J=5.1 Hz), 7.85 (1H, d, J=5.1 Hz), 8.42 (1H, s). [M+H] Calc'd for $C_{16}H_{15}FN_2O_3$, 302; found, 302.

Preparation 71A: 1-(8-fluoro-3,4-dihydro-2H-chromen-4-yl)methanamine

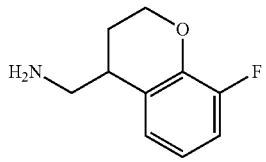 [SMILES: NCC1CCOc2c(F)cccc21]

The title compound was prepared in 24% overall yield from 8-fluoro-4-chromanone according to the procedure for Preparation 65A. [M+H] calc'd for $C_{10}H_{12}FNO$, 182; found 182.

Example 71: 3-{[(8-fluoro-3,4-dihydro-2H-chromen-4-yl)methyl]amino}pyridine-4-carboxylic acid

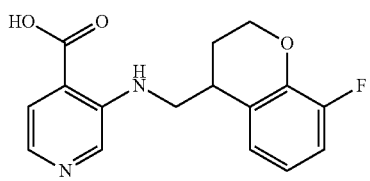

The title compound was prepared in 7% yield from Preparation 71A and 3-fluoroisonicotinic acid according to the procedure for the preparation of Example 3. $^1$H NMR (300 MHz, DMSO-$d_6$): δ 1.88-2.04 (2H, m), 3.19-3.23 (1H, m), 3.53-3.60 (1H, m), 3.69-3.75 (1H, m), 4.21-4.28 (2H, m), 6.79-6.86 (1H, m), 7.01-7.08 (1H, m), 7.13 (1H, d, J=3.6 Hz), 7.75 (1H, d, J=5.1 Hz), 7.92 (1H, s), 8.48 (1H, s). [M+H] Calc'd for $C_{16}H_{15}FN_2O_3$, 302; found, 302.

Preparation 72A: 1-(7-chloro-1,2,3,4-tetrahydronaphthalen-1-yl)methanamine, hydrochloride

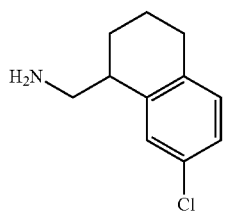 [SMILES: NCC1CCCc2ccc(Cl)cc21]

The title compound was prepared in 25% overall yield from 7-chloro-1-tetralone according to the procedure for Preparation 66A; however, the product was impure and contained significant amounts of over-reduced (de-chlorinated) material, as well as un-reduced (dihydronaphthalene) material. [M+H] calc'd for $C_{10}H_{12}ClNO$, 198; found 198.

Example 72: 3-{[(7-chloro-1,2,3,4-tetrahydronaphthalen-1-yl)methyl]amino}pyridine-4-carboxylic acid

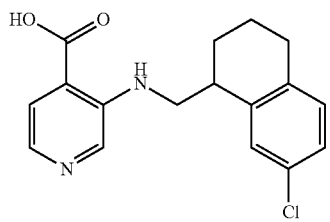

The title compound was prepared in 1% yield from Preparation 72A and 3-fluoroisonicotinic acid according to the procedure for the preparation of Example 5. $^1$H NMR (400 MHz, MeOD): δ 8.15 (s, 1H), 7.76-7.82 (m, 2H), 7.26 (s, 1H), 7.06-7.10 (m, 2H), 3.43-3.60 (m, 2H), 3.12-3.16 (m, 1H), 2.74-2.83 (m, 2H), 1.76-1.99 (m, 4H). [M+H] calc'd for $C_{17}H_{17}ClN_2O_2$, 317; found 317.

Preparation 73A: 7-phenyl-3,4-dihydronaphthalen-1(2H)-one

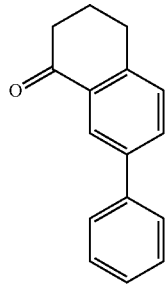 [SMILES: O=C1CCCc2ccc(-c3ccccc3)cc21]

The title compound was prepared in 79% yield from 6-bromo-chroman-4-one according to the general procedure for Preparation 69C. [M+H] calc'd for $C_{16}H_{14}O$, 223; found 223.

Preparation 73B: 1-(7-phenyl-1,2,3,4-tetrahydronaphthalen-1yl)methanamine, hydrochloride

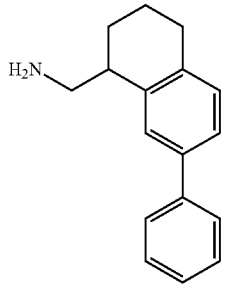 [SMILES: NCC1CCCc2ccc(-c3ccccc3)cc21]

The title compound was prepared in 42% yield from Preparation 73A according to the general procedure for Preparation 60A. $^1$H NMR (400 MHz, MeOD): δ 7.61 (dd, 2H, J=8.1, 1.2 Hz), 7.53 (d, 1H, J=1.7 Hz), 7.37-7.42 (m, 3H), 7.29-7.32 (m, 1H), 7.15 (d, 1H, J=8.0 Hz), 3.27-3.37 (m, 2H), 3.11-3.17 (m, 1H), 2.76-2.82 (m, 2H), 1.78-1.98 (m, 4H). [M+H] calc'd for $C_{17}H_{19}N$, 238; found 238.

Example 73: 3-{[(7-phenyl-1,2,3,4-tetrahydronaphthalen-1-yl)methyl]amino}pyridine-4-carboxylic acid

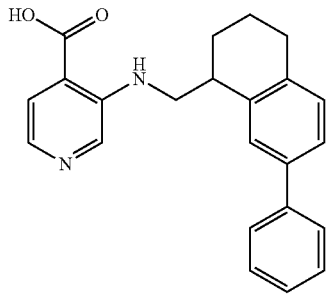 [SMILES: O=C(O)c1ccncc1NCC1CCCc2ccc(-c3ccccc3)cc21]

The title compound was prepared in 7% yield from Preparation 73B and 3-fluoroisonicotinic acid according to the procedure for the preparation of Example 5. $^1$H NMR (400 MHz, DMSO-d$_6$): δ 13.38 (br s, 1H), 8.42 (s, 1H), 7.83 (d, 1H, J=5.0 Hz), 7.76 (br s, 1H), 7.63 (d, 2H, J=7.2 Hz), 7.57 (d, 1H, J=5.0 Hz), 7.56 (s, 1H), 7.40-7.45 (m, 3H), 7.32 (t, 1H, J=7.4 Hz), 7.18 (d, 1H, J=8.0 Hz), 3.67-3.72 (m, 1H), 3.49-3.55 (m, 1H), 3.19-3.23 (m, 1H), 2.74-2.84 (m, 2H), 1.71-1.92 (m, 4H). [M+H] calc'd for $C_{23}H_{22}N_2O_2$, 359; found 359.

Preparation 74A: 5-methoxy-1,2,3,4-tetrahydronaphthalen-1-yl)methanamine

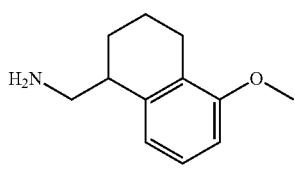

The title compound was prepared in 39% overall yield from 5-methoxy-1-tetralone according to the procedure for Preparation 63A. [M+H] calc'd for $C_{12}H_{17}NO$, 192; found 192.

Example 74: 3-{[(5-methoxy-1,2,3,4-tetrahydronaphthalen-1-yl)methyl]amino}pyridine-4-carboxylic acid

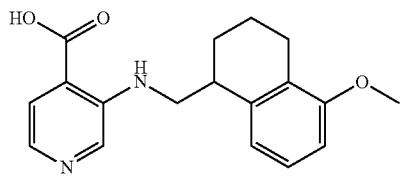 [SMILES: COc1cccc2c1CCCC2CNc1cnccc1C(=O)O]

The title compound was prepared in 22% yield from Preparation 74A and 3-fluoroisonicotinic acid according to the procedure for the preparation of Example 3. $^1$H NMR (300 MHz, DMSO-d$_6$): δ 1.68-1.78 (4H, m), 2.48-2.51 (1H, m), 2.61-2.65 (1H, m), 3.07-3.11 (1H, m), 3.42-3.56 (2H, m), 3.76 (3H, s), 6.77 (1H, d, J=7.8 Hz), 6.91 (1H, d, J=7.8 Hz), 7.11 (1H, t, J=8.1 Hz), 7.56 (1H, d, J=4.8 Hz), 7.83 (1H, d, J=5.1 Hz), 8.36 (1H, s). [M+H] Calc'd for $C_{18}H_{20}N_2O_3$, 313; found, 313.

Preparation 75A: methyl 3-{[(6-bromo-3,4-dihydronaphthalen-1-yl)methyl]amino}pyridine-4-carboxylate

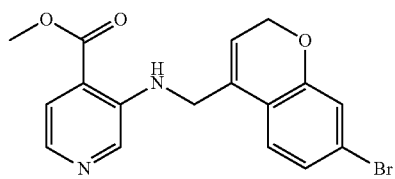 [SMILES: COC(=O)c1ccncc1NCC1=CCOc2cc(Br)ccc21]

To a solution of Preparation 69A (100 mg, 0.42 mmol) in DMA (5 mL) was added methyl 3-fluoroisonicotinate (65 mg, 0.42 mmol) at rt. The reaction was stirred at 170° C. for 1 h in a microwave. The reaction mixture was diluted with water extracted with EtOAc. Organics were washed with brine, dried (Na$_2$SO$_4$), and concentrated. Purification by silica gel chromatography (5:1 PE/EtOAc) gave 50 mg (32%) of the title compound as a yellow solid. $^1$H NMR (300 MHz, CDCl$_3$): δ 3.92 (3H, s), 4.27-4.28 (2H, m), 4.81-4.82 (2H, m), 5.78-5.80 (1H, m), 7.00-7.08 (3H, m), 7.65-7.69 (2H, m), 7.97 (1H, d, J=5.1 Hz), 8.20 (1H, s).

Preparation 75B: methyl 3-{[(6-cyclopropyl-3,4-dihydronaphthalen-1-yl)methyl]amino}pyridine-4-carboxylate

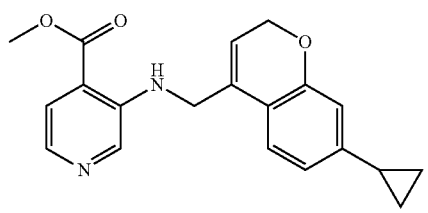 [SMILES: COC(=O)c1ccncc1NCC1=CCOc2cc(C3CC3)ccc21]

The title compound was prepared in 55% yield from Preparation 75A according to the general procedure for Preparation 19C. ¹H NMR (300 MHz, CDCl₃): δ 0.68-0.73 (2H, m), 0.94-1.00 (2H, m), 1.82-1.88 (1H, m), 3.92 (3H, s), 4.27-4.30 (2H, m), 4.76-4.79 (2H, m), 5.70-5.72 (1H, m), 6.55 (1H, d, J=1.8 Hz), 6.68 (1H, dd, J=1.8, 7.8 Hz), 7.06 (1H, d, J=7.8 Hz), 7.64-7.69 (2H, m), 7.96 (1H, d, J=5.1 Hz), 8.23 (1H, s).

Preparation 75C: methyl 3-{[(7-cyclopropyl-3,4-dihydro-2H-chromen-4-yl)methyl]amino}pyridine-4-carboxylate

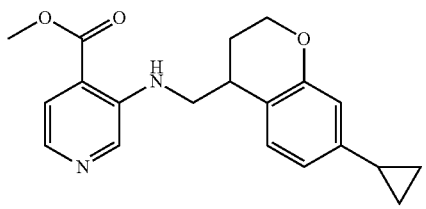 [SMILES: COC(=O)c1ccncc1NCC1CCOc2cc(C3CC3)ccc21]

To a solution of Preparation 75B (200 mg, 0.6 mmol) in MeOH (10 mL) and AcOH (2 mL) was added 10% Pd/C (30 mg) under N₂ at rt. The mixture was heated at 80° C. overnight under 2.0 MPa H₂. The reaction was filtered and concentrated in vacuo to give the crude title compound. [M+H] Calc'd for C₂₀H₂₂N₂O₃, 339; found, 339.

Example 75: 3-{[(7-cyclopropyl-3,4-dihydro-2H-chromen-4-yl)methyl]amino}pyridine-4-carboxylic acid

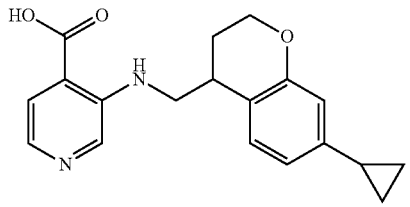

The title compound was prepared in 70% yield from Example 75C according to the general hydrolysis procedure outlined for Example 13. ¹H NMR (300 MHz, DMSO-d₆): δ 0.58-0.62 (2H, m), 0.87-0.92 (2H, m), 1.79-1.98 (3H, m), 3.05-3.10 (1H, m), 3.44-3.51 (1H, m), 3.63-3.68 (1H, m), 4.11-4.16 (2H, m), 6.46 (1H, s), 6.57 (1H, d, J=8.4 Hz), 7.16 (1H, d, J=7.8 Hz), 7.57 (1H, d, J=4.8 Hz), 7.85 (1H, d, J=3.6 Hz), 8.41 (1H, s). [M+H] Calc'd for C₁₉H₂₀N₂O₃, 325; found, 325.

Preparation 76A: 5-(cyclopropylmethoxy)-3,4-dihydronaphthalen-1(2H)-one

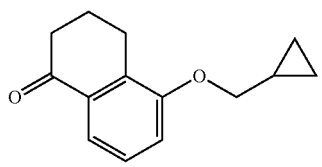 [SMILES: O=C1CCCc2c(OCC3CC3)cccc21]

To a solution of 5-hydroxy-1-tetralone (1.8 g, 11.0 mmol) in butanone was added (bromomethyl)cyclopropane (1.8 g, 13.2 mmol) and K₂CO₃ (3.0 g, 22.0 mmol) at rt. The mixture was heated at 80° C. overnight. The reaction was cooled to rt, diluted with EtOAc, filtered, and concentrated. The residue was purified by silica gel chromatography (20:1 PE/EtOAc) to give 1.9 g (78%) of the title compound as a tan oil. ¹H NMR (300 MHz, CDCl₃): δ 0.35-0.40 (2H, m), 0.62-0.68 (2H, m), 1.27-1.32 (1H, m), 2.05-2.17 (2H, m), 2.64 (2H, t, J=6.6 Hz), 2.96 (2H, t, J=6.0 Hz), 3.86 (2H, d, J=6.9 Hz), 6.98 (1H, d, J=8.1 Hz), 7.24 (1H, t, J=8.7 Hz), 7.65 (1H, d, J=8.1 Hz).

Preparation 76B: 1-[5-(cyclopropylmethoxy)-1,2,3,4-tetrahydronaphthalen-1-yl]methanamine

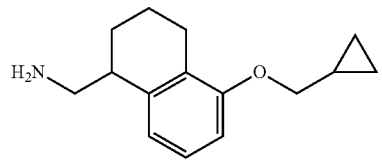 [SMILES: NCC1CCCc2c(OCC3CC3)cccc21]

The title compound was prepared in 33% overall yield from Preparation 76A according to the procedure for Preparation 63A, with the exception that the dehydration step ran for 2 hr instead of overnight. [M+H] calc'd for C₁₅H₂₁NO, 232; found 232.

Example 76: 3-({[(5-(cyclopropylmethoxy)-1,2,3,4-tetrahydronaphthalen-1-yl]methyl}amino)pyridine-4-carboxylic acid

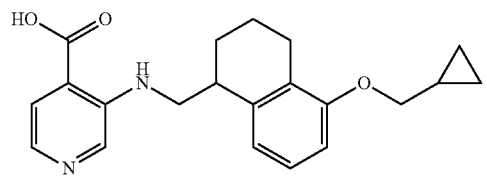 [SMILES: O=C(O)c1ccncc1NCC1CCCc2c(OCC3CC3)cccc21]

The title compound was prepared in 6% yield from Preparation 76B and 3-fluoroisonicotinic acid according to the procedure for the preparation of Example 3. ¹H NMR (300 MHz, DMSO-d₆): δ 0.30-0.35 (2H, m), 0.53-0.59 (2H, m), 1.19-1.24 (1H, m), 1.67-1.83 (4H, m), 2.53-2.57 (1H, m), 2.64-2.73 (1H, m), 3.07-3.09 (1H, m), 3.34-3.59 (2H, m), 3.75-3.85 (2H, m), 6.72 (1H, d, J=7.8 Hz), 6.88 (1H, d, J=4.8 Hz), 7.03-7.09 (1H, m), 7.55 (1H, d, J=4.8 Hz), 7.83 (1H, d, J=4.2 Hz), 8.36 (1H, s). [M+H] Calc'd for C₂₁H₂₄N₂O₃, 352; Found, 352.

Preparation 77A: 5-phenoxy-3,4-dihydronaphthalen-1(2H)-one

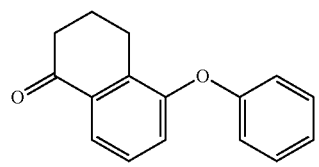 [SMILES: O=C1CCCc2c(Oc3ccccc3)cccc21]

To a solution of 5-hydroxy-1-tetralone (4.5 g, 28.0 mmol) and iodobenzene (24.0 g, 168.0 mmol) in DMF (50 mL) was added NaH (1.2 g, 30.0 mmol) at rt. The mixture was heated to 50° C. until the solid was dissolved and then cooled. To the mixture was added CuCl (2.8 g, 28.0 mmol); followed by tris(dioxa 3,6-heptyl)amine (2.7 g, 8.4 mmol). The mixture was heated at 145° C. overnight. The reaction was diluted with water, extracted with EtOAc, washed with brine, dried ($Na_2SO_4$), and concentrated. Purification by silica gel chromatography (20:1 PE/EtOAc) gave 1.2 g (18%) of the title compound as a yellow oil. [M+H] calc'd for $C_{16}H_{14}O_2$, 239; found 239.

Preparation 77B: 5-phenoxy-1,2,3,4-tetrahydronaphthalen-1-yl)methanamine

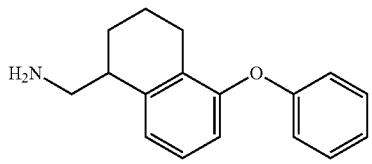 [SMILES: NCC1CCCc2c(Oc3ccccc3)cccc21]

The title compound was prepared in 81% overall yield from Preparation 77A according to the procedure for Preparation 63A. [M+H] calc'd for $C_{17}H_{19}NO$, 254; found 254.

Example 77: 3-{[(5-phenoxy-1,2,3,4-tetrahydronaphthalen-1-yl)methyl]amino}pyridine-4-carboxylic acid

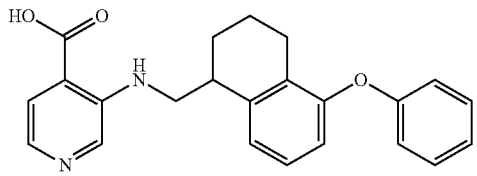 [SMILES: O=C(O)c1ccncc1NCC1CCCc2c(Oc3ccccc3)cccc21]

The title compound was prepared in 3% yield from Preparation 77B and 3-fluoroisonicotinic acid according to the procedure for the preparation of Example 3. $^1$H NMR (300 MHz, $CF_3CO_2D$): δ 1.71-1.95 (4H, m), 2.59-2.67 (2H, m), 3.22-3.26 (1H, m), 3.56-3.61 (2H, m), 6.74-6.83 (3H, m), 6.92-7.04 (3H, m), 7.14-7.19 (2H, m), 7.76-7.78 (1H, m), 8.05 (1H, s), 8.29 (1H, d, J=5.7 Hz). [M+H] Calc'd for $C_{23}H_{22}N_2O_3$, 374; found, 374.

Preparation 78A: 1-(3,4-dihydro-2H-thiochromen-4-yl)methanamine

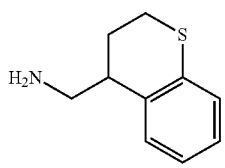 [SMILES: NCC1CCSc2ccccc21]

The title compound was prepared in 34% overall yield from thiochroman-4-one according to the procedure for Preparation 63A, with the exception that the dehydration step ran for 2 hr instead of overnight. [M+H] calc'd for $C_{10}H_{13}NS$, 180; found 180.

Example 78: 3-[(3,4-dihydro-2H-thiochromen-4-ylmethyl)amino]pyridine-4-carboxylic acid

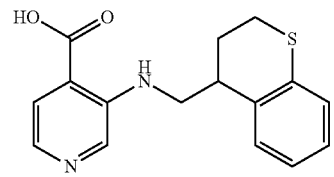

The title compound was prepared in 24% yield from Preparation 78A and 3-fluoroisonicotinic acid according to the procedure for the preparation of Example 3. $^1$H NMR (300 MHz, DMSO-$d_6$): δ 1.87-1.95 (1H, m), 2.21-2.28 (1H, m), 2.92-2.99 (1H, m), 3.18-3.27 (2H, m), 3.48-3.53 (2H, m), 6.97-7.02 (1H, m), 7.07-7.09 (2H, m), 7.21 (1H, d, J=7.8 Hz), 7.57 (1H, d, J=5.1 Hz), 7.83 (1H, d, J=5.1 Hz), 8.37 (1H, s). [M+H] Calc'd for $C_{16}H_{16}N_2O_2S$, 301; found, 301.

Preparation 79A: 6-(3,3,3-trifluoropropoxy)-3,4-dihydronaphthalen-1(2H)-one

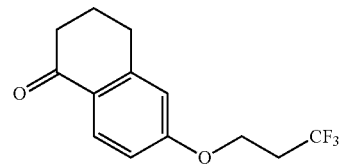 [SMILES: O=C1CCCc2cc(OCCC(F)(F)F)ccc21]

6-Hydroxy-1-tetralone (3.5 g, 21.6 mmol), 3,3,3-trifluoro-1-propanol (4.93 g, 43.2 mmol) and triphenylphosphine (11.3 g, 43.2 mmol) were combined in THF (80 mL). DIAD (8.7 g, 43.2 mmol) was added, and the reaction stirred overnight at rt. The solution was diluted with EtOAc (100 mL) and washed with brine. Organics were dried ($MgSO_4$) and concentrated. Purification by silica gel chromatography (10-50% EtOAc/hexanes) gave 2.93 g (53%) of the title compound as a clear oil. $^1$H NMR (400 MHz, DMSO-$d_6$): δ 8.02 (d, 1H, J=8.7 Hz), 6.82 (dd, 1H, J=8.7, 2.5 Hz), 6.71 (d, 1H, J=2.4 Hz), 4.25 (t, 2H, J=6.6 Hz), 2.93 (t, 2H, J=6.1 Hz), 2.59-2.71 (m, 4H), 2.08-2.16 (m, 2H). [M+H] calc'd for $C_{13}H_{13}F_3O_2$, 259; found 259.

Preparation 79B: 1-[6-(3,3,3-trifluoropropoxy)-1,2,3,4-tetrahydronaphthalen-1 yl]methanamine, hydrochloride

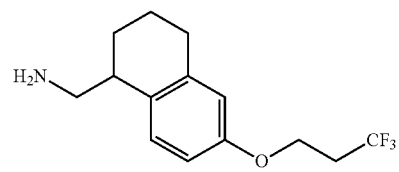 [SMILES: NCC1CCCc2cc(OCCC(F)(F)F)ccc21]

The title compound was prepared in 47% yield from Preparation 79A according to the general procedure for Preparation 60A. ¹H NMR (400 MHz, DMSO-d₆): δ 8.07 (br s, 3H), 7.17 (d, 1H, J=8.6 Hz), 6.76 (dd, 1H, J=8.5, 2.7 Hz), 6.69 (d, 1H, J=2.6 Hz), 4.16 (t, 2H, J=5.9 Hz), 3.00-3.06 (m, 2H), 2.5-2.0 (m, 5H), 1.61-1.86 (m, 4H). [M+H] calc'd for C₁₄H₁₈F₃NO, 274; found 274.

Example 79: 3-({[(6-(3,3,3-trifluoropropoxy)-1,2,3,4-tetrahydronaphthalen-1-yl]methyl}amino)pyridine-4-carboxylic acid

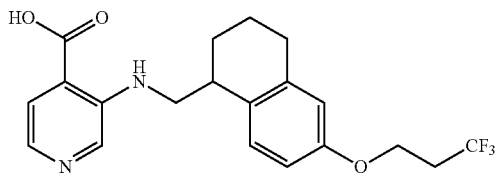

The title compound was prepared in 16% yield from Preparation 79B and 3-fluoroisonicotinic acid according to the procedure for the preparation of Example 5. ¹H NMR (400 MHz, DMSO-d₆): δ 8.29 (s, 1H), 7.80 (d, 1H, J=5.0 Hz), 7.56 (d, 1H, J=5.0 Hz), 7.23 (d, 1H, J=8.5 Hz), 6.68-6.75 (m, 2H), 4.16 (t, 2H, J=5.9 Hz), 3.49-3.55 (m, 1H), 3.34-3.41 (m, 1H), 3.02-3.06 (m, 1H), 2.67-2.81 (m, 4H), 1.64-1.83 (m, 4H). [M+H] calc'd for C₂₀H₂₁F₃N₂O₃, 395; found 395.

Preparation 80A:
6-phenoxy-3,4-dihydronaphthalen-1(2H)-one

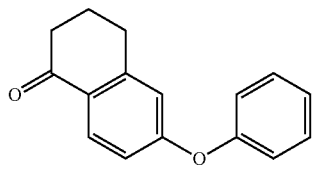 [SMILES: O=C1CCCc2cc(Oc3ccccc3)ccc21]

The title compound was prepared in 21% yield from 6-hydroxy-1-tetralone according to the procedure for Preparation 77A. ¹H NMR (300 MHz, CDCl₃): δ 2.09-2.18 (2H, m), 2.64 (2H, t, J=6.01 Hz), 2.91 (2H, t, J=6.01 Hz), 6.78 (1H, d, J=2.1 Hz), 6.88 (1H, dd, J=2.7, 8.7 Hz), 7.10 (2H, d, J=7.5 Hz), 7.22 (1H, t, J=7.5 Hz), 7.45 (2H, t, J=7.8 Hz), 8.05 (1H, d, J=8.7 Hz).

Preparation 80B: 6-phenoxy-1,2,3,4-tetrahydronaphthalen-1-yl)methanamine

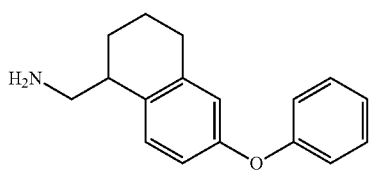 [SMILES: NCC1CCCc2cc(Oc3ccccc3)ccc21]

The title compound was prepared in 70% overall yield from Preparation 80A according to the procedure for Preparation 63A. [M+H] calc'd for C₁₇H₁₉NO, 254; found 254.

Example 80: 3-{[(5-phenoxy-1,2,3,4-tetrahydronaphthalen-1-yl)methyl]amino}pyridine-4-carboxylic acid

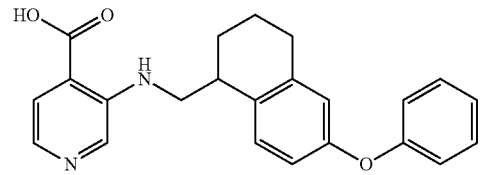 [SMILES: O=C(O)c1ccncc1NCC1CCCc2cc(Oc3ccccc3)ccc21]

The title compound was prepared in 27% yield from Preparation 80B and 3-fluoroisonicotinic acid according to the procedure for the preparation of Example 3. ¹H NMR (400 MHz, DMSO-d₆): δ ¹H NMR (300 MHz, DMSO-d₆): δ 1.62-1.86 (4H, m), 2.67-2.71 (2H, m), 3.09-3.13 (1H, m), 3.43-3.47 (1H, m), 3.50-3.58 (1H, m), 6.74-6.79 (2H, m), 6.97 (2H, d, J=7.5 Hz), 7.11 (1H, t, J=7.5 Hz), 7.32-7.40 (3H, m), 7.58 (1H, d, J=5.1 Hz), 7.84 (1H, d, J=5.1 Hz), 8.37 (1H, s). [M+H] Calc'd for C₂₃H₂₂N₂O₃, 375; found, 375.

Preparation 81A: 6-(cyclopropylmethoxy)-3,4-dihydronaphthalen-1(2H)-one

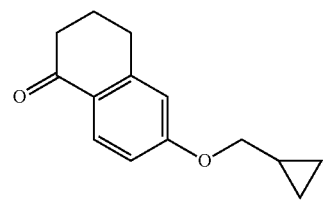 [SMILES: O=C1CCCc2cc(OCC3CC3)ccc21]

To a solution of 6-hydroxy-1-tetralone (2.0 g, 12.3 mmol) in ACN (30 mL) was added (bromomethyl)cyclopropane (2.0 g, 14.7 mmol) and K₂CO₃ (3.4 g, 24.6 mmol) at rt. The mixture was heated at 80° C. overnight. After the reaction was cooled to rt, it was diluted with EtOAc, filtered, and concentrated. The residue was purified by column chromatography (20:1 PE/EtOAc) to give 2.3 g (87%) of the title compound as a yellow solid. ¹H NMR (300 MHz, CDCl₃): δ 0.35-0.40 (2H, m), 0.65-0.71 (2H, m), 1.25-1.32 (1H, m), 2.08-2.16 (2H, m), 2.62 (2H, t, J=6.3 Hz), 2.93 (2H, t, J=6.0 Hz), 3.87 (2H, d, J=7.2 Hz), 6.71 (1H, s), 6.83 (1H, dd, J=2.1, 8.4 Hz), 8.01 (1H, d, J=8.4 Hz).

Preparation 81B: 1-[6-(cyclopropylmethoxy)-1,2,3,4-tetrahydronaphthalen-1-yl]methanamine

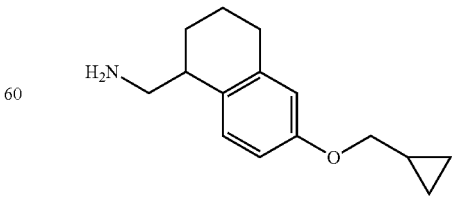

The title compound was prepared in 33% overall yield from Preparation 81A according to the procedure for Preparation 63A, with the exception that the dehydration step ran for 2 h instead of overnight. [M+H] calc'd for $C_{15}H_{21}NO$, 232; found 232.

Example 81: 3-({[(6-(cyclopropylmethoxy)-1,2,3,4-tetrahydronaphthalen-1-yl]methyl}amino)pyridine-4-carboxylic acid

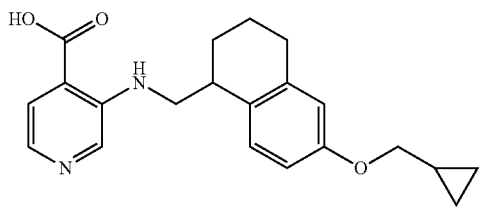 [SMILES: O=C(O)c1ccncc1NCC1CCCc2cc(OCC3CC3)ccc21]

The title compound was prepared in 22% yield from Preparation 81B and 3-fluoroisonicotinic acid according to the procedure for the preparation of Example 3. $^1$H NMR (300 MHz, DMSO-$d_6$): δ 0.29-0.34 (2H, m), 0.52-0.58 (2H, m), 1.16-1.20 (1H, m), 1.63-1.83 (4H, m), 2.66-2.70 (2H, m), 3.02-3.05 (1H, m), 3.40-3.45 (1H, m), 3.51-3.52 (1H, m), 3.75 (2H, d, J=6.9 Hz), 6.63 (1H, d, J=2.1 Hz), 6.68 (1H, dd, J=2.7, 8.4 Hz), 7.19 (1H, d, J=8.7 Hz), 7.55 (1H, d, J=5.1 Hz), 7.83 (1H, d, J=5.1 Hz), 8.35 (1H, s). [M+H] Calc'd for $C_{21}H_{24}N_2O_3$, 353; found, 353.

Example 82: 3{[(1-methyl-1,2,3,4-tetrahydroquinolin-4-yl)methyl]amino}pyridine-4-carboxylic acid

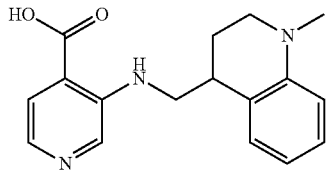 [SMILES: CN1CCC(CNc2cnccc2C(=O)O)c2ccccc21]

The title compound was prepared in 18% yield from 1-(1-methyl-1,2,3,4-tetrahydroquinolin-4-yl)methanamine and 3-fluoroisonicotinic acid according to the procedure for the preparation of Example 53. $^1$H NMR (400 MHz, DMSO-$d_6$): δ 13.36 (br s, 1H), 8.35 (s, 1H), 7.83 (d, 1H, J=5.0 Hz), 7.72 (br s, 1H), 7.56 (d, 1H, J=5.0 Hz), 7.01-7.08 (m, 2H), 6.52-6.62 (m, 2H), 3.45-3.51 (m, 2H), 3.04-3.32 (m, 3H), 2.85 (s, 3H), 1.89-1.95 (m, 2H). [M+H] calc'd for $C_{17}H_{19}N_3O_2$, 298; found 298.

Preparation 83A: methyl 3-{[(7-phenyl-3,4-dihydro-2H-chromen-4-yl)methyl]amino}pyridine-4-carboxylate

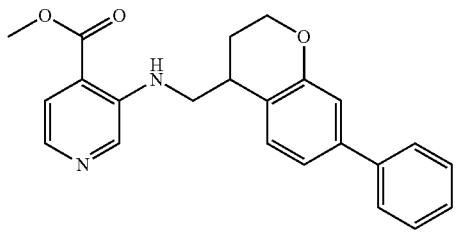 [SMILES: COC(=O)c1ccncc1NCC1CCOc2cc(-c3ccccc3)ccc21]

To a solution of Preparation 69D (700 mg, 2.9 mmol) in DMA (10 mL) was added methyl 3-fluoropyridine-4-carboxylate (500 mg, 3.2 mmol) at rt. The reaction was stirred at 170° C. for 1 hr in a microwave. Purification by silica gel chromatography (PE:EtOAc=2:1) gave 380 mg (35%) of the title compound as a yellow oil. [M+H] calc'd for $C_{23}H_{22}N_2O_3$, 375; found 375.

Preparation 83B and Preparation 84B: methyl 3-({[(4S)-7-phenyl-3,4-dihydro-2H-chromen-4-yl]methyl}amino)pyridine-4-carboxylate; methyl 3-({[(4R)-7-phenyl-3,4-dihydro-2H-chromen-4-yl]methyl}amino)pyridine-4-carboxylate

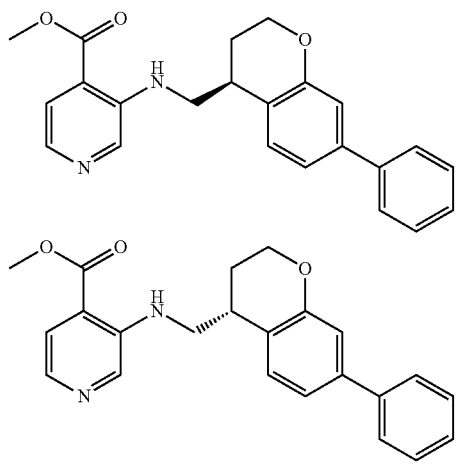

Preparation 83A (380 mg) was separated by chiral HPLC (Column: Chiralcel OD-H, 250 mm*4.6 mm 5 μm; Mobile phase: Hex:IPA=40:60; F: 1.0 mL/min; W: 230 nm; T=30° C.) to give to give the two enantiomers: 120 mg (32%) of the first isomer eluted at 10.39 min and 100 mg (26%) of the second isomer eluted at 13.88 min.

Example 83 and Example 84: 3-({[(4S)-7-phenyl-3,4-dihydro-2H-chromen-4-yl]methyl}-amino)pyridine-4-carboxylic acid; 3-({[(4R)-7-phenyl-3,4-dihydro-2H-chromen-4-yl]methyl}-amino)pyridine-4-carboxylic acid

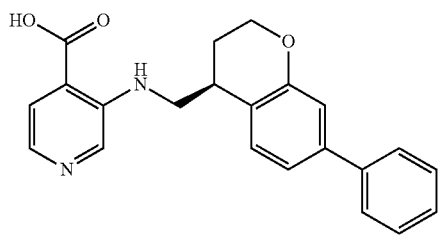

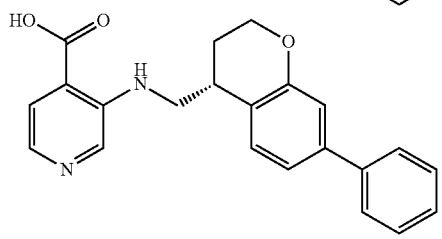

The title compounds were prepared in 83% to 85% yield from Preparation 83B and Preparation 84B according to the general hydrolysis procedure outlined for Example 61 and Example 62. NMR and MS for each of the title compounds matched Example 69.

Preparation 85A:
7-(3-fluorophenyl)-3,4-dihydro-2H-chromen-4-one

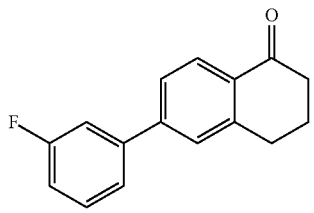 [SMILES: O=C1CCCc2cc(-c3cccc(F)c3)ccc21]

To a solution of 6-bromo-3,4-dihydro-2H-chromen-4-one (1.5 g, 6.6 mmol), 3-fluorophenylboronic acid (1.39 g, 9.9 mmol) and sodium carbonate (2.1 g, 19.8 mmol) in dioxane (20 mL) and water (1 mL) was added Pd(PPh$_3$)$_4$(382 mg, 0.3 mmol) at rt. The solution was heated at 100° C. overnight. The reaction was filtered, concentrated, and purified by silica gel chromatography (PE:EtOAc:DCM=10:1:2) to give 1.4 g (88%) of the title compound as a white solid. $^1$H NMR (300 MHz, CDCl$_3$): δ 2.86 (2H, t, J=6.6 Hz), 4.60 (2H, t, J=6.6 Hz), 7.11-7.14 (1H, m), 7.18 (1H, d, J=1.5 Hz), 7.23-7.29 (2H, m), 7.32-7.45 (2H, m), 7.98 (1H, d, J=8.1 Hz).

Preparation 85B: [7-(3-fluorophenyl)-3,4-dihydro-2H-chromen-4-yl]methanamine

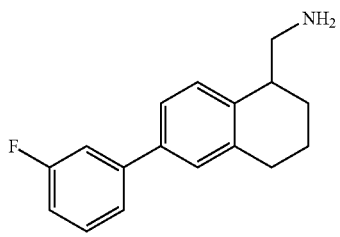 [SMILES: NCC1CCCc2cc(-c3cccc(F)c3)ccc21]

The title compound was prepared in 27% yield from Preparation 85A according to the general procedure for Preparation 63A. [M+H] calc'd for C$_{16}$H$_{16}$FNO, 258; found 258.

Preparation 85C: methyl 3-({[7-(3-fluorophenyl)-3,4-dihydro-2H-chromen-4-yl]methyl}amino)pyridine-4-carboxylate

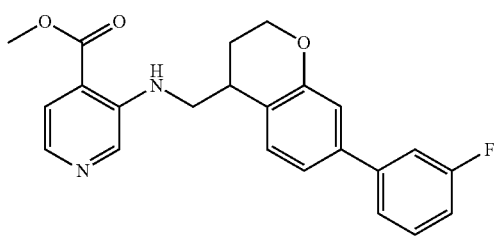 [SMILES: COC(=O)c1ccncc1NCC1CCOc2cc(-c3cccc(F)c3)ccc21]

The title compound was prepared from in 31% yield from Preparation 85B according to the general procedure outlined for Preparation 83A. [M+H] calc'd for C$_{23}$H$_{21}$FN$_2$O$_3$, 393; found 393.

Preparation 85D and Preparation 86D: methyl 3-({[(4S)-7-(3-fluorophenyl)-3,4-dihydro-2H-chromen-4-yl]methyl}amino)pyridine-4-carboxylate; methyl 3-({[(4R)-7-(3-fluorophenyl)-3,4-dihydro-2H-chromen-4-yl]methyl}amino)pyridine-4-carboxylate

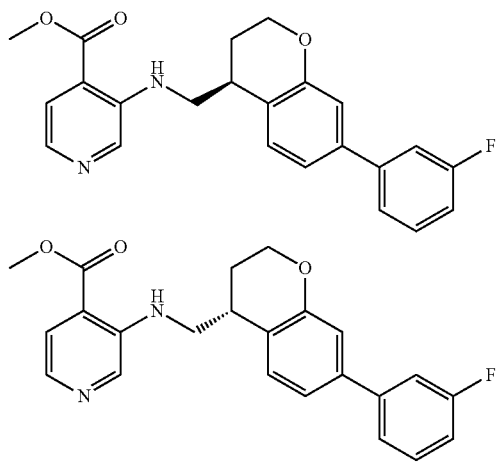

Preparation 85C (88 mg) was separated by chiral HPLC (Column: Chiralcel OD-H, 250 mm*4.6 mm 5 um; Mobile phase: Hex:IPA=70:30; F: 1.0 mL/min; W: 230 nm; T=30° C.) to give to give the two enantiomers: 27 mg (31%) of the first isomer eluted at 9.11 min and 25 mg (28%) of the second isomer eluted at 10.30 min.

Example 85 and Example 86: 3-({[(4S)-7-(3-fluorophenyl)-3,4-dihydro-2H-chromen-4-yl]methyl}amino)pyridine-4-carboxylic acid; 3-({[(4R)-7-(3-fluorophenyl)-3,4-dihydro-2H-chromen-4-yl]methyl}amino)pyridine-4-carboxylic acid

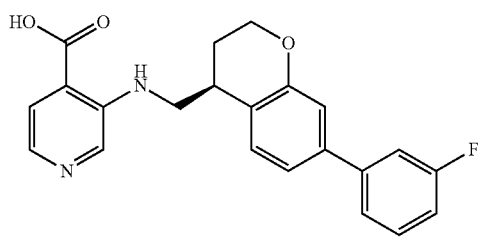

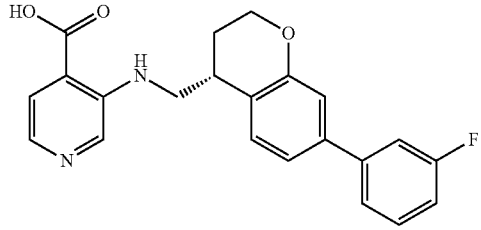

The title compounds were prepared in 78% to 83% yield from Preparation 85D and Preparation 86D according to the general hydrolysis procedure outline for Example 61 and Example 62. NMR and MS for each of the title compounds were identical: $^1$H NMR (300 MHz, DMSO-$d_6$): δ 1.92-2.03 (2H, m), 3.17-3.21 (1H, m), 3.56-3.59 (1H, m), 3.71-3.73 (1H, m), 4.21-4.26 (2H, m), 7.11 (1H, s), 7.16-7.21 (2H, m), 7.40-7.49 (4H, m), 7.58 (1H, d, J=4.8 Hz), 7.86 (1H, d, J=5.1 Hz), 8.46 (1H, s). [M+H] Calc'd for $C_{22}H_{19}FN_2O_3$, 379; Found, 379.

Preparation 87A and Preparation 88A: methyl 3-({[(4S)-7-cyclopropyl-3,4-dihydro-2H-chromen-4-yl]methyl}amino)pyridine-4-carboxylate; methyl 3-({[(4R)-7-cyclopropyl-3,4-dihydro-2H-chromen-4-yl]methyl}amino)pyridine-4-carboxylate

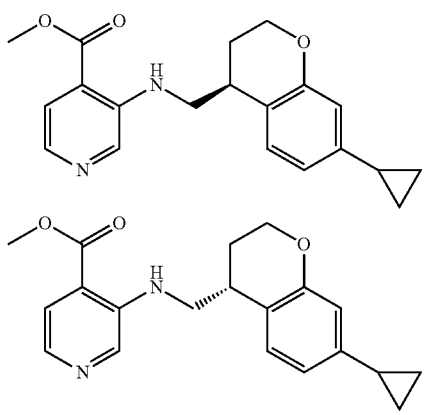

Preparation 75C (80 mg) was separated by chiral HPLC (Column: Chiralcel 1A, Mobile phase: $CO_2$:MeOH=60:40 (0.2% DEA) to give to give the two enantiomers: 20 mg (25%) of the first isomer eluted at 2.37 min and 22 mg (28%) of the second isomer eluted at 4.26 min.

Example 87 and Example 88: 3-({[(4S)-7-cyclopropyl-3,4-dihydro-2H-chromen-4-yl]methyl}amino)pyridine-4-carboxylic acid; 3-({[(4R)-7-cyclopropyl-3,4-dihydro-2H-chromen-4-yl]methyl}amino)pyridine-4-carboxylic acid

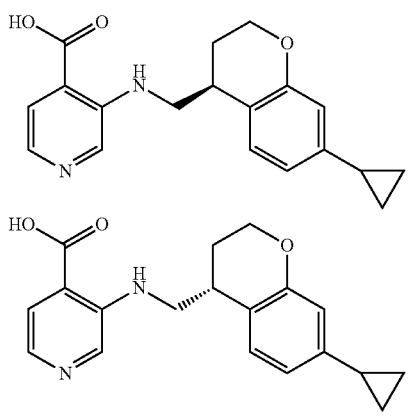

The title compounds were prepared in 48% to 68% yield from Preparation 87A and Preparation 88A according to the general hydrolysis procedure outlined for Example 61 and Example 62. NMR and MS for each of the title compounds matched Example 75.

Preparation 89A: 6-(2-phenylethoxy)-1,2,3,4-tetrahydronaphthalen-1-one

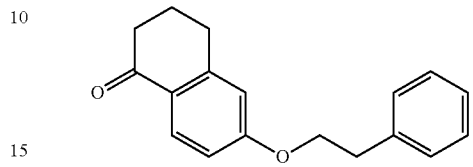

To a solution of 6-hydroxy-3,4-dihydro-1(2H)-naphthalenone (2.0 g, 12.3 mmol) and (2-bromoethyl)benzene (4.8 g, 25.8 mmol) in ACN (20 mL) was added potassium carbonate (3.4 g, 24.6 mmol) at rt. The solution was heated at reflux overnight. The reaction was filtered, concentrated, and purified by silica gel chromatography (PE:EtOAc:DCM=10:1:2) to give 2.0 g (61%) of the title compound as a brown oil. $^1$H NMR (300 MHz, CDCl$_3$): δ 2.08-2.16 (2H, m), 2.62 (2H, t, J=6.3 Hz), 2.92 (2H, t, J=6.3 Hz), 3.13 (2H, t, J=7.2 Hz), 2.92 (2H, t, J=7.2 Hz), 6.71 (1H, d, J=2.1 Hz), 6.83 (1H, dd, J=2.4, 8.7 Hz), 7.27-7.38 (5H, m), 8.01 (1H, dd, J=8.7 Hz).

Preparation 89B: [6-(2-phenylethoxy)-1,2,3,4-tetrahydronaphthalen-1-yl]methanamine

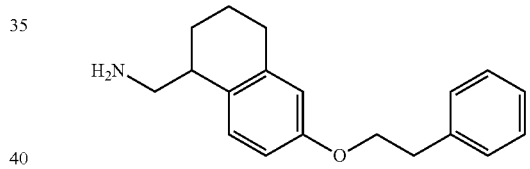

The title compound was prepared in 30% yield from Preparation 89A according to the general procedure for Preparation 63A, with the exception that the dehydration step reaction time was 10 min. [M+H] calc'd for $C_{19}H_{23}NO$, 282; found 282.

Example 89: 3-({[6-(2-phenylethoxy)-1,2,3,4-tetrahydronaphthalen-1-yl]methyl}amino)pyridine-4-carboxylic acid

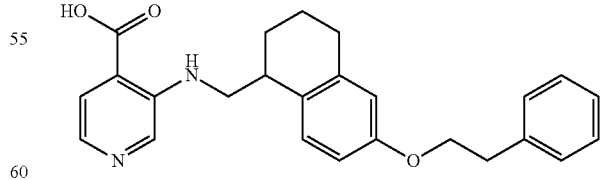

The title compound was prepared in 9% yield from Preparation 89B and 3-fluoroisonicotinic acid according to the procedure for the preparation of Example 3. $^1$H NMR (300 MHz, DMSO-$d_6$): δ 1.63-1.83 (4H, m), 2.66-2.71 (2H, m), 2.98-3.03 (3H, m), 3.40-3.44 (1H, m), 3.50-3.52 (1H, m), 4.13 (2H, t, J=6.6 Hz), 6.66-6.72 (2H, m), 7.19-7.21

(2H, m), 7.23-7.32 (4H, m), 7.54 (1H, d, J=5.1 Hz), 7.82 (1H, d, J=5.1 Hz), 8.35 (1H, s). [M+H] Calc'd for $C_{25}H_{26}N_2O_3$, 403; Found, 403.

Preparation 90A: 6-(2,2,2-trifluoroethoxy)-1,2,3,4-tetrahydronaphthalen-1-one

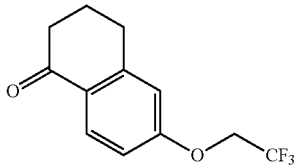

To a solution of 6-hydroxy-3,4-dihydro-1(2H)-naphthalenone (200 mg, 1.2 mmol) and 2,2,2-trifluoroethyl tosylate (345 mg, 1.4 mmol) in DMF (10 mL) was added potassium carbonate (339 mg, 2.5 mmol) at rt. The solution was heated at 100° C. overnight. The reaction was cooled, diluted with water (20 mL), and extracted with EtOAc (20 mL×3). Organics were dried ($Na_2SO_4$) and concentrated to give 250 mg (83%) of the title compound as a yellow solid. $^1$H NMR (300 MHz, $CDCl_3$): δ 2.12-2.16 (2H, m), 2.64 (2H, t, J=6.3 Hz), 2.95 (2H, t, J=6.3 Hz), 4.34-4.46 (2H, m), 6.78 (1H, d, J=2.4 Hz), 6.87 (1H, dd, J=2.4, 8.7 Hz), 8.05 (1H, dd, J=8.7 Hz).

Preparation 90B: [6-(2,2,2-trifluoroethoxy)-1,2,3,4-tetrahydronaphthalen-1-yl]methanamine

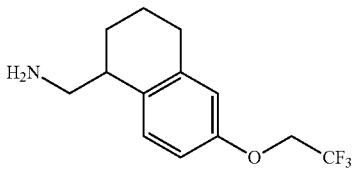 [SMILES: NCC1CCCc2cc(OCC(F)(F)F)ccc21]

The title compound was prepared in 13% yield from Preparation 90A according to the general procedure for Preparation 63A, with the exception that the dehydration step reaction time was 10 min. [M+H] calc'd for $C_{13}H_{16}F_3NO$, 260; found 260.

Example 90: 3-({[6-(2,2,2-trifluoroethoxy)-1,2,3,4-tetrahydronaphthalen-1-yl]methyl}amino)pyridine-4-carboxylic acid

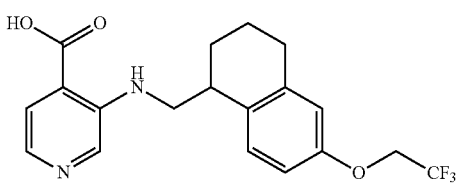

The title compound was prepared in 29% yield from Preparation 90B and 3-fluoroisonicotinic acid according to the procedure for the preparation of Example 3. $^1$H NMR (300 MHz, DMSO-$d_6$): δ 1.64-1.84 (4H, m), 2.68-2.72 (2H, m), 3.05-3.07 (1H, m), 3.41-3.46 (1H, m), 3.53-3.54 (1H, m), 4.65-4.74 (2H, m), 6.80-6.84 (2H, m), 7.27 (1H, d, J=8.1 Hz), 7.55 (1H, d, J=5.1 Hz), 7.83 (1H, d, J=5.1 Hz), 8.37 (1H, s). [M+H] Calc'd for $C_{19}H_{19}F_3N_2O_3$, 381; Found, 381.

Preparation 91A: 7-(2-cyclopropylethynyl)-3,4-dihydro-2H-1-benzopyran-4-one

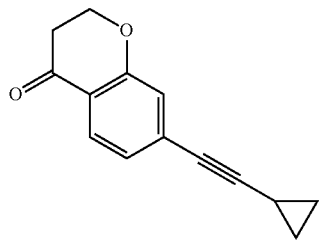 [SMILES: O=C1CCOc2cc(C#CC3CC3)ccc21]

To a solution of 7-bromochroman-4-one (2.0 g, 8.8 mmol) in DMF (10 mL) was added CuI (380 mg, 1.7 mmol), $Pd(PPh_3)Cl_2$ (540 mg, 0.8 mmol) and triethylamine (5 mL) under nitrogen at rt. The suspension was warmed to 100° C. and then cyclopropylacetylene (1.1 g, 17.6 mmol) was added dropwise. The mixture was stirred at 100° C. under nitrogen for 2 hr. The reaction mixture was cooled to rt, poured into water, and extracted with EtOAc. Organics were separated and washed with brine, dried ($Na_2SO_4$), and concentrated. The residue was purified by silica gel chromatography to give 1.65 g (88%) of the title compound as a tan solid. $^1$H NMR (300 MHz, $CDCl_3$): δ 0.83-0.93 (4H, m), 1.44-1.49 (1H, m), 2.79 (2H, t, J=6.6 Hz), 4.52 (2H, t, J=6.6 Hz), 6.96-7.00 (2H, m), 7.79 (1H, d, J=7.8 Hz). [M+H] calc'd for $C_{14}H_{12}O$, 213; found 213.

Preparation 91B: 7-(2-cyclopropylethyl)-3,4-dihydro-2H-1-benzopyran-4-one

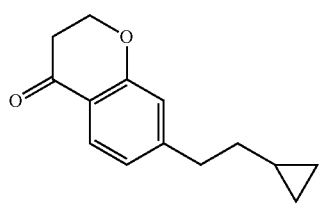 [SMILES: O=C1CCOc2cc(CCC3CC3)ccc21]

To a solution of Preparation 91A (520 mg, 2.4 mmol) in MeOH (15 mL) was added 10% Pd/C (190 mg) at rt under nitrogen. The suspension was stirred overnight at rt under 50 psi of hydrogen. The reaction mixture was filtered and concentrated. The residue was purified by silica gel chromatography to give 460 mg (86%) of the title compound as a colorless oil. [M+H] calc'd for $C_{14}H_{16}O$, 217; found 217.

Preparation 91C: [7-(2-cyclopropylethyl)-3,4-dihydro-2H-1-benzopyran-4-yl]methanamine

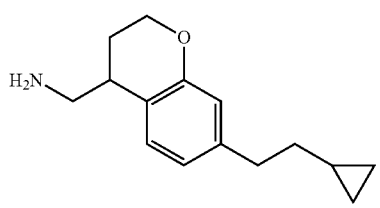 [SMILES: NCC1CCOc2cc(CCC3CC3)ccc21]

The title compound was prepared in 14% yield from Preparation 91B according to the general procedure for Preparation 63A, with the exception that the dehydration step reaction time was 1 hr. [M+H] calc'd for $C_{15}H_{21}NO$, 232; found 232.

Example 91D: methyl 3-({[7-(2-cyclopropylethyl)-3,4-dihydro-2H-chromen-4-yl]methyl}amino)pyridine-4-carboxylate

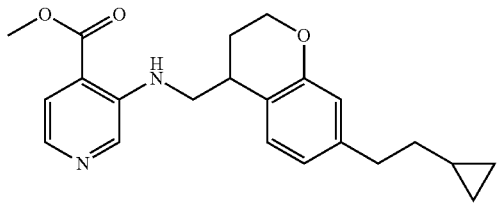 [SMILES: COC(=O)c1ccncc1NCC1CCOc2cc(CCC3CC3)ccc21]

The title compound was prepared from in 21% yield from Preparation 91C according to the general procedure outlined for Preparation 83A. [M+H] calc'd for $C_{22}H_{26}N_2O_3$, 367; found 367.

Example 91: 3-({[7-(2-cyclopropylethyl)-3,4-dihydro-2H-chromen-4-yl]methyl}amino)pyridine-4-carboxylic acid

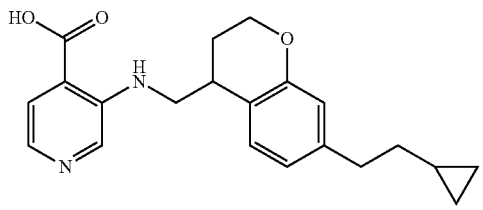 [SMILES: O=C(O)c1ccncc1NCC1CCOc2cc(CCC3CC3)ccc21]

The title compound was prepared in 63% yield from Preparation 91D according to the general hydrolysis procedure outlined for Examples 61 and 62. $^1$H NMR (300 MHz, CD$_3$OD): δ 0.01-0.05 (2H, m), 0.38-0.44 (2H, m), 0.65-0.70 (1H, m), 1.41-1.49 (2H, m), 1.96-2.03 (1H, m), 2.11-2.17 (1H, m), 2.61 (2H, t, J=7.5 Hz), 3.19-3.23 (1H, m), 3.53-3.60 (1H, m), 3.69-3.75 (1H, m), 4.16-4.27 (2H, m), 6.63 (1H, s), 6.69 (1H, d, J=7.5 Hz), 7.14 (1H, d, J=8.1 Hz), 7.92 (1H, d, J=5.4 Hz), 8.21 (1H, d, J=5.4 Hz), 8.35 (1H, s). [M+H] Calc'd for $C_{21}H_{24}N_2O_3$, 352; Found, 352.

Preparation 92A: ethyl 4-[3-(trifluoromethoxy)phenyl]butanoate

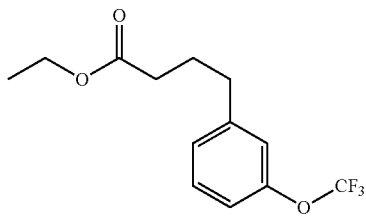 [SMILES: CCOC(=O)CCCc1cccc(OC(F)(F)F)c1]

4-Ethoxy-4-oxobutylzinc bromide solution (25 mL, 0.5 M in THF, 12.5 mmol) was added to a solution of 1-bromo-3-(trifluoromethoxy)benzene (2.6 g, 10.8 mmol) in THF (10 mL) under N$_2$. Pd(dppf)Cl$_2$ (1.18 g, 1.62 mmol) was added, and the reaction was heated at reflux for 3 hr. The solution was concentrated and purified by silica gel chromatography (0-20% EtOAc/hexanes) to give 1.22 g (41%) of the title compound as a clear oil. $^1$H NMR (400 MHz, DMSO-d$_6$): δ 1.26 (3H, t, J=7.2 Hz), 1.91-2.00 (2H, m), 2.32 (2H, t, J=7.4 Hz), 2.67 (2H, t, J=7.4 Hz), 4.13 (2H, q, J=7.2 Hz), 7.03-7.07 (2H, m), 7.11 (1H, d, J=7.7 Hz), 7.30 (1H, t, J=7.7 Hz).

Preparation 92B: 4-[3-(trifluoromethoxy)phenyl]butanoic acid

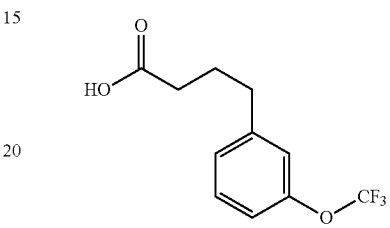

Preparation 92A (1.22 g, 4.42 mmol) was stirred in MeOH (10 mL) with 5N NaOH (2 mL) at rt overnight. The solution was neutralized with HOAc and concentrated. Purification by silica gel chromatography (5-10% MeOH/DCM) gave 1.02 g (92%) of the title compound as a clear oil. $^1$H NMR (400 MHz, DMSO-d$_6$): δ 1.93-2.01 (2H, m), 2.39 (2H, t, J=7.4 Hz), 2.70 (t, 2H, J=7.4 Hz), 7.04-7.13 (3H, m), 7.30 (1H, t, J=7.7 Hz), 11.33 (1H, br s).

Preparation 92C: 6-(trifluoromethoxy)-1,2,3,4-tetrahydronaphthalen-1-one

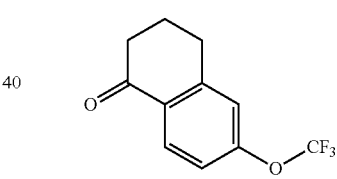

Preparation 93B (1.02 g, 4.11 mmol) was heated in PPA (5 mL) at 82° C. for 2 hr. The reaction was cooled, slowly quenched with sat NaHCO$_3$, and extracted with EtOAc (3×). Organics were dried (MgSO$_4$) and concentrated. Purification by silica gel chromatography (20-60% EtOAc/hexanes) gave 630 mg (67%) of the title compound as a clear oil. $^1$H NMR (400 MHz, DMSO-d$_6$): δ 2.13-2.20 (2H, m), 2.67 (2H, t, J=6.4 Hz), 2.99 (2H, t, J=6.1 Hz), 7.09 (1H, s), 7.13 (1H, d, J=8.7 Hz), 8.08 (1H, d, J=8.6 Hz). [M+H] calc'd for $C_{11}H_9F_3O_2$, 231; found 231.

Preparation 92D: [6-(trifluoromethoxy)-1,2,3,4-tetrahydronaphthalen-1-yl]methanamine

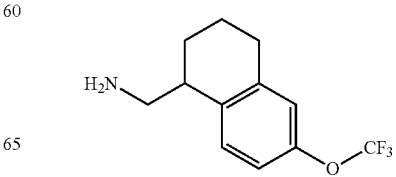

The title compound was prepared in 34% overall yield from Preparation 92C according to the procedure for Preparation 63A, with the exception that the dehydration step ran for 2 hr instead of overnight. ¹H NMR (400 MHz, Me₃OD): δ 1.78-2.00 (4H, m), 2.76-2.90 (2H, m), 3.07-3.15 (1H, m), 3.20-3.33 (2H, m), 7.02 (1H, s), 7.07 (1H, d, J=8.6 Hz), 7.37 (1H, d, J=8.5 Hz). [M+H] calc'd for C₁₂H₁₄F₃NO, 246; found 246.

Example 92: 3-({[6-(trifluoromethoxy)-1,2,3,4-tetra-hydronaphthalen-1-yl]methyl}amino)pyridine-4-carboxylic acid

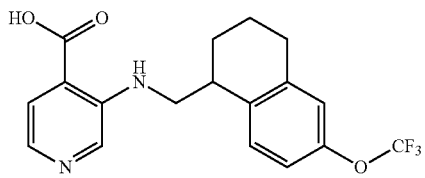

The title compound was prepared in 14% yield from Preparation 92D and 3-fluoroisonicotinic acid according to the procedure for the preparation of Example 3. ¹H NMR (400 MHz, DMSO-d₆): δ 1.66-1.88 (4H, m), 2.73-2.84 (2H, m), 3.12-3.16 (1H, m), 3.44-3.62 (2H, m), 7.09-7.12 (2H, m), 7.44 (1H, d, J=9.1 Hz), 7.57 (1H, d, J=5.0 Hz), 7.71 (1H, br s), 7.84 (1H, d, J=5.0 Hz), 8.37 (1H, s). [M+H] calc'd for C₁₈H₁₇F₃N₂O₃, 367; found 367.

Preparation 93A:
7-(4-fluorophenyl)-3,4-dihydro-2H-chromen-4-one

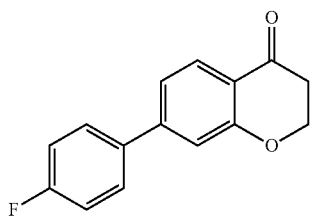 [SMILES: O=C1CCOc2cc(-c3ccc(F)cc3)ccc21]

The title compound was prepared in 99% yield using 4-fluorophenylboronic acid in the general procedure for Preparation 85A. ¹H NMR (300 MHz, CDCl₃): δ 2.86 (2H, t, J=6.3 Hz), 4.95 (2H, t, J=6.3 Hz), 7.13-7.24 (4H, m), 7.58 (2H, dd, J=5.7, 8.4 Hz), 7.96 (1H, d, J=8.1 Hz).

Preparation 93B: [7-(4-fluorophenyl)-3,4-dihydro-2H-chromen-4-yl]methanamine

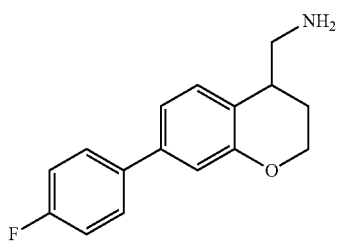 [SMILES: NCC1CCOc2cc(-c3ccc(F)cc3)ccc21]

The title compound was prepared in 17% yield from Preparation 93A according to the general procedure for Preparation 63A. [M+H] calc'd for C₁₆H₁₆FNO, 258; found 258.

Preparation 93C: methyl 3-({[7-(4-fluorophenyl)-3,4-dihydro-2H-chromen-4-yl]methyl}amino)pyridine-4-carboxylate

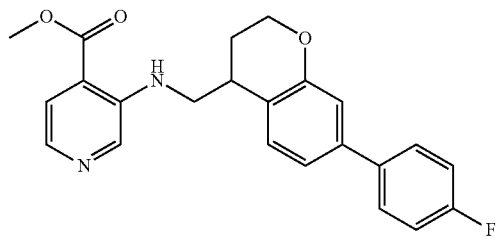 [SMILES: COC(=O)c1ccncc1NCC1CCOc2cc(-c3ccc(F)cc3)ccc21]

The title compound was prepared from in 35% yield from Preparation 93B according to the general procedure outlined for Preparation 83A. [M+H] calc'd for C₂₃H₂₁FN₂O₃, 393; found 393.

Preparation 93D and Preparation 94D: methyl 3-({[(4S)-7-(4-fluorophenyl)-3,4-dihydro-2H-chromen-4-yl]methyl}amino)pyridine-4-carboxylate; methyl 3-({[(4R)-7-(4-fluorophenyl)-3,4-dihydro-2H-chromen-4-yl]methyl}amino)pyridine-4-carboxylate

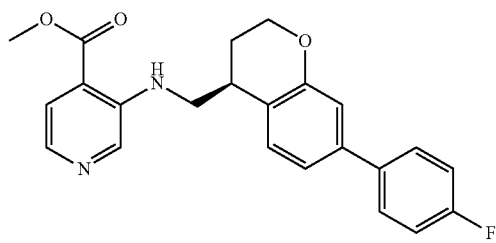

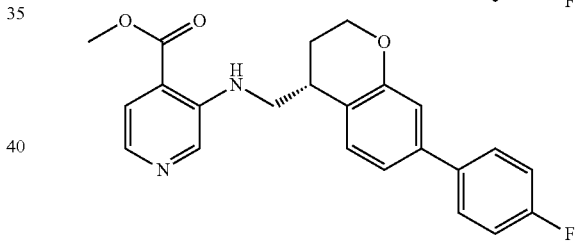

Preparation 93C (200 mg) was separated by chiral HPLC (Column: Chiralcel ID; Mobile phase: CO₂:MeOH=60:40 with −0.2% DEA) to give to give the two enantiomers: 50 mg (25%) of the first isomer eluted at 3.92 min and 60 mg (30%) of the second isomer eluted at 5.55 min.

Example 93 and Example 94: 3-({[(4S)-7-(4-fluorophenyl)-3,4-dihydro-2H-chromen-4-yl]methyl}amino)pyridine-4-carboxylic acid; 3-({[(4R)-7-(4-fluorophenyl)-3,4-dihydro-2H-chromen-4-yl]methyl}amino)pyridine-4-carboxylic acid

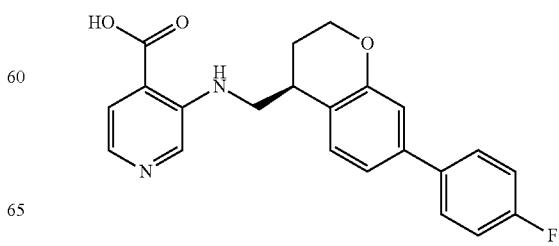

-continued

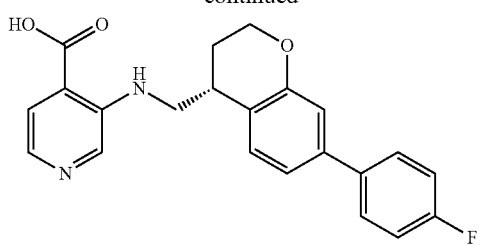

The title compounds were prepared in 70% to 92% yield from Preparation 93D and Preparation 94D according to the general hydrolysis procedure outline for Example 61 and Example 62. NMR and MS for each of the title compounds were identical: ¹H NMR (300 MHz, DMSO-$d_6$): δ 1.87-2.04 (2H, m), 3.14-3.20 (1H, m), 3.50-3.59 (1H, m), 3.70-3.77 (1H, m), 4.16-4.25 (2H, m), 7.04 (1H, d, J=1.8 Hz), 7.14 (1H, dd, J=1.5, 7.8 Hz), 7.26 (2H, t, J=9.0 Hz), 7.39 (1H, d, J=8.1 Hz), 7.58 (1H, d, J=4.8 Hz), 7.64-7.68 (2H, m), 7.85 (1H, d, J=5.1 Hz), 8.45 (1H, s). [M+H] Calc'd for $C_{22}H_{19}FN_2O_3$, 379; Found, 379.

Preparation 95A:
7-(2-fluorophenyl)-3,4-dihydro-2H-chromen-4-one

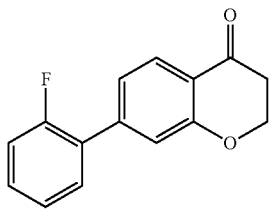 [SMILES: O=C1CCOc2cc(-c3ccccc3F)ccc21]

The title compound was prepared in 36% yield using 2-fluorophenylboronic acid in the general procedure for Preparation 85A.

Preparation 95B: [7-(2-fluorophenyl)-3,4-dihydro-2H-chromen-4-yl]methanamine

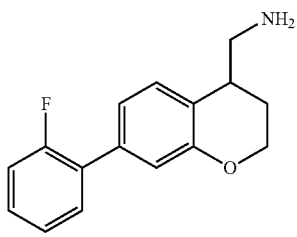 [SMILES: NCC1CCOc2cc(-c3ccccc3F)ccc21]

The title compound was prepared in 33% yield from Preparation 95A according to the general procedure for Preparation 63A. [M+H] calc'd for $C_{16}H_{16}FNO$, 258; found 258.

Preparation 95C: methyl 3-({[7-(2-fluorophenyl)-3,4-dihydro-2H-chromen-4-yl]methyl}amino)pyridine-4-carboxylate

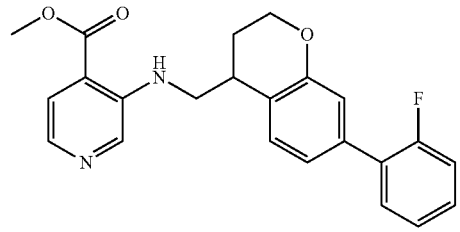

The title compound was prepared from in 36% yield from Preparation 95B according to the general procedure outlined for Preparation 83A. [M+H] calc'd for $C_{23}H_{21}FN_2O_3$, 393; found 393.

Preparation 95D and Preparation 96D: methyl 3-({[(4S)-7-(2-fluorophenyl)-3,4-dihydro-2H-chromen-4-yl]methyl}amino)pyridine-4-carboxylate; methyl 3-({[(4R)-7-(2-fluorophenyl)-3,4-dihydro-2H-chromen-4-yl]methyl}amino)pyridine-4-carboxylate

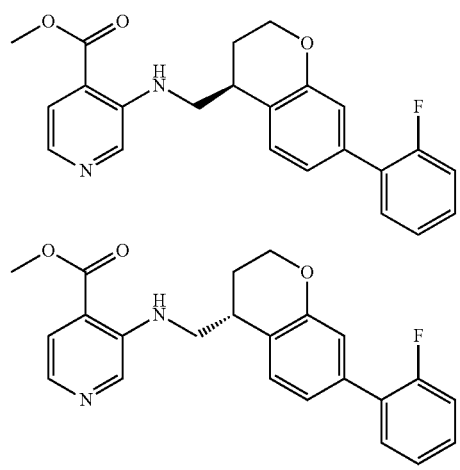

Preparation 95C (200 mg) was separated by chiral HPLC (Column: Chiralcel ID, 250 mm*4.6 mm 5 μm; Mobile phase: Hex:IPA=80:20; F: 1.0 mL/min; W: 230 nm; T=30° C.) to give to give the two enantiomers: 70 mg (35%) of the first isomer eluted at 4.52 min and 69 mg (34%) of the second isomer eluted at 5.68 min.

Example 95 and Example 96: 3-({[(4S)-7-(2-fluorophenyl)-3,4-dihydro-2H-chromen-4-yl]methyl}amino)pyridine-4-carboxylic acid; 3-({[(4R)-7-(2-fluorophenyl)-3,4-dihydro-2H-chromen-4-yl]methyl}amino)pyridine-4-carboxylic acid

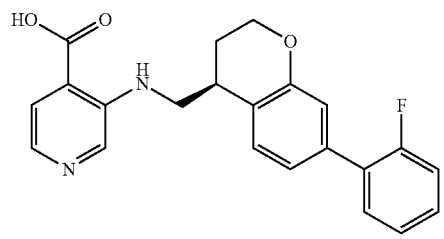

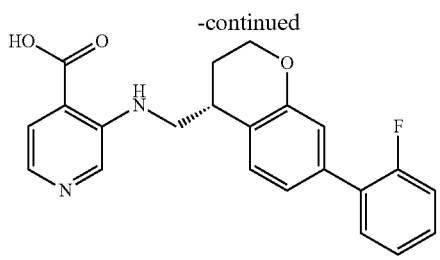

The title compounds were prepared in 77% to 91% yield from Preparation 95D and Preparation 96D according to the general hydrolysis procedure outline for Example 61 and Example 62. NMR and MS for each of the title compounds were identical: $^1$H NMR (300 MHz, DMSO-d$_6$): δ 1.91-2.04 (2H, m), 3.18-3.23 (1H, m), 3.53-3.61 (1H, m), 3.73-3.79 (1H, m), 4.17-4.26 (2H, m), 6.94 (1H, s), 7.04 (1H, d, J=8.1 Hz), 7.25-7.32 (2H, m), 7.36-7.52 (3H, m), 7.72 (1H, d, J=5.1 Hz), 7.90 (1H, d, J=4.5 Hz), 8.49 (1H, s). [M+H] Calc'd for C$_{22}$H$_{19}$FN$_2$O$_3$, 379; Found, 379.

Preparation 97A: 6-(2-cyclopropylethoxy)-1,2,3,4-tetrahydronaphthalen-1-one

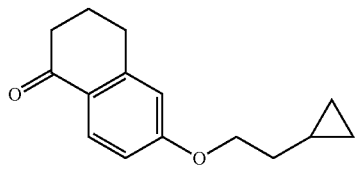 [SMILES: O=C1CCCc2cc(OCCC3CC3)ccc21]

To a suspension of 6-hydroxy-3,4-dihydro-1(2H)-naphthalenone (1.0 g, 6.0 mmol), 2-cyclopropylethanol (640 mg, 7.0 mmol) and triphenylphosphine (3.25 g, 12 mmol) in THF (100 mL) was added DEAD (2.13 g, 12 mmol) at 0° C. The reaction was stirred at rt overnight. The solution was concentrated and purified by silica gel chromatography (PE:EtOAc=12:1) to give 470 mg (33%) of the title compound as a red oil. $^1$H NMR (300 MHz, CDCl$_3$): δ 0.13-0.15 (2H, m), 0.50-0.52 (2H, m), 0.86-0.93 (1H, m), 1.68-1.74 (2H, m), 2.11-2.15 (2H, m), 2.64 (2H, t, J=6.3 Hz), 2.93 (2H, t, J=6.0 Hz), 4.10 (2H, t, J=6.6 Hz), 6.73 (1H, s), 6.83 (1H, dd, J=2.4, 8.7 Hz), 8.02 (1H, d, J=8.7 Hz).

Preparation 97B: [6-(2-cyclopropylethoxy)-1,2,3,4-tetrahydronaphthalen-1-yl]methanamine

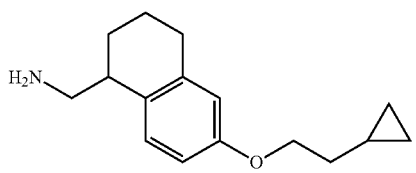 [SMILES: NCC1CCCc2cc(OCCC3CC3)ccc21]

The title compound was prepared in 73% yield from Preparation 97A according to the general procedure for Preparation 63A, with the exception that the dehydration step reaction time was 10 min. [M+H] calc'd for C$_{16}$H$_{23}$NO, 246; found 246.

Preparation 97C: methyl 3-({[6-(2-cyclopropylethoxy)-1,2,3,4-tetrahydronaphthalen-1-yl]methyl}amino)pyridine-4-carboxylate

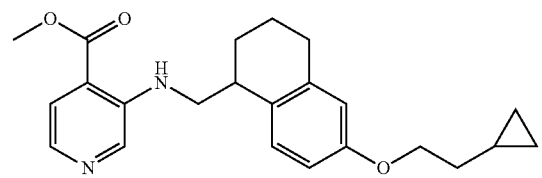 [SMILES: COC(=O)c1ccncc1NCC1CCCc2cc(OCCC3CC3)ccc21]

The title compound was prepared in 18% yield from Preparation 97B and methyl 3-fluoroisonicotinate according to the procedure for the preparation of Example 83A. [M+H] Calc'd for C$_{23}$H$_{28}$N$_2$O$_3$, 381; Found, 381.

Preparation 97D and Preparation 98D: methyl 3-({[(1S)-6-(2-cyclopropylethoxy)-1,2,3,4-tetrahydronaphthalen-1-yl]methyl}amino)pyridine-4-carboxylate; methyl 3-({[(1R)-6-(2-cyclopropylethoxy)-1,2,3,4-tetrahydronaphthalen-1-yl]methyl}amino)pyridine-4-carboxylate

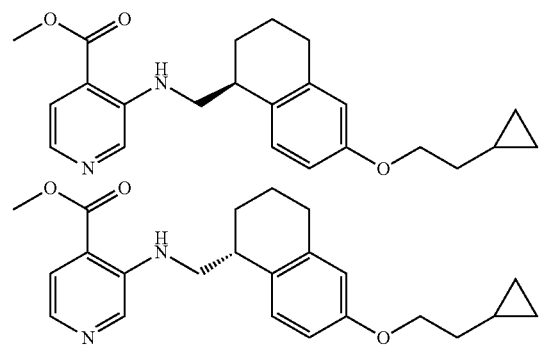

Preparation 97C (100 mg) was separated by chiral HPLC (Column: Chiralcel ID, 250 mm*4.6 mm 5 μm; Mobile phase: CO$_2$:MeOH (0.2% DEA)=70:30; F: 1.0 mL/min; W: 230 nm; T=30° C.) to give to give the two enantiomers: 15 mg (15%) of the first isomer eluted at 3.82 min and 20 mg (20%) of the second isomer eluted at 4.94 min.

Example 97 and Example 98: 3-({[(1 S)-6-(2-cyclopropylethoxy)-1,2,3,4-tetrahydronaphthalen-1-yl]methyl}amino)pyridine-4-carboxylic acid; 3-({[(1R)-6-(2-cyclopropylethoxy)-1,2,3,4-tetrahydronaphthalen-1-yl]methyl}amino)pyridine-4-carboxylic acid

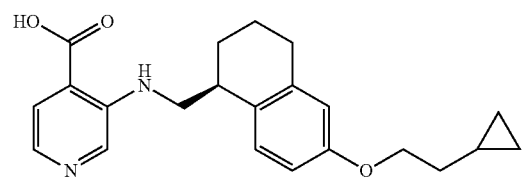

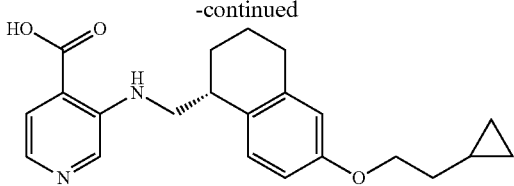

The title compounds were prepared in 71% to 74% yield from Preparation 97D and Preparation 98D according to the general hydrolysis procedure outline for Example 61 and Example 62. NMR and MS for each of the title compounds were identical: $^1$H NMR (300 MHz, DMSO-d$_6$): δ 0.09-0.12 (2H, m), 0.40-0.44 (2H, m), 0.77-0.86 (1H, m), 1.58-1.65 (3H, m), 1.75-1.84 (3H, m), 2.66-2.71 (2H, m), 3.00-3.05 (1H, m), 3.38-3.44 (1H, m), 3.50-3.56 (1H, m), 3.96 (2H, t, J=6.6 Hz), 6.65-6.72 (2H, m), 7.20 (1H, d, J=8.1 Hz), 7.55 (1H, d, J=4.8 Hz), 7.82 (1H, d, J=4.8 Hz), 8.35 (1H, s). [M+H] Calc'd for C$_{22}$H$_{26}$N$_2$O$_3$, 367; Found, 367.

Preparation 99A: methyl 3-({[(6-(3,3,3-trifluoropropoxy)-1,2,3,4-tetrahydronaphthalen-1-yl]methyl}amino)pyridine-4-carboxylate

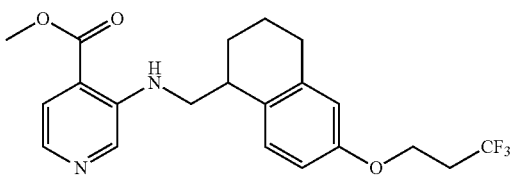 [SMILES: COC(=O)c1ccncc1NCC1CCCc2cc(OCCC(F)(F)F)ccc21]

The title compound was prepared from in 45% yield from Preparation 79B according to the general procedure outlined for Preparation 83A. [M+H] Calc'd for C$_{21}$H$_{23}$F$_3$N$_2$O$_3$, 407; Found, 407.

Preparation 99B and Preparation 100B: methyl 3-({[(1S)-6-(3,3,3-trifluoropropoxy)-1,2,3,4-tetrahydronaphthalen-1-yl]methyl}amino)pyridine-4-carboxylate; methyl 3-({[(1R)-6-(3,3,3-trifluoropropoxy)-1,2,3,4-tetrahydronaphthalen-1-yl]methyl}amino)pyridine-4-carboxylate

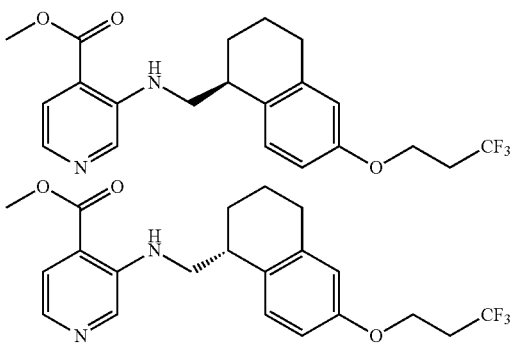

Preparation 99A (380 mg) was separated by chiral HPLC (Column: Chiralcel IF, 250 mm*4.6 mm 5 μm; Mobile phase: CO$_2$:MeOH (0.2% DEA)=60:40; F: 1.0 mL/min; W: 230 nm; T=30° C.) to give to give the two enantiomers: 80 mg (21%) of the first isomer eluted at 2.83 min and 70 mg (18%) of the second isomer eluted at 3.84 min.

Example 99 and Example 100: 3-({[(1S)-6-(3,3,3-trifluoropropoxy)-1,2,3,4-tetrahydronaphthalen-1-yl]methyl}amino)pyridine-4-carboxylic acid; 3-({[(1R)-6-(3,3,3-trifluoropropoxy)-1,2,3,4-tetrahydronaphthalen-1-yl]methyl}amino)pyridine-4-carboxylic acid

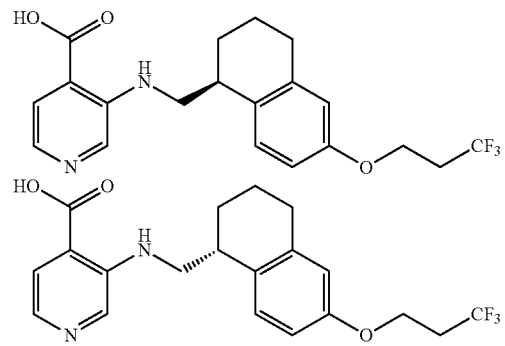

The title compounds were prepared in 74% to 78% yield from Preparation 99B and Preparation 100B according to the general hydrolysis procedure outline for Example 61 and Example 62. NMR and MS for each of the title compounds were identical: $^1$H NMR (300 MHz, DMSO-d$_6$): δ 1.63-1.84 (4H, m), 2.67-2.82 (4H, m), 3.02-3.06 (1H, m), 3.41-3.45 (1H, m), 3.51-3.58 (1H, m), 4.15 (2H, t, J=6.0 Hz), 6.69-6.75 (2H, m), 7.21 (1H, d, J=8.4 Hz), 7.57 (1H, d, J=4.8 Hz), 7.83 (1H, d, J=4.8 Hz), 8.36 (1H, s). [M+H] Calc'd for C$_{20}$H$_{21}$F$_3$N$_2$O$_3$, 395; Found, 395.

Example 101: 3-({[6-(3,3,3-trifluoropropoxy)-1,2,3,4-tetrahydronaphthalen-1-yl]methyl}amino)pyridazine-4-carboxylic acid

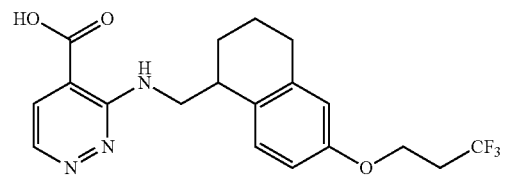 [SMILES: O=C(O)c1ccnnc1NCC1CCCc2cc(OCCC(F)(F)F)ccc21]

To a solution of Preparation 79B (150 mg, 0.55 mmol) in DMA (5 mL) was added 3-chloropyridazine-4-carbonitrile (84 mg, 0.6 mmol) at rt. The reaction was stirred for 1 hr at 170° C. in a microwave. The solution was diluted with H$_2$O (10 mL) and extracted with EtOAc (20 mL×3). Organics were washed with brine (30 mL), dried (Na$_2$SO$_4$), and concentrated to give crude 3-({[6-(3,3,3-trifluoropropoxy)-1,2,3,4-tetrahydronaphthalen-1-yl]methyl}amino)pyridazine-4-carbonitrile as a brown oil. This crude intermediate was stirred in EtOH (5 mL) and H$_2$O (5 mL). NaOH (110 mg, 2.8 mmol) was added, and the reaction was stirred at 90° C. for 3 hr. The solution was concentrated and purified by prep-HPLC to give 50 mg (23%) of the title compound as a brown solid. $^1$H NMR (300 MHz, CD$_3$OD): δ 1.77-1.99 (4H, m), 2.62-2.83 (4H, m), 3.19-3.23 (1H, m), 3.64-3.67 (1H, m), 3.77-3.79 (1H, m), 4.18 (2H, t, J=6.0 Hz), 6.69-

6.75 (2H, m), 7.23 (1H, d, J=8.1 Hz), 8.05 (1H, d, J=4.5 Hz), 8.48 (1H, d, J=4.2 Hz). [M+H] Calc'd for $C_{19}H_{20}F_3N_3O_3$, 396; Found, 396.

Preparation 102A: 5-fluoro-6-methoxy-1,2,3,4-tetrahydronaphthalen-1-one

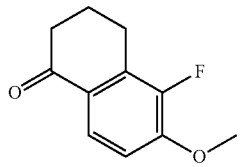

To a solution of 6-methoxy-1-tetralone (200 mg, 1.1 mmol) in ACN (20 mL) was added Selectfluor (603 mg, 1.7 mmol) at rt, and the reaction was stirred at 40° C. overnight. The reaction was filtered and concentrated. The residue was dissolved in EtOAc (40 mL), filtered, and concentrated. Purification by silica gel chromatography (PE:EtOAc:DCM=20:1:2) gave 90 mg (41%) of the title compound as a yellow solid. [M+H] Calc'd for $C_{11}H_{11}FO_2$, 195; Found, 195.

Preparation 102B: (5-fluoro-6-methoxy-1,2,3,4-tetrahydronaphthalen-1-yl)methanamine

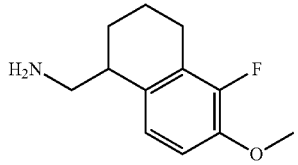

The title compound was prepared in 16% yield from Preparation 90A according to the general procedure for Preparation 63A, with the exception that the dehydration step reaction time was 10 min. [M+H] calc'd for $C_{12}H_{16}FNO$, 210; found 210.

Example 102: 3-{[(5-fluoro-6-methoxy-1,2,3,4-tetrahydronaphthalen-1-yl)methyl]amino}pyridine-4-carboxylic acid

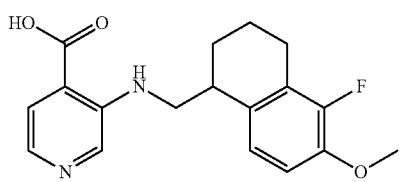 [SMILES: COc1ccc2c(c1F)CCCC2CNc1cnccc1C(=O)O]

The title compound was prepared in 25% yield from Preparation 102B and 3-fluoroisonicotinic acid according to the procedure for the preparation of Example 3. $^1$H NMR (300 MHz, DMSO-d$_6$): δ 1.68-1.82 (4H, m), 2.62-2.70 (2H, m), 3.06-3.10 (1H, m), 3.41-3.48 (1H, m), 3.53-3.58 (1H, m), 3.79 (3H, s), 6.95 (1H, t, J=8.4 Hz), 7.10 (1H, d, J=8.7 Hz), 7.55 (1H, d, J=5.1 Hz), 7.83 (1H, d, J=4.8 Hz), 8.36 (1H, s). [M+H] Calc'd for $C_{18}H_{19}FN_2O_3$, 331; Found, 331.

Preparation 103A: (3E)-4-(2,3-dimethylphenyl)but-3-enoic acid

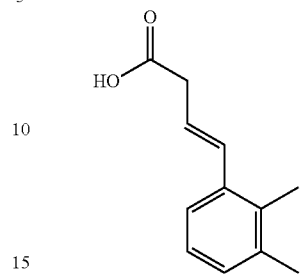

To a solution of 2,3-dimethylbenzaldehyde (17.0 g, 41.0 mmol) in THF (40 mL) was added NaHMDS (41.1 mL, 82.1 mmol) at −20° C., and the reaction was stirred for 20 min. (2-Carboxyethyl)triphenylphosphonium bromide (5.0 g, 37.3 mmol) was added to the reaction at −78° C., and reaction was stirred while warming to rt overnight. The solution was diluted with water (50 mL) and extracted with EtOAc (50×3 mL). Organics were washed with brine (50 mL), dried (Na$_2$SO$_4$), and concentrated to give 7.00 g (99%) of the crude title compound as a yellow solid. [M+H] calc'd for $C_{12}H_{14}O_2$, 191; found 191.

Preparation 103B: 4-(2,3-dimethylphenyl)butanoic acid

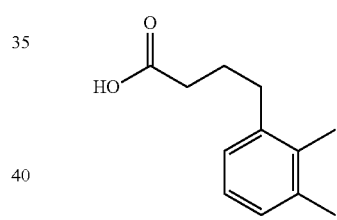

To a solution of Preparation 103A (7.0 g, 36.8 mmol) in MeOH (30 mL) was added 10% Pd/C (300 mg) under N$_2$ at rt. The mixture was stirred at rt overnight under 50 psi of H$_2$. The reaction was filtered through Celite and concentrated to give 6.5 g (92%) of the title compound as a white solid. [M+H] calc'd for $C_{12}H_{16}O_2$, 193; found 193.

Preparation 103C: 5,6-dimethyl-1,2,3,4-tetrahydronaphthalen-1-one

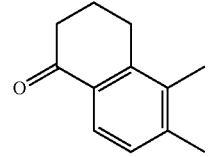

Preparation 103B (6.5 g, 33.9 mmol) was heated in PPA (5 mL) at 95° C. for 1.5 hr. The reaction was cooled, slowly quenched with sat NaHCO$_3$, and extracted with EtOAc (3×). Organics were dried (Na$_2$SO$_4$) and concentrated. Purification by silica gel chromatography (PE:EtOAc=15:1) gave 4.0 g (68%) of the title compound as a brown solid. ¹H NMR (300 MHz, CDCl₃): δ 2.11-2.19 (2H, m), 2.23 (3H, s), 2.36 (3H, s), 2.62 (2H, d, J=6.3 Hz), 2.91 (2H, t, J 6.3 Hz), 7.14 (1H, d, J=7.8 Hz), 7.87 (1H, d, J=7.8 Hz).

Preparation 103D: (5,6-dimethyl-1,2,3,4-tetrahydronaphthalen-1-yl)methanamine

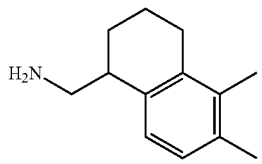

The title compound was prepared in 49% overall yield from Preparation 103C according to the procedure for Preparation 63A, with the exception that the dehydration step ran for 10 min instead of overnight. [M+H] calc'd for $C_{13}H_{19}N$, 190; found 190.

Example 103: 3-{[(5,6-dimethyl-1,2,3,4-tetrahydronaphthalen-1-yl)methyl]amino}pyridine-4-carboxylic acid

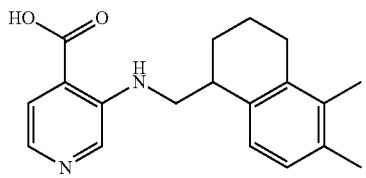 [SMILES: Cc1ccc2c(c1C)CCCC2CNc1cnccc1C(=O)O]

The title compound was prepared in 20% yield from Preparation 103D and 3-fluoroisonicotinic acid according to the procedure for the preparation of Example 3. ¹H NMR (400 MHz, DMSO-d₆): δ 1.72-1.78 (4H, m), 2.08 (3H, s), 2.20 (3H, s), 2.50-2.64 (2H, m), 3.04-3.07 (1H, m), 3.39-3.55 (2H, m), 6.93 (1H, d, J=7.8 Hz), 7.03 (1H, d, J=7.8 Hz), 7.56 (1H, d, J=5.1 Hz), 7.83 (1H, d, J=5.4 Hz), 8.36 (1H, s). [M+H] calc'd for $C_{19}H_{22}N_2O_2$, 311; Found, 311.

Preparation 104A: 6-{[6-(trifluoromethyl)pyridin-2-yl]oxy}-1,2,3,4-tetrahydronaphthalen-1-one

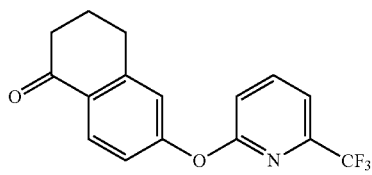 [SMILES: O=C1CCCc2cc(Oc3cccc(C(F)(F)F)n3)ccc21]

To a solution of 6-hydroxy-3,4-dihydro-1(2H)-naphthalenone (5.0 g, 30.8 mmol) and 2-chloro-6-(trifluoromethyl)pyridine (5.87 g, 32.3 mmol) in ACN (100 mL) was added potassium carbonate (6.39 g, 46.2 mmol), and the reaction was heated at 120° C. in a sealed vessel overnight. The reaction was cooled, diluted with water (100 mL), and extracted with EtOAc (100 mL×3). Organics were dried (Na₂SO₄), and concentrated. Purification by silica gel chromatography (10%-80% EtOAc/hexanes) gave 5.8 g (61%) of the title compound as a yellow oil. ¹H NMR (400 MHz, CDCl₃): δ 2.13-2.20 (2H, m), 2.67 (2H, t, J=6.2 Hz), 2.97 (2H, t, J=6.0 Hz), 7.07-7.14 (2H, m), 7.45 (1H, d, J=7.4 Hz), 7.89 (1H, t, J=8.0 Hz), 8.09 (1H, d, J=8.3 Hz). [M+H] calc'd for $C_{16}H_{12}F_3NO_2$, 308; found 308.

Preparation 104B: (6-{[6-(trifluoromethyl)pyridin-2-yl]oxy}-1,2,3,4-tetrahydronaphthalen-1-yl)methanamine

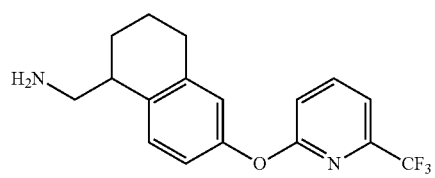 [SMILES: NCC1CCCc2cc(Oc3cccc(C(F)(F)F)n3)ccc21]

The title compound was prepared in 30% yield from Preparation 104A according to the general procedure for Preparation 63A, with the exception that the dehydration step reaction time was 1 hr. ¹H NMR (400 MHz, CDCl₃): δ 1.75-1.93 (4H, m), 2.74-2.78 (2H, m), 2.85-2.94 (1H, m), 2.96-3.03 (m, 2H), 6.89-6.99 (3H, m), 7.22 (1H, d, J=8.4 Hz), 7.36 (1H, d, J=7.4 Hz), 7.80 (1H, t, J=7.8 Hz). [M+H] calc'd for $C_{17}H_{17}F_3N_2O$, 323; found 323.

Example 104: 3-{[(6-{[6-(trifluoromethyl)pyridin-2-yl]oxy}-1,2,3,4-tetrahydronaphthalen-1-yl)methyl]amino}pyridine-4-carboxylic acid

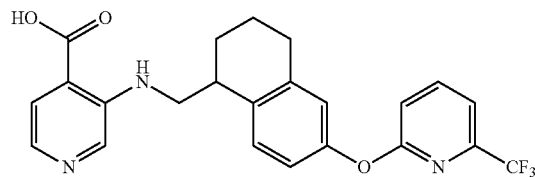 [SMILES: O=C(O)c1ccncc1NCC1CCCc2cc(Oc3cccc(C(F)(F)F)n3)ccc21]

The title compound was prepared in 15% yield from Preparation 104B and 3-fluoroisonicotinic acid according to the procedure for the preparation of Example 3. ¹H NMR (400 MHz, DMSO-d₆): δ 1.67-1.88 (4H, m), 2.72-2.77 (2H, m), 3.14-3.19 (1H, m), 3.45-3.51 (1H, m), 3.61-3.66 (1H, m), 6.95-6.99 (2H, m), 7.23 (1H, d, J=8.4 Hz), 7.41 (1H, d, J=8.2 Hz), 7.57-7.64 (2H, m), 7.83 (1H, d, J=4.7 Hz), 8.10 (1H, t, J=7.9 Hz), 8.38 (1H, s). [M+H] Calc'd for $C_{23}H_{20}F_3N_3O_3$, 444; Found, 444.

II. Biological Evaluation

Example 1: In Vitro Enzyme Inhibition Assay

This assay determines the ability of a test compound to inhibit Jarid1A, Jarid1B, and JMJD2C demethylase activity. Baculovirus expressed Jarid1A (GenBank Accession #NM_001042603, AA1-1090) was purchased from BPS Bioscience (Cat#50110). Baculovirus expressed Jarid1B (GenBank Accession #NM_006618, AA 2-751) was purchased from BPS Bioscience (Cat #50121) or custom made by MolecularThroughput. Baculovirus-expressed JMJD2C (GenBank Accession #BC143571, AA 2-372) was purchased from BPS Bioscience (Cat#50105).

Jarid1A Assay

The enzymatic assay of Jarid1A activity is based upon Time Resolved-Fluorescence Resonance Energy Transfer (TR-FRET) detection. The ability of test compounds to inhibit the activity of Jarid1A was determined in 384-well plate format under the following reaction conditions: 1 nM Jarid1A, 300 nM H3K4me3-biotin labeled peptide (Anaspec cat #64357), 2 µM alpha-ketoglutaric acid in assay buffer of 50 mM HEPES, pH 7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-mono-or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 µl of the mixture of 900 nM H3K4me3-biotin labeled peptide and 6 µM alpha-ketoglutaric acid with 2 µl of 11-point serial diluted inhibitor in 3% DMSO was added to each well of plate, followed by the addition of 2 µl of 3 nM Jarid1A to initiate the reaction. The reaction mixture was incubated at rt for 30 min, and terminated by the addition of 6 µl of 5 mM EDTA in LANCE detection buffer containing 50 nM Phycolink Streptavidin-allophycocyanin and 2 nM Europium-anti-H3K4me1-2 antibody. Plates were read by EnVision-Multilabel Reader in TR-FRET mode (excitation at 320 nm, emission at 615 nm and 665 nm) after 1 hr incubation at rt. A ratio was calculated (665/615) for each well and fitted to determine inhibition constant ($IC_{50}$).

Jarid1B Assay

The ability of test compounds to inhibit the activity of Jarid1B was determined in 384 well plate format under the following reaction conditions: 0.8 nM Jarid1B, 300 nM H3K4me3-biotin labeled peptide (Anaspec cat #64357), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-mono-or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 µl of the mixture of 900 nM H3K4me3-biotin labeled peptide and 6 µM alpha-ketoglutaric acid with 2 µl of 11-point serial diluted inhibitor in 3% DMSO was added to each well of the plate, followed by the addition of 2 µl of 2.4 nM Jarid1B to initiate the reaction. The reaction mixture was incubated at rt for 30 min, and terminated by the addition of 6 µl of 5 mM EDTA in LANCE detection buffer containing 50 nM Phycolink Streptavidin-allophycocyanin and 2 nM Europium-anti-H3K4me1-2 antibody. Plates were read by EnVision-Multilabel Reader in TR-FRET mode (excitation at 320 nm, emission at 615 nm and 665 nm) after 1 hr incubation at rt. A ratio was calculated (665/615) for each well and fitted to determine inhibition constant ($IC_{50}$).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 µl of the mixture of 900 nM H3K9me3-biotin labeled peptide and 6 µM alpha-ketoglutaric acid with 2 µl of 11-point serial diluted inhibitor in 3% DMSO were added to each well of the plate, followed by the addition of 2 µl of 0.9 nM JMJD2C to initiate the reaction. The reaction mixture was incubated at room temperature for 30 min, and terminated by the addition of 6 µl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hr incubation at rt. A ratio was calculated (665/615) for each well and fitted to determine inhibition constant ($IC_{50}$).

An assay to determine the ability of test compounds to inhibit the activity of JMJD2A was developed and disclosed in U.S. Provisional Application 61/792,930 and is incorporated by reference herein.

The ability of the pyridine and pyridazine compounds disclosed herein to inhibit demethylase activity was quantified and the respective $IC_{50}$ value was determined. Table 3 provides the $IC_{50}$ values of various compounds disclosed herein.

TABLE 3

| Chemical Synthesis Example | Name | JARID1A $IC_{50}$ (µM) | JARID1B $IC_{50}$ (µM) | JMJD2C $IC_{50}$ (µM) |
|---|---|---|---|---|
| 1 | 3-(benzylamino)pyridazine-4-carboxylic acid | A | B | A |
| 2 | 3-[(2-fluorobenzyl)amino] pyridine-4-carboxylic acid | A | A | A |
| 3 | 3-[(3-fluorobenzyl)amino] pyridine-4-carboxylic acid | A | A | A |
| 4 | 3-[(4-fluorobenzyl)amino] pyridine-4-carboxylic acid | A | A | A |
| 5 | 3-[(4-cyanobenzyl)amino] pyridine-4-carboxylic acid | A | A | A |
| 6 | 3-{[4-hydroxymethyl)benzyl]amino}pyridine-4-carboxylic acid | A | A | A |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 7 | 3-[(4-methoxybenzyl)amino] pyridine-4-carboxylic acid | A | A | A |
| 8 | 3-{[4-(trifluoromethyl)benzyl]amino} pyridine-4-carboxylic acid | A | A | A |
| 9 | 3-[(biphenyl-4-ylmethyl) amino]pyridine-4-carboxylic acid | A | B | C |
| 10 | 3-[(4-chlorobenzyl)amino] pyridine-4-carboxylic acid | A | A | A |
| 11 | 3-{[4-(propan-2-yloxy)benzyl] amino}pyridine-4-carboxylic acid | A | A | B |
| 12 | 3-[(4-phenoxybenzyl)amino] pyridine-4-carboxylic acid | A | A | B |
| 13 | 3-({2-[(dimethylamino)methyl] benzyl}amino)pyridine-4-carboxylic acid | A | A | A |
| 14 | 3-[(3,4-dichlorobenzyl)amino] pyridine-4-carboxylic acid | A | A | A |
| 15 | 3-[(4-chloro-2-methylbenzyl) amino]pyridine-4-carboxylic acid | A | A | A |
| 16 | 3-[(2,4-dimethyoxybenzyl)amino] pyridine-4-carboxylic acid | A | A | B |
| 17 | 3-[(2-hydroxybenzyl)amino] pyridine-4-carboxylic acid | A | A | A |
| 18 | 3-[(2,4-dichlorobenzyl)amino] pyridine-4-carboxylic acid | A | A | A |
| 19 | 3-[(2-cyclopropylbenzyl)amino] pyridine-4-carboxylic acid | A | A | A |
| 20 | 3-[(4-chloro-2-methoxybenzyl) amino]pyridine-4-carboxylic acid | A | A | B |
| 21 | 3-[(4-chloro-2-hydroxybenzyl) amino]pyridine-4-carboxylic acid | A | A | A |
| 22 | 3-[(2-aminobenzyl)amino] pyridine-4-carboxylic acid | A | A | A |
| 23 | 3-[(4-bromobenzyl)amino] pyridine-4-carboxylic acid | A | A | A |
| 24 | 3-[(4-methylbenzyl)amino] pyridine-4-carboxylic acid | A | A | A |
| 25 | 3-[(4-cyclopropylbenzyl)amino] pyridine-4-carboxylic acid | A | A | B |
| 26 | 3-[(4-chloro-2-cyclopropylbenzyl) amino]pyridine-4-carboxylic acid | A | A | B |
| 27 | 3-{[2-cyclopropyl-4-(trifluoro-methl) benzyl]amino}pyridine-4-carboxylic acid | A | A | B |
| 28 | 3-[(naphthalene-1-ylmethyl) amino]pyridine-4-carboxylic acid | A | A | A |
| 29 | 3-[(1H-indol-7-ylmethyl) amino]pyridine-4-carboxylic acid | A | A | A |
| 30 | 3-[(2-cyclopropyl-3-methylbenzyl) amino]pyridine-4-carboxylic acid | A | A | A |
| 31 | 3-{[(4-cyclopropylpyridin-3-yl)-methyl] amino}pyridine-4-carboxylic acid | A | A | A |
| 32 | 3-{[3-(trifluoromethyl)benzyl] amino}pyridine-4-carboxylic acid | A | A | A |
| 33 | 3-[(2-phenoxybenzyl)amino] pyridine-4-carboxylic acid | A | A | B |
| 34 | 3-[(2-cyclopropyl-5-methylbenzyl) amino]pyridine-4-carboxylic acid | A | A | B |
| 35 | 3-{[3-(trifluoromethoxy) benzyl]amino}pyridine-4-carboxylic acid | B | B | B |
| 36 | 3-{[2-(phenylaminol)benzyl] amino}pyridine-4-carboxylic acid | A | A | B |
| 37 | 3-{[3-(cyclopropylmethoxy) benzyl]amino}pyridine-4-carboxylic acid | B | A | B |
| 38 | 3-[(1-benzofuran-3-ylmethyl) amino]pyridine-4-carboxylic acid | A | A | B |
| 39 | 3-{[(5-methylthiophen-2-yl) methyl]amino}pyridine-4-carboxylic acid | A | A | A |
| 40 | 3-{[(5-methylfuran-2-yl)methyl] amino}pyridine-4-carboxylic acid | A | A | A |
| 41 | 3-[(1-benzofuran-2-ylmethyl)amino] pyridine-4-carboxylic acid | A | A | A |

TABLE 3-continued

| Chemical Synthesis Example | Name | JARID1A IC$_{50}$ (µM) | JARID1B IC$_{50}$ (µM) | JMJD2C IC$_{50}$ (µM) |
|---|---|---|---|---|
| 42 | 3-[(adamantan-1-ylmethyl) amino]pyridine-4-carboxylic acid | B | B | A |
| 43 | 3-[(2,3-dihydro-1-benzofuran-2-ylmethyl)amino]pyridine-4-carboxylic acid | A | A | A |
| 44 | 3-[(2,3-dihydro-1,4-benzodioxin-2-ylmethyl)amino]pyridine-4-carboxylic acid | A | A | A |
| 45 | 3-[(2,3-dihydro-1H-inden-1-ylmethylbenzyl) amino]pyridine-4-carboxylic acid | A | A | A |
| 46 | 3-[(1,2,3,4-tetrahydronaphthalen-1-ylmethyl) amino]pyridine-4-carboxylic acid | A | A | B |
| 47 and 48 | 3-{[(1S)-1,2,3,4-tetrahydro-naphthalen-1-yl methyl]amino} pyridine-4-carboxylic acid; 3-{[(1R)-1,2,3,4-tetrahydro-naphthalen-1-yl methyl]amino} pyridine-4-carboxylic acid | A/B | A/B | B/B |
| 49 | 3-{[(1-methyl-1,2,3,4-tetrahydro-naphthalen-1-yl)methyl]amino}pyridine-4-carboxylic acid | B | B | B |
| 50 | 3-{[(7-fluoro-1,2,3,4-tetrahydro-naphthalen-1-yl)methyl]amino}pyridine-4-carboxylic acid | — | A | B |
| 51 | 3-{[(7-fluoro-3,4-dihydronaphthalen-1-yl)methyl]amino}pyridine-4-carboxylic acid | — | — | B |
| 52 | 3-{[(5,7-dimethyl-1,2,3,4-tetra-hydronaphthalen-1-yl)methyl] amino}pyridine-4-carboxylic acid | — | — | C |
| 53 | 3-{[(7-cyclopropyl-1,2,3,4-tetra-hydro-naphthalen-1-yl)methyl]amino}pyridine-4-carboxylic acid | A | A | B |
| 54 | 3-{[(5-fluoro-1,2,3,4-tetrahydro-naphthalen-1-yl)methyl]amino} pyridine-4-carboxylic acid | — | — | B |
| 55 | 3-{[(5-fluoro-1-hydroxy-1,2,3,4-tetrahydronaphthalen-1-yl)methyl] amino}pyridine-4-carboxylic acid | — | — | B |
| 56 and 57 | 3-({[(1S)-5-fluoro-1,2,3,4-tetrahydro-naphthalen-1-yl]methyl}amino)pyridine-4-carboxylic acid; 3-({[(1R)-5-fluoro-1,2,3,4-tetrahydro-naphthalen-1-yl]methyl}amino) pyridine-4-carboxylic acid | — | — | A/B |
| 58 | 3-[(3,4-dihydro-2H-chromen-4-ylmethyl) amino]pyridine-4-carboxylic acid | A | A | A |
| 59 | 3-{[(4,4-dimethyl-1,2,3,4-tetrahydro-naphthalen-1-yl)methyl]amino}pyridine-4-carboxylic acid | — | — | B |
| 60 | 3-{[(6-methoxy-1,2,3,4-tetrahydronaphthalen-1-yl)methyl] amino}pyridine-4-carboxylic acid | A | A | B |
| 61 and 62 | 3-({[(1S)-6-methoxy-1,2,3,4-tetrahydro-naphthalen-1-yl]methyl} amino)pyridine-4-carboxylic acid; 3-({[(1R)-6-methoxy-1,2,3,4-tetrahydro-naphthalen-1-yl]methyl} amino)pyridine-4-carboxylic acid | — | — | B/B |
| 63 | 3-{[(6-methyl-3,4-dihydro-2H-chromen-4-yl) methyl]amino}pyridine-4-carboxylic acid | A | A | B |
| 64 | 3-({[(6-(propan-2-yloxy)-1,2,3,4-tetrahydronaphthalen-1-yl]methyl} amino)pyridine-4-carboxylic acid | — | — | B |
| 65 | 3-{[(7-fluoro-3,4-dihydro-2H-chromen-4-yl) methyl]amino}pyridine-4-carboxylic acid | — | — | A |
| 66 | 3-{[(7-chloro-3,4-dihydro-2H-chromen-4-yl) methyl]amino}pyridine-4-carboxylic acid | — | — | B |

TABLE 3-continued

| Chemical Synthesis Example | Name | JARID1A IC$_{50}$ (µM) | JARID1B IC$_{50}$ (µM) | JMJD2C IC$_{50}$ (µM) |
|---|---|---|---|---|
| 67 | 3-{[(6-chloro-1-hydroxy-1,2,3,4-tetrahydronaphthalen-1-yl)methyl]amino}pyridine-4-carboxylic acid | — | — | B |
| 68 | 3-{[(6-chloro-1,2,3,4-tetrahydronaphthalen-1-yl)methyl]amino}pyridine-4-carboxylic acid | — | — | B |
| 69 | 3-{[(7-phenyl-3,4-dihydro-2H-chromen-4-yl)methyl]amino}pyridine-4-carboxylic acid | — | — | B |
| 70 | 3-{[(7-fluoro-3,4-dihydro-2H-chromen-4-yl) methyl]amino}pyridine-4-carboxylic acid | — | — | B |
| 71 | 3-{[(8-fluoro-3,4-dihydro-2H-chromen-4-yl) methyl]amino}pyridine-4-carboxylic acid | — | — | A |
| 72 | 3-{[(7-chloro-1,2,3,4-tetrahydronaphthalen-1-yl)methyl]amino}pyridine-4-carboxylic acid | — | — | B |
| 73 | 3-{[(7-phenyl-1,2,3,4-tetrahydronaphthalen-1-yl)methyl]amino}pyridine-4-carboxylic acid | — | — | B |
| 74 | 3-{[(5-methoxy-1,2,3,4-tetrahydronaphthalen-1-yl)methyl]amino}pyridine-4-carboxylic acid | — | — | B |
| 75 | 3-{[(7-cyclopropyl-3,4-dihydro-2H-chromen-4-yl)methyl]amino}pyridine-4-carboxylic acid | — | — | B |
| 76 | 3-({[(5-(cyclopropylmethoxy)-1,2,3,4-tetra-hydronaphthalen-1-yl]methyl}amino)pyridine-4-carboxylic acid | — | — | C |
| 77 | 3-{[(5-phenoxy-1,2,3,4-tetrahydronaphthalen-1-yl)methyl]amino}pyridine-4-carboxylic acid | — | — | C |
| 78 | 3-[(3,4-dihydro-2H-thiochromen-4-yl-methyl)amino]pyridine-4-carboxylic acid | — | — | B |
| 79 | 3-({[(6-(3,3,3-trifluoropropoxy)-1,2,3,4-tetrahydronaphthalen-1-yl]methyl}amino)pyridine-4-carboxylic acid | — | — | B |
| 80 | 3-{[(5-phenoxy-1,2,3,4-tetrahydronaphthalen-1-yl)methyl]amino}pyridine-4-carboxylic acid | — | — | B |
| 81 | 3-({[(6-(cyclopropylmethoxy)-1,2,3,4-tetrahydronaphthalen-1-yl]methyl}amino) pyridine-4-carboxylic acid | — | — | B |
| 82 | 3{[(1-methyl-1,2,3,4-tetrahydroquinolin-4-yl) methyl]amino}pyridine-4-carboxylic acid | — | — | B |
| 83 and 84 | 3-({[(4R)-7-phenyl-3,4-dihydro-2H-chromen-4-yl]methyl}amino)pyridine-4-carboxylic acid; 3-({[(4S)-7-phenyl-3,4-dihydro-2H-chromen-4-yl]methyl}amino)pyridine-4-carboxylic acid | — | — | B/B |
| 85 and 86 | 3-({[(4S)-7-(3-fluorophenyl)-3,4-dihydro-2H-chromen-4-yl]methyl}amino)pyridine-4-carboxylic acid; 3-({[(4R)-7-(3-fluorophenyl)-3,4-dihydro-2H-chromen-4-yl]methyl}amino)pyridine-4-carboxylic acid | — | — | B/C |
| 87 and 88 | 3-({[(4S)-7-cyclopropyl-3,4-dihydro-2H-chromen-4-yl]methyl}amino) pyridine-4-carboxylic acid; 3-({[(4R)-7-cyclopropyl-3,4-dihydro-2H-chromen-4-yl]methyl}amino) pyridine-4-carboxylic acid | — | — | A/B |
| 89 | 3-({[6-(2-phenylethoxy)-1,2,3,4-tetrahydro-naphthalen-1-yl]methyl}amino)pyridine-4-carboxylic acid | — | — | B |
| 90 | 3-({[6-(2,2,2-trifluoroethoxy)-1,2,3,4-tetrahydronaphthalen-1-yl]methyl}amino) pyridine-4-carboxylic acid | — | — | B |
| 91 | 3-({[7-(2-cyclopropylethyl)-3,4-dihydro-2H-chromen-4-yl]methyl}amino)pyridine-4-carboxylic acid | — | — | B |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 92 | 3-({[6-(trifluoromethoxy)-1,2,3,4-tetrahydronaphthalen-1-yl]methyl}amino)pyridine-4-carboxylic acid | — | — | C |
| 93 and 94 | 3-({[(4S)-7-(4-fluorophenyl)-3,4-dihydro-2H-chromen-4-yl]methyl}amino)pyridine-4-carboxylic acid; 3-({[(4R)-7-(4-fluorophenyl)-3,4-dihydro-2H-chromen-4-yl]methyl}amino)pyridine-4-carboxylic acid | — | — | B/C |
| 95 and 96 | 3-({[(4S)-7-(2-fluorophenyl)-3,4-dihydro-2H-chromen-4-yl] methyl}amino)pyridine-4-carboxylic acid; 3-({[(4R)-7-(2-fluorophenyl)-3,4-dihydro-2H-chromen-4-yl] methyl}amino)pyridine-4-carboxylic acid | — | — | B/C |
| 97 and 98 | 3-({[(1S)-6-(2-cyclopropylethoxy)-1,2,3,4-tetrahydronaphthalen-1-yl]methyl}amino)pyridine-4-carboxylic acid; 3-({[(1R)-6-(2-cyclopropylethoxy)-1,2,3,4-tetrahydronaphthalen-1-yl]methyl}amino)pyridine-4-carboxylic acid | — | — | B/C |
| 99 and 100 | 3-({[(1S)-6-(3,3,3-trifluoro-propoxy)-1,2,3,4-tetrahydro-naphthalen-1-yl] methyl}amino) pyridine-4-carboxylic acid; 3-({[(1R)-6-(3,3,3-trifluoro-propoxy)-1,2,3,4-tetra-hydronaphthalen-1-yl] methyl} amino)pyridine-4-carboxylic acid | — | — | B/B |
| 101 | 3-({[6-(3,3,3-trifluoropropoxy)-1,2,3,4-tetrahydronaphthalen-1-yl] methyl} amino)pyridazine-4-carboxylic acid | — | — | B |
| 102 | 3-{[(5-fluoro-6-methoxy-1,2,3,4-tetrahydro-naphthalen-1-yl)methyl]amino}pyridine-4-carboxylic acid | — | — | B |
| 103 | 3-{[(5,6-dimethyl-1,2,3,4-tetrahydro-naphthalen-1-yl)methyl]amino}pyridine-4-carboxylic acid | — | — | B |
| 104 | 3-{[(6-{[6-(trifluoromethyl)pyridin-2-yl]oxy}-1,2,3,4-tetrahydro-naphthalen-1-yl)methyl] amino}pyridine-4-carboxylic acid | — | — | B |

Note:
Biochemical assay IC$_{50}$ data are designated within the following ranges:
A: ≤0.10 μM;
B: >0.10 μM to ≤1.0 μM;
C: >1.0 μM to ≤10 μM;
D: >10 μM

Example 2: In Vitro Cell-Based Assay

The primary cellular assay for JMJD2C inhibition is an assay which measures cellular proliferation via Bromodeoxyuridine (BrdU) incorporation after 168 hours of compound incubation. Cell lines tested include the JMJD2C gene amplified cell line KYSE-150. This is a quantitative ELISA assay measuring DNA incorporation of BrdU during S-phase as a direct readout of cellular proliferation.

Assay Principle: This is a colorimetric immunoassay for the quantification of cell proliferation. Cells treated for 168 hr with test compounds are assayed for their ability to go through S-phase as a measure of their proliferative potential.

Assay Method: The human KYSE-150 (SMAD4 mut, TP53 mut) esophageal carcinoma cell line was seeded at 2,000 cells/well on a 96-well tissue culture treated plate. After an overnight incubation, cells were treated with compound in an 11-point dilution series with final concentrations ranging from 100 μM to 2 nM. Cells were then incubated in the presence of compound for 168 hr. After compound incubation the cells were assayed using a BrdU Cell Proliferation ELISA (Roche). The cells were first incubated with BrdU labeling reagent for 2 hours. After 2 hours, the BrdU incorporated cells were fixed and denatured, probed with an anti-BrdU-Peroxidase antibody for 1.5 hr and washed. Finally, a tetramethylbenzidine peroxidase substrate was added to each well for 15 min followed by a H$_2$SO$_4$ stop solution. The plate was read at 450 nm, and the raw optical density data was transferred into XLFit (IDBS) for IC$_{50}$ calculation using the formula:

$$\text{fit} = (D + ((V\text{max} * (x\hat{\,}n))/((x\hat{\,}n) + (Km\hat{\,}n))))$$

A fluorometric immunoassay for the quantification of tri-methyl H3K4 extracted from cells treated with test compound and used as a measure of the cellular inhibition of KDM5A/B was developed and disclosed in U.S. Provisional Application 61/792,930 and is incorporated by reference herein.

Table 4 provides the cellular $IC_{50}$ values of various compounds disclosed herein.

TABLE 4

| Example | Cellular $IC_{50}$ (μM) |
|---|---|
| 5 | D |
| 5A | D |
| 8A | D |
| 10 | D |
| 10A | D |
| 14 | D |
| 14A | C |
| 15 | D |
| 16 | D |
| 17 | D |
| 18 | D |
| 19 | D |
| 23 | D |
| 25 | D |
| 25A | D |
| 26 | D |
| 26A | C |
| 28 | D |
| 30 | D |
| 30A | D |
| 32A | D |
| 38 | D |
| 39 | D |
| 40 | D |
| 41 | D |
| 42 | D |
| 42A | C |
| 45 | D |
| 46 | C |
| 47/48 | C/D |
| 49 | D |
| 50 | C |
| 51 | D |
| 52 | B |
| 53 | C |
| 54 | D |
| 56/57 | C/D |
| 58 | D |
| 59 | D |
| 60 | C |
| 61/62 | B/D |
| 63 | D |
| 64 | C |
| 66 | D |
| 67 | C |
| 69 | C |
| 72 | C |
| 75 | C |
| 79 | C |
| 80 | A |
| 81 | C |
| 82 | D |
| 83/84 | B/— |
| 85/86 | B/— |
| 87/88 | C/— |
| 89 | B |
| 90 | C |
| 91 | B |
| 99/100 | C/— |

Biochemical assay $IC_{50}$ data are designated within the following ranges:
A: ≤0.10 μM;
B: >0.10 μM to ≤1.0 μM;
C: >1.0 μM to ≤10 μM;
D: >10 μM Example 3: In Vivo Xenograph Study Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1 \times 10^7$ cells/mL. MCF-7 cells are subcutaneously injected (100 μL/animal) on the right flank 2-3 days post pellet implantation and tumor volume (length× $width^2/2$) is monitored bi-weekly. When tumors reach an average volume of ~200 $mm^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1: Oral Tablet

A tablet is prepared by mixing 48% by weigh of a compound of Formula (I) or a pharmaceutically acceptable salt thereof, 45% by weight of microcrystalline cellulose, 5% by weight of low-substituted hydroxypropyl cellulose, and 2% by weight of magnesium stearate.

Tablets are prepared by direct compression. The total weight of the compressed tablets is maintained at 250-500 mg.

We claim:

1. A compound of Formula (XI), or a pharmaceutically acceptable salt thereof,

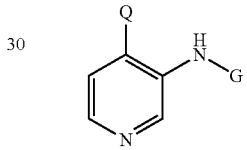

Formula (XI)

wherein:
Q is carboxylic acid; and
G is —X—Y, wherein
X is —$C_1$ alkylene;
Y is tetralinyl, optionally substituted with at least one halogen, hydroxyl, alkyl, carbocyclylalkyl, carbocyclylalkoxy, alkoxy, aryloxy, arylalkoxy, haloalkyloxy, or pyridinyl.

2. The compound of claim 1, wherein Y is substituted with halogen.

3. The compound of claim 1, wherein Y is substituted with at least one methyl.

4. The compound of claim 1, wherein Y is substituted with halogen selected from chloro or fluoro.

5. The compound of claim 1, wherein Y is further substituted with hydroxyl.

6. The compound of claim 1, wherein Y is substituted with phenyl.

7. The compound of claim 1, wherein Y is substituted with aryloxy or arylalkoxy selected from phenoxy, or phenylethoxy.

8. The compound of claim 1, wherein Y is substituted with trifluoromethoxy, or trifluoroethoxy.

9. The compound of claim 1, wherein Y is substituted with cyclopropyl, cyclopropylmethyl, or cyclopropylethyl.

10. The compound of claim 1, wherein Y is substituted with trifluoropropynyl or cyclopropylethynyl.

11. The compound of claim 1, wherein Y is substituted with pyridinyl.

12. A pharmaceutical composition comprising the compound of claim 1 and at least one pharmaceutically acceptable carrier.

13. A method of treating cancer in a subject in need thereof comprising administering to the subject the pharmaceutical composition of claim 12.

14. A method of inhibiting a histone demethylase enzyme comprising contacting the histone demethylase enzyme with the compound of claim 1.

* * * * *